US012252719B2

(12) United States Patent
Schlachter et al.

(10) Patent No.: US 12,252,719 B2
(45) Date of Patent: Mar. 18, 2025

(54) CHIMERIC AND OTHER VARIANT β-GLUCURONIDASE ENZYMES WITH ENHANCED PROPERTIES

(71) Applicant: INTEGRATED MICRO-CHROMATOGRAPHY SYSTEMS, INC., Irmo, SC (US)

(72) Inventors: Caleb Reece Schlachter, Irmo, SC (US); John Tomashek, Columbia, SC (US); Lim Andrew Lee, Columbia, SC (US)

(73) Assignee: INTEGRATED MICRO-CHROMATOGRAPHY SYSTEMS, INC., Irmo, SC (US)

( * ) Notice: Subject to any disclaimer, the term of this patent is extended or adjusted under 35 U.S.C. 154(b) by 0 days.

(21) Appl. No.: 17/865,099

(22) Filed: Jul. 14, 2022

(65) Prior Publication Data

US 2023/0060620 A1     Mar. 2, 2023

Related U.S. Application Data

(62) Division of application No. 16/596,568, filed on Oct. 8, 2019, now Pat. No. 11,421,210.

(Continued)

(51) Int. Cl.
    *C12N 9/24*   (2006.01)
    *C12N 9/42*   (2006.01)
    (Continued)

(52) U.S. Cl.
    CPC ........ *C12N 9/2402* (2013.01); *C07K 2319/00* (2013.01); *C12N 9/2445* (2013.01);
    (Continued)

(58) Field of Classification Search
    CPC ............ C12P 19/14; C12Y 302/01031; C12N 9/2402; C12N 9/2445; C12N 15/70; C07K 2319/00
    See application file for complete search history.

(56) References Cited

U.S. PATENT DOCUMENTS

4,994,390 A    2/1991  Wiatr
5,071,765 A   12/1991  Wiatr
(Continued)

FOREIGN PATENT DOCUMENTS

EP       1175495 B1    10/2006
WO     00/55333 A1     9/2000
(Continued)

OTHER PUBLICATIONS

U.S. Appl. No. 16/596,568, filed Oct. 8, 2019, Caleb Reece Schlachter, U.S. Pat. No. 9,920,306.
(Continued)

*Primary Examiner* — Soren Harward
*Assistant Examiner* — Naghmeh Nina Moazzami
(74) *Attorney, Agent, or Firm* — Nelson Mullins Riley & Scarborough LLP; Jill Gorny Sloper, Esq.

(57) ABSTRACT

Chimeric and other variant β-glucuronidase enzymes with enhanced properties as compared to unmodified enzyme are provided. The enzymes of the invention advantageously exhibit enhanced enzymatic activity, enhanced substrate range, enhanced pH range, enhanced temperature range and/or enhanced enzyme stability. Methods of using the variant enzymes for hydrolysis of glucuronide substrates, including opiates and benzodiazepines, are also provided.

26 Claims, 45 Drawing Sheets

Specification includes a Sequence Listing.

Related U.S. Application Data

(60) Provisional application No. 62/742,779, filed on Oct. 8, 2018.

(51) Int. Cl.
 *C12N 15/70* (2006.01)
 *C12P 19/14* (2006.01)
(52) U.S. Cl.
 CPC .............. *C12N 15/70* (2013.01); *C12P 19/14* (2013.01); *C12Y 302/01031* (2013.01)

(56) References Cited

U.S. PATENT DOCUMENTS

| | | |
|---|---|---|
| 6,391,547 B1 | 5/2002 | Jefferson et al. |
| 6,641,996 B1 | 11/2003 | Jefferson et al. |
| 6,664,097 B2 | 12/2003 | Russell et al. |
| 7,087,420 B1 | 8/2006 | Jefferson et al. |
| 7,141,719 B2 | 11/2006 | Jefferson et al. |
| 7,148,407 B2 | 12/2006 | Wenzl |
| 7,176,006 B2 | 2/2007 | Jefferson et al. |
| 8,491,891 B2 | 7/2013 | Roffler et al. |
| 9,719,075 B2 | 8/2017 | Lee |
| 9,909,111 B2 | 3/2018 | Yang et al. |
| 9,920,306 B2 | 3/2018 | Lee |
| 11,161,107 B2 | 11/2021 | Mullis et al. |
| 11,268,079 B2 | 3/2022 | Tomashek et al. |
| 11,421,210 B2 | 8/2022 | Schlachter et al. |
| 11,807,879 B2 | 11/2023 | Tomashek et al. |
| 2003/0003562 A1 | 1/2003 | Russell et al. |
| 2003/0157684 A1* | 8/2003 | Jefferson .............. C12N 9/2402 435/320.1 |
| 2004/0091922 A1 | 5/2004 | Russell et al. |
| 2005/0153448 A1 | 7/2005 | Wenzl |
| 2005/0227306 A1 | 10/2005 | Fox et al. |
| 2007/0037246 A1 | 2/2007 | Butt et al. |
| 2007/0081986 A1 | 4/2007 | Tomatsu et al. |
| 2009/0041741 A1 | 2/2009 | Sly et al. |
| 2010/0129367 A1 | 5/2010 | Roffler et al. |
| 2011/0237506 A1 | 9/2011 | Garigapati et al. |
| 2013/0011381 A1 | 1/2013 | Sly et al. |
| 2015/0086526 A1 | 3/2015 | Xie et al. |
| 2016/0090582 A1 | 3/2016 | Lee |
| 2016/0237415 A1 | 8/2016 | Lee |
| 2017/0267985 A1 | 9/2017 | Yang et al. |
| 2017/0354966 A1 | 12/2017 | Mullis et al. |
| 2018/0067116 A1 | 3/2018 | Rozas Andreu et al. |
| 2020/0002458 A1 | 1/2020 | Kajita |
| 2020/0024586 A1 | 1/2020 | Lee et al. |
| 2020/0040319 A1 | 2/2020 | Tomashek et al. |
| 2020/0109386 A1 | 4/2020 | Schlachter et al. |
| 2022/0090037 A1 | 3/2022 | Tomashek et al. |

FOREIGN PATENT DOCUMENTS

| | | |
|---|---|---|
| WO | 2010/138522 A2 | 12/2010 |
| WO | 2015/016124 A1 | 2/2015 |
| WO | 2016100871 A1 | 6/2016 |
| WO | 2018/136082 A1 | 7/2018 |

OTHER PUBLICATIONS

U.S. Appl. No. 15/076,134, filed Mar. 21, 2016, Lim Andrew Lee, U.S. Pat. No. 9,719,075.
U.S. Appl. No. 14/867,710, filed Sep. 28, 2015, Lim Andrew Lee, U.S. Pat. No. 9,920,306.
U.S. Appl. No. 15/076,183, filed Mar. 21, 2016, Jia Yang, U.S. Pat. No. 9,909,111.
U.S. Appl. No. 16/478,674, filed Jul. 17, 2019, Lim Andrew Lee, US 2020-0024586.
U.S. Appl. No. 16/528,292, filed Jul. 31, 2019, Lim Andrew Lee, U.S. Pat. No. 11,268,079.
U.S. Appl. No. 17/547,854, filed Dec. 10, 2021, Lim Andrew Lee, US 20220090037.
Rana, S. et al., "A New Method for Simultaneous Determination of Cyclic Antidepressants and their Metabolites in Urine Using Enzymatic Hydrolysis and Fast GC-MS," J. Anal. Toxicol., vol. 32:355 (2008).
Roberts, A. et al., "Molecular Insights into Microbial ?-Glucuronidase Inhibition to Abrogate CPT-11 Toxicity," Mol. Pharmacol. 84:208 (2013).
Romberg, R.W. et al., Comparison of the Hydrolysis Rates of Morphine-3-Glucuronide and Morphine-6-Glucuronide with Acid and ?-Glucuronidase,: J. Anal. Toxicol., vol. 19:157 (1995).
Russell W.M., et al., "Identification and cloning of gusA, Encoding a New Beta-Glucuronidase from Lactobacillus Gasseri ADH," Applied and Environmental Microbiology, vol. 67(3), pp. 1253-1261 (2001).
Sakurama, H. et al., "?-Glucuronidase from Lactobacillus brevis useful for baicalin hydrolysis belongs to glycoside hydrolase family 30," Appl Microbiol Biotechnol., vol. 98:4021-4032 (2014).
Sanchez, P. et al., "Fetal exposure to arsenic results in hyperglycemia, hypercholesterolemia, and nonalcoholic fatty liver disease in adult mice," J. Anal. Toxicol., vol. 36:162 (2014).
Schlachter, C. et al., "Variants of glycosyl hydrolase family 2 ?-glucuronidases have increased activity on recalcitrant substrates," Enzyme and Microbial Technology, vol. 145 (109742): 11 pages (2021).
Singh, R. et al., Protein Engineering Approaches in the Post-Genomic Era,: Curr Protein Pept Sci., vol. 18: 1-11 (2017).
Sitasuwan, P. et al., "Degradation of Opioids and Opiates During Acid Hydrolysis Leads to Reduced Recovery Compared to Enzymatic Hydrolysis," J. Anal. Toxicol., vol. 40:601 (2016).
Stahl, P. et al., "?-Glucuronidase of Rat Liver Lysosomes," J. Biol. Chem., vol. 246:5398 (1971).
Steffens, DL et al., "Efficient Site-Directed Saturation Mutagenesis Using Degenerate Oligonucleotides," J. Biomol. Tech., vol. 18:147-149 (2007).
Sudan, C. et al., "Ubiquitous presence of ?-glucuronidase (GUS) in plants and its regulation in some model plants," Planta, vol. 224:853 (2006).
Ulrich, A. et al., "Exponential megapriming PCR (EMP) cloning—seamless DNA insertion into any target plasmid without sequence constraints.," PLoS One, vol. 7:e53360 (2012).
Wallace, B. et al., "Alleviating Cancer Drug Toxicity by Inhibiting a Bacterial Enzyme," Science, vol. 330:831 (2010).
Wallace, B. et al., "Structure and Inhibition of Microbiome ?-Glucuronidases Essential to the Alleviation of Cancer Drug Toxicity," Chem. Biol. , vol. 22(9):1238-1249 (2015).
Wang et al., "Incomplete Recovery of Prescription Opioids in Urine using Enzymatic Hydrolysis of Glucuronide Metabolites," J. Anal. Toxicol., vol. 30:570 (2006).
Wang, C. et al., "Studies of Catalysis by ?-Glucuronidase," J. Biol. Chem., vol. 247:2644 (1972).
Waterhouse, A. et al., "Swiss-Model: homology modelling of protein structures and complexes," Nucleic Acids Res., vol. 46(W1):W296-W303 (2018).
Wierenga, R.K. et al., "The TIM barrel fold: a versatile framework for efficient enzymes," FEBS Letters, vol. 492:193-198 (2001).
Xiong, A.S. et al., "Directed evolution of a beta-galactosidase from Pyrococcus woesei resulting in increased thermostable beta-glucuronidase activity," Appl Microbiol Biotechnoly, vol. 77(3), pp. 569-578 (2007).
Xiong, A., et al. "Concurrent mutations in six amino acids in beta-glucuronidase improve its thermostability," Protein Engineering, Design & Selection, vol. 20(7) pp. 319-325 (2007).
Yang, HS et al., "Development and Validation of a Novel LC-MS/MS Opioid Confirmation Assay: Evaluation of ?-glucuronidase Enzymes and Sample Cleanup Methods," J. Anal. Toxicol., vol. 40:323 (2016).
Yeom, S.J. et al., "Controlled Aggregation and Increased Stability of ?-Glucuronidase by Cellulose Binding Domain Fusion.," PLoS One, vol. 12:e0170398 (2017).

(56) References Cited

OTHER PUBLICATIONS

Zhang, X. et al., "Increased activity of j3-glucuronidase variants produced by site-directed mutagenesis," Enzyme and Microbial Technology, vol. 109:20-24 (2018).
Naz, H. et al., "Human ß-glucuronidase: structure, function, and application in enzyme replacement therapy," Rej Research, vol. 16(5): 1-12. (2013).
Mutsumura et al., "In vitro evolution of beta-glucuronidase into a beta-galactosidase proceeds through non-specific intermediates," JMB vol. 305:331-339 (2001).
Devos et al., "Practical limits of function prediction," Proteins: Structure, Function and Genetics, vol. 41: 98-107 (2000).
Whisstock et al., "Prediction of protein function from protein sequence and structure," Quarterly Reviews of Biophysics, vol. 36 (3): 307-340 (2003).
Witkowski et al., "Conversion of a beta-ketoacyl synthase to a malonyl decarboxylase by replacement of the active-site cysteine with glutamine," Biochemistry 38:11643-11650 (1999).
Kisselev L., "Polypeptide release factors in prokaryotes and eukaryotes: same function, different structure," Structure, vol. 10: 8-9 (2002).
Accession C4Z6Z2. Jul. 28, 2009 (Year: 2009).
Accession KOJGG2. Nov. 28, 2012 (Year: 2012).
Aich S. et al., "Expression and Purification of *Escherichia coli* beta-Glucuronidase," Protein Expression and Purification, vol. 22 (1), pp. 75-81, (2001).
Benkert et al., "Toward the estimation of the absolute quality of individual protein structure models," Bioinformatics, vol. 27:343-350 (2011).
Bertoni, M. et al., "Modeling protein quaternary structure of homo- and hetero-oligomers beyond binary interactions by homology," Sci. Reports, vol. 7: 10480: 15 pages (2017).
Bienert, S. et al., "The Swiss-Model Repository—new features and functionality," Nucleic Acid Res. vol. 45:D313-D319 (2017).
Burchett, G. et al., "Native Electrophoresis-Coupled Activity Assays Reveal Catalytically-Active Protein Aggregates of *Escherichia coli* ?Glucuronidase," PLoS One, vol. 10(6): e0130269 (2015).
Callanan, M.J. et al. , "Modification of Lactobacillus beta-glucuronidase activity by random mutagenesis," Gene, vol. 389, pp. 122-127 (2007).
Chen, C. et al., "Ecstasy, an adjustable membrane-tethered/soluble protein expression system for the directed evolution of mammalian proteins," Protein Engineering, Design & Selection, vol. 25(7), pp. 367-375 (2012).
Chen, G. J. et al., "Restriction Site-Free Insertion of PCR Products Directionally into Vectors," BioTechniques, vol. 28:498-500 (2000).
Chica, R. et al. "Semi-rational approaches to engineering enzyme activity: combining the benefits of directed evolution and rational design," Curr Opin Biotechnol., vol. 16(4):378-384 (2005).
Chronopoulou, E. et al., "Site saturation Mutagenesis: A Powerful Tool for Structure Based Design of Combinatorial Mutation Libraries," Curr. Protocols Protein Sci., vol. 63:26.6.1-26.6.10 (2011).
Cummings, O. et al., "Impact of ?-Glucuronidase Mediated Hydrolysis on Haldol® Urinalysis," J. Anal. Toxicol., vol. 42:214 (2018).
Davies, G. et al., "Structures and mechanisms of glycosyl hydrolases," Structure, vol. 3:853 (1995).
Feng, X. et al., "Enhancing the Thermostability of ?-Glucuronidase by Rationally Redesigning the Catalytic Domain Based on Sequence Alignment Strategy," Ind. Eng. Chem. Res., vol. 55:5474-5483 (2016).
Flores, H. et al., "Increasing the thermal stability of an oligomeric protein, beta-glucuronidase.," J. Mol. Biol., vol. 315, Issue 3, pp. 325-337 (2002).
Folz. R-J. et al., "Substrate specificity of eukaryotic signal peptidase. Site-saturation mutagenesis at position-1 regulates cleavage between multiple sites in human pre (delta pro) apolipoprotein A-II.," J. Biol. Chem., vol. 263:2070-2078 (1988).
Fukao, M. et al., "Genomic Analysis by Deep Sequencing of the Probiotic Lactobacillus brevis KB290 Harboring Nine Plasmids Reveals Genomic Stability," PLoS One 8(3): e60521. doi:10.1371/journal.pone.0060521 (2013).

Geddie, M. et al., "Rapid Evolution of beta-Glucuronidase Specificity by Saturation Mutagenesis of an Active Site Loop," The Journal Of Biological Chemistry, vol. 279(25) pp. 26462-26468 (2004).
GenBank Accession No. WP 015255760.1, published May 28, 2013.
Genseq Accession No. AAW93825, published Jun. 15, 2007.
Graef, V. et al., "Hydrolysis of steroid glucuronides with beta-glucuronidase preparations from bovine liver, Helix pomatia, and *E. coli*.," Clin. Chem., vol. 23:532 (1977).
Guex, N. et al., "Automated comparative protein structure modeling with Swiss Model and SwissPdbViewer: A historical perspective," Electrophoresis, vol. 30:S162-S173 (2009).
Hassan, I. et al., "High resolution crystal structure of human ?-glucuronidase reveals structural basis of lysosome targeting," PLoS One 8:e79687 (2013).
Hernandez et al., "Control of protein immobilization: Coupling immobilization and site-directed mutagenesis to improve biocatalyst or biosensor performance," Enzyme and Microbial Technology, vol. 48:107-122 (2011).
Hochuli, E. et al., "Genetic Approach to Facilitate Purification of Recombinant Proteins with a Novel Metal Chelate Adsorbent," Nature Biotech., vol. 6:1321-1325 (1988).
International Preliminary Report on Patentability, PCT/US2017/014387, dated Jul. 23, 2019, 6 pages.
International Search Report and Written Opinion, PCT/US2017/014387, dated Apr. 19, 2017, 10 pages.
Jain, S. et al., "Structure of human ?-glucuronidase reveals candidate lysosomal targeting and active-site motifs," Nature Struct. Biol., vol. 3:375 (1996).
Joshi, M. et al., "Dissecting the Electrostatic Interactions and pH-Dependent Activity of a Family 11 Glycosidase†,‡," Biochemistry 40:10115 (2001).
Kim H.S. et al., "Cloning and expression of beta-glucuronidase from Lactobacillus brevis in *E. coli* and application in the bioconversion of baicalin and wogonoside," J Microbiol Biotechnol., vol. 19(12), pp. 1650-1655 (2009).
Kotronoulas, A. et al., "Evaluation of two glucuronides resistant to enzymatic hydrolysis as markers of testosterone oral administration," J. Steroid Biochem. Mol. Biol., vol. 167B:212 (2017).
Kuiper, H.A., et al., "Illegal use of ?-adrenergic agonists: European Community," J. Animal Sci., vol. 76:195-207 (1998).
Lin, Z. et al., "Evaluation of Analytical Procedures for Urinary Codeine and Morphine Measurements," J. Anal. Toxicol. 18:129-133 (1994).
Liu, M. et al., "Improving the activity and thermostability of GH2 beta glucuronidases via domain reassembly," Biotechnol Bioeng., 1-11. (2021).
Lv, B. et al., "Structure-guided engineering of the substrate specificity of a fungal ?-glucuronidase toward triterpenoid saponins," J. Biol. Chem., vol. 293(2):433-443 (2018).
Masuo, Y. et al., "Characterization of Inhibitory Effect of Carbapenem Antibiotics on the Deconjugation of Valproic Acid Glucuronide," Drug Metab. Disp., vol. 38:1828 (2010).
Matsumura, I. et al., "Directed evolution of the surface chemistry of the reporter enzyme beta-glucuronidase," Nat. Biotechnol., vol. 17(7), pp. 696-701 (1999).
Matsumura, I., et al., "In vitro evolution of beta-glucuronidase into a beta-galactosidase proceeds through non-specific intermediates," J. Mol. Biol. vol. 305(2), pp. 331-339 (2001).
McIntosh, L. et al., "The pKa of the General Acid/Base Carboxyl Group of a Glycosidase Cycles during Catalysis:? A 13C-NMR Study of Bacillus circulans Xylanase†," Biochemistry, vol. 35:9958 (1996).
Morris, A. et al., "Opioid Hydrolysis by a Novel Recombinant Beta-Glucuronidase for Urinalysis," Ameritox Medication Monitoring Solutions, Poster Presentation, 2014, Society of Forensic Toxicologists Annual Meeting, held in Grand Rapids, Michigan, Oct. 19-24, 2014, 1 page.
Morris, A.A. et al., "Rapid Enzymatic Hydrolysis Using A Novel Recombinant beta-Glucuronidase in Benzodiazepine Urinalysis," Journal of Analytical Toxicology, vol. 38, pp. 610-614 (2014).

(56) References Cited

OTHER PUBLICATIONS

Morris, A.A. et al., "Rapid Enzyme Hydrolysis Using A Novel Recombinant beta-Glucuronidase in Benzodiazepine Urinalysis," Ameritox Medication Monitoring Solutions, Poster Presentation, 2014, American Association of Clinical Chemistry Annual Meeting in Chicago, Illinois, Jul. 30, 2014, 1 page.

Morris, A.A. et al., Buprenorphine Hydrolysis Using a Novel Recombinant Beta-glucuronidase for Urine Drug Testing, Ameritox Medication Monitoring Solutions, Poster Presentation, 2014, Society of Forensic Toxicologists Annual Meeting, held in Grand Rapids, Michigan, Oct. 19-24, 2014, 1 page.

Nakamura, T. et al., "Possible Evidence of Contamination by Catechins in Deconjugation Enzymes from Helix pornatia and Abalone entrails," Biosci. Biotechnol. Biochem., vol. 75:1506 (2011).

Ngo et al. in The Protein Folding Problem and Tertiary Structure Prediction, 1994, Merz et al. (ed.), Birkhauser, Boston, MA, pp. 433 and 492-495.

Pellock, S. et al., "Gut Microbial ?-Glucuronidase Inhibition via Catalytic Cycle Interception," ACS Central Science, vol. 4: 868-879 (2018).

PIR Accession No. A25047, published Jun. 30, 1988.

PIR Accession No. A72300, published Jun. 11, 1999.

Pollet, R. et al., "An Atlas of ?-Glucuronidases in the Human Intestinal Microbiome," Structure, vol. 25:967 (2017).

\* cited by examiner

```
EeGUS    ------------------------------MLYPVLTQSRL-LSDLSGVWDFKLDNG---------      26
AoGUS    -----------------------------MLKPQQTTTRD-LISLDGLWKFALAS---------      25
Rxn3     -----------------------------MLKPQQTTTRD-LISLDGLWKFALAS---------      25
AtGUS    -----------------------------MLKPRQTPFRD-LISLDGLWKFALDSG--------      26
EcE1F    -----------------------------MLRPVETPTRE-IKKLDGLWAFSLDREN-------      27
BpGUS    -------------------------MVNSMLYPRESRTRR-VVDISGMWEFKIDIN--------      30
BmGUS    -------------------------MVNSMLYPRESRTRR-VVDISGMWEFKIDSN--------      30
CpGUS    -----------------------------MLYPIITESRQ-LIDLSGIWKFKLNEG--------      26
StpGUS   -----------------------------MLYPINTETRG-VFDLNGVWNFKLDYG--------      26
LbLR2D   -----------------------------MLYPMETASRV-VLDLSGVWRFMIDKE--------      26
SaGUS    -----------------------------MLYPLLTKTRN-TYDLGGIWNFKLG----------      24
HsGUS    MARGSAVAWAALGPLLWGCALGLQGGMLYPQESPSRE-CKELDGLWSFRADFSDN------      54
BfGUS    --MKKLLAAAMLFMLNSWSCFSADTPRAEYPRPQFEREQWVNLNGTWTFDFDFGK-------      53
PmGUS    -MKRISIAFLSLFLCVASVWSMPRP---EYPRPQFERAGWVNLNGEWTCSFDFGG-------      51
BuGUS    ----MKTLLKNSLIFLLMLMPVLAFAQQAPQIMNVSARQTTSLDGQWKTIVDPFENGYYDY      57
                                        .:.*  *

EeGUS    --------------KGFEEKWYEKPLKD----ADTMPVPASYNDLKEGTDFRDHYGWVFYQRNI      72
AoGUS    --------------DDNNTQPWTSQLKT----SLECPVPASYNDIFADSKIHDHVGWVYYQRDV      71
Rxn3     --------------DDNNTQPWTSQLKT----SLECPVPASYNDIFADSKIHDHVGWVYYQRDV      71
AtGUS    --------------DNATAAPWTGPLTT----DLECPVPASYNDIFVDRQIRDHVGWVYYQREA      72
EcE1F    --------------CGIDQRWWESALQE----SRAIAVPGSFNDQFADADIRNYAGNVWYQREV      73
BpGUS    --------------NEGRNSGYANGLKD----TTFIPVPSSFNDLFTDKNIREHAGDVWYETSF      76
BmGUS    --------------NEGRKNGYANGLKD----TTFIPVPSSFNDLFTDKNIREHAGDIWYETSF      76
CpGUS    --------------NGLTEELSKAPLED----TIEMAVPSSYNDLVESQEVRDHVGWVWYERNF      72
StpGUS   --------------KGLEEKWYESKLTD----TISMAVPSSYNDIGVTKEIRNHIGYVWYEREF      72
LbLR2D   ------------Q---IPVDVTRPLPA----TLSMAVPASFNDQTASKEIREHVGYVWYERCF      70
SaGUS    -----------------EHNPNELLPS----DEVMVIPTSFNDLMVSKEKRDYIGDFWYEKVI      66
HsGUS    ---------RRRGFEEQWYRRPLWESGPTVDMPVPSSFNDISQDWRLRHFVGWVWYEREV      105
BfGUS    -----------SGKDRRLQSAEKFD------KNITVPFCPESKLSGVGYTDFIEQMWYQRNI      98
PmGUS    -----------SGMEREFYKSKGFD----KKITVPFCPESKLSGIGYTDFINHFWYQRPI      96
BuGUS    RLKPYDGGYAQDKTYSDKTKLQEYDFETDKLLFVPGDWN---TQRPQLYYYEGTVWYRKHF      115
                      :*     :             . .:*.

EeGUS    SVPEYVKS---QRIVLRCAAVTHYAMIYLNGKLICEHKGGFLPFEVELNDDLQDGD-----      125
AoGUS    IVPKGWSE---ERYLVRCEAATHHGRIYVNGNLVADHVGGYTPFEADITDLVAAGEQ---      125
Rxn3     IVPKGWSE---ERYLVRCEAATHHGRIYVNGNLVADHVGGYTPFEADITDLVAAGEQ---      125
AtGUS    IVPRAWSQ---QQYLVRVDAATHQGRIYINDNLVAEHRGGYTPFEADITGLVSAGDS---      126
EcE1F    FIPKGWAG---QRIVLRFDAVTHYGKVWVNNQEVMEHQGGYIPFEADVTPYVIAGKS---      127
BpGUS    YLPLEWKD---KDVNVRFGCATHEATVYINGKEVCTHVGGFMPFNAPVNEAGIFGEK---      130
BmGUS    YLPLEWKD---KNVNIRFGCATHEAAVYINGKEVCTHVGGFMPFNAPVNEAGIFGEK---      130
CpGUS    TIPKTLLN---ERIVLRFGSATHEAKVYLNGELLVEHKGGFTPFEAEINDLLVSGD----      125
StpGUS   TVPAYLKD---QRIVLRFGSATHKAIVYNGELVVEHKGGFLPFEAEINNSLRDGM-----      125
LbLR2D   ELPQLLRQ---ERLVLRFGSATHEAWVYLNGHLITHHKGGFTPFEVEINDDLVTGE----      123
SaGUS    EVPKVSEG---EEMVLRFGSVTHQAKIYVDGILVGEHKGGFTPFEVLVPECKYNNEK---      120
HsGUS    ILPERWTQDLRTRVVLRIGSAHSYAIVWVNGVDTLEHEGGYLPFEADISNLVQVGPLPSR      165
BfGUS    TIPSDWNG---KKIFLNFGAVDYCAEIYVDGKFVQRHFGGSSSFAVDLTRYVTPGKT---      152
PmGUS    TIPQEWNG---KNILLNFGAVYYKSEVYIDGVLASRHFGGTSSFAVDITSLVKPGQT---      150
BuGUS    EYSLQPGK---RLFLNFGAVNYEAIVWLNGKRLGRHIGGFTPFNFEITNLLKEGTN---      168
                  :. ..  . ::::.    *  **  .*   :  .
```

Figure 1

```
EeGUS    NLLTIAVNNVIDYTTLPVGGKANMMSGMMGGMGAGASDKPQNNPNFDFFNYCGITRPVKI    185
AoGUS    FRLTIAVDNELTYQTIPPGK-----------VEILEATGKKVQTYQHDFYNYAGLARSVWL    175
Rxn3     FRLTIAVDNELTYQTIPPGK-----------VEILEATGKKVQTYQHDFYNYAGLARSVWL    175
AtGUS    FRLTIAVNNELTHETIPPGR-----------IEVEEYTGKRVQVYQHDFFNYAGLARSVWL    176
EcE1F    VRITVCVNNELNWQTIPPG------------MVITDENGKKKQSYFHDFFNYAGIHRSVML    176
BpGUS    NKLVVVVNNELSNTTIPCG------------HTETKPSGKKYIKPSFDFFNYAGLNRPVKI    179
BmGUS    NKLVVVVNNELSNTTLPCG------------HTETKPSGKKYIKPSFDFFNYAGLNRPVKI    179
CpGUS    NRLTVAVNNIIDETTLPVG---------LVKEVEVDGK-KVIKNSVNFDFFNYAGIHRPVKI    177
StpGUS   NRVTVAVDNILDDSTLPVG---------LYSERHEEGLGKVIRNKPNFDFFNYAGLHRPVKI    178
LbLR2D   NRLTVKLSNMLDYTTLPVG---------HYKETQNETGQRVRQLDENFDFFNYAGLQRPVKI    176
SaGUS    IKVSICANNVLDYTTLPVG---------NYSEIIQEDGSIKKKVRENFDFFNYAGVHRPLKL    173
HsGUS    LRITIAINNTLTPTTLPPGT------IQYLTDTSKYPKGYFVQNTYFDFFNYAGLQRSVLL    220
BfGUS    HNLVVFVQDDLRSGLQTGGK---------------------QCGNYYSGGCSYTRTTGIWQTVWM    196
PmGUS    HSLVVYESDVRGAKQAAGK-----------------QNLQYASYGCNYTRTTGIWQTVWM    194
BuGUS    -SLVVKVDNKRLPEAVPTVN---------------------------ADWWNFGGITRPVTL    202
             : :  ..    .                       .:  . *: :.:  :

EeGUS    YTTPETYINDITVTADIDFTKEEPSAVLNYNVEIKGKDYNNITCKVELFDEEGTKLSETE    245
AoGUS    YSVPQQHIQDITVRTDVQG--------TTGLIDYNVVAS-TTQGTIQVAVIDEDGTTVATSS    228
Rxn3     YSVPQQHIQDITVRTDVQG--------TTGLIDYNVVAS-TTQGTIQVAVIDEDGTTVATSS    228
AtGUS    YSVPQQHIQDIKVVTHVKG-------SAGLINYLVTVSNSTTGRVKIDVIDKDGTTVAEAS    230
EcE1F    YTTPNTWVDDITVVTHVAQD-------CNHASVDWQVVAN----GDVSVELRDADQQVVATGQ    228
BpGUS    TVTNKEYIHDIDILSDVNGS----DGIVNYEVHTTGENK----VYIKINDEEGCKEVASCE    231
BmGUS    TVTNKEYIYDIDILSDINGS----DGIVNYEVHTTGENK----VFVKIYDEEGKEAASAE    231
CpGUS    YTTPKSYIEDITIVTDFKEN-----NGYVNYEVQAVGKCN------IKVTIIDEENNIVAEGE    229
StpGUS   YTTPFTYVEDISVVTDFNGP----TGTVTYTVDFQGKAET---VKVSVVDEEGKVVASTE    231
LbLR2D   YSTPHSYIRDITLTPKVNLT---NHSAVVNGEIETVGDVEQ----VVVTILDEDNQVVGTTS    231
SaGUS    MIRPKNHISDITITSRLSDD--LQSADLHFLVETNQKVDE----VRISVFDEDNKLVGETK    228
HsGUS    YTTPTTYIDDITVTTSVEQD--------SGLVNYQISVKGSNLFKLEVRLLDAENKVVANGT    274
BfGUS    EAVSADGLKSVFVRPDIDQK-----QLVIEPEFYNESANTLEITLKDRNKTVAKKSVNCAN    252
PmGUS    EAVHPEGLQSIQLLTDIDQQ------QLVVRPRFYKEAGGKLQVTLKDNGKVVASRTVSASS    250
BuGUS    IEMPATYIRDYYVQLAKDDK-----NMIEGWVQLEGSDKEQKITLDIPELKVKKEVTTDAN    258
             : .      :

EeGUS    GSEGTFEISNVRLWQP------LNAYLYKIKVTAG---------QDVYTLPYGVRSVRVDGT    292
AoGUS    GSNGTIHIPSVHLWQP------GAAYLYQLHASIIDS---SKKTIDYKLATGIRTVKVQGT    281
Rxn3     GSNGTIHIPSVHLWQP------GAAYLYQLHASIIDS---SKKTIDYKLATGIRTVKVQGT    281
AtGUS    GARGSVTIDSVKLWQP------GEAYLYQFRASIVGL---NDSVVDTYCVETGVRTVKVSGN    283
EcE1F    GTSGTLQVVNPHLWQP------GEGYLYELCVTAKS-----QTECDIYPLRVGIRSVAVKGE    279
BpGUS    GKSGKIVIKDAKLWNP------KAAYLYKFIACIKN----GDELIDEYYLDFGIRTVKVEGT    283
BmGUS    GKNGKIVIKNAKLWNP------KAAYLYKFEACIKN----GEELIDEYYLDFGIRTIKVEGT    283
CpGUS    GKEGKLTINNVHLWEP------MNAYLYKLKVELLD----DEEIIDTYFEEFGVRTVEVKDG    281
StpGUS   GLSGNVEIPNVILWEP------LNTYLYQIKVELVN----DGLTIDVYEEPFGVRTVEVNDG    283
LbLR2D   GKTLAIELNSVHLWQP------GKAYLYRAKVELYQ---AGQVIDTYIETFGIRQIAVKAG    283
SaGUS    --DSRLFLSDVHLWEV------LNAYLYTARVEIFV---DNQLQDVYEENFGLREIEVTNG    278
HsGUS    GTQGQLKVPGVSLWWPYLMHERPAYLYSLEVQLTAQTSLGPVSDFYTLPVGIRTVAVTKS    334
BfGUS    SSVVVLPVKNMKLWSP------EDPFLYDLVYQVKDA--KGNVLDEVKSYAGMRKVHTANG    305
PmGUS    LSSVVLPVKKMKTWSP------ESPFLYDLEYKVLDK--NGNIIDEVNGYAGMRKVHIEGN    303
BuGUS    GYASFLIKSKPILWTP------ENPKLYAVNLASET--------DKVSDEIGFRTIRTEGI    305
             .         *      **           *       *.*  :
```

Figure 1 (cont'd.)

```
EeGUS    KFLINEKPFYFKGYGKH-EDTFPNGRGINLPMNTKDISIMKWQHANSFRTSHYPYSEEMM  351
AoGUS    QFLINDKPFYFTGFGKH-EDTNIRGKGHDDAYMVHDFQLLHWMGANSFRTSHYPYAEEVM  340
Rxn3     QFLINDKPFYFTGFGKH-EDSAVRGKGYDPAYMVHDFQLMDWMGANSFRTSHYPYAEEVM  340
AtGUS    RFLINDKPFYFTGFGKH-EDSAVRGKGYDPAYMVHDFQLMDWMGANSFRTSHYPYAEEVM  342
EcE1F    QFLINHKPFYFTGFGRH-EDADLRGKGFPDNVLMVHDHALMDWIGANSYRTSHYPYAEEML 338
BpGUS    KFLINGKPFYFTGFGKH-EDSEIAGRGYNPPVIKRDFELIKWVGANSFRTSHYPYSEEIM  342
BmGUS    KFLINGKPFYFTGFGKH-EDSETAGRGYNPPVIKRDFELIKWIGANSFRTSHYPYSEEIM  342
CpGUS    KFLINNKPFYFKGFGKH-EDSYVNGRGINEAINIKDFNLMKWIGANSFRTSHYPYSEEIM  340
StpGUS   KFLINNKPFYFKGFGKH-EDTPINGRGFNEASNVMDFNILKWIGANSFRTAHYPYSEELM  342
LbLR2D   KFLINGQPFYFKGFGKH-EDAYIHGRGLSEPQNVLDLSLMKQMGANSFRTSHYPYSEEMM  342
SaGUS    QFLLNRKPIYFKGFGKH-EDTFINGRGLNEAANLMDLNLLKDIGANSFRTSHYPYSEEMM  337
HsGUS    QFLINGKPFYFHGVNKH-EDADIRGKGFDWPLLVKDFNLLRWLGANAFRTSHYPYAEEVM  393
BfGUS    RFYLNNQPYFQRLVLDQGFYPEGIWTAPSDEDLKNDIVLGKEAGFNGARLHQKVFEERYY  365
PmGUS    KIYLNNKPYYQRLVLDQGFYPDGIWTAPSDEALKRDIELSMEAGFNGARLHQKVFEERFY  363
BuGUS    KILLNDKEIFCRGISIHEETPYYSGRAYSKDHAHTLLSWAKELGCNFVRLAHYPHNEEMV  365
           ::  :*     :              :   .  .       *     *   :   . *.

Variant
                                                                    Site 1

EeGUS    RLCDEEGIVVIDETTAVGVNLQFGGGANFGGERIGTFDKEHG-VQTQEHHKDVIRDLISR  410
AoGUS    EYADRQGIVVIDETPAVGLAFSIGAGAQTSNPP--ATFSPDRINNKTREAHAQAIRELIHR 399
Rxn3     EFADRHGIVVIDETPAVGLAFSIGSGVSSEDSP--QTFTPEGINNNTREAHRQAIRELIAR 399
AtGUS    EFADRHGIVVIDETPAVGLAFSIGSGVSSEDSP--QTFTPEGINNNTREAHKQAIRELIAR 401
EcE1F    DWADEHGIVVIDETAAVGFNLSLGIGFEAGNKPKELYSEEAVNGETQQAHLQAIKELIAR  398
BpGUS    QAADREGIVIIDEVAAVGMFDVGSVLNPSASKTDYFSLDEVH-SKTKEVHRKAVEELIKR  401
BmGUS    QAADREGIVIIDEIAAVGMFDVGSVLNPGASKADYFSLEEVH-TKTKEIHKKAVEELIIR  401
CpGUS    RLADREGIVVIDETPAVGLHLNFMATG-FGGDAP-KRDTWKE-IGTKEAHERILRELVSR  397
StpGUS   RLADREGLVVIDETPAVGVHLNFMATTGLGEGSE-RVSTWEK-IRTFEHHQDVLRELVSR  400
LbLR2D   RLCDREGIVVIDEVPAVGLMLSFTFDVSALEKDDFEDDTWEK-LRTAEAHRQAITEMIDR  401
SaGUS    RLADRMGVLVIDEVPAVGLFQNFNASLDLSPKD------NGTWSL-MQTKAAHEQAIQELVKR 393
HsGUS    QMCDRYGIVVIDECPGVGLALPQFFNN-------------------VSLHHHMQVMEEVVRR 436
BfGUS    YWADKLGYITWGESASWMLDVNK----------------------ELAARNFLGEWSEVVVR 405
PmGUS    YWADKMGYLTWGEASSWGMDCND----------------------TETARNFITEWSEIVQR 403
BuGUS    REAEPMGFLVWSEIPVYWTIHWEN--------------------KDTYQNAEQQLCDMIAR 406
           .:.  *  :   . * .                          :             ::: *

EeGUS    DKNHACVVMWSIANEPDSAAEGAYDYFKPLYDLARELDPQKRPCTLVS----VQGITADT  466
AoGUS    DKNHPSVVMWSIANEPASNEDGAREYFAPLPKLARQLDPT-RPVTFAN----VGLATYKA  454
Rxn3     DKNHASVVMWSIANEPASQEVGAREYFAPLVDLAHELDPS-RPVCFAN----YGDATYEV  454
AtGUS    DKNHASVVMWSIANEPASQEVGAREYFAPLVDLAHELDPS-RPVCFAN----YGDATYEV  456
EcE1F    DKNHPSVVMWSIANEPDTRPQGAREYFAPLAEATRKLDPT-RPITCVN----VMFCDAHT  453
BpGUS    DKNHPSVVMWSLFNEPDTSKDEAVPYFEDIFNFAKSQDKQNLPKTFAA----IQASSPGK  457
BmGUS    DKNHPSVVMWSLFNEPDTSKDEALPYFEDIFNFAKSIDKQNLPKTFAA----IQASAPGK  457
CpGUS    DKNHPCVVMWSVANEPDSDSEGAKEYFEPLIKLTKELDPQKRPVTVVT----YLMSTPDR  453
StpGUS   DKNHPSVVMWSIANEAATEEEGAYEYFKPLVELTKELDPQKRPVTIVL----FVMATPET  456
LbLR2D   DKNHASVVMWSISNEAANFSKGAYEFKPLFDLARKLDPQQRPCTYTS-----IMMTTLKT  457
SaGUS    DKNHPSVVMWVVANEPASHEAGAHDYFEPLVKLYKDLDPQKRPVTLVN----ILMATPDR  449
HsGUS    DKNHPAVVMWSVANEPASHLESAGYYLKMVIAHTKSLDPS-RPVTFVS----NSN---YAA 489
BfGUS    DRNHPSLVTWTPFNEIWGGGPDAYIRLVRDVYNITKAIDPTRPVNDASGD--NHVITDIW  463
PmGUS    DRNHPSLLIWTPTNEEFWPDRVQYPRLMHDLYNLTKMIDPTRPFHGASGG--THIATDIW  461
BuGUS    DKNRCNIIIWSIANETP-HSETRLTFLSNLANKARSLDSVRLIGAAMEKEEVQPGVLTVN  465
         *:*:    :: *    **             :         .

Variant
                                                                    Site 2
                                                                    (M-loop)
```

Figure 1 (cont'd.)

```
EeGUS    DCSSQLSDVICLNRYYG----------WYFGGPDLEVSEIGLR-KELSDWGKLG--KPVM  513
AoGUS    DRIADLFDVLCLNRYFG----------WYTQTAELDEAEAALE-EELRGWTEKYD-KPIV  502
Rxn3     DRISDMFDVLCLNRYFG----------WYSQTGEVEEAEAALE-KELLGWEGKYG-KPIV  502
AtGUS    DRISDMFDVLCLNRYFG----------WYSQTGEVEEAEAALE-KELLGWEGKYG-KPIV  504
EcE1F    DTISDLFDVLCLNRYYG----------WYVQSGDLETAEKVLE-KELLAWQEKLH-QPII  501
BpGUS    CKCMHLCDVITLNRYYG----------WYFLGG-YEIDMSEEK-FREEMNLYSNMNKPVM  505
BmGUS    CKCMHLCDVITLNRYYG----------WYFLGG-YEIDMSEEK-FREEMNLYKDMNKPVM  505
CpGUS    CKVGDIVDVLCLNRYYG----------WYVAGGDLEEAKRMLE-DELKGWEERCPKTPIM  502
StpGUS   DKVAELIDVIALNRYNG----------WYFDGGDLEAAKVHLR-QEFHAWNKRCPGKPIM  505
LbLR2D   DRCLALADVIALNRYYG----------WYMGNGDLKAAETATR-EELLAYQAKFPDKPIM  506
SaGUS    DQVMDLVDVVCLNRYYG----------WYVDHGDLTNAEVGLR-KELLEWQDKFPDKPII  498
HsGUS    DKGAPYVDVICLNSYYS----------WYHDYGHLELIQLQLA-TQFENWYKKYQ-KPII  537
BfGUS    SVHNYEQDRAKLTEQLK---------------MEEGKEPYRNARDKDFLAVYEGQPYM    506
PmGUS    TVHNYEQDPAKLKEKLYNGGKLMEAPKWEIHLMPMNIGYNGLKYTDQYAFPEYKKDMPYL  521
BuGUS    DPLGELLDIISFNEYVG-----------WYDGDSEKCDR-----------VNWTFDTQKPVF  505
                 *  :.                                              *  .

EeGUS    FTEYGADTVSGLHDTTSVMYTEEYQVEYYEMNNKVFD---EFDFVVGEQAWNFADFATSQ--  570
AoGUS    MTEYGADTVAGLHSVMVTPWSEEFQVEMLDMYHRVFD---RFEAMAGEQVWNFADFQTAV-  559
Rxn3     ITEYGADTMAGLHSVLALPWSEEFQVQLLDMYHRVFD---RIDSVVGEHVWNFADFQTAV-  559
AtGUS    ITEYGADTMAGLHSVLALPWSEEFQVQLLDMYHRVFD---RIDSVVGEHVWNFADFQTAV-  561
EcE1F    ITEYGVDTLAGLHSMYTDMWSEEYQCAWLDMYHRVFD---RVSAVVGEQVWNFADFATSQ-  558
BpGUS    FTEYGADTYAGVHKLPSVMWSEEYQCEYYEMNFKVFD---SYDFIVGEQLWNFADFQTTE-  562
BmGUS    FTEYGADTYAGVHKLPSVMWSEEYQCEYYEMNFKVFD---SYDFIIGEQLWNFADFQTTE-  562
CpGUS    FTEYGADTVAGLHDTVPVMFTEEYQVEYYKANHEVMD---KCKNFVGEQVWNFADFATSQ-  559
StpGUS   ITEYGADTVAGFHDIDPVMFTEEYQVEYYQANHVVFD---EEPENFVGEQAWNFADFATSQ-  562
LbLR2D   YTEYGADTIAGLHSNYDEPFSEEFQEDYYRMCSRVFD---EVTNFVGEQLWNFADFQTKF-  563
SaGUS    ITEYGADTLPGLHSTWNIPYTEEFQCDFYEMSHRVFD---GIPNLVGEQWNFADFETNL-  555
HsGUS    QSEYGAETIAGFHQDPPLMFTEEYQKSLLEQYHLGLDQKRRKYVVGELIWNFADFMTEQ-  596
BfGUS    VDEFGGIPWMAEK------DRKNSWGYGGMPENAEAFYKRLEGQIDAFIDSP--HVTGFCYT-  560
PmGUS    VDEFGGIKWNPSQQMESAQNTSWGYGEPPRSLEEFYARLEGQVDAVLSLSNDIWGYCYT-  580
BuGUS    ISELGGGALYGRHGSPKERFTEEYQEDLYIRHVNMLK--RIPGLAGTTPWILKDFRSPRR  563
           *  *        :      ..

EeGUS    ---SLLRVQGNKKGLFTRDRKPKMVAHYFRNRWSTIPEFGYKTK-----------------  611
AoGUS    ---GVSRVDGNKKGVFTRDRKPKAAAHLLRKRWTNLHNGTAEGSKTFQ-----------  604
Rxn3     ---GIIRVDGNKKGVFTRERKPKAAAHTLKTRWSGMLGSDH-----------------  597
AtGUS    ---GIIRVDGNKKGVFTRERKPKAAAHTLKTRWSGMLGSDH-----------------  599
EcE1F    ---SILRVGGNKKGIFTRDRKPKSAAFLLQKRWTGMNFGEKPQQGSKQGLCGR------  608
BpGUS    ---GIFRVDGNKKGIFTRNRQPKAVAHLIRSRWNKLPLDYKSKK---------------  603
BmGUS    ---GIFRVDGNKKGIFTRTRQPKAVAHYIRSRWTKLPLDYKK----------------  601
CpGUS    ---GIIRVQGNKKGIFTRERKPKMIAHSLRERWTNIPEFGYKK---------------  599
StpGUS   ---GVMRVQGNKKGVFTRDRKPKLAAHVFRERWTNIPDFGYKN--------------  602
LbLR2D   ---GIQRVQGNKKGIFTRAREPKMVVRYLTQRWRNIPDFNYKK---------------  603
SaGUS    ---MILRVQGNHKGLFSRNRQPKQVVKEFKKRWMTIPHYHNKKNSVK-----------  599
HsGUS    ---SPTRVLGNKKGIFTRQRQPKSAAFLLRERYWKIANETRYPHSVAKSQCLENSLFT  651
BfGUS    ---QLTDVEQEKNGIYYYDRTPKLDMKRIKAIFEKIK----------------------  594
PmGUS    ---QLTDVEQEQNGIYYYDRTPKFDMKRIHAIFSKTPESK-----------------  617
BuGUS    HVPEIQDDFNRKGLVSDKGQKKAFFVLQKWYKELTEAYK-------------------  603
           :::*:              *          :      :
```

Variant Site 3

Figure 1 (cont'd.)

```
CpGUS    MLYPIITESRQLIDLSGIWKFKLN-EGNGLTEELSKAPLEDTIEMAVPSSYNDLVESQEV     59
EeGUS    MLYPVLTQSRLLSDLSGVWDFKLD--NGKGFEEKWYEKPLKDADTMPVPASYNDLKEGTDF    59
EcGUS    MLRPVETPTREIKKLDGLWAFSLDRENCGIDQRWWESALQESRAIAVPGSFNDQFADADI     60
AoGUS    MLKPQQTTTRDLISLDGLWKFALASDDN--NTQPWTSQLKTSLECPVPASYNDIFADSKI     58
         **  *  *  :* :   *.:*:*  *  *       :.       :* :  .**.*:**   ...

CpGUS    RDHVGWVWYERNFTIPKTLLNERIVLRFGSATHEAKVYLNGELLVEHKGGFTPFEAEIND     119
EeGUS    RDHYGWVFYQRNISVPEYVKSQRIVLRCAAVTHYAMIYLNGKLICEHKGGFLPFEVELND    119
EcGUS    RNYAGNVWYQREVFIPKGWAGQRIVLRFDAVTHYGKVWVNNQEVMEHQGGYTPFEADVTP    120
AoGUS    HDHVGWVYYQRDVIVPKGWSEERYLVRCEAATHHGRIYVNGNLVADHVGGYTPFEADITD    118
         :::  * *: *:*:. *:    :  **  .*       :. :::*.:  : ** ***.:::.

CpGUS    LLVSGDNR-LTVAVNNIIDETTI PVG--------LVKEVEVDGKKVIKNSVNFDFPNYAG   170
EeGUS    DLQDGDNL-LTIAVNNVIDYTTI PVGGKANMMSGMMGGMGAGASDKPQNNPNFDFFNYCG   178
EcGUS    YVIAGKSVRITVCVNNELNWQTI PPG---------------MVITDENGKKKQSYFHDFPNYAG   169    C-Loop
AoGUS    LVAAGEQFRLTIAVDNELTYQTI PGK---------VBILEATGKKVQTYQHDFNYAG    168
         :  *. .   :*.:*::   *  *               .                 : .:.**.*

CpGUS    IHRPVKIYTTPKSYIEDITIVTDFKEN----NGYVNYEVQAVGKCN----IKVTIIDEEN    222
EeGUS    ITRPVKIYTTPETYINDITVTADIDFTKEEPSAVLNYNVEIKGKDYNNITCKVELFDEEG   238
EcGUS    IHRSVMLYTTPNTWVDDITVVTHVAQDCNHASVDWQVVANG--------DVSVELRDADQ    221
AoGUS    LARSVWLYSVPQQHIQDITVRTDVQGTTGLIDYNVVASTTQG-------TIQVAVIDEDG   221
         : *.*  *:.*   *:**:  :.  .                            .* *

CpGUS    NIVAEGEGKEGKLTINNVHLWEPMNAYLYKLKVELLDD-EEIIDTYFEEFGVRTVEVRDG   281
EeGUS    TKLSETEGSEGTFEISNVRLWQPLNAYLYKIKVTAG----QDVYTLPYGVRSRVDGT    292
EcGUS    QVVATGQGTSGTLQVVNPHLWQPGEGYLELCVTAKS---QTECDIYPLRVGIRSVAVKGE   279
AoGUS    TTVATSSGSNGTIHIPSVHLWQPGAAYLYQLHASIIDSSKKTIDTYKLATGIRTVKVQGT   281
         ::  . *. .*.:  . *:** .  ** :  .:           * *   *:. * ..

CpGUS    KFLINNKPFYFKGFGKHEDSYVNGRGINEAINIKDFNLMKWIGANSFRTSHYPYSEEIMR   341
EeGUS    KFLINEKPFYFKGYGKHEDTFPNGRGINLPMNTKDISIMKWQHANSFRTSHYPYSEEMMR   352
EcGUS    QFLINHKPFYFTGFGRHEDADLRGKGFDNVLMVHDHALMDWIGANSYRTSHYPYAEEMLD   339
AoGUS    QFLINDKPFYFTGFGKHEDTNIRGKGHDDAYMVHDFQLLHWMGANSFRTSHYPYAEEVME   341
         :****.******.*:***    * :*. :    :*   :: .* ***:********:**::

CpGUS    LADREGIVVIDETPAVGLHL NFMATG--FGGDAP KRD-TWKEIGTKEAHERILRELVSRD   398
EeGUS    LCDEEGIVVIDETTAVGVNL QFGGGANFGGERI GTFD-KEHGVQTQEHHKDVIRDLISRD   411    Loop1
EcGUS    WADEHGIVVIDETAAVGFNL SLGIGFEAGNKPK ELYSEEAVNGETQQAHLQAIKELIARD   399
AoGUS    YADRQGIVVIDETPAVGLAF SIGAGAQTSNPP- ATFSPDRINNKTREAHAQAIRELIBRD   400
         .*..:********.***.:     .  ::     *::  *   :::*::.  **

CpGUS    KNHPCVVMWSVANEPD SDSEG AKEYFEPLIKLTKELDPQKRPVTVV YLMSTPDRCKVGD   458    Loop2
EeGUS    KNHACVVMWSIANEPD SAAEG AYDYFKPLYDLARELDPQKRPCTLV VQGTTADTDCSSQ   471
EcGUS    KNHPSVVMWSIANEPD TRPQG AREYFAPLAEATRKLDP-TRPITCV VMFCDAHTDTISD   458    M-loop
AoGUS    KNHPSVVMWSIANEPA SNEDG AREYFAPLPKLARQLDP-TRPVTFAN VLATYKADRIAD   459
         ***..:****:****.      .::** **  .  ::*** .** . :

CpGUS    IVDVLCI NRYYGWYVAG DLEEAKRMLEDELKGWEERCPKTPIMFTEYGADTVAGLHDTV   518
EeGUS    LSDVICI NRYYGWYFGG PDLEVSEIGLRKELSDWGKLG---KPVMFTEYGADTVSGLHDTT   529    Y-loop
EcGUS    LFDVLCI NRYYGWYVQS GDLETAEKVLEKELLAWQEKLH--QPIITEYGHVTAGLHSMY   517
AoGUS    LFDVLCI NRYFGWYTQT AELDEAEAALEEELRGWTEKYD--KPIVMTEYGADTVAGLHSVM   518
         : **:*** ***:*  :*: ::  *..**  *   *::***. **::***.

CpGUS    PVMFTEEYQVEYYKANHEVMDRCKNFVGEQVWNFADFATSQGIIRVQG NKK GIFTRERKP   578
EeGUS    SVMYTEEYQVEYYEMNNHKVFDEFDFVGEQAWNFADFATSQGLLRVQQ NKK DLFTRDRKP   589    N-K Motif
EcGUS    TDMWSEEYQCAWLDMYHRVFDRVSAVVGEQVWNFADFATSQGILRVGG NKK GIFTRDRKP   577
AoGUS    VTPWSEEFQVEMLDMYHRVFDRFEAMAGEQVWNFADFQTAVGVSRVDG NKK EVFTRDRKP   578
         :  ::**:*       .  :*:  . . ***.*****:*:.:: ** **** .:***.***

CpGUS    KMIAHSLRERWTNIPEFGYKK-----   599
EeGUS    KMVAHYFRNRWTSIPEFGYKTK----   611
EcGUS    KSAAFLLQKRWTGMNFGEKPQQGGKQ   603
AoGUS    KAAAHLLRKRWTNLHNGTAEGSKTFQ   604
         *   :  ::.:**.   .
```

Figure 2

```
AoGUS   .MLKPQQTTTRDLISLDGLWKFALAS--DDNNTQPWTSQLKTSLECPVPASYNDIFADSKI   58
AtGUS   .MLKPRQTPFRDLISLDGLWKFALDSG--DNATAAPWTGPLTTDLECPVPASYNDIFVDRQI   59
EcElF   .MLRPVETPTREIKKLDGLWAFSLDRENCGIDQRWWESALQESRAIAVPGSFNDQFADADI   60
         *:*   *:.  *:: .:****:**:. .  .  *  . .  . :.**.:****..*..*

AoGUS   HDHVGWVYYQRDVIVPKGWSEERYLVRCEAATHHGRIYVNGNLVADHVGGYTPFEADITD    118
AtGUS   RDHVGWVYYQREAIVPPAWSQQQYLVRVDAATHQGRIYINDNLVAEHRGGYTPFEADITG    119
EcElF   RNYAGNVWYQREVFIPKGWAGQRIVLRFDAVTHYGKVWVNNQEVMEHQGGYTPFEADVTP    120
         ::.* *:***::.::*:.*   ::**.**.**:*::::.:  : *:*  *********:*

AoGUS   LVAAGEQFRLTIAVDNELTYQTIPPGKVEILEATGKKVQTYQHDFYNYAGLARSVWLYSV    178
AtGUS   LVSAGDSFRLTIAVNNELTHETIPPGRIEVEEYTGKRVQVYQHDFFNYAGLARSVWLYSV    179
EcElF   YVIAGKSVRITVCVNNELNWQTIPPG-MVITDENGKRKQSYFHDFFNYAGIHRSVMLYTT    179
         * **. .:*:*: *:***  :*****  :* : .**: * * *** **** ***::*:.

AoGUS   PQQHIQDITVPTDVQGTTGLIDYNVVAS-TTQGTIQVAVIDEDGTTVATSSGSNGTIHIP    237
AtGUS   PQQHIQDIKVVTHVKGSAGLINYLVTVSNSTTGRVKIDVIDKDGTTVAEASGARGSVTID    239
EcElF   PNTWVDDITVVTHVAQDCNHAS---VDWQVVANGDVSVELRDADQQVVATGQGTSGTLQVV    237
         *:  :  **.:::*.*  . :: :    . .  :  *  . *.*.:* :.. ..::.: :

AoGUS   SVHLWQPGAAYLYQLHASIIDSSKKTIDTYKLATGIRTVKVQGTQFLINDKPFYFTGFGK    297
AtGUS   SVKLWQPGEAYLYQFRASIVGLNDSVVDTYCVETGVRTVKVSGNRFLINDKPFYFTGFSK    299
EcElF   NPHLWQPGEGYLYELCVTAKS---QTECDIYPLRVGIRSVAVKGEQFLINHKPFYFTGFGR    295
         . :****. .***:: ::: . .: .  :*   .*:*:*.*.*.:****:******.*.

AoGUS   HEDTNIRGKGHDDAYMVHDFQLLHWMGANSFRTSHYPYAEEVMEYADRQGIVVIDETPAV    357
AtGUS   HEDSAVRGKGYDPAYMVHDFQLMDWMGANSFRTSHYPYAEEVMEFADRHGIVVIDETPAV    359
EcElF   HEDADLRGKGFDNVLMVHDHALMDWIGANSYRTSHYPYAEEMLDWADEHGIVVIDETAAV    355
         ***: :****:*  :****:.*::*:****:*********::::**.:********.**

AoGUS   GLAFSIGAGAQTSNPP--ATFSPDRINNKTREAHAQAIRELIHRDKNHPSVVMWSIANEPA    416
AtGUS   GLAFSIGSGVSSEDSP-QTFTPEGINNNTREAHKQAIRELIARDKNHASVVMWSIANEPA    418
EcElF   GFNLSLGIGFEAGNKPKELYSEEAVNGETQQAHLQAIKELIARDKNHPSVVMWSIANEPD    415
         *:.:*:* * :: : * :. .   :* :*:.** **:***.*****.********:**

AoGUS   SNEDGAREYFAPLPKLARQLDPTRPVTFANVGLATYKADRIADLFDVLCLNRYFGWYTQT    476
AtGUS   SQEVGAREYFAPLVDLAHELDPSRPVCFANYGDATYEVDRISDMFDVLCLNRYFGWYSQT    478
EcElF   TRFQGAREYFAPLAEATRKLDPTRPITCVNVMFCDAHTDTISDLFDVLCLNRYYGWYVQS    475
         :.  ******** :   ::**:**:*:.* .   ::  **.:::********:*** *:

AoGUS   AELDEAEAALEEELRGWTEKYDKPIVMTEYGADTVAGLHSVMVTPWSEEFQVEMLDMYHR    536
AtGUS   GEVEEAEAALEKELLGWEGKYGKPIVITEYGADTMAGLHSVLALPWSEEFQVQLLDMYHR    538
EcElF   GDLETAEKVLEKELLAWQEKLHQPIIITEYGVDTLAGLHSMYTDMWSEEYQCAWLDMYHR    535
         .::: **: **:** .*: *  :**::****.**:*****:   :****:*  ******

AoGUS   VFDRFEAMAGEQVWNFADFQTAVGVSRVDGNKKGVFTRDRKPKAAAHLLRKRWTNLHNGT    596
AtGUS   VFDRIDSVVGEHVWNFADFQTAVGIIRVDGNKKGVFTREPKPKAAAHTLKTRWSGML----    595
EcElF   VFDRVSAVVGEQVWNFADFATSQSILRVGGNKKGIFTRDRKPKSAAFLLQKRWTGMNFGE   595
         ****:.::.**:*******.*: .: **.*****:***: ***:**  *:.**:.:

AoGUS   AE--GGKTFQ------.   604
AtGUS   ----GSDH--------.   599
EcElF   KPQQGEKQGLCGR---.   608
             * :  *:
```

Restriction Site 1

Restriction Site 2

Loop 1 Site A

Loop 1 Site B

Restriction site 3

Restriction Site 4

Figure 3

```
BpGUS   MVNSMLYPRESRTR&VVDISGMWEFKIDINNEGRNSGYANGLKDTTFIPVPSSFNDLFTD    60
EeGUS   ----MLYPVLTQSRLLSDLSGVWDFKLDNGKGFEEKWYEKPLKDADTMPVPASYNDLKEG    56
            ****  :::* :  *:**:*:**:*  .:   .. *  : ***:   ;***:*:***   .

BpGUS   KNIREHAGDVWYETSFYLPLEWKDKDVNVRFGCATHEATVYINGKEVCTHVGGFMPFNAP   120
EeGUS   TDFRDHYGWVFYQRNISVPEYVKSQRIVLRCAAVTHYAMIYLNGKLICEHKGGFLFFEVE   116
         .: :*:*  *:*:  .: :*   *.: :  *...:*  :*:*** :* * ***:*:*:

BpGUS   VNEAGIFGEKNKLVVVVNNELSNTTIPCGHTETKPSGKK-----------YIKPSFDFFN   169
EeGUS   LNDDLQDGD-NLLTIAVNNVIDYTTLPVGGKANMMSGMMGGMGAGASDKPQNNPNFDFFN   175
         :*:   *: *  *:  .*** :. **:* *   . **           :*:.****

BpGUS   YAGLNRPVKITVTNKEYIHDIDILSDVNGSD----GIVNYEVHTTGENK----VYIKIND   221
EeGUS   YCGITRPVKIYTTPETYINDITVTADIDFTKEEPSAVLNYNVEIKGKDYNNITCKVELFD   235
        *.*:******  *:  **:**  : :*::  .       .:**:*:  .*::    ::: *

BpGUS   EEGKEVASCEGKSGKIVIKQAKLWNPKAAYLYKFIACIKNGDELIDEYYLDFGIRTVKVE   281
EeGUS   EEGTKLSETEGSEGTFEISNVELWQPLNAYLYKIKVTAG------QDVYTLPYGVRSVRVD   290
        ***.::.   **..*.  *.:.:**:*  *****: .             *  *  *:*:*:*:

BpGUS   GTKFLINGKPFYFTGFGKHEDSEIAGRGYNPPVIKRDFELIKWVGANSFRTSHYPYSEEI   341
EeGUS   GTKFLINEKPFYFKGYGKHEDTFPNGRGINLPMNTKDISIMKWQHANSFRTSHYPYSEEM   350
        ******* ***** *:*****.:   *** * *: :**::;:** ************** ;

BpGUS   MQAADREGIVIIDEVAAVGMFDVGGVLNPSASKTDYFSLDEVFSKTKEVHKKAVEELIKR   401
EeGUS   MRLCDEEGIVVIDETTAVGVNLDFGGGANFGGERIGTFDKEHGVQTQEHHKDVIRDLISR   410
        *:  .* ****:***: :***   :.:   ..  :   *  *.:* :* **.::*::**.*

BpGUS   DKNHPSVVMWSLFNEPDTSKDEAVPYFEDIFNFAKSQDKQNLFKTFAAIQASSPGKCKCM   461
EeGUS   DKNHACVVMWSIANEPDSAAEGAYDYFKPLYDLARELDPQKRPCTLVSVQGTTADTDCSS   470
        ****  :.****: :****:: :*.   **: :   *  *: * .*:.. :. ...    .

BpGUS   HLCDVITLNRYYGWYFLGGYEIDMSEEKFREEMNLYSNMNKPVMFTEYGADTYAGVHKLP   521
EeGUS   QLSDVICLNRYYGWYFGG-PDLEVSEIGLRKELSDWGKLGKPVMFTEYGADTVSGLHDTT   529
        :*.*** ********* *   :::::**  :**:;:.  .:::.**********  *:*:. .

BpGUS   SVMWSEEYQCEYYEMNFKVFDSYDFIVGEQLWNFADFQTTEGIFRVDGNKKGIFTRNRQF   581
EeGUS   SVMYTEEYQVEYYEMNNKVFDEFDFVVGEQAWNFADFATSQSLLRVQGNKKGLFTRDPKP   589
        ***; ;**** ******.**** :***:***.****** *::::;**:*****:***:*:*

BpGUS   KAVAHLIRSRWNKLPLDYKSKK   603
EeGUS   KMVAHYFRNRWSTIPEFGYKTK   611
        * ***  :*.**..:*      ..*
```

C-loop Site

Loop 1 Swap1

Loop 1 Swap2

Figure 4

CHIMERIC AND OTHER VARIANT β-GLUCURONIDASE ENZYMES WITH ENHANCED PROPERTIES

CROSS-REFERENCE TO RELATED APPLICATIONS

This application is a Division of U.S. patent application Ser. No. 16/596,568, filed Oct. 8, 2019, pending, which application claims the benefit of the filing date under 35 U.S.C. § 119(e) to U.S. Provisional Patent Application No. 62/742,779, filed Oct. 8, 2018, the entire contents of which are incorporated herein by reference.

SEQUENCE LISTING

The Sequence Listing is provided as a file entitled IMJ-010DV_SequenceListing_2022-08-09, created on Aug. 9, 2022, which is 225 kilobytes in size. The information in the electronic format of the sequence listing is incorporated herein by reference in its entirety.

BACKGROUND OF THE INVENTION

In mammals, glucuronidation via the UDP glucuronyl transferase system is one principle means of detoxifying or inactivating compounds. Compounds are conjugated by the glucuronyl transferase system to form glucuronides, which are then secreted in urine or into the lower intestine in bile. The beta-glucuronidase (BGUS) enzyme catalyzes the hydrolysis of a wide variety of beta-glucuronides. Given the key role of glucuronidation in detoxification of compounds, the BGUS enzyme has been used for detection of drugs in bodily samples, such as to detect the presence of therapeutic drugs in bodily samples of hospital patients. For example, a bodily sample can be tested for the presence of a drug by treating the sample with BGUS and detecting the hydrolysis product of the glucuronide form of the drug. The hydrolysis of the glucuronide by the BGUS enzyme facilitates the analysis of the drug by methods such as mass spectrometry, since this analytical instrument is less sensitive to the glucuronide.

Beta-glucuronidases (BGUS; EC 3.2.1.31) hydrolyze the beta-glycosidic bond between the anomeric reducing end of glucuronic acid (GlcU or gluc) and a broad range of possible aglycones. Enzymes with this activity are found predominantly in glycosyl hydrolase family 2 (GH2), although other examples can also be found in GH30 (Sakurama et al. (2014), *Appl. Microbiol. Biotechnol.* 98: 4021), GH1, GH79 and GH137. All BGUS enzymes characterized thus far are retaining enzymes utilizing a double displacement reaction, with a covalent enzyme-glucuronic acid intermediate, to add water across the glycosidic bond (Wang and Trouser (1972) *J. Biol. Chem.* 247:2644; Davies and Henrissat (1995) *Structure* 3:853). Well characterized examples come from bacteria, particularly *E. coli* gusA (formerly uidA), mammalian species (bovine, mouse, rat, human), where the enzyme normally localizes to lysosomes and defects may contribute to lysosomal storage disorders, and mollusks (snail, abalone, limpet), the source of crude hydrolytic extracts utilized for both research and applications in forensic and clinical medicine (Graef et al. (1977) *Clin. Chem.* 23:532; Romberg and Lee (1995) *J. Anal. Toxicol.* 19:157; Yang et al. (2016) *J. Anal. Toxicol.* 40:323). Additional applications for the preparation of food additives and traditional remedies are under consideration (Kim et al. (2009) *J. Microbiol. Biotechnol.* 19:1650; Sakurama et al. (2014) *Appl. Microbiol. Biotechnol.* 98:4021).

Genes for BGUS, especially gusA, have been favored as reporters in gene regulation studies because of the wide range of substrates with easily detected aglycone products (non-limiting examples of aglycones include p-nitrophenol, phenolphthalein, 4-methylumbelliferone, indigo-blue, fluorescein). This is particularly true for studies in plants, where for many years BGUS activity was believed to be absent. Evidence of naturally occurring BGUS in plants has been discovered, but plant enzymes generally have lower pH optima and growth-specific expression patterns (Sudan et al. (2006) *Planta* 224:853).

As discussed above, one significant application for BGUS enzymes is in clinical and forensic analysis of biological samples for the quantitative measurement of drugs and metabolites. In the body, toxic metabolites and foreign molecules such as drugs are glucuronidated by enzymes in the liver to increase their solubility and tag them for excretion. Thus, a broad range of glucuronidated molecules end up in the urine and other bodily fluids. To identify and quantify these molecules ("target substrates"), the preferred approach is to remove excretion tags such as glucuronic acids (some molecules are sulfated as well) and quantify the free aglycones by separation methods such as liquid chromatography (LC) and gas chromatography (GC), and methods for detection, identification and quantitation such as mass spectrometry (MS). Protocols for de-glucuronidation of excretion products initially favored acid hydrolysis (Romberg and Lee (1995) *J. Anal. Toxicol.* 19:157; Wang et al. (2006) *J. Anal. Toxicol.* 30:570). However, though simple and broadly applicable, acid hydrolysis is slow, messy and harsh, suffering from side reactions that break down some molecules targeted for analysis (Romberg and Lee (1995) *J. Anal. Toxicol.* 19:157; Sitasuwan et al. (2016) *J. Anal. Toxicol.* 40:601). In contrast, enzymatic hydrolysis is specific, potentially fast and can be accomplished under gentle conditions (Rana et al. (2008) *J. Anal. Toxicol.* 32:355; Sanches et al. (2012) *J. Anal. Toxicol.* 36:162; Morris et al. (2014) *J. Anal. Toxicol.* 38:610; Yang et al. (2016) *J. Anal. Toxicol.* 40:323; Cummings et al. (2017) *J. Anal. Toxicol.* 42:214). Thus, enzymatic methods have largely superseded acid hydrolysis.

Although the specificity of BGUS is determined by its ability to recognize glucuronic acid and the anomeric bond (Pollet et al. (2017) *Structure* 25:967), interactions between an aglycone and an enzyme are unique to the aglycone and enzyme pair in question, likely due to steric interactions that are not yet well characterized (Masuo et al. (2010) *Drug Metab. Disp.* 38:1828; Kotronoulas et al. (2016) J. Steroid Biochein. *Mol. Biol.* 167B:212). Crude enzyme preparations of BGUS from mollusks (e.g. snail, abalone, limpet) are commercially available and thus have been used for clinical and forensic analysis purposes. In some instances, however, crude enzyme preparations contain contaminants that interfere with either enzyme activity or downstream measurement of products (Nakamura et al. (2011) *Biosci. Biotechnol. Biochem.* 75:1506).

More recently, purified recombinant BGUS enzymes have been described, including variant forms of recombinant BGUS enzymes that have been modified to enhance enzymatic activity, temperature stability or both (see e.g., US Patent Publication 20160090582, issued as U.S. Pat. No. 9,920,306; US Patent Publication 20160237415, issued as U.S. Pat. No. 9,719,075; US Patent Publication 20170267985, issued as U.S. Pat. No. 9,909,111; Xiong, A-S. et al. (2007) *Prot. Eng. Design Select.* 20:319-325). For example, a genetically modified recombinant *E. coli* K12 BGUS enzyme is commercially available (IMCSzyme®; IMCS).

Accordingly, while variant forms of BGUS have been reported, there is still a need in the art for additional modified forms of BGUS enzymes having enhanced properties that are more efficient for use in drug testing.

SUMMARY OF THE INVENTION

The invention provides chimeric and other variant forms of BGUS enzymes that exhibit enhanced properties as compared to the parental enzymes from which they have been derived. In particular, the chimeric and other variant BGUS enzymes of the disclosure exhibit enhanced enzymatic activity, and/or an increased effective substrate range, and/or an increased effective pH range and/or an increased effective temperature range as compared to the parental enzymes from which they have been derived. Furthermore, the variant enzymes of the invention are produced recombinantly and thus can be prepared in a highly purified form without contaminating non-BGUS proteins.

Accordingly, in one aspect, the disclosure pertains to chimeric BGUS enzymes, which comprise at least one domain from a first BGUS enzyme and at least one domain from a second (different) BGUS enzymes. For example, in one aspect, the disclosure pertains to a chimeric beta-glucuronidase (BGUS) enzyme, which comprises at least one domain from a first BGUS enzyme operatively linked to at least one domain from a second BGUS enzyme, wherein the chimeric BGUS enzyme exhibits:
  (i) an increased level of enzymatic activity for one or more substrates as compared to the first or second BGUS enzyme; or
  (ii) an increased effective range of substrates catalyzed as compared to the first or second BGUS enzyme; or
  (iii) an increased effective pH range for one or more substrates as compared to the first or second BGUS enzyme; or
  (iv) an increased effective temperature range for one or more substrates as compared to the first or second BGUS enzyme; or
  (v) an increase in enzyme stability as compared to the first or second BGUS enzyme; or
  (vi) any combination of (i)-(v).

In one embodiment, the first and second BGUS enzymes used in the chimeric BGUS enzyme are each from a species independently selected from the group consisting of *Aspergillus oryzae*, *Aspergillus terreus*, *Bacteroides fragilis*, *Bacteroides uniformis*, *Brachyspira murdochii*, *Brachyspira pilosicoli*, *Clostridium perfringens*, *Escherichia coli*, *Eubacterium eligens*, *Homo sapiens*, *Lactobacillus brevis*, *Mus musculus*, *Parabacteroides* sp., *Staphylococcus* sp, and *Streptococcus agalactiae*. In one embodiment, the first BGUS enzyme is from *Aspergillus oryzae* and the second BGUS enzyme is from *Aspergillus terreus*. In one embodiment, the first BGUS enzyme is from *Brachyspira pilosicoli* and the second BGUS enzyme is from *Eubacterium* eligens.

In one embodiment, the chimeric BGUS enzyme comprises an N-terminal sugar-binding/Ig-like domain (SBI domain) and a C-terminal TIM-Barrel domain (TIMB domain) comprising a Loop 1 domain, wherein the chimeric BGUS enzyme comprises an SBI domain from the first BGUS enzyme and a TIMB domain and Loop 1 domain from the second BGUS enzyme. In one embodiment, the chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 17-24 and 121-137. In one embodiment, the chimeric BGUS enzyme is at least 95% homologous to an amino acid sequence shown in SEQ ID NOs: 17-24 and 121-137. In one embodiment, the chimeric BGUS enzyme is at least 90% (or 91%, 92%, 93%, 94%, 95%, 96%, 97%, 98% or 99%) homologous to an amino acid sequence shown in the SEQ ID NOs: 19 or 121-137. In one embodiment, the chimeric BGUS enzyme comprises an amino acid sequence shown in SEQ ID NOs: 19 or 121-137.

In another embodiment, the chimeric BGUS enzyme comprises an N-terminal sugar-binding/Ig-like domain (SBI domain) and a C-terminal TIM-Barrel domain (TIMB domain) comprising a Loop 1 domain, wherein the chimeric BGUS enzyme comprises an SBI domain from the first BGUS enzyme, a TIMB domain from the second BGUS enzyme, and a Loop 1 domain from the first BGUS enzyme. In one embodiment, the chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 25-30. In one embodiment, the chimeric BGUS enzyme is at least 95% homologous to an amino acid sequence shown in SEQ ID NOs: 25-30. In one embodiment, the chimeric BGUS enzyme is at least 90% (or 91%, 92%, 93%, 94%, 95%, 96%, 97%, 98% or 99%) homologous to the amino acid sequence shown in the SEQ ID NO: 26. In one embodiment, the chimeric BGUS enzyme comprises the amino acid sequence shown in SEQ ID NO: 26.

In another embodiment, the chimeric BGUS enzyme comprises an N-terminal sugar-binding/Ig-like domain (SBI domain) and a C-terminal TIM-Barrel domain (TIMB domain) comprising a Loop 1 domain, wherein the chimeric BGUS enzyme comprises an SBI domain and a TIMB domain from the first BGUS enzyme and a Loop 1 domain from the second BGUS enzyme. In one embodiment, the chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 31-36. In one embodiment, the chimeric BGUS enzyme is at least 95% homologous to an amino acid sequence shown in SEQ ID NOs: 31-36. In one embodiment, the chimeric BGUS enzyme is at least 90% (or 91%, 92%, 93%, 94%, 95%, 96%, 97%, 98% or 99%) homologous to the amino acid sequence shown in the SEQ ID NO: 31. In one embodiment, the chimeric BGUS enzyme comprises the amino acid sequence shown in SEQ ID NO: 31.

In another embodiment, the chimeric BGUS enzyme comprises a TIM-Barrel domain (TIMB domain) comprising a Counter-loop domain and a Loop 1 domain, wherein the chimeric BGUS enzyme comprises:
  (a) a TIMB domain from a first BGUS enzyme, a Counter-loop domain from a second BGUS enzyme and a Loop 1 domain from the first BGUS enzyme; or
  (b) a TIMB domain from a first BGUS enzyme, a Counter-loop domain from the first BGUS enzyme and a Loop 1 domain from a second BGUS enzyme; or
  (c) a TIMB domain from a first BGUS enzyme, a Counter-loop domain from a second BGUS enzyme and a Loop 1 domain from the second BGUS enzyme.

In one embodiment, the chimeric BGUS enzyme is at least 80% (or 85%, or 90%, or 91% or 92% or 93% or 94% or 95% or 96% or 97% or 98% or 99%) homologous to amino acid sequence shown in SEQ ID NOs: 37-46. In one embodiment, the chimeric BGUS enzyme is at least 95% homologous to an amino acid sequence shown in SEQ ID NOs: 37-36. In one embodiment, the chimeric BGUS enzyme comprises an amino acid sequence shown in SEQ ID NOs: 37-46.

In another aspect, the invention pertains to a chimeric beta-glucuronidase (BGUS) enzyme, which comprises an N-terminal sugar-binding/Ig-like domain (SBI domain) and a C-terminal TIM-Barrel domain (TIMB domain) comprising a Loop 1 domain, wherein the chimeric BGUS enzyme comprises:
- (a) an SBI domain from a first BGUS enzyme and a TIMB domain and Loop 1 domain from a second BGUS enzyme; or
- (b) an SBI domain from a first BGUS enzyme, a TIMB domain from a second BGUS enzyme, and a Loop 1 domain from the first BGUS enzyme; or
- (c) an SBI domain and a TIMB domain from a first BGUS enzyme and a Loop 1 domain from a second BGUS enzyme.

In various embodiments, the chimeric enzyme exhibits:
- (i) an increased level of enzymatic activity for one or more substrates as compared to the first or second BGUS enzyme; or
- (ii) an increased effective range of substrates catalyzed as compared to the first or second BGUS enzyme; or
- (iii) an increased effective pH range for one or more substrates as compared to the first or second BGUS enzyme; or
- (iv) an increased effective temperature range for one or more substrates as compared to the first or second BGUS enzyme; or
- (v) an increase in enzyme stability as compared to the first or second BGUS enzyme; or
- (vi) any combination of (i)-(v).

In various embodiments, the first and second BGUS enzymes are each from a species independently selected from the group consisting of *Aspergillus oryzae, Aspergillus terreus, Bacteroides fragilis, Bacteroides uniformis, Brachyspira murdochii, Brachyspira pilosicoli. Clostridium perfringens, Escherichia coli, Eubacterium eligens, Homo sapiens, Lactobacillus brevis, Mus musculus, Parabacteroides* sp., *Staphylococcus* sp, and *Streptococcus agalactiae*. In one embodiment, the first BGUS enzyme is from *Aspergillus oryzae* and the second BGUS enzyme is from *Aspergillus terreus*.

In one embodiment, the chimeric BGUS enzyme comprises an SBI domain from a first BGUS enzyme and a TIMB domain and Loop 1 domain from a second BGUS enzyme. In one embodiment, this chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 17-24 and 121-137. In another embodiment, this chimeric BGUS enzyme is at least 90% (or 91%, 92%, 93%, 94%, 95%, 96%, 97%, 98% or 99%) homologous to an amino acid sequence shown in SEQ ID NO: 19. In yet another embodiment, this chimeric BGUS enzyme is at least 95% homologous to an amino acid sequence shown in SEQ ID NO: 19. In one embodiment, the chimeric BGUS enzyme comprises an amino acid sequence shown in SEQ ID NOs: 19 and 121-137.

In one embodiment, the chimeric BGUS enzyme comprises an SBI domain from a first BGUS enzyme, a TIMB domain from a second BGUS enzyme, and a Loop 1 domain from the first BGUS enzyme. In one embodiment, this chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 25-30. In another embodiment, this chimeric BGUS enzyme is at least 90% (or 91%, 92%, 93%, 94%, 95%, 96%, 97%, 98% or 99%) homologous to an amino acid sequence shown in SEQ ID NO: 26. In yet another embodiment, this chimeric BGUS enzyme is at least 95% homologous to an amino acid sequence shown in SEQ ID NO: 26. In one embodiment, the chimeric BGUS enzyme comprises the amino acid sequence shown in SEQ ID NO: 26.

In one embodiment, the chimeric BGUS enzyme comprises an SBI domain and a TIMB domain from a first BGUS enzyme and a Loop 1 domain from a second BGUS enzyme. In one embodiment, this chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 31-36. In another embodiment, this chimeric BGUS enzyme is at least 90% (or 91%, 92%, 93%, 94%, 95%, 96%, 97%, 98% or 99%) homologous to an amino acid sequence shown in SEQ ID NO: 31. In yet another embodiment, this chimeric BGUS enzyme is at least 95% homologous to an amino acid sequence shown in SEQ ID NO: 31. In one embodiment, the chimeric BGUS enzyme comprises the amino acid sequence shown in SEQ ID NO:31.

In another aspect, the disclosure pertains to a chimeric BGUS enzyme, which comprises a TIM-Barrel domain (TIMB domain) comprising a Counter-loop domain and a Loop 1 domain, wherein the chimeric BGUS enzyme comprises:
- (a) a TIMB domain from a first BGUS enzyme, a Counter-loop domain from a second BGUS enzyme and a Loop 1 domain from the first BGUS enzyme; or
- (b) a TIMB domain from a first BGUS enzyme, a Counter-loop domain from the first BGUS enzyme and a Loop 1 domain from a second BGUS enzyme; or
- (c) a TIMB domain from a first BGUS enzyme, a Counter-loop domain from a second BGUS enzyme and a Loop 1 domain from the second BGUS enzyme.

In various embodiments, the chimeric BGUS enzyme exhibits:
- (i) an increased level of enzymatic activity for one or more substrates as compared to the first or second BGUS enzyme; or
- (ii) an increased effective range of substrates catalyzed as compared to the first or second BGUS enzyme; or
- (iii) an increased effective pH range for one or more substrates as compared to the first or second BGUS enzyme; or
- (iv) an increased effective temperature range for one or more substrates as compared to the first or second BGUS enzyme; or
- (v) an increase in enzyme stability as compared to the first or second BGUS enzyme; or
- (vi) any combination of (i)-(v).

In various embodiments, the first and second BGUS enzymes are each from a species independently selected from the group consisting of *Aspergillus oryzae, Aspergillus terreus. Bacteroides fragilis, Bacteroides uniformis, Brachyspira murdochii, Brachyspira pilosicoli, Clostridium perfringens, Escherichia coli, Eubacterium eligens, Homo sapiens, Lactobacillus brevis, Mus musculus, Parabacteroides* sp., *Staphylococcus* sp, and *Streptococcus agalactiae*. In one embodiment, the first BGUS enzyme is from *Brachyspira pilosicoli* and the second BGUS enzyme is from *Eubacterium* eligens or the first BGUS enzyme is from *Eubacterium* eligens and the second BGUS enzyme is from *Brachyspira pilosicoli*.

In one embodiment, this chimeric BGUS enzyme is at least 80% (or 85%, or 90%, or 91% or 92% or 93% or 94% or 95% or 96% or 97% or 98% or 99%) homologous to an amino acid sequence shown in SEQ ID NOs: 37-46. In one embodiment, this chimeric BGUS enzyme is at least 90% (or 91%, 92%, 93%, 94%, 95%, 96%, 97%, 98% or 99%) homologous to an amino acid sequence shown in SEQ ID NO: 40 or 45. In another embodiment, this chimeric BGUS enzyme is at least 95% homologous to an amino acid sequence shown in SEQ ID NO: 40 or 45. In yet another embodiment, this chimeric BGUS enzyme comprises the amino acid sequence shown in SEQ ID NO: 40 or 45.

In yet another aspect, the disclosure pertains to BGUS enzymes (including the chimeric enzymes described before) that comprise one or more point mutations (i.e., amino acid substitutions at specified amino acid positions) as compared to the parental enzyme from which the variant is derived. Accordingly, in another aspect, the disclosure pertains to a variant beta-glucuronidase (BGUS) enzyme derived from a parental BGUS enzyme, the variant BGUS enzyme comprising an amino acid sequence at least 80% (or 85%, or 90%, or 91% or 92% or 93% or 94% or 95% or 96% or 97% or 98% or 99%) homologous to an amino acid sequence shown in SEQ ID NOs: 1-46 and 138, and comprising (i) at least one amino acid substitution, as compared to the parental BGUS enzyme, at at least one amino acid position corresponding to F294, T295, I450, Q451, A452 and/or G563 of SEQ ID NO: 5; or (ii) at least one cysteine substitution, as compared to the parental BGUS enzyme, at at least one amino acid position corresponding to Q8, S73, P489, Q570 or K588 of SEQ ID NO: 10, wherein the variant BGUS enzyme exhibits:
(i) an increased level of enzymatic activity for one or more substrates as compared to the parental BGUS enzyme; or
(ii) an increased effective range of substrates catalyzed as compared to the parental BGUS enzyme; or
(iii) an increased effective pH range for one or more substrates as compared to the parental BGUS enzyme; or
(iv) an increased effective temperature range for one or more substrates as compared to the parental BGUS enzyme; or
(v) an increase in enzyme stability as compared to the parental BGUS enzyme; or
(vi) any combination of (i)-(v).
In one embodiment, the variant comprises an amino acid sequence at least 90% homologous to a sequence shown in SEQ ID NOs: 47-137. In one embodiment, the variant comprises an amino acid sequence selected from the group consisting of the amino acid sequences shown in SEQ ID NOs: 47-137.

In yet another aspect, the disclosure pertains to a variant beta-glucuronidase (BGUS) enzyme derived from a parental BGUS enzyme, the variant BGUS enzyme comprising an amino acid sequence at least 80% (or 85%, or 90%, or 91% or 92% or 93% or 94% or 95% or 96% or 97% or 98% or 99%) homologous to an amino acid sequence shown in SEQ ID NOs: 1-46 and 138, and comprising at least one amino acid substitution, as compared to the parental BGUS enzyme, at at least one amino acid position corresponding to F294, T295, I450, Q451, A452 and/or G563 of SEQ ID NO: 5, wherein the variant BGUS enzyme exhibits:
(i) an increased level of enzymatic activity for one or more substrates as compared to the parental BGUS enzyme; or
(ii) an increased effective range of substrates catalyzed as compared to the parental BGUS enzyme; or
(iii) an increased effective pH range for one or more substrates as compared to the parental BGUS enzyme; or
(iv) an increased effective temperature range for one or more substrates as compared to the parental BGUS enzyme; or
(v) an increase in enzyme stability as compared to the parental BGUS enzyme; or
(vi) any combination of (i)-(v).
In one embodiment, the variant BGUS enzyme is at least 90% homologous to an amino acid sequence shown in SEQ ID NOs: 1-46 and 138. In another embodiment, the variant BGUS enzyme is at least 95% homologous to an amino acid sequence shown in SEQ ID Nos: 1-46 and 138. In another embodiment, the variant BGUS enzyme is at least 98% homologous to an amino acid sequence shown in SEQ ID NOs: 1-46 and 138. In other embodiments, the variant BGUS enzyme is at least 90%, 91%, 92%, 93%, 94%, 95%, 96%, 97%, 98%, 99% or 99.5% homologous to an amino acid sequence shown in SEQ ID Nos: 1-46 and 138.

In various embodiments of the point variants, the parental BGUS enzyme is from a species selected from the group consisting of *Aspergillus oryzae, Aspergillus terreus, Bacteroides fragilis, Bacteroides uniformis, Brachyspira murdochii, Brachyspira pilosicoli, Clostridium perfringens, Escherichia coli, Eubacterium eligens, Homo sapiens, Lactobacillus brevis, Mus musculus, Parabacteroides* sp., *Staphylococcus* sp, and *Streptococcus agalactiae*.

In one embodiment, the variant BGUS enzyme comprises an amino acid substitution, as compared to the parental BGUS enzyme, at an amino acid position corresponding to F294 of SEQ ID NO: 5. In specific embodiments, this variant BGUS enzyme comprises an amino acid sequence selected from the group consisting of the amino acid sequences shown in SEQ ID NOs: 47-54 (corresponding to BpF294A, BpF294I, BpF294V, BpF294Y, BpF294L, BpF294W, EeF303W and EeF303S, respectively).

In another embodiment, the variant BGUS enzyme comprises an amino acid substitution, as compared to the parental BGUS enzyme, at an amino acid position corresponding to T295 of SEQ ID NO: 5. In specific embodiments, this variant BGUS enzyme comprises an amino acid sequence selected from the group consisting of the amino acid sequences shown in SEQ ID NOs: 55-63, (corresponding to BpT295A, BpT295C, BpT295F, BpT295I, BpT295K, BpT295S, BpT295V, EeK304A and EeK304V, respectively).

In another embodiment, the variant BGUS enzyme comprises an amino acid substitution, as compared to the parental BGUS enzyme, at an amino acid position corresponding to I450 of SEQ ID NO: 5. In specific embodiments, this variant BGUS enzyme comprises an amino acid sequence selected from the group consisting of the amino acid sequences shown in SEQ ID NOs: 64-76 and 121-124 (corresponding to BpI450F, BpI450K, BpI450L, BpI450M, BpI450Q, BpI450D, BpI450V, EeV459F, EeV459L, EeV459W, EeV459C, EeV459G, EeV459E, Rxn3Y447L, Rxn3Y447P, Rxn3Y447I and Rxn3Y447Q, respectively).

In another embodiment, the variant BGUS enzyme comprises an amino acid substitution, as compared to the parental BGUS enzyme, at an amino acid position corresponding to Q451 of SEQ ID NO: 5. In specific embodiments, this variant BGUS enzyme comprises an amino acid sequence selected from the group consisting of the amino acid sequences shown in SEQ ID NOs: 77-82 and 125-130

(corresponding to BpQ451D, BpQ451E, BpQ451G, BpQ451S, BpQ451V, BpQ451K, Rxn3G448E, Rxn3G448K, Rxn3G448F, Rxn3G448L, Rxn3G448C and Rxn3G448W, respectively).

In another embodiment, the variant BGUS enzyme comprises an amino acid substitution, as compared to the parental BGUS enzyme, at an amino acid position corresponding to A452 of SEQ ID NO: 5. In specific embodiments, this variant comprises an amino acid sequence selected from the group consisting of the amino acid sequences shown in SEQ ID NOs: 83-92 and 131-137 (corresponding to BpA452D, BpA452K, BpA452N, BpA452G, BpA452E, BpA452Q, EeG461A, EeG461H, EeG461N, EeG461S, Rxn3D449Q, Rxn3D449G, Rxn3D449R, Rxn3D449K, Rxn3D449S, Rxn3D449C and Rxn3D449E, respectively.

In another embodiment, the variant BGUS enzyme comprises an amino acid substitution, as compared to the parental BGUS enzyme, at an amino acid position corresponding to G563 of SEQ ID NO: 5. In specific embodiments, this variant comprises an amino acid sequence selected from the group consisting of the amino acid sequences shown in SEQ ID NOs: 93-100 (corresponding to BpG563E, BpG563A, BpG563D, BpG563Y, EeS571G, EeS571N, Rxn3G560V and Rxn3G560E, respectively).

In another embodiment, the variant BGUS enzyme comprises amino acid substitutions, as compared to the parental BGUS enzyme, at amino acid positions corresponding to F294 and T295 of SEQ ID NO: 5. In specific embodiments, the variant comprises an amino acid sequence selected from the group consisting of the amino acid sequences shown in SEQ ID NOs: 101-106 (corresponding to BpF294Y/T295C, BpF294Y/T295I, BpF294Y/T295V, BpF294Y/T295F, BpF294Y/T295M and BpF294Y/T295K, respectively).

In another embodiment, the variant BGUS enzyme comprises amino acid substitutions, as compared to the parental BGUS enzyme, at amino acid positions corresponding to T295 and I450 of SEQ ID NO: 5. In specific embodiments, the variant comprises an amino acid sequence selected from the group consisting of the amino acid sequences shown in SEQ ID NOs: 107-110 (corresponding to BpT295V/I450L, BpT295V/I450M, BpT295V/I450Y and BpT295V/I450V, respectively).

In another embodiment, the variant BGUS enzyme comprises amino acid substitutions, as compared to the parental BGUS enzyme, at amino acid positions corresponding to I450 and Q451 of SEQ ID NO: 5. In specific embodiments, the variant comprises an amino acid sequence selected from the group consisting of the amino acid sequences shown in SEQ ID NOs: 111 and 112 (corresponding to BpI450M/Q451D and BpI450Q/Q451D, respectively).

In another embodiment, the variant BGUS enzyme comprises amino acid substitutions, as compared to the parental BGUS enzyme, at amino acid positions corresponding to Q451 and A452 of SEQ ID NO: 5. In specific embodiments, the variant comprises an amino acid sequence selected from the group consisting of the amino acid sequences shown in SEQ ID NOs: 113-117 (corresponding to BpQ451D/A452E, BpQ451D/A452G, BpQ451D/A452Q, BpQ451D/A452S and BpQ451D/A452R, respectively).

In another aspect, the disclosure pertains to a variant beta-glucuronidase (BGUS) enzyme derived from a parental BGUS enzyme, the variant BGUS enzyme comprising an amino acid sequence at least 80% (or 85%, or 90%, or 91% or 92% or 93% or 94% or 95% or 96% or 97% or 98% or 99%) homologous to an amino acid sequence shown in SEQ ID NOs: 1-46 and 138, and comprising at least one cysteine substitution, as compared to the parental BGUS enzyme, at at least one amino acid position corresponding to Q8, S73, P489, Q570 or K588 of SEQ ID NO: 10, wherein the variant BGUS enzyme exhibits:

(i) an increased level of enzymatic activity for one or more substrates as compared to the parental BGUS enzyme; or
(ii) an increased effective range of substrates catalyzed as compared to the parental BGUS enzyme; or
(iii) an increased effective pH range for one or more substrates as compared to the parental BGUS enzyme; or
(iv) an increased effective temperature range for one or more substrates as compared to the parental BGUS enzyme; or
(v) an increase in enzyme stability as compared to the parental BGUS enzyme; or
(vi) any combination of (i)-(v).

In specific embodiments, the cysteine-substituted variant BGUS enzyme comprises an amino acid sequence selected from the group consisting of the amino acid sequences shown in SEQ ID NOs: 118-120 (corresponding to EeQ8C/S73C, EeK588C and EeP489C/Q570C, respectively).

Formulations comprising any of the chimeric or other variant BGUS enzymes are also provided. In one embodiment, the formulation comprises the chimeric or variant BGUS enzyme and at least one excipient. In one embodiment, the at least one excipient is selected from the group consisting of water, salts, buffers, sugars and amino acids. In one embodiment, the formulation is free of polymers and detergents. In one embodiment, the formulation is an aqueous formulation. In one embodiment, the formulation is a lyophilized formulation. Packaged formulations, comprising the BGUS enzyme formulation and a container, are also provided.

In other aspects, the disclosure pertains to DNA constructs encoding the chimeric or variant BGUS enzymes of the disclosure, including expression vectors comprising such DNA constructs, as well as host cells comprising such expression vectors. Methods for expressing (i.e., producing) the chimeric or variant BGUS enzymes using such host cells are also provided.

In yet another aspect, the disclosure pertains to methods of hydrolyzing a substrate comprising a glucuronide linkage. In one embodiment, the method comprises contacting the substrate with any of the chimeric or variant BGUS enzymes of the disclosure such that hydrolysis of the glucuronide linkage occurs. In various embodiments, the substrate is selected from the group consisting of morphine-3-β-D-glucuronide (MOR), oxymorphone-3-β-D-glucuronide (OMOR), hydromorphone-3-β-D-glucuronide (HMOR), codeine-6-β-D-glucuronide (COD), dihydrocodeine-6-β-D-glucuronide (DCOD), buprenorphine-3-β-D-glucuronide (BUP gluc), norbuprenorphine-3-β-D-glucuronide (NBUP gluc), tapentadol glucuronide (TAP gluc), O-desmethyltramadol glucuronide (ODT gluc), O-desmethylvenlafaxine glucuronide (ODV gluc), amitriptyline-N-β-D-glucuronide (AMT gluc), oxazepem glucuronide (OXZ gluc), lorazepam glucuronide (LOR gluc), and/or temazepam glucuronide (TEM gluc).

In one embodiment, the disclosure provides a method of hydrolyzing codeine-6-β-D-glucuronide (COD), the method comprising contacting the substrate with a variant BGUS enzyme that comprises an amino acid substitution, as compared to its parental BGUS enzyme, at an amino acid position corresponding to Q451 of SEQ ID NO: 5, such that hydrolysis of the glucuronide linkage occurs. In one embodiment, the variant BGUS enzyme comprises the amino acid sequence shown in SEQ ID NO: 76 (corresponding to the BpQ451D variant). In another embodiment of this method, the variant BGUS enzyme comprises the amino acid sequence shown in SEQ ID NO: 113 (BpGUS comprising Q451D/A452E mutations). In another embodiment of this method, the variant BGUS enzyme comprises the amino acid sequence shown in SEQ ID NO: 114 (BpGUS comprising Q451D/A452G mutations). In another embodiment of this method, the variant BGUS enzyme comprises the amino acid sequence shown in SEQ ID NO: 115 (BpGUS comprising Q451D/A452Q mutations). In another embodiment of this method, the variant BGUS enzyme comprises the amino acid sequence shown in SEQ ID NO: 116 (BpGUS comprising Q451D/A452S mutations). In another embodiment of this method, the variant BGUS enzyme comprises the amino acid sequence shown in SEQ ID NO: 117 (BpGUS comprising Q451D/A452R mutations).

Other features and aspects of the invention are described in further detail herein.

BRIEF DESCRIPTION OF THE DRAWINGS

FIG. 1 shows an alignment of the amino acid sequences for the EeGUS (SEQ ID NO: 10), AoGUS (SEQ ID NO: 1), Rxn3 (SEQ ID NO: 19). AtGUS (SEQ ID NO: 2), EcE1F (SEQ ID NO: 9), BpGUS (SEQ ID NO: 5). BmGUS (SEQ ID NO: 6). CpGUS (SEQ ID NO: 7), StpGUS (SEQ ID NO: 15), LbLR2D (SEQ ID NO: 12). SaGUS (SEQ ID NO: 16). HsGUS (SEQ ID NO: 11), BfGUS (SEQ ID NO: 3), PmGUS (SEQ ID NO: 14) and BuGUS (SEQ ID NO: 4) enzymes. Amino acid residue numbering is shown on the right. Key conserved residues are indicated by (.) (:) and (*) beneath the sequences. Variant Sites 1, 2 and 3 that were used for point mutagenesis indicated in black.

FIG. 2 is an alignment of the CpGUS (SEQ ID NO: 7), EeGUS (SEQ ID NO: 10), EcGUS (SEQ ID NO: 8) and AoGUS (SEQ ID NO: 1) amino acid sequences showing the locations of the C-Loop. Loop 1. Loop 2. M-Loop. Y-loop and N-K motif regions.

FIG. 3 is an alignment of the AoGUS (SEQ ID NO: 1). AtGUS (SEQ ID NO: 2) and EcE1F (SEQ ID NO: 9) amino acid sequences showing the locations of the Restriction Site 1, Restriction Site 2. Loop 1 Site A. Loop 1 Site B. Restriction Site 3 and Restriction Site 4 regions used to create chimeric enzymes.

FIG. 4 is an alignment of the BpGUS (SEQ ID NO: 5) and EeGUS (SEQ ID NO: 10) amino acid sequences showing the C-Loop Site, the Loop 1 Swap 1 and Loop 1 Swap 2 locations used to create chimeric enzymes.

DETAILED DESCRIPTION OF THE INVENTION

Figure 5:
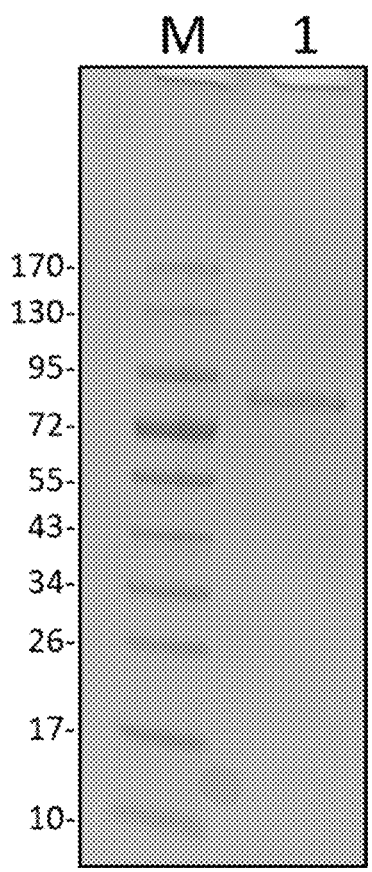
FIG. 5 is a photograph of a 4-20% gradient SDS-PAGE showing the enzyme purity observed by purifying BGUS enzymes, chimeras, and variants via IMCStips tip technologies. Lane M=molecular weight markers. Lane 1=purified BGUS enzyme.

The invention pertains to mutated β-glucuronidase enzymes, in particular chimeric and other variant forms of BGUS enzymes, having enhanced properties as compared to the parental enzyme from which the variant form was derived, as well as packaged formulations thereof and methods of using the enzymes for hydrolysis of glucuronide linkages.

Structures for GH2 BGUS enzymes have been solved from multiple sources, both with and without ligands in the active site (Jain et al. (1996) *Nature Struct. Biol.* 3:375; Wallace et al. (2010) *Science* 330:831; Roberts et al. (2013) *Mol. Pharmacol.* 84:208; Hassan et al. (2013) *PLoS ONE* 8:e79687; Wallace et al. (2015) *Chem. Biol.* 22:1238; Pollet et al. (2017) *Structure* 25:967; Pellock et al. (2018) *ACS Central Science*). The approximately 70 kD enzyme monomer (approximately 600 amino acids) has three domains: an N-terminal beta-sandwich described as a sugar-binding domain or jelly-roll barrel (approximately 180 amino acids); a second beta-sandwich described as an immunoglobulin-like domain (approximately 110 amino acids); and an alpha/beta eight-strand TIM barrel (approximately 310 amino acids). The monomers form dimers with the individual active sites directly opposite each other. The dimers form tetramers, which are thought to be the active form (Stahl and Touster (1971) *J. Biol. Chem.* 246:5398; see also Yeom et al. (2017) *PLoS ONE* 12:e0170398). Additionally, higher order complexes have been observed, although their physiological relevance, if any, is unknown.

The function of each domain in BGUS can be inferred from their structural homologies and similarities to other proteins sharing similar domains. The sugar-binding domain contains residues that are possibly important in lysosome targeting based on similarities of human BGUS to cathepsin D (Hassan et al. (2013) *PLoS ONE* 8:e79687). The immunoglobulin-like domain possibly facilitates protein-protein interactions, promoting the formation of multimeric BGUS structures (Burchett et al. (2015) *PLoS ONE*). The TIM-barrel domain, which contains the active site, is physicochemically similar to clusters of residues (that determine the common TIM-barrel folding pattern) in both the GH2 family of enzymes and non-homologous enzyme families (Wierenga (2001) *FEBS Letters* 492:193-198). Furthermore, TIM-barrels can contain several flexible loops that are involved in binding different substrates (Wierenga (2001) *FEBS Letters* 492:193-198).

Several bacterial BGUS active site loops have been characterized and their conservation and flexibility vary, depending on the loop and its relationship to the active site. Some bacterial BGUS have "Loop 1," believed involved with processing small substrates (Pollet et al. (2017) *Structure*). By contrast, other BGUS, including a majority of bacterial and eukaryotic enzymes (especially mammalian and mollusk enzymes), have a gap ("No Loop" or NL) in sequence alignments of GH2 beta-glucuronidase enzymes. It has been suggested this makes NL enzymes better able to process larger substrates (Wallace et al. (2015) *Chem. Biol.*). The length of Loop 1 ranges from approximately 15 to 30 amino acids (Pollet et al. (2017) Structure), and the sequence of Loop 1 is generally non-conserved (Wallace et al. (2015) *Chem. Biol.*; Pollet et al. (2017) Structure). Adjacent to Loop 1 in the active site is "Loop 2," which also has variability in length and amino acid composition (Pollet et al. (2017) Structure). Pollet et al. further describe "mini-Loop 1" (mLU) and "mini-Loop 2" (mL2) which are shorter versions of Loop 1 and Loop 2, respectively (Pollet et al. (2017) *Structure*).

A unique conserved region in BGUS called the "N-K motif" distinguishes them from other activities in the GH2 family, especially beta-galactosidases (BGAL), which otherwise often share significant homology with BGUS enzymes (Wallace et al. (2015) *Chem. Biol.*; Pollet et al. (2017) Structure). The N-K motif contains two conserved residues, asparagine and lysine, that form contacts with the carboxylic acid of glucuronic acid in the active site (Wallace et al. (2015) *Chem. Biol.*). The "Y-loop" is a region conserved in all BGUS sequences identified so far; it contains several aromatic residues that are implicated in substrate binding (Wallace et al. (2015) *Chem. Biol.*). In addition. BGUS, in contrast to BGAL, contain a tyrosine residue near the glucuronic acid binding site that only permits the processing of β-linked substrates due to steric occlusion (Wallace et al. (2015) *Chem. Biol.*). Furthermore, based on the *Escherichia coli* BGUS structure, an "M-loop" region has been described near one of the catalytic glutamic acid residues in the active site (Wallace et al. (2015) *Chem. Biol.*).

Analogous regions have been described for the GH2 BGUS from *Aspergillus oryzae* (AoGUS) such as "Loop B" (N-K motif), "Loop C" (Y-loop), "Loop D" (Loop 1). "Loop E" (Loop 2), and "Loop F" (M-loop) (Lv et al. (2017) *J. Biol. Chem.*). Furthermore. Lv et al. (2017) describe a "Loop A" they claim participates with the N-K motif in polar interactions with the GlcU moiety of 3-O-mono-beta-D-glucuronide (GAMG) substrate.

Furthermore, as described herein, a sequence referred to herein as the Counter-loop (C-loop) precedes and overlaps with Loop A described by Lv et al. (2017). As described herein, the C-loop corresponds to residues 142-163 in AoGUS, whereas Loop A consist of residues 159-172 (Lv et al. (2017) *J. Biol. Chem.*); both are located near the active site in the crystal structure of AoGUS (Lv et al. (2017) *J. Biol. Chem.*). Without being bound by theory, it is hypothesized that the C-loop, which is poorly conserved among BGUS enzymes, may be important for substrate binding and interactions with the aglycone. For example, it has been observed that the C-loop of one enzyme in particular, EeGUS from *Eubacterium eligens*, is unusually long and contains an unusually high content of methionine and glycine residues. Furthermore, without being bound by theory, it is hypothesized that, due to flexibility and residue composition, this C-loop is important for substrate recognition and activity.

An amino acid alignment of fifteen BGUS enzymes is shown in FIG. 1. FIG. 2 shows an alignment of four BGUS sequences indicating the C-loop. Loop 1, Loop 2. M-loop, Y-loop and NK motif regions.

Mutagenesis is a powerful approach for determining residues that are important in protein structure and function, and can be used to possibly produce favorable properties of a target protein such as improved thermostability or function. The mutations can be made in the nucleotide sequence of the gene coding for the protein, and the modified gene can be expressed to produce variants of the original template sequence. Directed Evolution (DE) is a technique whereby amino acids are randomly changed throughout a sequence and then improvements, such as thermostability, pH range, or substrate profile, are identified in a subsequent screen of variants. This technique has been used successfully to create glutaraldehyde and formaldehyde resistant EcGUS variants (Matsumura et al. (1999) *Nature Biotech.* 17:696-701). Key residues that substantially impact a property of an enzyme can be altered specifically, if they are known or can be predicted based on sequence and structural data, by using site-directed saturation mutagenesis (Folz et al. (1988) *J. Biol. Chem.* 263:2070-2078). Substitution of a single key residue in a sequence will yield 20 possible variants (including the original template). This can be achieved by using site-saturation mutagenesis such that codons for all 20 possible amino acids are each substituted at the same key position in the sequence (Steffens et al. (2007) *J. Biomol. Tech.* 18:147-149; Chronopoulou et al. (2011) *Curr. Protocols Protein Sci.* 63:26.6.1-26.6.10).

Some key residues have been described and partially characterized in certain BGUS. In *E. coli* BGUS, residue 559 has been shown to alter activity and thermostability of the protein (Flores et al. (2002) *J. Mol. Biol.* 315:325-337; US Patent Publication 20160090582A1 issued as U.S. Pat. No. 9,920,306). In Li-3 from *A. oryzae*, variants of residues 292 and 293 have been described to shift the geometry of the active site glutamic acid residues and also alter protein thermostability (Feng et al. (2016) *Ind. Eng. Chem. Res.* 55:5474-5483). M-loop residues have been described in Li-3 (residue 447) and EcGUS (residues 446 and 448) as having interactions with the aglycone of substrates and BGUS inhibitors (Roberts et al. (2013) *Mol. Pharm.* 84:208-217; Wallace et al. (2015) *Chem. Biol.* 22(9):1238-1249; Lv et al. (2017) *J. Bio. Chem.*). Furthermore, addition of the residues glycine-leucine-cysteine (GLC) to the C-terminal end of an EcGUS variant has been shown to improve protein stability (US Patent Publication 20160090582A1, issued as U.S. Pat. No. 9,920,306).

While some BGUS are currently available and suitable for forensic and clinical applications, as described herein the activity of BGUS has been further improved by domain-swapping among different BGUS and using site-saturation mutagenesis on key residues. Described herein are novel BGUS chimeras and other variants generated by domain-swapping and site-saturation mutagenesis. These variants have improved activities against target substrates, and/or demonstrate valuable changes in their pH range and/or stability.

Various aspects of the invention are described in further detail in the following subsections.

I. Variant β-Glucuronidase Enzymes

As used herein, the term "β-glucuronidase enzyme", also referred to as "β-glucuronidase" or "BGUS", refers to an enzyme that hydrolyzes glucuronide linkages. A "parental" or "template" BGUS enzyme refers to the starting enzyme that is modified to create a "variant" BGUS enzyme. A "variant" BGUS enzyme refers to a modified form of the enzyme in which one or more modifications, such as amino acid swaps, substitutions, deletions and/or insertions, have been made such that the amino acid sequence of the variant BGUS enzyme differs from the parental or template amino acid sequence. Thus, the "variant" BGUS enzyme is derived from the "parental" or "template" BGUS enzyme through introduction of one or more modifications. The parental or template BGUS amino acid sequence can be a "wild-type" BGUS sequence, i.e., a naturally-occurring unmodified BGUS enzyme. Alternatively, the parental or template BGUS amino acid sequence may itself be modified as compared to a "wild-type" sequence. For example, a chimeric BGUS enzyme as described herein can be used as the template enzyme for introducing additional modification, such as one or more amino acid substitutions.

In certain embodiments, the chimeric and other variant BGUS enzymes are described as having substantial homology to a specified amino acid sequence disclosed herein. The term "substantial homology" indicates that two amino acid sequences, when optimally aligned and compared, are identical, with appropriate insertions or deletions, in at least about 80% of the amino acids, usually at least about 90% to 95%, and more preferably at least about 98% to 99% to 99.5% of the nucleotides.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using mathematical algorithm, as described in the non-limiting examples below. Methods and algorithms for determining the % homology between two protein sequences are well established in the art.

For example, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. Furthermore, a protein amino acid sequence can be used as a "query sequence" to perform a search against public databases to, for example, identify related sequences. Such searches can be performed using the XBLAST programs (version 2.0) of Altschul, et al. (1990) *J. Mol. Biol.* 215:403-10. BLAST protein searches can be performed with the XBLAST program, score=50, word-length=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The amino acid sequences of fifteen BGUS enzymes suitable for use as parental or template enzymes are shown in the alignment of FIG. 1. Moreover, the alignment shown in FIG. 1 can be used as a model alignment for determining % homology (i.e., % identity), between two BGUS enzyme sequences. Cloning, expression and purification of BGUS enzymes is described in Examples 1-2.

In one embodiment, a variant BGUS enzyme of the disclosure is a chimeric BGUS enzyme, which comprise at least one domain from a first BGUS enzyme and at least one domain from a second (different) BGUS enzymes. A chimeric BGUS enzyme of the disclosure typically exhibits altered, and typically enhanced, activity as compared to one or both of the BGUS enzymes from which it is derived. For example, in one aspect, the disclosure pertains to a chimeric beta-glucuronidase (BGUS) enzyme, which comprises at least one domain from a first BGUS enzyme operatively linked to at least one domain from a second BGUS enzyme, wherein the chimeric BGUS enzyme exhibits:
  (i) an increased level of enzymatic activity for one or more substrates as compared to the first or second BGUS enzyme; or
  (ii) an increased effective range of substrates catalyzed as compared to the first or second BGUS enzyme; or
  (iii) an increased effective pH range for one or more substrates as compared to the first or second BGUS enzyme; or
  (iv) an increased effective temperature range for one or more substrates as compared to the first or second BGUS enzyme; or
  (v) an increase in enzyme stability as compared to the first or second BGUS enzyme; or
  (vi) any combination of (i)-(v).

Various embodiments of chimeric BGUS enzymes are described in further detail below in subsections A and B below.

In one embodiment, a variant BGUS enzyme of the disclosure comprises one or more point mutations (i.e., amino acid substitutions) as compared to a parental BGUS enzyme from which it is derived. Various embodiments of point mutant BGUS enzymes are described in further detail below in subsection C.

In yet another embodiment, a variant BGUS enzyme of the disclosure comprises a combination of modifications, such as being a chimeric enzymes, having at least one domain from a first BGUS enzyme and at least one domain from a second BGUS enzyme, as well as comprising one or more point mutations (i.e., amino acid substitutions) as compared to the parental BGUS enzyme(s) from which it is derived. Various embodiments of combination mutant BGUS enzymes are described in further detail below in subsection D.

A. Sugar-Binding Domain/Ig-Like Domain, TIM-Barrel and/or Loop1 Swaps

In one aspect, the disclosure provides chimeric BGUS enzymes in which the sugar-binding domain/Ig-like domain, TIM-barrel domain and/or Loop 1 have been swapped between two different BGUS enzymes. Accordingly, in one embodiment, the invention provides a chimeric beta-glucuronidase (BGUS) enzyme, which comprises an N-terminal sugar-binding/Ig-like domain (SBI domain) and a C-terminal TIM-Barrel domain (TIMB domain) comprising a Loop 1 domain, wherein the chimeric BGUS enzyme comprises:
  (a) an SBI domain from a first BGUS enzyme and a TIMB domain and Loop 1 domain from a second BGUS enzyme; or
  (b) an SBI domain from a first BGUS enzyme, a TIMB domain from a second BGUS enzyme, and a Loop 1 domain from the first BGUS enzyme; or
  (c) an SBI domain and a TIMB domain from a first BGUS enzyme and a Loop 1 domain from a second BGUS enzyme.

For BGUS enzymes, which contain approximately 600 amino acids, the sugar-binding domain corresponds to the approximately 180 amino acids at the N-terminus, with the Ig-like binding domain corresponding to the next approximately 110 residues and the TIM-barrel domain corresponding to the approximately 310 amino acids at the C-terminus. Accordingly, the combined sugar-binding/Ig-like domain (SBI domain) corresponds to the approximately 290 amino acids at the N-terminus and the TIM-barrel domain (TIMB) corresponds to the approximately 310 amino acids at the C-terminus. To swap the SBI domain of one BGUS enzyme and the TIMB domain of a second BGUS enzyme, one of ordinarily skill in the art can readily identify the appropriate regions based on the known BGUS structures/amino acid sequences and recombinantly link the N-terminal approximately 290 amino acids from one BGUS enzyme to the C-terminal approximately 310 amino acids from a second BGUS enzyme. Furthermore, the Loop 1 region, located within the TIMB domain, is indicated in FIGS. 2 and 3. Approaches for creating the SBI domain, TIMB domain and/or Loop 1 swaps are described in detail in Example 5, using the restriction sites shown in FIG. 3.

In various embodiments, the chimeric enzyme exhibits:
  (i) an increased level of enzymatic activity for one or more substrates as compared to the first or second BGUS enzyme; or
  (ii) an increased effective range of substrates catalyzed as compared to the first or second BGUS enzyme; or
  (iii) an increased effective pH range for one or more substrates as compared to the first or second BGUS enzyme; or
  (iv) an increased effective temperature range for one or more substrates as compared to the first or second BGUS enzyme; or
  (v) an increase in enzyme stability as compared to the first or second BGUS enzyme; or
  (vi) any combination of (i)-(v).

As used herein, an "increased effective range of substrates" means that the chimeric enzyme is active across a broader panel (i.e., higher number) of substrates under the same reaction conditions as compared to one or both parental enzymes (i.e., the unmodified first and/or second BGUS enzyme). Typically, an enzyme is "active" when it has at least 50% activity (or at least 60%, at least 70% or at least 80% activity) against each substrate in the range under the same defined reaction conditions (e.g., at a particular temperature and pH). For example, a parental enzyme 1 may have an effective substrate range of A, B and C at a specified temperature and pH, and a parental enzyme 2 may have an effective substrate range of C, D and E at that same temperature and pH. A chimeric enzyme composed of a mixture of the SBI domain, TIMB domain and/or Loop 1 domain of enzymes 1 and 2 may have an effective substrate range of A, B, C, D and E at that temperature and pH. Thus, this effective substrate range of the chimeric enzyme (i.e., A, B, C, D and E) is greater than the effective substrate range of each of the parental enzymes (i.e., greater than A, B and C for enzyme 1 and greater than C, D and E for enzyme 2).

As used herein, an "increased effective pH range for one or more substrates" means that the chimeric enzyme is active across a wider spectrum of pH values for the same substrate(s) under the same reaction conditions as compared to one or both parental enzymes (i.e., the unmodified first and/or second BGUS enzyme). For example, a parental enzyme 1 may have an effective pH range of 5.0-6.5, and a parental enzyme 2 may have an effective pH range of 6.0-7.5. A chimeric enzyme composed of a mixture of the SBI domain, TIMB domain and/or Loop 1 domain of enzymes 1 and 2 may have an effective pH range of 5.0-7.5. Thus, this effective pH range of the chimeric enzyme (i.e., 5.0-7.5) is greater than the effective pH range of each of the parental enzymes (i.e., greater than 5.0-6.5 for enzyme 1 and greater than 6.0-7.5 for enzyme 2).

As used herein, an "increased effective temperature range for one or more substrates" means that the chimeric enzyme is active across a wider spectrum of temperatures for the same substrate(s) under the same reaction conditions as compared to one or both parental enzymes (i.e., the unmodified first and/or second BGUS enzyme). For example, a parental enzyme 1 may have an effective temperature range of 25-30° C., and a parental enzyme 2 may have an effective temperature range of 30-35° C. A chimeric enzyme composed of a mixture of the SBI domain, TIMB domain and/or Loop 1 domain of enzymes 1 and 2 may have an effective temperature range of 25-35° C. Thus, this effective temperature range of the chimeric enzyme (i.e., 25-35° C.) is greater than the effective pH range of each of the parental enzymes (i.e., greater than 25-30° C. for enzyme 1 and greater than 30-35° C. for enzyme 2).

As used herein, an "increase in enzyme stability" means that the chimeric enzyme is more stable (e.g., better retains its conformational integrity), as compared to one or both parental enzymes (i.e., the unmodified first and/or second BGUS enzymes) under one or more reaction conditions (e.g., reaction conditions that promote denaturation of enzymes), such as temperatures above 37° C. (e.g., 65° C., 100° C.) and/or reducing conditions (e.g., TCEP buffer) and/or denaturing reagents (e.g., urea and guanidine). Additionally or alternatively, an "increase in enzyme stability" can mean that the chimeric enzyme retains its stability (e.g., conformational integrity) across a wider spectrum of temperatures and/or buffer conditions as compared to one or both parental enzymes (i.e., the unmodified first and/or second BGUS enzymes).

In various embodiments, the first and second BGUS enzymes are each from a species independently selected from the group consisting of *Aspergillus oryzae, Aspergillus terreus, Bacteroides fragilis, Bacteroides uniformis, Brachyspira murdochii, Brachyspira pilosicoli, Clostridium perfringens, Escherichia coli, Eubacterium eligens, Homo sapiens, Lactobacillus brevis, Mus musculus, Parabacteroides* sp., *Staphylococcus* sp, and *Streptococcus agalactiae*. In one embodiment, the first BGUS enzyme is from *Aspergillus oryzae* and the second BGUS enzyme is from *Aspergillus terreus*. Specific chimeric enzymes and their activities are described in detail in Example 5.

In one embodiment, the chimeric BGUS enzyme comprises an SBI domain from a first BGUS enzyme and a TIMB domain and Loop 1 domain from a second BGUS enzyme. In one embodiment, this chimeric BGUS enzyme is at least 80% (or at least 85%, 90%, 91%, 92%, 93%, 94%, 95%, 96%, 97%, 98%, 98.5%, 99% or 99.5%) homologous to an amino acid sequence shown in SEQ ID NOs: 17-24 and 121-137. In another embodiment, this chimeric BGUS enzyme is at least 90% homologous to an amino acid sequence shown in SEQ ID NO: 19 or 121-137. In yet another embodiment, this chimeric BGUS enzyme is at least 95% homologous to an amino acid sequence shown in SEQ ID NO: 19 or 121-137. In yet other embodiment, this chimeric BGUS enzyme is at least 90%, 91%, 92%, 93%, 94%, 95%, 96%, 97%, 98%, 98.5%, 99% or 99.5% homologous to an amino acid sequence shown in SEQ ID NO: 19 or 121-137. In one embodiment, the chimeric BGUS enzyme comprises the amino acid sequence shown in SEQ ID NO: 17-24 or 121-137. In one embodiment, the chimeric BGUS enzyme comprises the amino acid sequence shown in SEQ ID NO: 19 or 121-137. In one embodiment, the chimeric BGUS enzyme comprises the amino acid sequence shown in SEQ ID NO: 19.

In one embodiment, the chimeric BGUS enzyme comprises an SBI domain from a first BGUS enzyme, a TIMB domain from a second BGUS enzyme, and a Loop 1 domain from the first BGUS enzyme. In one embodiment, this chimeric BGUS enzyme is at least 80% (or at least 85%, 90%, 91%, 92%, 93%, 94%, 95%, 96%, 97%, 98%, 98.5%, 99% or 99.5%) homologous to an amino acid sequence shown in SEQ ID NOs: 25-30. In another embodiment, this chimeric BGUS enzyme is at least 90% homologous to an amino acid sequence shown in SEQ ID NO: 26. In yet another embodiment, this chimeric BGUS enzyme is at least 95% homologous to an amino acid sequence shown in SEQ ID NO: 26. In yet other embodiment, this chimeric BGUS enzyme is at least 90%, 91%, 92%, 93%, 94%, 95%, 96%, 97%, 98%, 98.5%, 99% or 99.5% homologous to an amino acid sequence shown in SEQ ID NO: 26. In one embodiment, the chimeric BGUS enzyme comprises the amino acid sequence shown in SEQ ID NO: 26.

In one embodiment, the chimeric BGUS enzyme comprises an SBI domain and a TIMB domain from a first BGUS enzyme and a Loop 1 domain from a second BGUS enzyme. In one embodiment, this chimeric BGUS enzyme is at least 80% (or at least 85%, 90%, 91%, 92%, 93%, 94%, 95%, 96%, 97%, 98%, 98.5%, 99% or 99.5%) homologous to an amino acid sequence shown in SEQ ID NOs: 31-36. In another embodiment, this chimeric BGUS enzyme is at least 90% homologous to an amino acid sequence shown in SEQ ID NO: 31. In yet another embodiment, this chimeric BGUS enzyme is at least 95% homologous to an amino acid sequence shown in SEQ ID NO: 31. In yet other embodiment, this chimeric BGUS enzyme is at least 90%, 91%, 92%, 93%, 94%, 95%, 96%, 97%, 98%, 98.5%, 99% or 99.5% homologous to an amino acid sequence shown in SEQ ID NO: 31. In one embodiment, the chimeric BGUS enzyme comprises the amino acid sequence shown in SEQ ID NO: 31.

B. Counter-Loop and Loop 1 Swaps

In one aspect, the disclosure provides chimeric BGUS enzymes in which the Counter-Loop (C-Loop) and Loop 1, both of which are located within the TIM-barrel (TIMB) domain, have been swapped between two different BGUS enzymes.

Accordingly, in one embodiment, the disclosure provides a chimeric BGUS enzyme, which comprises a TIM-Barrel domain (TIMB domain) comprising a Counter-loop domain and a Loop 1 domain, wherein the chimeric BGUS enzyme comprises:

(a) a TIMB domain from a first BGUS enzyme, a Counter-loop domain from a second BGUS enzyme and a Loop 1 domain from the first BGUS enzyme; or (b) a TIMB domain from a first BGUS enzyme, a Counter-loop domain from the first BGUS enzyme and a Loop 1 domain from a second BGUS enzyme; or (c) a TIMB domain from a first BGUS enzyme, a Counter-loop domain from a second BGUS enzyme and a Loop 1 domain from the second BGUS enzyme.

As discussed herein, for BGUS enzymes, the TIM-barrel domain corresponds to the approximately 310 amino acids at the C-terminus. The C-loop and Loop 1 regions located within the TIMB domain are indicated in FIG. 2 and FIG. 4, wherein FIG. 4 illustrates two possible regions of Loop 1 (one longer and one shorter) for swapping. Approaches for creating the Counter-Loop and Loop 1 swaps arm described in detail in Example 6.

In one embodiment, the chimeric enzyme comprises a TIMB domain from a first BGUS enzyme, a Counter-loop domain from a second BGUS enzyme and a Loop 1 domain from the first BGUS enzyme. In this chimeric enzyme, the upstream sugar-binding/Ig-like (SBI) domain can be from the first BGUS enzyme, the second BGUS enzyme or from a different BGUS enzyme. When the SBI domain is from the first BGUS enzyme, then the structure of this chimeric is entirely the first BGUS enzyme except for the Counter-loop domain, which is from the second BGUS enzyme. Such a chimeric enzyme can be created using the first BGUS enzyme as the template and swapping in the C-loop from the second BGUS enzyme by recombinant means as described in Example 6.

In another embodiment, the chimeric enzyme comprises a TIMB domain from a first BGUS enzyme, a Counter-loop domain from the first BGUS enzyme and a Loop 1 domain from a second BGUS enzyme. In this chimeric enzyme, the upstream sugar-binding/Ig-like (SBI) domain can be from the first BGUS enzyme, the second BGUS enzyme or from a different BGUS enzyme. When the SBI domain is from the first BGUS enzyme, then the structure of this chimeric is entirely the first BGUS enzyme except for the Loop 1 domain, which is from the second BGUS enzyme. Such a chimeric enzyme can be created using the first BGUS enzyme as the template and swapping in the Loop 1 from the second BGUS enzyme by recombinant means as described in Example 6.

In another embodiment, the chimeric enzyme comprises a TIMB domain from a first BGUS enzyme, a Counter-loop domain from a second BGUS enzyme and a Loop 1 domain from the second BGUS enzyme. In this chimeric enzyme, the upstream sugar-binding/Ig-like (SBI) domain can be from the first BGUS enzyme, the second BGUS enzyme or from a different BGUS enzyme. When the SBI domain is from the first BGUS enzyme, then the structure of this chimeric is entirely the first BGUS enzyme except for the C-loop and Loop 1 domains, which are from the second BGUS enzyme. Such a chimeric enzyme can be created using the first BGUS enzyme as the template and swapping in the C-loop and Loop 1 domains from the second BGUS enzyme by recombinant means as described in Example 6.

In various embodiments, the chimeric BGUS enzyme exhibits:

(i) an increased level of enzymatic activity for one or more substrates as compared to the first or second BGUS enzyme; or (ii) an increased effective range of substrates catalyzed as compared to the first or second BGUS enzyme; or (iii) an increased effective pH range for one or more substrates as compared to the first or second BGUS enzyme; or (iv) an increased effective temperature range for one or more substrates as compared to the first or second BGUS enzyme; or (v) an increase in enzyme stability as compared to the first or second BGUS enzyme; or (vi) any combination of (i)-(v).

These properties are described further in Subsection 1A above.

In various embodiments, the first and second BGUS enzymes are each from a species independently selected from the group consisting of *Aspergillus oryzae, Aspergillus terreus. Bacteroides fragilis, Bacteroides uniformis, Brachyspira murdochii, Brachyspira pilosicoli. Clostridium perfringens. Escherichia coli, Eubacterium eligens, Homo sapiens. Lactobacillus brevis. Mus musculus, arabacteroides* sp., *Staphylococcus* sp, and *Streptococcus agalactiae*. In one embodiment, the first BGUS enzyme is from *Brachyspira pilosicoli* and the second BGUS enzyme is from *Eubacterium* eligens or the first BGUS enzyme is from *Eubacterium* eligens and the second BGUS enzyme is from *Brachyspira pilosicoli*.

In one embodiment, this chimeric BGUS enzyme is at least 80% (or at least 85%, 90%, 91%, 92%, 93%, 94%, 95%, 96%, 97%, 98%, 98.5%, 99% or 99.5%) homologous to an amino acid sequence shown in SEQ ID NOs: 37-46. In one embodiment, this chimeric BGUS enzyme is at least 90% homologous to an amino acid sequence shown in SEQ ID NO: 40 or 45. In another embodiment, this chimeric BGUS enzyme is at least 95% homologous to an amino acid sequence shown in SEQ ID NO: 40 or 45. In yet another embodiment, this chimeric BGUS enzyme is at least 90%, 91%, 92%, 93%, 94%, 95%, 96%, 97%, 98%, 98.5%, 99% or 99.5% homologous to an amino acid sequence shown in SEQ ID NO: 40 or 45. In yet another embodiment, this chimeric BGUS enzyme comprises the amino acid sequence shown in SEQ ID NO: 40 or 45.

C. Amino Acid Substitutions

In one aspect, the disclosure provides variant BGUS enzymes in which one or more key residues have been substituted with a different amino acid than is present in the parental (template) enzyme. Non-limiting exemplary methods of preparing and screening such variants are described in detail in Example 7. Other suitable methods for preparing single or multiple point mutations within the BGUS enzyme are well established in the art.

In one embodiment, amino acid substitution(s) is made at one or more positions within Variant Site 1, 2 or 3 shown in FIG. 1. Variant BGUS enzymes having single and double point mutations at these residues, and their activities, are described in detail in Examples 8-14.

Accordingly, in one embodiment, the disclosure provides a variant beta-glucuronidase (BGUS) enzyme derived from a parental BGUS enzyme, the variant BGUS enzyme comprising an amino acid sequence at least 80% (or at least 85%, 90%, 91%, 92%, 93%, 94%, 95%, 96%, 97%, 98%, 98.5%, 99% or 99.5%) homologous to an amino acid sequence shown in SEQ ID NOs: 1-46 and 138 and comprising at least one amino acid substitution, as compared to the parental BGUS enzyme, at at least one amino acid position corresponding to F294, T295, I450, Q451, A452 and/or G563 of SEQ ID NO: 5, wherein the variant BGUS enzyme exhibits:

(i) an increased level of enzymatic activity for one or more substrates as compared to the parental BGUS enzyme; or (ii) an increased effective range of substrates catalyzed as compared to the parental BGUS enzyme; or (iii) an increased effective pH range for one or more substrates as compared to the parental BGUS enzyme; or (iv) an increased effective temperature range for one or more substrates as compared to the parental BGUS enzyme; or (v) an increase in enzyme stability as compared to the parental BGUS enzyme; or (vi) any combination of (i)-(v).

These properties are described further in Subsection 1A above.

In one embodiment, the variant BGUS enzyme is at least 90% homologous to an amino acid sequence shown in SEQ ID NOs: 1-46 and 138. In another embodiment, the variant BGUS enzyme is at least 95% homologous to an amino acid sequence shown in SEQ ID Nos: 1-46 and 138. In another embodiment, the variant BGUS enzyme is at least 90%, 91%, 92%, 93%, 94%, 95%, 96%, 97%, 98%, 98.5%, 99% or 99.5% homologous to an amino acid sequence shown in SEQ ID NOs: 1-46 and 138.

In various embodiments of the point variants, the parental BGUS enzyme is from a species selected from the group consisting of *Aspergillus oryzae, Aspergillus terreus, Bacteroides fragilis, Bacteroides uniformis, Brachyspira murdochii, Brachyspira pilosicoli. Clostridium perfringens, Escherichia coli, Eubacterium eligens, Homo sapiens, Lactobacillus brevis, Mus musculus, Parabacteroides* sp., *Staphylococcus* sp, and *Streptococcus agalactiae.*

In one embodiment, the variant BGUS enzyme comprises an amino acid substitution, as compared to the parental BGUS enzyme, at an amino acid position corresponding to F294 of SEQ ID NO: 5. In specific embodiments, this variant BGUS enzyme comprises an amino acid sequence selected from the group consisting of the amino acid sequences shown in SEQ ID NOs: 47-54 (corresponding to BpF294A, BpF294I. BpF294V, BpF294Y, BpF294L, BpF294W, EeF303W and EeF303S, respectively).

In another embodiment, the variant BGUS enzyme comprises an amino acid substitution, as compared to the parental BGUS enzyme, at an amino acid position corresponding to T295 of SEQ ID NO: 5. In specific embodiments, this variant BGUS enzyme comprises an amino acid sequence selected from the group consisting of the amino acid sequences shown in SEQ ID NOs: 55-63, (corresponding to BpT295A, BpT295C. BpT295F. BpT295I, BpT295K, BpT295S. BpT295V. EeK304A and EeK304V, respectively).

In another embodiment, the variant BGUS enzyme comprises an amino acid substitution, as compared to the parental BGUS enzyme, at an amino acid position corresponding to I450 of SEQ ID NO: 5. In specific embodiments, this variant BGUS enzyme comprises an amino acid sequence selected from the group consisting of the amino acid sequences shown in SEQ ID NOs: 64-76 and 121-124 (corresponding to BpI450F, BpI450K. BpI450L, BpI450M, BpI450Q, BpI450D, BpI450V, EeV459F, EeV459L, EeV459W, EeV459C, EeV459G, EeV459E, Rxn3Y447L, Rxn3Y447P, Rxn3Y447I and Rxn3Y447Q, respectively).

In another embodiment, the variant BGUS enzyme comprises an amino acid substitution, as compared to the parental BGUS enzyme, at an amino acid position corresponding to Q451 of SEQ ID NO: 5. In specific embodiments, this variant BGUS enzyme comprises an amino acid sequence selected from the group consisting of the amino acid sequences shown in SEQ ID NOs: 77-82 and 125-130 (corresponding to BpQ451D, BpQ451E, BpQ451G, BpQ451S, BpQ451V. BpQ451K. Rxn3G448E. Rxn3G448K. Rxn3G448F, Rxn3G448L. Rxn3G448C and Rxn3G448W, respectively).

In another embodiment, the variant BGUS enzyme comprises an amino acid substitution, as compared to the parental BGUS enzyme, at an amino acid position corresponding to A452 of SEQ ID NO: 5. In specific embodiments, this variant comprises an amino acid sequence selected from the group consisting of the amino acid sequences shown in SEQ ID NOs: 83-92 and 131-137 (corresponding to BpA452D, BpA452K, BpA452N, BpA452G, BpA452E, BpA452Q, EeG461A, EeG461H, EeG461N, EeG461S, Rxn3D449Q, Rxn3D449G, Rxn3D449R, Rxn3D449K, Rxn3D449S, Rxn3D449C and Rxn3D449E, respectively).

In another embodiment, the variant BGUS enzyme comprises amino acid substitutions, as compared to the parental BGUS enzyme, at amino acid positions corresponding to F294 and T295 of SEQ ID NO: 5. In specific embodiments, the variant comprises an amino acid sequence selected from the group consisting of the amino acid sequences shown in SEQ ID NOs: 101-106 (corresponding to BpF294Y/T295C, BpF294Y/T295I, BpF294Y/T295V, BpF294Y/T295F, BpF294Y/T295M and BpF294Y/T295K, respectively).

In another embodiment, the variant BGUS enzyme comprises amino acid substitutions, as compared to the parental BGUS enzyme, at amino acid positions corresponding to T295 and I450 of SEQ ID NO: 5. In specific embodiments, the variant comprises an amino acid sequence selected from the group consisting of the amino acid sequences shown in SEQ ID NOs: 107-110 (corresponding to BpT295V/I450L, BpT295V/I450M, BpT295V/I450Y and BpT295V/I450V, respectively).

In another embodiment, the variant BGUS enzyme comprises amino acid substitutions, as compared to the parental BGUS enzyme, at amino acid positions corresponding to I450 and Q451 of SEQ ID NO: 5. In specific embodiments, the variant comprises an amino acid sequence selected from the group consisting of the amino acid sequences shown in SEQ ID NOs: 111 and 112 (corresponding to BpI450M/Q451D and BpI450Q/Q451D, respectively).

In another embodiment, the variant BGUS enzyme comprises amino acid substitutions, as compared to the parental BGUS enzyme, at amino acid positions corresponding to Q451 and A452 of SEQ ID NO: 5. In specific embodiments, the variant comprises an amino acid sequence selected from the group consisting of the amino acid sequences shown in SEQ ID NOs: 113-117 (corresponding to BpQ451D/A452E, BpQ451D/A452G, BpQ451D/A452Q, BpQ451D/A452S and BpQ451D/A452R, respectively).

In another aspect, the disclosure provides variant BGUS enzymes having one or more cysteine substitutions at key residues. Variant BGUS enzymes having single and double point mutations substituting cysteine at key residues, and their activities, are described in detail in Example 15.

Accordingly, in another embodiment, the disclosure pertains to a variant beta-glucuronidase (BGUS) enzyme derived from a parental BGUS enzyme, the variant BGUS enzyme comprising an amino acid sequence at least 80% (or at least 85%, 90%, 91%, 92%, 93%, 94%, 95%, 96%, 97%, 98%, 98.5%, 99% or 99.5%) homologous to an amino acid sequence shown in SEQ ID NOs: 1-46 and 138, and comprising at least one cysteine substitution, as compared to the parental BGUS enzyme, at at least one amino acid position corresponding to Q8, S73, P489, Q570 or K588 of SEQ ID NO: 10, wherein the variant BGUS enzyme exhibits:

(i) an increased level of enzymatic activity for one or more substrates as compared to the parental BGUS enzyme; or
(ii) an increased effective range of substrates catalyzed as compared to the parental BGUS enzyme; or
(iii) an increased effective pH range for one or more substrates as compared to the parental BGUS enzyme; or
(iv) an increased effective temperature range for one or more substrates as compared to the parental BGUS enzyme; or
(v) an increase in enzyme stability as compared to the parental BGUS enzyme; or
(vi) any combination of (i)-(v).

These properties are described further in Subsection 1A above.

In specific embodiments, the cysteine-substituted variant BGUS enzyme comprises an amino acid sequence selected from the group consisting of the amino acid sequences shown in SEQ ID NOs: 118-120 (corresponding to EeQ8C/S73C, EeK588C and EeP489C/Q570C, respectively).

D. Combination Variants

In another aspect, the invention pertains to variant BGUS enzymes that contain two or more of the above described modifications, referred to herein as combination variants. For example, a chimeric enzyme as described in Subsection 1A or 1B above can be used as the parental (template) enzyme for introduction of one or more amino acid substitutions as described in Subsection 1C above.

Non-limiting examples of such combination variants include the BGUS enzymes having the amino acid sequences shown in SEQ ID NOs: 99 and 100 (corresponding to Rxn3G560V and Rxn3G560E, respectively, in which the chimeric Rxn3 enzyme also has a point mutation at position 0560). Additional non-limiting examples of such combination variants include the BGUS enzymes having the amino acid sequences shown in SEQ ID NOs: 121-124 (corresponding to Rxn3Y447L, Rxn3Y447P, Rxn3Y447I and Rxn3Y447Q, respectively, in which the chimeric Rxn3 enzyme also has a point mutation at position Y447). Additional non-limiting examples of such combination variants include the BGUS enzymes having the amino acid sequences shown in SEQ ID NOs: 125-130 (corresponding to Rxn3G448E, Rxn3G448K, Rxn3G448F, Rxn3G448L, Rxn3G448C and Rxn3G448W, respectively, in which the chimeric Rxn3 enzyme also has a point mutation at position G448). Additional non-limiting examples of such combination variants include the BGUS enzymes having the amino acid sequences shown in SEQ ID NOs: 131-137 (corresponding to Rxn3D449Q, Rxn3D449G, Rxn3D449R, Rxn3D449K, Rxn3D449S, RxnD449C and Rxn3D449E, respectively, in which the chimeric Rxn3 enzyme also has a point mutation at position D449).

Still further, a combination variant can comprise one or more of the modifications described above in Subsections 1A, 1B and/or 1C, and additionally can have a cysteine residue appended at the carboxy terminus. For example, a tripeptide Glycine-Leucine-Cysteine (GLC) can be appended at the carboxy terminus. Combination variants comprising a chimeric enzyme as described in Subsection 1A above and having a GLC tripeptide appended at the carboxy terminus are described in Example 5. Furthermore, BGUS variant having a cysteine residue appended at the carboxy terminus, such as a GLC peptide, have been described in the art (see U.S. Pat. No. 9,920,306).

II. Preparation of Variant Enzymes

The BGUS enzymes of the invention can be prepared using standard recombinant DNA techniques. Exemplary methods for preparing chimeric enzymes or amino acid-substituted variants are described in the Examples, although other methods known in the art for protein mutagenesis by standard recombinant DNA techniques are also suitable. Once a nucleic acid fragment encoding the desired variant BGUS enzyme has been obtained, the fragment can be inserted into a suitable expression vector, transformed into a suitable host cell and the variant protein expressed recombinantly by culturing of the host cell, e.g., as described in Example 1. Suitable DNA constructs, expression vectors and host cells are well established in the art.

Accordingly, in another aspect, the disclosure provides a DNA construct encoding a chimeric or other variant BGUS enzyme of the disclosure, including plasmid constructs. In another aspect, the disclosure provides an expression vector comprising the DNA construct encoding the chimeric or other variant BGUS enzyme, including plasmid expression vectors and viral expression vectors. In another aspect, the disclosure provides a host cell comprising an expression vector encoding the chimeric or other variant BGUS enzyme, including prokaryotic (e.g., bacterial) and eukaryotic (e.g., yeast) host cells. In yet another aspect, the disclosure provides a method of expressing (i.e., producing) the chimeric or other variant BGUS enzymes by culturing the host cells such that the enzyme is expressed. Suitable culture conditions for host cells are well established in the art.

Following recombinant expression of the variant BGUS enzyme, the protein can be purified using standard protein purification techniques, such as those described in Example 2. For example, standard affinity chromatography methods, such as immunoaffinity chromatography using an anti-BGUS antibody or metal ion affinity chromatography using nickel, cobalt or copper resin, can be used. Furthermore, dispersive pipette extraction technology, such as IMC-Stips™, can be used for enzyme purification (e.g., as described in Example 2 and shown in FIG. 5). Recombinant variant enzyme typically exhibits a significantly higher degree of purity than commercially available extracts from abalone, snail or humans. Thus, the recombinant variant enzymes of the disclosure advantageously lack contaminating proteins found in commercially available crude extract preparations, which contaminating proteins could interfere with enzyme activity or efficiency.

III. Formulations

The variant BGUS enzymes of the disclosure can be included in formulations that contain additional substances and/or that are formulated in a particular way. For example, the formulations of the disclosure can be either liquid (aqueous) or lyophilized (freeze-dried). Liquid formulations typically allow for maintenance of enzymatic activity even after cycles of freezing/thawing. Lyophilized formulations typically maintain enzymatic activity over a wide temperature range, including high temperatures. Typically, a formulation comprises the enzyme blend composition and at least one excipient. Non-limiting examples of excipients that can be included in a formulation include water, salts, buffers, sugars and amino acids. Certain BGUS enzyme formulations have been described in the art, such as in PCT Application No. PCT/US2017/14387, the entire contents of which is expressly incorporated herein by reference.

Aqueous and lyophilized formulations can be prepared using methods well established in the art. Typically, an aqueous formulation is prepared by combining the enzymes and the excipient(s) at the desired concentrations. A lyophilized formulation can be made by freeze-drying the aqueous formulation using techniques well established in the art.

In certain embodiments, one or more sugars are used in the formulation. In one embodiment, the sugar is a polyol. In certain embodiments, the sugar(s) used in the formulation is selected from the group consisting of sucrose, sorbitol, xylitol, glycerol, 2-hydroxypropyl-β-cyclodextrin and α-cyclodextrin. In a preferred embodiment, the sugar is sucrose.

In certain embodiments, the sugar is present in the formulation at a concentration of at least 10 mM, or at least 25 mM or at least 50 mM or at least 100 mM. In other embodiments, the sugar is present in the formulation at a concentration of 10-1000 mM, or 25-500 mM or 50 mM-250 mM or 50 mM-500 mM or 50 mM-1000 mM. In other embodiments, the sugar is present in the formulation at a concentration of 50 mM or 75 mM or 100 mM or 200 mM or 250 mM or 300 mM or 400 mM or 500 mM or 600 mM or 700 mM or 750 mM or 800 mM or 900 mM or 1000 mM.

In certain embodiments, one or more amino acids (e.g., beta-alanine, L-histidine) is present in the formulation at a concentration of at least 25 mM or at least 50 mM. In other embodiments, the amino acid(s) is present in the formulation at a concentration of 25-500 mM or 50 mM-250 mM or 50 mM-500 mM. In other embodiments, the amino acid(s) is present in the formulation at a concentration of 25 mM or 30 mM or 40 mM or 50 mM or 75 mM or 100 mM or 200 mM or 250 mM or 300 mM or 400 mM or 500 mM.

In certain embodiments, the variant BGUS enzyme is present in the formulation at a concentration of at least 0.1 mg/mL. In certain embodiments, the variant BGUS enzyme is present in the formulation at a concentration of at least 1 mg/mL or at least 2.5 mg/mL or at least 5 mg/mL or at least 10 mg/mL. In other embodiments, the variant BGUS enzyme is present in the formulation at a concentration of 1-10 mg/mL or 1-5 mg/mL or 2.5-10 mg/mL or 2.5-5 mg/mL. In other embodiments, the variant BGUS enzyme is present in the formulation at a concentration of 1 mg/mL or 2 mg/mL or 3 mg/mL or 4 mg/mL or 5 mg/mL or 6 mg/mL or 7 mg/mL or 8 mg/mL or 9 mg/mL or 10 mg/mL.

In certain embodiments, the variant BGUS enzyme in the formulation has an enzymatic activity of at least 5,000 Units/mL or 5,000 Units/mg, more preferably at least 10,000 Units/mL or 10,000 Units/mg, even more preferably at least 25,000 Units/mL or 25,000 Units/mg and even more preferably 50,000 Units/mL or 50,000 Units/mg. The specific activity of the enzyme in the preparation, in Units/mL or Units/mg, can be determined using a standardized glucuronide linkage hydrolysis assay using phenolphthalein-glucuronide as the substrate. The standardization of the specific activity of BGUS has been well established in the art. Thus, 1 Fishman unit of BGUS activity is defined as an amount of enzyme that liberates 1 μg of phenolphthalein from phenolphthalein-glucuronide in 1 hour. Exemplary standardized assays that can be used to determine the specific activity (in Units/mL or Units/mg) of an enzyme preparation are described in further detail in Example 3. The skilled artisan will appreciate that other protocols for the enzyme assay are also suitable (e.g., such as those described by Sigma Aldrich Chemical Co.).

In one embodiment, the formulation is free of detergents, such as surfactants (e.g., Tween compounds and the like). Since the presence of detergents in a BGUS formulation can interfere with mass spectrometry (MS) analysis, the lack of detergent(s) in the formulation of the invention imparts the advantage that the formulation can be used directly in analysis of biological samples to be assayed by MS.

In one embodiment, the formulation is free of polymers (e.g., synthetic polymers and the like). Since the presence of polymers in a BGUS formulation can interfere with mass spectrometry (MS) analysis, the lack of polymer(s) in the formulation of the invention imparts the advantage that the formulation can be used directly in analysis of biological samples to be assayed by MS.

Packaged formulations, comprising a formulation of the disclosure and a container, are also encompassed. Non-limiting examples of suitable containers for use in a packed formulation include, bottles, tubes, vials, ampules and the like. Preferably, the container is glass or plastic, although other suitable materials are known in the art. Non-limiting examples of suitable instruction media include labels, pamphlets, inserts, and digital media.

IV. Methods of Use

The variant BGUS enzymes of the invention exhibit enhanced properties in their ability to hydrolyze glucuronide linkages as compared to the parental enzymes from which they are derived. Accordingly, the variant enzymes can be used in methods for hydrolysis of gluruonide substrates. The variant enzymes can be used, for example, for clinical purposes, for forensic purposes, for industrial manufacturing purposes or for agricultural purposes. These methods are particularly useful for analyzing bodily samples for the presence of drugs through detection of the glucuronide detoxification products of the drugs, e.g., for clinical or forensic purposes. Additionally, beta-agonists have been used in meat husbandry, since they can promote muscle growth instead of fat growth in animals (see e.g., *J. Animal Sci.* (1998) 76:195-207). Thus, the variant enzyme also can be used for agricultural purposes in detecting beta-agonist residues in meat products.

Thus, in another aspect the invention pertains to a method of hydrolyzing a substrate comprising a glucuronide linkage, the method comprising contacting the substrate with a variant β-glucuronidase enzyme of the disclosure under conditions such that hydrolysis of the glucuronide linkage occurs. Any of the variant enzymes of the invention, including the chimeric enzymes, those having a single amino acid substitution, those having double amino acid substitutions and those having more than one modification (i.e., combination variants) can be used in the method.

In one embodiment, the substrate comprises opiate glucuronides. Non-limiting examples of suitable opiate glucuronide substrates include morphine-3-β-D-glucuronide, morphine-6-β-D-glucuronide, codeine-6-β-D-glucuronide, hydromorphone-3-β-D-glucuronide, oxymorphone-3-β-D-glucuronide, and combinations thereof.

In another embodiment, the substrate comprises benzodiazepine glucuronides. Non-limiting examples of suitable benzodiazepine glucuronide substrates include the glucuronides of oxazepam, lorazepam, temazepam, and alpha-hydroxy-alprazolam.

Other suitable ranges of substrates include the glucuronides of buprenorphine, norbuprenorphine, 11-nor-Δ9-tetrahydrocannabinol-9-carboxylic acid, testosterone, androsterone, tapentadol, cyclobenzaprine, amitriptyline and combinations thereof.

In another embodiment, the substrate catalyzed by the variant BGUS enzyme comprises glucuronidated metabolites of drugs comprising opiates, synthetic opioids, antidepressants and benzodiazepines. In another embodiment, the substrate catalyzed by the variant BGUS enzyme comprises glucuronidated opiates comprising morphine-3-β-D-glucuronide, hydromorphone-3-β-D-glucuronide, oxymorphone-3-β-D-glucuronide, codeine-6-β-D-glucuronide and dihydrocodeine-6-β-D-glucuronide. In another embodiment, the substrate catalyzed by the variant BGUS enzyme comprises glucuronidated opioids comprising buprenorphine glucuronide, norbuprenorphine glucuronide and tapentadol glucuronide. In another embodiment, the substrate catalyzed by the BGUS variant enzyme comprises glucuronidated anti-depressants comprising O-desmethyl-venlafaxine glucuronide and amitriptyline-N-β-D-glucuronide. In another embodiment, the substrates catalyzed by the variant BGUS enzyme comprises glucuronidated benzodiazepines comprising temazepam glucuronide, oxazepam glucuronide and lorazepam glucuronide.

In one embodiment, the substrate catalyzed by the BGUS variant enzyme comprises at least one beta-agonist (e.g., for meat product analysis). Non-limiting examples of suitable beta-agonist glucuronidated substrates include clenbuterol, ractopamine and salbutamol.

In yet another embodiment, the substrate catalyzed by the variant BGUS enzyme comprises morphine-3-β-D-glucuronide (MOR), oxymorphone-3-β-D-glucuronide (OMOR), hydromorphone-3-β-D-glucuronide (HMOR), codeine-6-β-D-glucuronide (COD), dihydrocodeine-6-β-D-glucuronide (DCOD), buprenorphine-3-β-D-glucuronide (BUP gluc), norbuprenorphine-3-β-D-glucuronide (NBUP gluc), tapentadol glucuronide (TAP gluc), O-desmethyltramadol glucuronide (ODT gluc), O-desmethylvenlafaxine glucuronide (ODV gluc), amitriptyline-N-β-D-glucuronide (AMT gluc), oxazepem glucuronide (OXZ gluc), lorazepam glucuronide (LOR gluc), and/or temazepam glucuronide (TEM gluc).

In certain embodiments of the method of hydrolyzing a substrate, one or more particular substrates are used in combination with a particular variant BGUS enzyme that exhibits enhanced enzymatic activity against that particular substrate as compared to the parental BGUS enzyme from which the variant is derived. For example, in one embodiment, the disclosure pertains to a method of hydrolyzing codeine-6-β-D-glucuronide (COD), the method comprising contacting the substrate with a variant BGUS enzyme comprising an amino acid substitution, as compared to the parental BGUS enzyme, at an amino acid position corresponding to Q451 of SEQ ID NO: 5, such that hydrolysis of the glucuronide linkage occurs. In one embodiment of this method, the variant BGUS enzyme comprises the amino acid sequence shown in SEQ ID NO: 76 (BpGUS comprising a Q451D mutation). In another embodiment of this method, the variant BGUS enzyme comprises the amino acid sequence shown in SEQ ID NO: 113 (BpGUS comprising Q451D/A452E mutations). In another embodiment of this method, the variant BGUS enzyme comprises the amino acid sequence shown in SEQ ID NO: 114 (BpGUS comprising Q451D/A452G mutations). In another embodiment of this method, the variant BGUS enzyme comprises the amino acid sequence shown in SEQ ID NO: 115 (BpGUS comprising Q451D/A452Q mutations). In another embodiment of this method, the variant BGUS enzyme comprises the amino acid sequence shown in SEQ ID NO: 116 (BpGUS comprising Q451D/A452S mutations). In another embodiment of this method, the variant BGUS enzyme comprises the amino acid sequence shown in SEQ ID NO: 117 (BpGUS comprising Q451 D/A452R mutations).

In another embodiment, the disclosure pertains to a method of hydrolyzing amitriptyline-N-β-D-glucuronide (AMT gluc), the method comprising contacting the substrate with a variant BGUS enzyme comprising an amino acid substitution, as compared to the parental BGUS enzyme, at an amino acid position corresponding to I450 of SEQ ID NO: 5, such that hydrolysis of the glucuronide linkage occurs. In one embodiment of this method, the variant BGUS enzyme comprises the amino acid sequence shown in SEQ ID NO: 64 (BpGUS comprising an I450F mutation). In another embodiment of this method, the variant BGUS enzyme comprises the amino acid sequence shown in SEQ ID NO: 65 (BpGUS comprising an I450K mutation). In another embodiment of this method, the variant BGUS enzyme comprises the amino acid sequence shown in SEQ ID NO: 67 (BpGUS comprising an I450M mutation). In another embodiment of this method, the variant BGUS enzyme comprises the amino acid sequence shown in SEQ ID NO: 68 (BpGUS comprising an I450Q mutation). In another embodiment of this method, the variant BGUS enzyme comprises the amino acid sequence shown in SEQ ID NO: 69 (BpGUS comprising an I450D mutation). In another embodiment of this method, the variant BGUS enzyme comprises the amino acid sequence shown in SEQ ID NO: 71 (EeGUS comprising a V459F mutation). In another embodiment of this method, the variant BGUS enzyme comprises the amino acid sequence shown in SEQ ID NO: 72 (EeGUS comprising a V459L mutation). In another embodiment of this method, the variant BGUS enzyme comprises the amino acid sequence shown in SEQ ID NO: 74 (EeGUS comprising a V459C mutation). In another embodiment of this method, the variant BGUS enzyme comprises the amino acid sequence shown in SEQ ID NO: 75 (EeGUS comprising a V459G mutation).

In another embodiment, the disclosure pertains to a method of hydrolyzing morphine-3-β-D-glucuronide (MOR), the method comprising contacting the substrate with a variant BGUS enzyme comprising an amino acid substitution, as compared to the parental BGUS enzyme, at an amino acid position corresponding to I450 of SEQ ID NO: 5, such that hydrolysis of the glucuronide linkage occurs. In one embodiment of this method, the variant BGUS enzyme comprises the amino acid sequence shown in SEQ ID NO: 64 (BpGUS comprising an I450F mutation). In another embodiment of this method, the variant BGUS enzyme comprises the amino acid sequence shown in SEQ ID NO: 67 (BpGUS comprising an I450M mutation). In another embodiment of this method, the variant BGUS enzyme comprises the amino acid sequence shown in SEQ ID NO: 68 (BpGUS comprising an I450Q mutation).

In one embodiment, the range of substrates is in a sample of blood, urine, tissue or meconium obtained from a subject. The methods of the invention can be used on a variety of different bodily samples. Non-limiting examples of suitable bodily samples include blood, urine, tissue or meconium obtained from a subject. For meat product analysis, the bodily sample can be a meat sample. Bodily samples can be obtained, stored and prepared for analysis using standard methods well established in the art.

Following hydrolysis by the enzyme, the cleavage products in the sample can be analyzed by standard methodologies, such as high performance liquid chromatography (HPLC), gas chromatography (GC) and/or mass spectrometry (MS). Such approaches for analysis of bodily samples for the presence of drugs are well established in the art. For example, a completely automated workflow for the hydrolysis and analysis of urine samples by LC-MS/MS, which can be applied using the variant enzymes of the invention for hydrolysis, is described in Cabrices, O. G. et al., GERSTEL AppNote AN/2014/4-7. Additional liquid chromatography and tandem mass spectrometry (LC-MS/MS) methodologies suitable for use with the invention are described in Sitasuwan et al. (2016) *J. Analytic. Toxicol.* 40:601-607. Methods for detecting beta-agonist residues in meat products using UPLC-MS/MS have also been described (www.waters.com/webassets/cms/library/docs/720004388en.pdf).

The present invention is further illustrated by the following examples, which should not be construed as further limiting. The contents of Sequence Listing, figures and all references, patents and published patent applications cited throughout this application are expressly incorporated herein by reference.

EXAMPLES

Example 1: Gene Synthesis, Cloning, and Protein Expression

Genes for beta-glucuronidase enzymes were synthesized, placed in plasmid expression vectors, and expressed *E. coli* using standard recombinant DNA techniques established in the art. The DNA sequence coding for a protein sequence can be reconstructed from the protein sequence by standard methods well known in the art. For example, amino acid sequences for BGUS enzymes from *Aspergillus oryzae* (AoGUS), *Aspergillus terreus* (AtGUS), *Bacteroides fragilis* (BfGUS), *Bacteroides uniformis* (BuGUS), *Brachyspira murdochii* (BmGUS), *Brachyspira pilosicoli* (BpGUS), *Clostridium perfringens* (CpGUS), *Escherichia coli* (EcGUS), IMCSzyme® variant *Escherichia coli* K12 (EcE1F), *Eubacterium* eligens (EeGUS), *Homo sapiens* (HsGUS). *Lactobacillus brevis* (LbLR2D), *Mus musculus* (MmGUS), *Parabacteroides* sp. (PmGUS). *Staphylococcus* sp. (StpGUS) and *Streptococcus agalactiae* (SaGUS) are shown in SEQ ID Nos: 1-16, respectively, and can be used to design appropriate DNA sequences coding for the enzymes.

It is noted that the AoGUS amino acid sequence shown in SEQ ID NO: 1 contains a G600S substitution at residue 600 as compared to the wild-type AoGUS amino acid sequence, which is shown in SEQ ID NO: 138. This substitution was made to introduce a restriction site for cloning purposes at the C-terminus of the sequence (as shown in FIG. 3) without affecting the enzymatic function of the AoGUS enzyme. Thus, to make variants that use an AoGUS enzyme as a parental enzyme (e.g., for making a chimeric enzyme and/or an amino acid-substituted variant comprising AoGUS sequences) either SEQ ID NO: 1 or SEQ ID NO: 138 is a suitable parental enzyme.

FIG. 1 show the amino acid sequence alignment for the EeGUS. AoGUS, Rxn3, AtGUS, EcE1F, BpGUS, BmGUS, CpGUS, StpGUS, LbLR2D, SaGUS, HsGUS, BfGUS, PmGUS and BuGUS enzymes.

These DNA sequences can be codon optimized for the organism in which they are to be expressed, and linked to appropriate regulatory sequences that enable transcription and translation of the gene and enzyme product. The sequence may include protein sequences known to those skilled in the art that facilitate purification to near homogeneity (Hochuli et al. (1988) *Nature Biotech.* 6:1321-1325). A non-limiting example is the His$_6$-tag, six histidine residues in a row (SEQ ID NO: 139), usually attached to either the N-terminal or C-terminal of an enzyme, which enables specific purification on chromatography resins containing divalent metal cations, such as nickel, cobalt, copper, or zinc.

Typically, the enzyme-encoding DNA sequence is synthesized with consideration for the codon bias of the expression host, an approach also well established in the art (Maloy et al. (1996) *Cold Spring Harbor Lab. Press*; Gouy and Gautier (1982) *Nucleic Acids Res.* 10:22). Using such methods, genes for EcE1F, AoGUS. AtGUS. BpGUS and EeGUS were synthesized with a codon bias compatible for expression in *Escherichia coli* host cells. Using standard molecular biology techniques, the genes were assembled in plasmid vectors under the control of an inducible promoter and expressed in a bacterial strain supportive of the construct. Enzymes were expressed intracellularly, the cells were lysed by a combination of physical and chemical means, and the lysates clarified by centrifugation. The lysates were then adjusted with buffer compatible with subsequent purification steps.

Example 2: Protein Purification of BGUS Enzymes

Following recombinant expression, the BGUS enzymes, chimeras and variants described in the Examples were purified by standard immobilized metal affinity chromatography (IMAC) techniques known to those skilled in the art, either on an AKTA™ Pure FPLC or with IMCStips tip technologies. Protein elution was monitored by absorbance at 280 nm, protein purity was evaluated by SDS-PAGE (Laemmli (1970) *Nature* 227:680-685), and protein concentration in pure fractions was determined by Bradford protein assay (Bradford (1976) *Anal. Biochem.* 72:248-254). The SDS-PAGE shown in FIG. 5 revealed purified protein bands of the expected molecular weights, demonstrating effective purification of the recombinant enzymes. Typically a 4-20% gradient SDS-PAGE was used to determine protein purity and about 1.0 μg of protein was used. Protein purity was assessed by using ImageQuantTL 8.1 Software.

Example 3: pH Optima and Enzymatic Activity Measurements Using Various Substrates Activity of recombinant BGUS enzymes was measured, at two or more pH, using the substrate phenolphthalein-β-D-glucuronide (PTGlcU), a standard substrate for monitoring and reporting BGUS activity (Talalay et al. (1946) *J. Biol. Chem.* 166:757-72). The pH profile for some of the chimeras and variants was determined using a buffer system described in the art (Ellis and Morrison (1982) *Methods Enzymol.* 87:405-426), with phenolphthalein-β-D-glucuronide as the substrate. All enzymes were tested with 1.0 mM PTGlcU in 10% ethanol. For set up, 25 μL of enzyme and 25 μL of 1.0 mM PTGlcU were mixed in a 96-well microtiter plate at room temperature, and the reactions were stopped by addition of 150 μL 0.2 M glycine, pH 10.4. The buffer pH range tested was from pH 4.5-8.0. Thirty minutes after stopping the reaction, the absorbance of each well was read at 540 nm.

Additionally, activity of recombinant BGUS enzymes was measured, at two or more pH, using the substrate 4-methylumbelliferyl-β-D-glucuronide (4MUG). Enzymes were tested with 1.0 mM 4MUG in 10% ethanol. For set up, 25 μL of enzyme and 25 μL of 1.0 mM 4MUG were mixed in a 96-well microtiter plate at room temperature, and the reactions were stopped by addition of 150 μL 0.2 M glycine, pH 10.4. Product of 4MUG was measured by excitation wavelength at 365 nm and emission wavelength at 455 nm.

Additionally, activity of recombinant BGUS enzymes was measured, at two or more pH, using the substrate fluorescein-di-β-D-glucuronide (FDGlcU). Enzymes were tested with 170 µM FDGlcU in 5% methanol. For set up, 25 µL of enzyme and 25 µL of 170 µM FDGlcU were mixed in a 96-well microtiter plate at room temperature, and the reactions were stopped by addition of 150 µL 0.2 M glycine, pH 10.4. Product of FDGlcU was measured by excitation at 490 nm and emission at 514 nm.

Example 4: Liquid Chromatography-Mass Spec and Drug Glucuronides

In this example, liquid chromatography-Mass Spec (LC-MS) was used to measure the activity of BGUS chimeras and variants on various opiate and opioid drug glucuronides. Each recombinant beta-glucuronidase was used to deconjugate up to fourteen glucuronidated drugs frequently tested in urine drug-testing applications. The substrates represent a wide variety of drug classes, such as opiates, synthetic opioids, benzodiazepines, and anti-depressants. The substrates included morphine-3-β-D-glucuronide (MOR), oxymorphone-3-β-D-glucuronide (OMOR), hydromorphone-3-β-D-glucuronide (HMOR), codeine-6-β-D-glucuronide (COD), dihydrocodeine-6-β-D-glucuronide (DCOD), buprenorphine-3-β-D-glucuronide (BUP gluc), norbuprenorphine-3-β-D-glucuronide (NBUP gluc), tapentadol glucuronide (TAP gluc), O-desmethyltramadol glucuronide (ODT gluc), O-desmethylvenlafaxine glucuronide (ODV gluc), amitriptyline-N-β-D-glucuronide (AMT gluc), oxazepam glucuronide (OXZ gluc), lorazepam glucuronide (LOR gluc) or temazepam glucuronide (TEM gluc). The substrates were fortified in synthetic urine at a concentration equivalent to 500 ng/mL when liberated.

The hydrolysis buffer used was 0.2 M sodium acetate, pH 5.5. The internal standard solution was prepared at 1.0 µg/mL of each deuterated drug standard in methanol, 50 µL of urine containing the substrates was mixed with 150 µL of hydrolysis buffer, 20 µL enzyme solution, and 10 µL internal standard solution. The incubations were performed at 23° C. for various times, depending on the chimeras or variants being tested. Samples were extracted using dispersive pipette extraction tips with WAX/RP resins as described in the art. Samples were eluted twice, each in 200 µL of acetonitrile with 1% formic acid. Prior to LC-MS/MS analysis, samples were dried down to 100 µL and diluted with 700 µL of water.

Ultra-performance liquid chromatography was performed on a Thermo-Scientific™ Vanquish™ UHPLC system using a Phenomenex Kinetex® Phenyl-Hexyl 100 Å column (4.6×50 mm, 2.6 µm). The column was heated to 40° C. with a gradient elution with a flow rate of 0.6 mL/min. Mobile phase A consisted of 0.1% formic acid in ultrapure water and mobile phase B consisted of 0.1% formic acid in acetonitrile. The system was equilibrated in 95% A for the first 0.5 minutes and the gradient consisted of 5-95% B from 0.5-3.0 minutes and re-equilibrated at initial conditions from 4.0-6.0 minutes. The liquid chromatography (LC) system was connected to a Thermo-Scientific™ Endura™ Triple Quadrupole mass spectrometer with an electrospray ionization source, operated in positive mode. Detection was performed by multiple reaction monitoring (MRM) analysis of the most intense transitions originating from the protonated molecular ion [M+1] of each analyte. The aglycone species was quantified and enzyme activity was expressed as pmol·min$^{-1}$·mg$^{-1}$.

Data were plotted as significance (negative logarithm base 10 of p-value) versus change in activity (logarithm base 2 change in activity relative to template). A horizontal dashed line at the logarithm base 10 of 0.05 is used to distinguish data is that has a significant change, i.e. the p-value<0.05; any data plotted above this line are considered significant.

Example 5: Chimeric BGUS Enzymes Having Sugar-Binding/Ig-Like Domain, TIM-Barrel Domain and/or Loop 1 Swaps In this example, chimeric BGUS enzymes were prepared in which domains were swapped between AoGUS. AtGUS and/or EcE1F by using DNA restriction enzyme cloning techniques, plasmid DNA expression, DNA purification, and DNA fragment ligation known by those skilled in the art. Fusion sites for domain-swapping were determined by considering the amino acid sequence alignments and crystal structures for AoGUS and EcGUS (PDB codes: 4JHZ and 5C70, respectively). Also, the DNA sequences were engineered to include restriction enzyme DNA sequences at the fusion sites for swapping (see FIG. 3). Domains include the sugar-binding domain, the immunoglobulin-like domain, and the TIM-barrel domain. The sugar-binding and immunoglobulin domains were often exchanged as a pair between AoGUS, AtGUS, and EcE1F. using Restriction Sites 1 and 2 as shown in FIG. 3 to generate chimeras referred to herein as "Rxn" chimeras, wherein the N-terminal portion of the Rxn chimera comprises the sugar-binding/immunoglobulin domains from one BGUS enzyme and the C-terminal portion of the Rxn chimera comprised the TIM-Barrel domain from a second BGUS enzyme. Furthermore, Loop 1 of AoGUS, AtGUS, and/or EcE1F, located within the TIM-Barrel domain, was also swapped between them to generate chimeras referred to herein as "Save" and "L" chimeras, in addition to domain-swapping, by using the combinations of Restriction Site 2 and Loop Site B or Loop Site A and Loop Site B as shown in FIG. 3. Also, the C-terminal residues GLC were swapped into AoGUS and AtGUS using Restriction Site 3 and Restriction Site 4 shown in FIG. 3. All DNA sequences were confirmed by using DNA sequencing techniques known to those skilled in the art.

A summary of the structure of the panel of Rxn, Save and L chimeras is shown below in Table 1:

TABLE 1

Chimeras of AoGUS, AtGUS, and EcE1F.

| Chimera | Domain | | | C-Terminal |
| | SB/IgG-like | TIM-Barrel | Loop1 | GLC residues |
| --- | --- | --- | --- | --- |
| Rxn1 | AtGUS | AoGUS | AoGUS | No |
| Rxn2 | AtGUS | EcE1F | EcE1F | No |
| Rxn3 | AoGUS | AtGUS | AtGUS | No |
| Rxn4 | AtGUS | EcE1F | EcE1F | No |
| Rxn5 | AoGUS | EcE1F | EcE1F | Yes |
| Rxn8 | AtGUS | EcE1F | EcE1F | Yes |
| Rxn9 | EcE1F | AoGUS | AoGUS | Yes |
| Rxn10 | EcE1F | AtGUS | AtGUS | Yes |
| Save1 | AtGUS | AoGUS | AtGUS | No |
| Save3 | AoGUS | AtGUS | AoGUS | No |
| Save4 | AtGUS | EcE1F | AtGUS | No |
| Save5 | AoGUS | EcE1F | AoGUS | Yes |
| Save9 | EcE1F | AoGUS | EcE1F | Yes |
| Save10 | EcE1F | AtGUS | EcE1F | Yes |
| L1 | AoGUS | AoGUS | AtGUS | No |
| L2 | AoGUS | AoGUS | EcE1F | No |
| L3 | AtGUS | AtGUS | AoGUS | No |
| L4 | AtGUS | AtGUS | EcE1F | No |

TABLE 1-continued

Chimeras of AoGUS, AtGUS, and EcE1F.

| Chimera | Domain | | | C-Terminal |
| | SB/IgG-like | TIM-Barrel | Loop1 | GLC residues |
| --- | --- | --- | --- | --- |
| L5 | EcE1F | EcE1F | AoGUS | Yes |
| L6 | EcE1F | EcE1F | AtGUS | Yes |

The amino acid sequences of the Rxn1, Rxn2, Rxn3, Rxn4, Rxn5, Rxn8, Rxn9 and Rxn10 chimeras are shown in SEQ ID NOs: 17-24, respectively. The amino acid sequences of the Save1, Save3, Save4, Save5, Save9 and Save10 chimeras are shown in SEQ ID NOs: 25-30, respectively. The amino acid sequences of the L1, L2, L3, L4, L5 and L6 chimeras are shown in SEQ ID NOs: 31-36, respectively.

Figure 6:
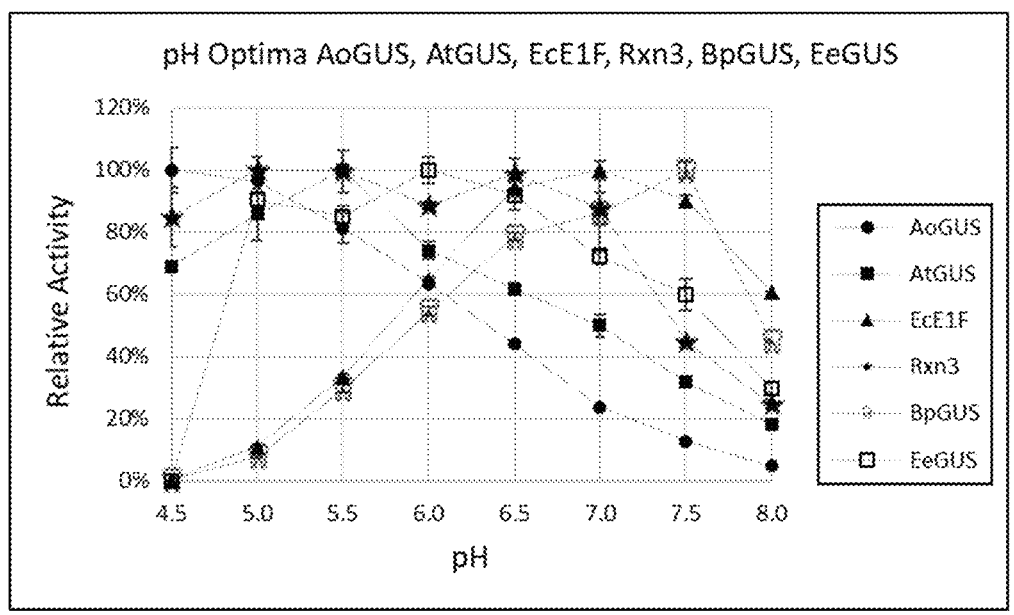
FIG. 6 is a graph showing the pH optima of the AoGUS, AtGUS, EcE1F, Rxn3, BpGUS and EeGUS enzymes.

To study the activity of the chimeric enzymes, in a first series of experiments, the pH range of the chimeras versus the parental enzymes was examined, as described in Example 3. The results for the Rxn3 chimera are shown in FIG. 6 and summarized below in Table 2, which shows the optimum pH range (range in which enzyme maintains 80% or greater activity):

TABLE 2

Optimum pH Range of Rxn3 Chimera versus Parental Enzymes

| BGUS Enzyme | Optimum pH Range (>80% activity) |
| --- | --- |
| AoGUS | pH 4.5-5.5 |
| AtGUS | pH 5.0-5.5 |
| EcE1F | pH 6.5-7.5 |
| Rxn3 | pH 4.5-7.0 |

The data summarized in Table 2 demonstrates that the Rxn3 chimera (composed of the sugar binding/Ig-like domains of AoGUS and the TIM-Barrel/Loop 1 of AtGUS) has a broader optimum pH range (pH 4.5-7.0) than either the AoGUS parental enzyme (pH 4.5-5.5) or the AtGUS parental enzyme (pH 5.0-5.5).

Additionally, the enzymatic activity of the panel of chimeras was tested using two different substrates, phenolphthalein-β-D-glucuronide (PTGlcU) and 4-methylumbelliferyl-β-D-glucuronide (4MUG) as described in Example 3.

Figure 7:
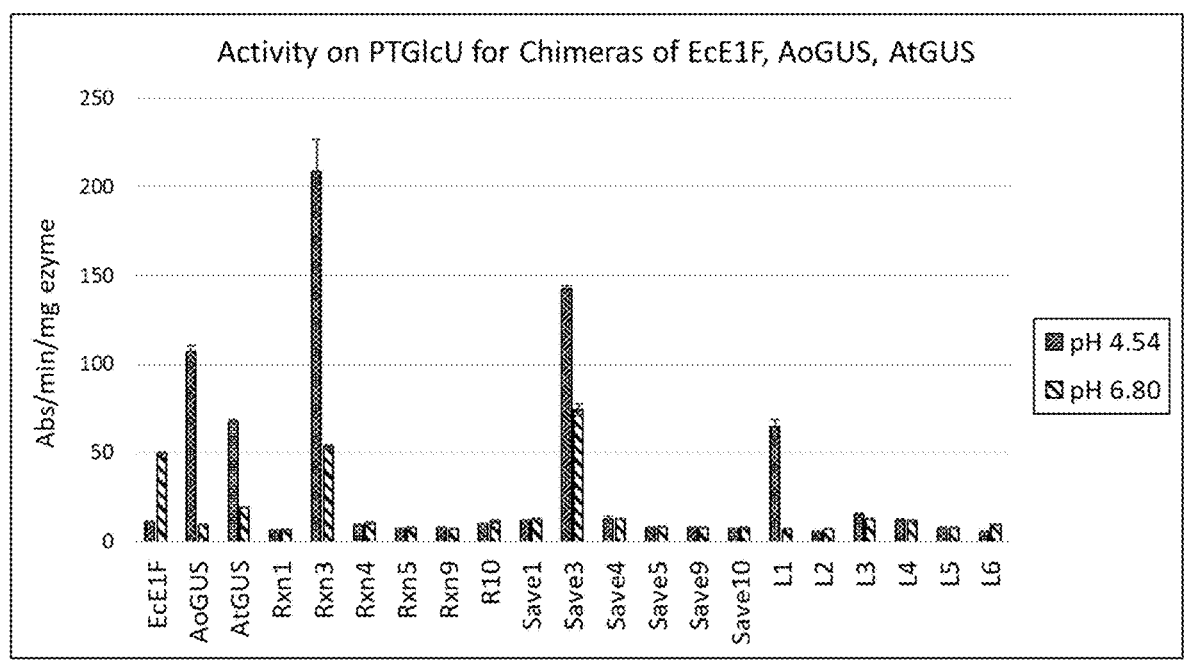
FIG. 7 is a bar graph showing the enzymatic activity of the Rxn. Save and L chimeric enzymes on the PTGlcU substrate.

The results for PTGlcU are shown in FIG. 7. The results in FIG. 7 demonstrate that the Rxn3 chimera and the Save3 chimera (composed of the sugar binding/Ig-like domains of AoGUS, the TIM-Barrel domain of AtGUS and the Loop 1 domain of AoGUS) each exhibit higher enzymatic activity against the PTGlcU substrate than either the AoGUS parental enzyme or the AtGUS parental enzyme at both pH 4.54 and pH 6.80.

Figure 8:
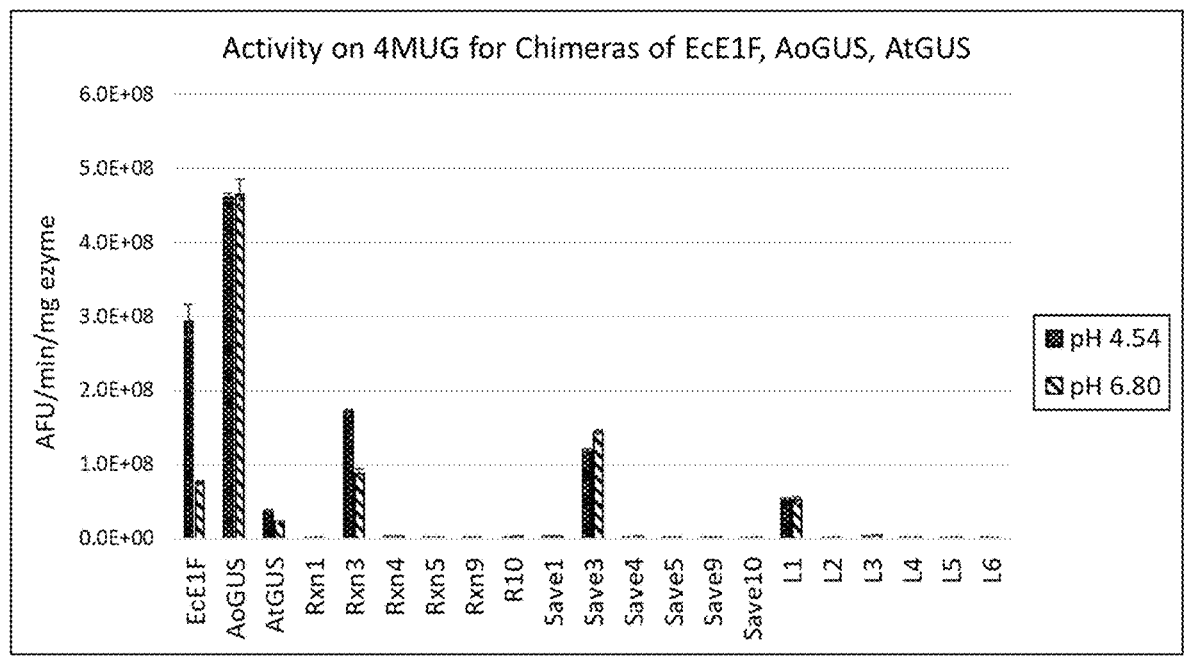
FIG. 8 is a bar graph showing the enzymatic activity of the Rxn, Save and L chimeric enzymes on the 4MUG substrate.

The results for 4MUG are shown in FIG. 8. The results in FIG. 8 demonstrate that the Rxn3 chimera, the Save3 chimera and the L1 chimera (composed of the sugar binding/Ig-like domain and TIM-Barrel domain of AoGUS and the Loop 1 domain of AtGUS) each exhibited higher enzymatic activity against the 4MUG substrate than the AtGUS parental enzyme at both pH 4.54 and pH 6.80.

In summary, this example demonstrates chimeric enzymes comprising various swaps of the sugar binding/Ig-like domain, TIM-Barrel domain and Loop 1 domain from two different BGUS parental enzymes that exhibited an increased effective pH range and/or increased enzymatic activity against a substrate as compared to either or both of the parental enzymes from which the chimera was derived.

Example 6: Chimeric BGUS Enzymes Having C-Loop and Loop 1 Swaps

In this example, the C-loop. Loop 1, or both were swapped between BpGUS and EeGUS using either restriction-free cloning (Chen et al. (2000) BioTechniques. 28:498-500) or exponential mega-priming polymerase chain reaction (PCR) (Ulrich et al. (2012) PLoS ONE. 7:e53360). The residue lengths of Loop 1 and C-loop to be swapped were determined by using amino acid sequence alignments and by observing predicted crystal structures of BpGUS and EeGUS created by the online software SWISS-MODEL (Waterhouse et al. (2018) Nucleic Acids Res. 46(W1):W296-W303; Bienert et al. (2017) Nucleic Acid Res. 45:D313-D319; Guex et al. (2009) Electrophoresis 30:S162-S173; Benkert et al. (2011) Bioinformatics 27:343-350; Bertoni et al. (2017) Sci. Reports 7). Furthermore, residues for Loop 1 were chosen based on comparisons of flexibility and homology to known BGUS crystal structures. The length of residues swapped for Loop 1 between BpGUS and EeGUS was varied. FIG. 4 shows the C-loop region and the two different Loop 1 swap regions (Loop 1 Swap 1 and Loop 1 Swap 2) of differing lengths that were used to create the chimeras. Ten chimeras of BpGUS and EeGUS were produced, having the structures set forth in Table 3 below. All DNA sequences were confirmed by sequencing.

TABLE 3

BpGUS and EeGUS chimeras for Counter-loop and Loop 1 swaps.

| Chimera | Template | Counter-loop | Loop 1 (amino acid length) |
| --- | --- | --- | --- |
| BpChimera1 | BpGUS | EeGUS | BpGUS (template) |
| BpChimera2 | BpGUS | BpGUS | EeGUS (21 residues) |
| BpChimera3 | BpGUS | EeGUS | EeGUS (21 residues) |
| BpChimera4 | BpGUS | BpGUS | EeGUS (10 residues) |
| BpChimera5 | BpGUS | EeGUS | EeGUS (10 residues) |
| EeChimera1 | EeGUS | BpGUS | EeGUS (template) |
| EeChimera2 | EeGUS | EeGUS | BpGUS (21 residues) |
| EeChimera3 | EeGUS | BpGUS | BpGUS (21 residues) |
| EeChimera4 | EeGUS | EeGUS | BpGUS (10 residues) |
| EeChimera5 | EeGUS | BpGUS | BpGUS (10 residues) |

The amino acid sequences of the BpChimera1, BpChimera2, BpChimera3, BpChimera4 and BpChimera5 chimeras are shown in SEQ ID NOs: 37-41, respectively. The amino acid sequences of the EeChimera1. EeChimera2, EeChimera3, EeChimera4 and EeChimera5 chimeras are shown in SEQ ID NOs: 42-46, respectively.

Figure 9:
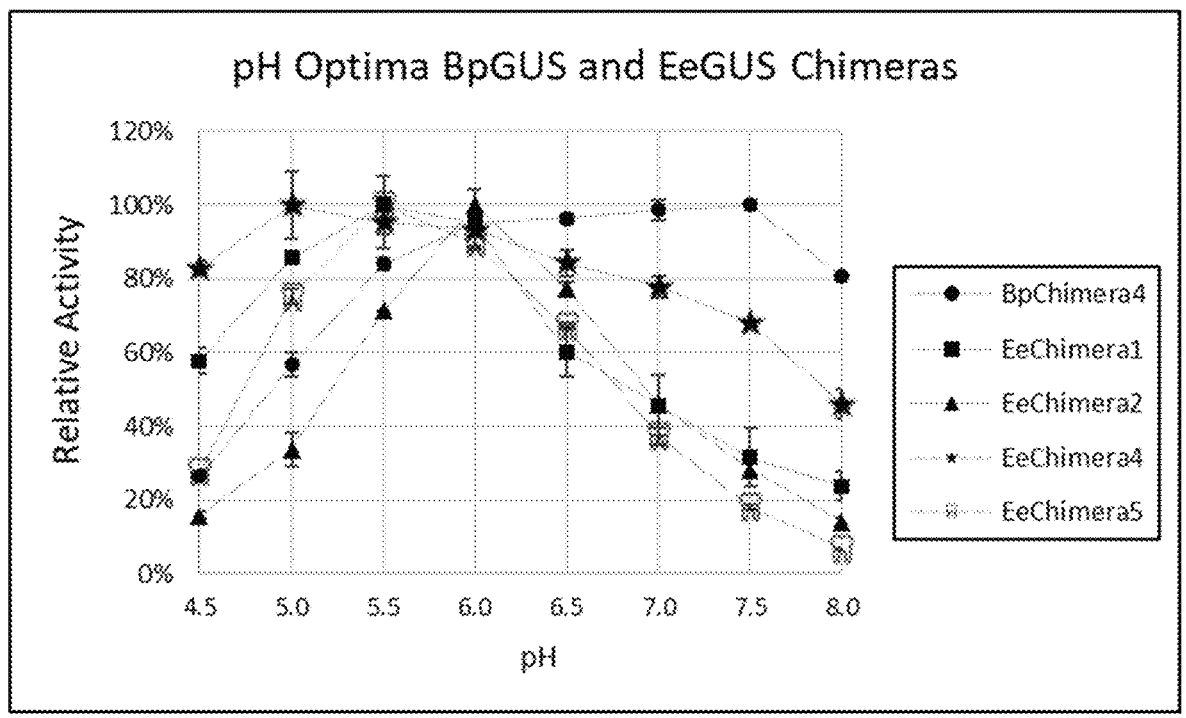
FIG. 9 is a graph showing the pH optima of the BpGUS and EeGUS chimeric enzymes.

To study the activity of the chimeric enzymes, in a first series of experiments, the pH range of the chimeras versus the parental enzymes was examined, as described in Example 3. The results for the BpChimera4, EeChimera1, EeChimera2, EeChimera4 and EeChimera5 chimeric enzymes are shown in FIG. 9. The pH optima for certain BpChimera and EeChimera chimeric enzymes as compared to the parental BpGUS and EeGUS enzymes are summarized below in Table 4, which shows the optimum pH range (range in which enzyme maintains 80% or greater 5 activity):

TABLE 4

Optimum pH Range of BpChimera and EeChimera versus Parental Enzymes

| BGUS Enzyme | Optimum pH Range (>80% activity) |
| --- | --- |
| BpGUS | pH 7.0-7.5 |
| EeGUS | pH 5.0-6.5 |
| BpChimera4 | pH 5.5-8.0 |
| EeChimera1 | pH 5.0-6.0 |
| EeChimera2 | pH 6.0 |
| EeChimera4 | pH 4.5-6.5 |
| EeChimera5 | pH 5.5-6.0 |

The data summarized in Table 4 demonstrates that the BpChimera4 chimera (composed of the 10 amino acid Loop 1 of EeGUS swapped into BpGUS) has a broader optimum pH range (pH 5.5-8.0) than either the BpGUS parental enzyme (pH 7.0-7.5) or the EeGUS parental enzyme (pH 5.0-6.5). Moreover, the EeChimera4 chimera (composed of the 10 amino acid Loop 1 of BpGUS swapped into EeGUS) has a broader pH range at the lower end of the pH spectrum (pH 4.5-6.5) than either the BpGUS parental enzyme (pH 7.0-7.5) or the EeGUS parental enzyme (pH 5.0-6.5).

Figure 10:
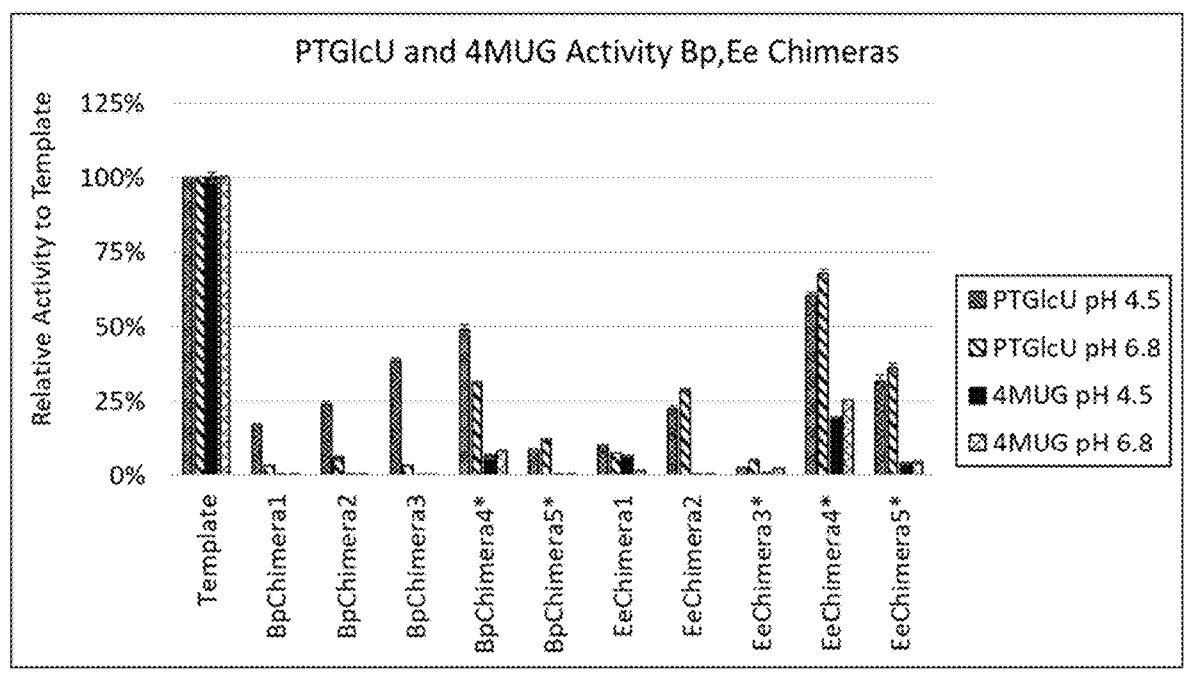
FIG. 10 is a bar graph showing the enzymatic activity of the BpGUS and EeGUS chimeric enzymes on the PTGlcU and 4MUG substrates. The asterisk (*) on certain chimeras indicates the reactions were performed at pH 5.5 and 7.0 for both substrates.

Additionally, the enzymatic activity of the panel of chimeras was tested using two different substrates, phenolphthalein-β-D-glucuronide (PTGlcU) and 4-methylumbelliferyl-β-D-glucuronide (4MUG), as described in Example 3. The results are shown in FIG. 10, which demonstrates that the chimeric enzymes did not exhibit enhanced activity against PTGlcU or 4MUG as compared to the parental enzymes (referred to as Template in FIG. 10).

Figure 11:
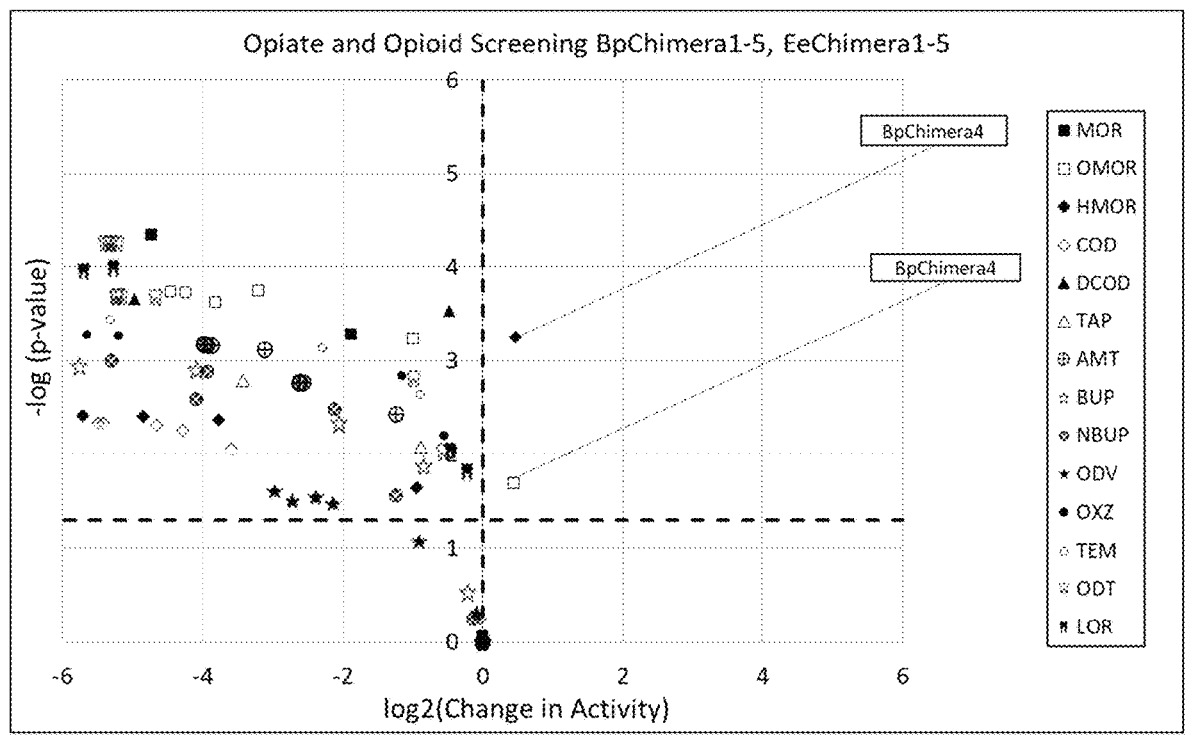
FIG. 11 is a graph showing the significant enzymatic activity of the BpChimera1-5 and EeChimera1-5 chimeric enzymes on a panel of opiate and opioid substrates.

The enzymatic activity of the panel of chimeras also was tested using a panel of opiate and opioid substrates, as described in Example 4. The results for the panel of opiates/opioids are shown in FIG. 11. The results in FIG. 11 demonstrate that the BpChimera4 chimera exhibited enhanced enzymatic activity against the HMOR and OMOR substrates as compared to the parental (template) enzymes.

In summary, this example demonstrates chimeric enzymes comprising various swaps of the C-Loop and Loop 1 domain from two different BGUS parental enzymes that exhibited an increased effective pH range and/or increased enzymatic activity against a substrate as compared to either or both of the parental enzymes from which the chimera was derived.

Example 7: Mutagenesis of Key Residues in BGUS

In this example, key residues within various BGUS enzymes were selected for site-saturation mutagenesis. This is a method whereby all possible amino acid substitutions are made at a single residue site using degenerate oligonucleotides. Oligonucleotides were designed so that only one codon was used for each possible amino acid (Pines et al. (2014) *ACS Synth. Bio.* 4:604-614). Variants were produced from the following templates (i.e., parental enzymes) at the residues indicated: AoGUS (G560); AtGUS (G562); Rxn3 (G560, Y447, G448, D449); BpGUS (G563, F294, T295, I450, Q451, A452); EeGUS (5571, F303, K304, V459, Q460, G461). These key residue positions for mutagenesis are highlighted as Variant Sites 1, 2 and 3 in the alignment of 15 BGUS enzymes shown in FIG. 1.

In addition, key residues in EeGUS were mutated to cysteine in an effort to improve enzyme function and stability: Q8C, S73C, Q8C/S73C, L53C, K326C, L53C/K326C, H526C, K588C, H526C/K588C, P489C, Q570C, P489C/Q570C.

Over 90 clones from each site-saturation mutagenesis library of each key residue were screened for activity to ensure that every possible amino acid was tested at each site. At this level of coverage, statistical calculations predict a >99% chance that each amino acid would be screened at least once. Active clones were selected by in vivo assay using the fluorescent substrates 4-methylumbelliferyl-β-D-glucuronide (4MUG) or fluorescein-di-β-D-glucuronide (FDGlcU). This assay was performed by growing the clones for about 16 hours at 37° C. in a 96-well plate where each well contains the appropriate anti-biotic and 150 µL of LB with shaking at 300 RPM. Next, 150 µL of media containing IPTG (0.2 mM), glucose (1.2%), and glycerol (0.8%) was added to the 96-well plate and the cells incubated for 3-4 hours at 37° C. and 300 RPM. After expression induction, the optical density ($OD_{600}$) of the cells was determined by measuring the absorbance at 600 nm. The activity assay was performed by mixing 25 µL of cells with 25 µL of substrate, incubating the reactions at room temperature for 5 minutes, then stopping the reactions with the addition of 150 µL 0.2 M glycine, pH 10.4. The stock concentration of 4MUG was 1.0 mM in 10% EtOH with either 100 mM potassium acetate (pH 4.5) or potassium phosphate (pH 6.8), and the stock 5 concentration of FDGlcU was 170 µM in 5% MeOH with either 100 mM potassium acetate (pH 4.5) or potassium phosphate (pH 6.8). The pH of the buffer used was chosen based on the pH optimum of the variant template. The product of 4MUG was measured by excitation at 365 nm and emission at 445 nm, and the product of FDGlcU was measured by excitation at 490 nm and emission at 514 nm. Activity was calculated as arbitrary fluorescent units (AFU) per minute per OD. The 10 most active variants were selected for plasmid isolation and DNA sequencing.

Example 8: Point Mutation at Residue Position Corresponding to BpF294

Figure 12:
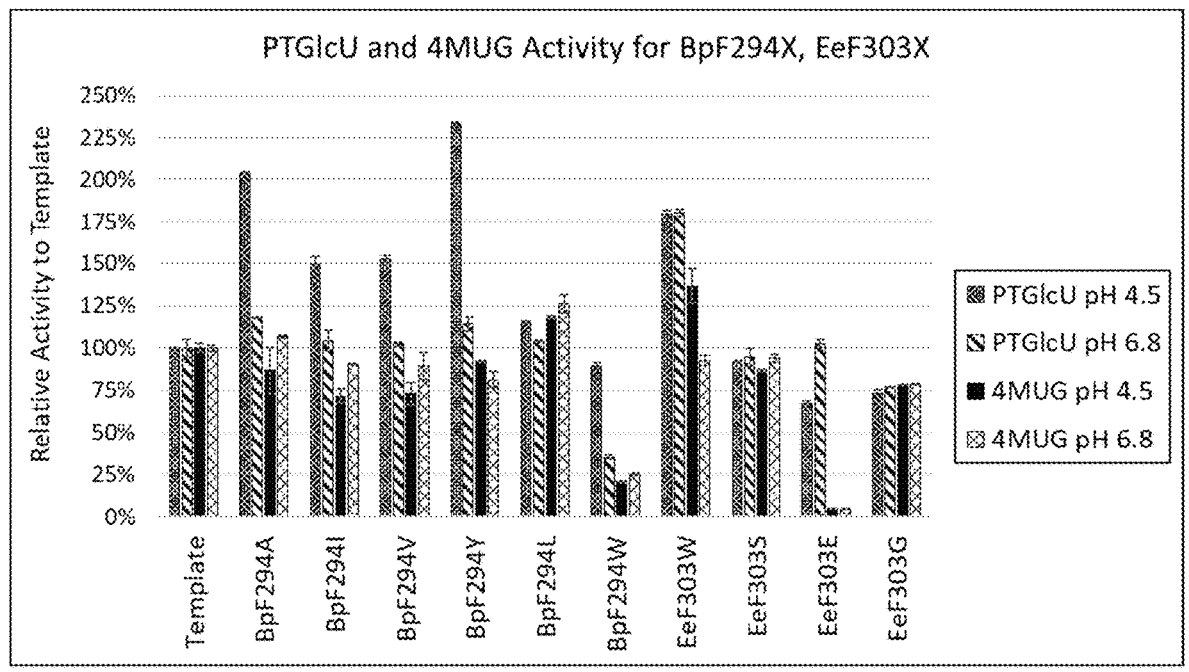
FIG. 12 is a bar graph showing the enzymatic activity of the BpF294X and EeF303X variant enzymes on the PTGlcU and 4MUG substrates.
Figure 13:
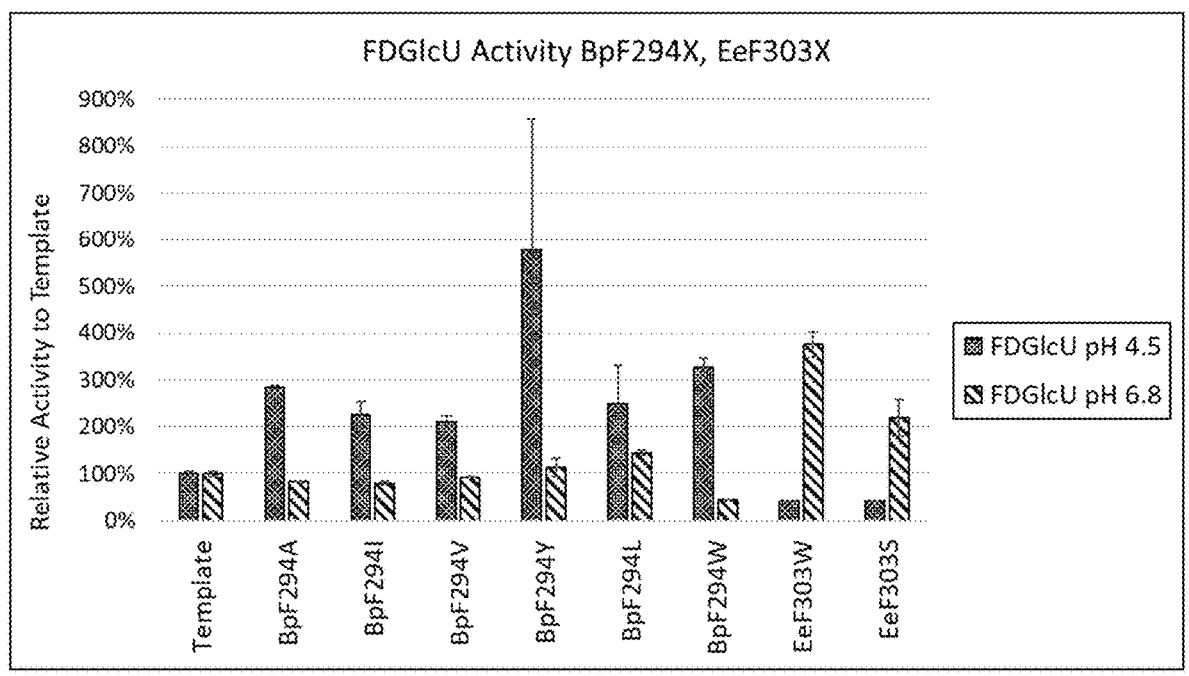
FIG. 13 is a bar graph showing the enzymatic activity of the BpF294X and EeF303X variant enzymes on the FDGlcU substrate.
Figure 14:
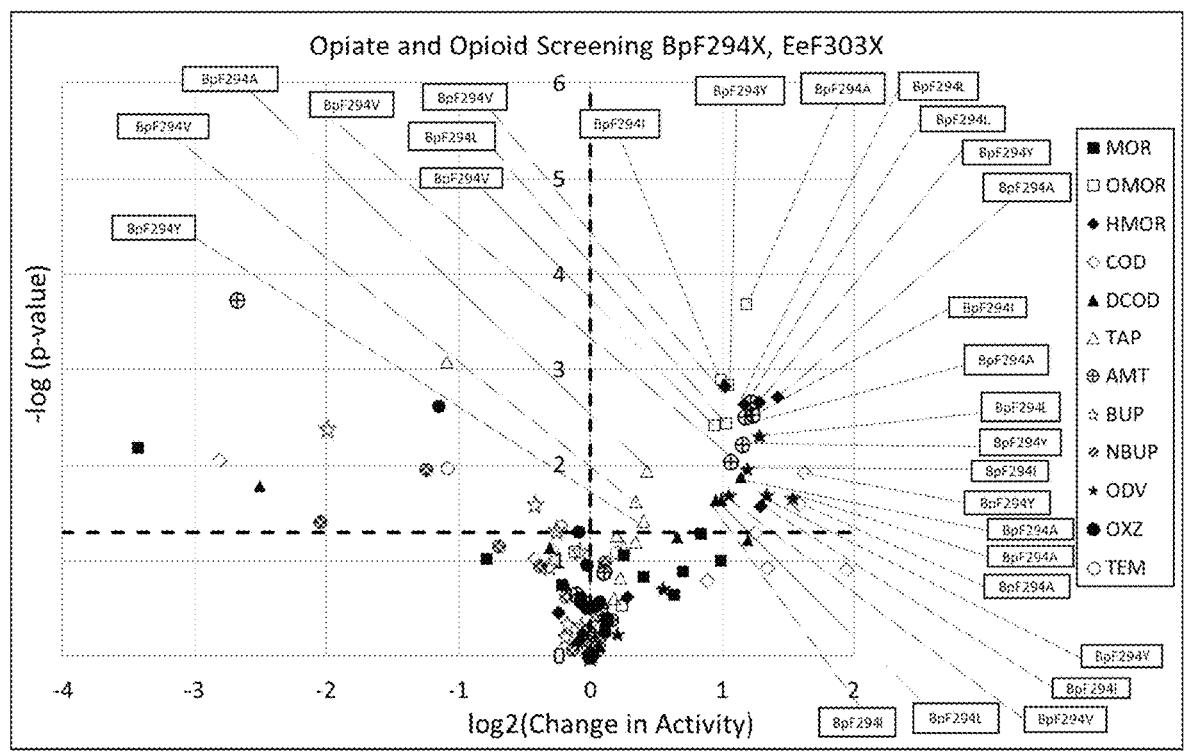
FIG. 14 is a graph showing the significant enzymatic activity of the BpF294X and EeF303X variant enzymes on a panel of opiate and opioid substrates.

In this example, the first amino acid residue within Variant Site 1 shown in FIG. 1 was mutated and the enzymatic activity of the variants tested on a panel of substrates. This residue corresponds to positions BpF294 and EeF303. Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 12. The results for the FDGlcU substrate, as compared to template, are shown in FIG. 13. The results for a panel of opiates and opioids are shown in FIG. 14. In FIG. 14, variants indicated in the upper right quadrant of the graph exhibited increased activity as compared to template.

In summary, the results from FIGS. 12-14 demonstrate that the following BpGUS single point variants exhibited enhanced enzymatic activity against at least one, and often multiple, substrates as compared to the template from which the variant was derived: BpF294A, BpF294I, BpF294V, BpF294Y, BpF294L and BpF294W, the amino acid sequences of which are shown in SEQ ID NOs: 47-52, respectively.

In summary, the results from FIGS. 12-14 demonstrate that the following EeGUS single point variants exhibited enhanced enzymatic activity against at least one, and often multiple, substrates as compared to the template from which the variant was derived: EeF303W and EeF303S, the amino acid sequences of which are shown in SEQ ID NOs: 53 and 54, respectively.

Example 9: Point Mutation at Residue Position Corresponding to BpT295

Figure 15:
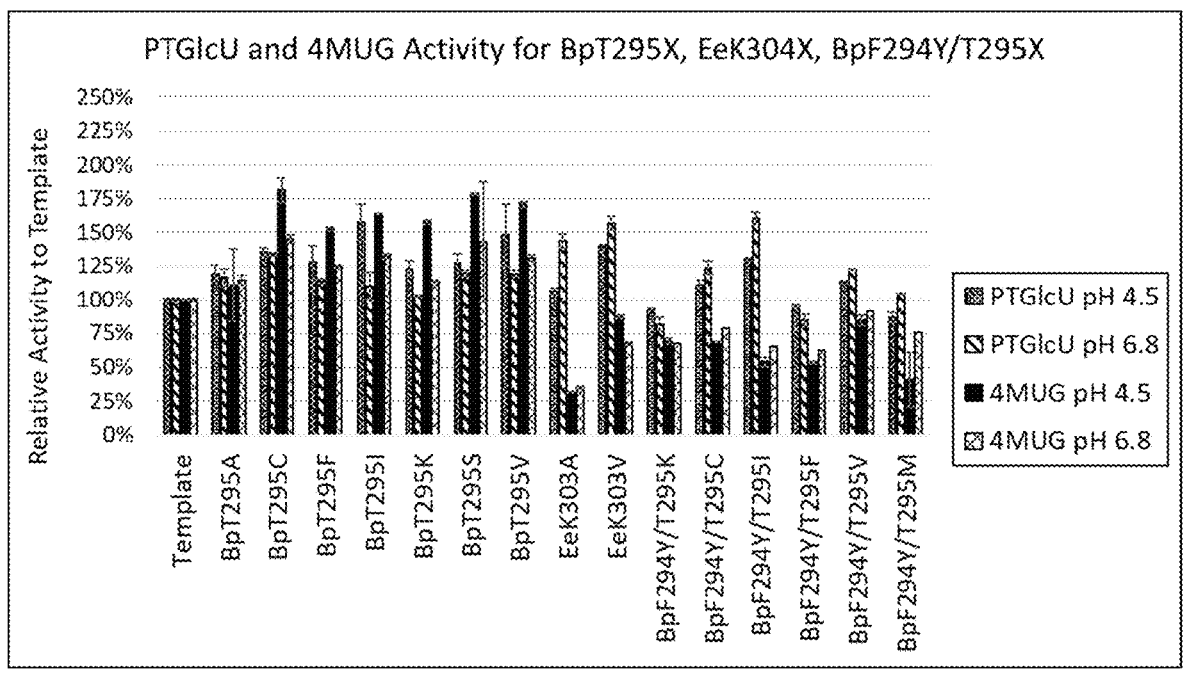
FIG. 15 is a bar graph showing the enzymatic activity of the BpT295X. EeK304X and BpF294Y/T295X variant enzymes on the PTGlcU and 4MUG substrates.
Figure 16:
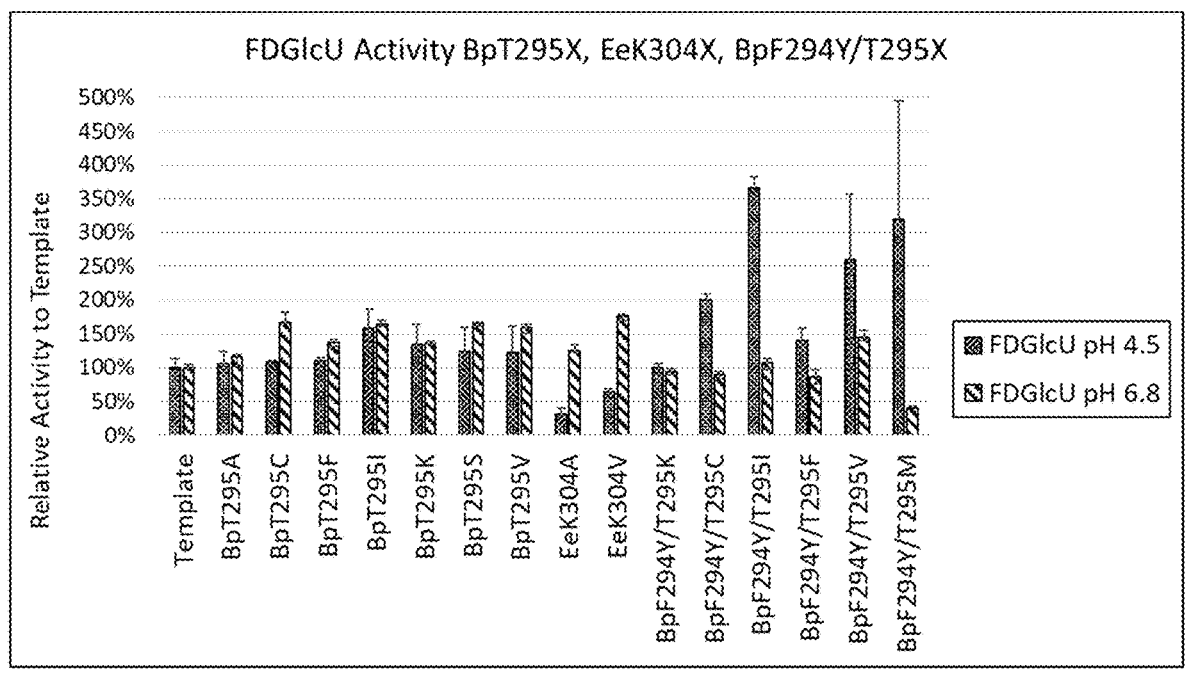
FIG. 16 is a bar graph showing the enzymatic activity of the BpT295X. EeK304X and BpF294Y/T295X variant enzymes on the FDGlcU substrate.
Figure 17:
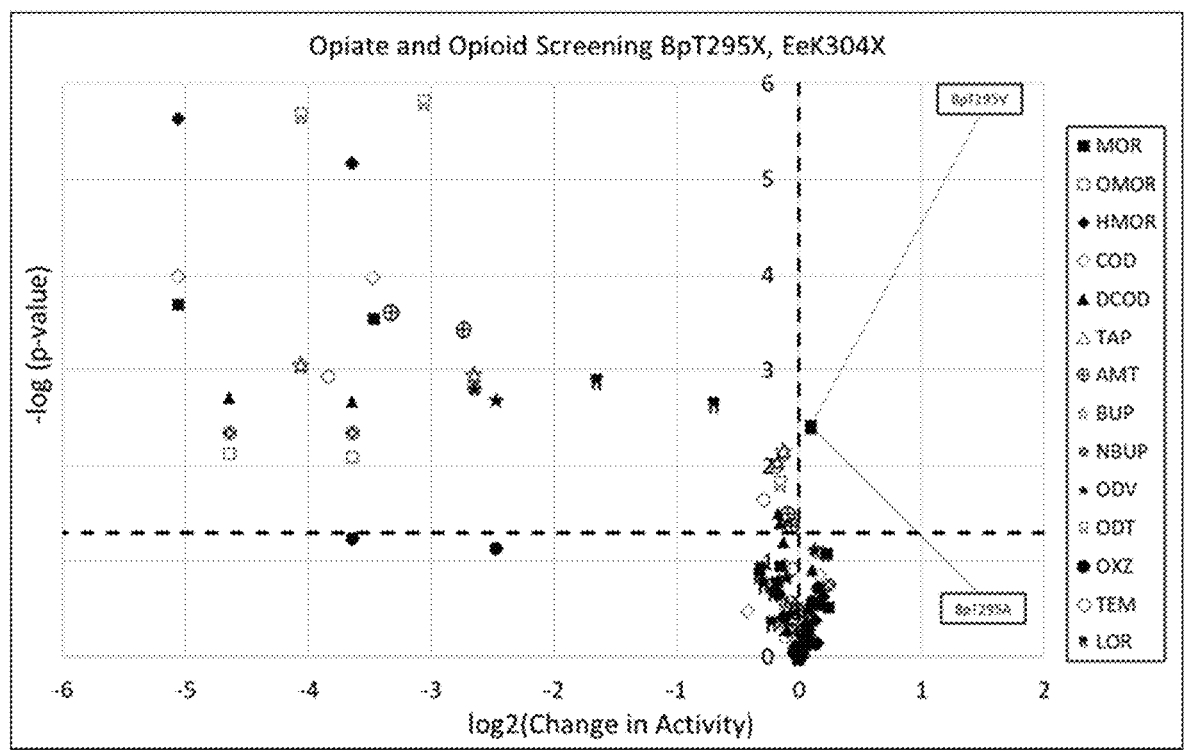
FIG. 17 is a graph showing the significant enzymatic activity of the BpT295X and EeK304X variant enzymes on a panel of opiate and opioid substrates.

In this example, the second amino acid residue within Variant Site 1 shown in FIG. 1 was mutated and the enzymatic activity of the variants tested on a panel of substrates. This residue corresponds to positions BpT295 and EeK304. Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 15. The results for the FDGlcU substrate, as compared to template, are shown in FIG. 16. The results for a panel of opiates and opioids are shown in FIG. 17. In FIG. 17, variants indicated in the upper right quadrant of the graph exhibited increased activity as compared to template.

In summary, the results from FIGS. 15-17 demonstrate that the following BpGUS single point variants exhibited enhanced enzymatic activity against at least one, and often multiple, substrates as compared to the template from which the variant was derived: BpT295A, BpT295C, BpT295F, BpT295I, BpT295K, BpT295S and BpT295V, the amino acid sequences of which are shown in SEQ ID NOs: 55-61, respectively.

In summary, the results from FIGS. 15-17 demonstrate that the following EeGUS single point variants exhibited enhanced enzymatic activity against at least one, and often multiple, substrates as compared to the template from which the variant was derived: EeK304A and EeK304V, the amino acid sequences of which are shown in SEQ ID NOs: 62 and 63, respectively.

Example 10: Point Mutation at Residue Position Corresponding to BpI450

Figure 18:
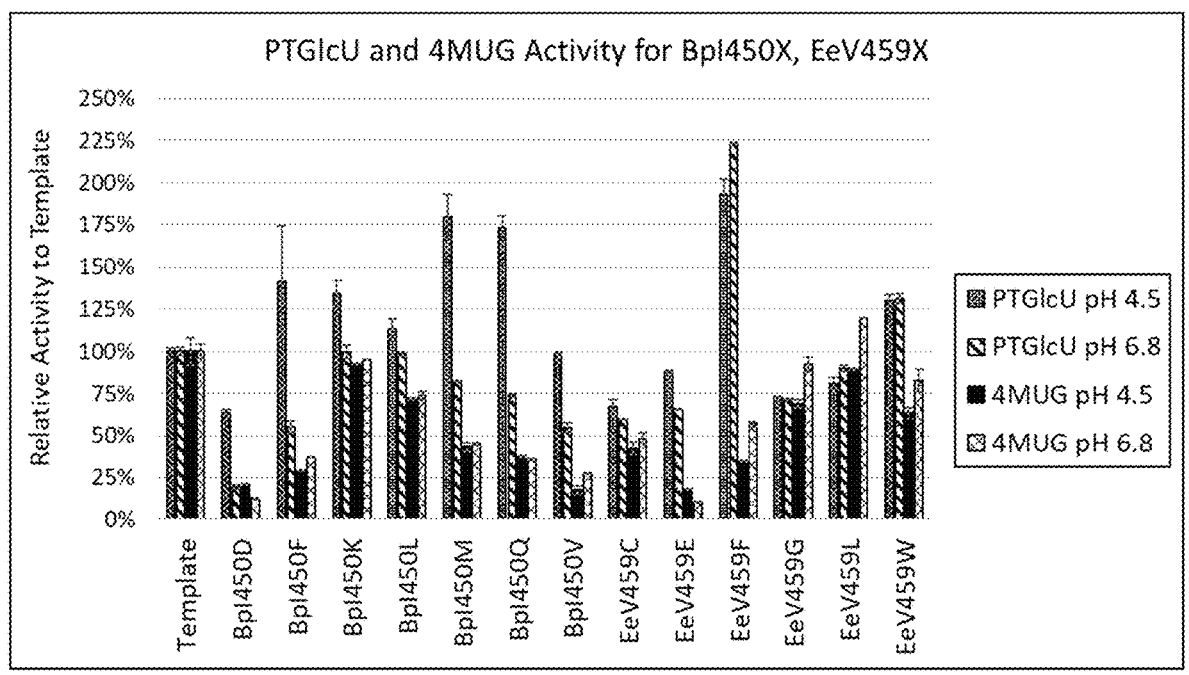
FIG. 18 is a bar graph showing the enzymatic activity of the BpI450X and EeV459X variant enzymes on the PTGlcU and 4MUG substrates.
Figure 19:
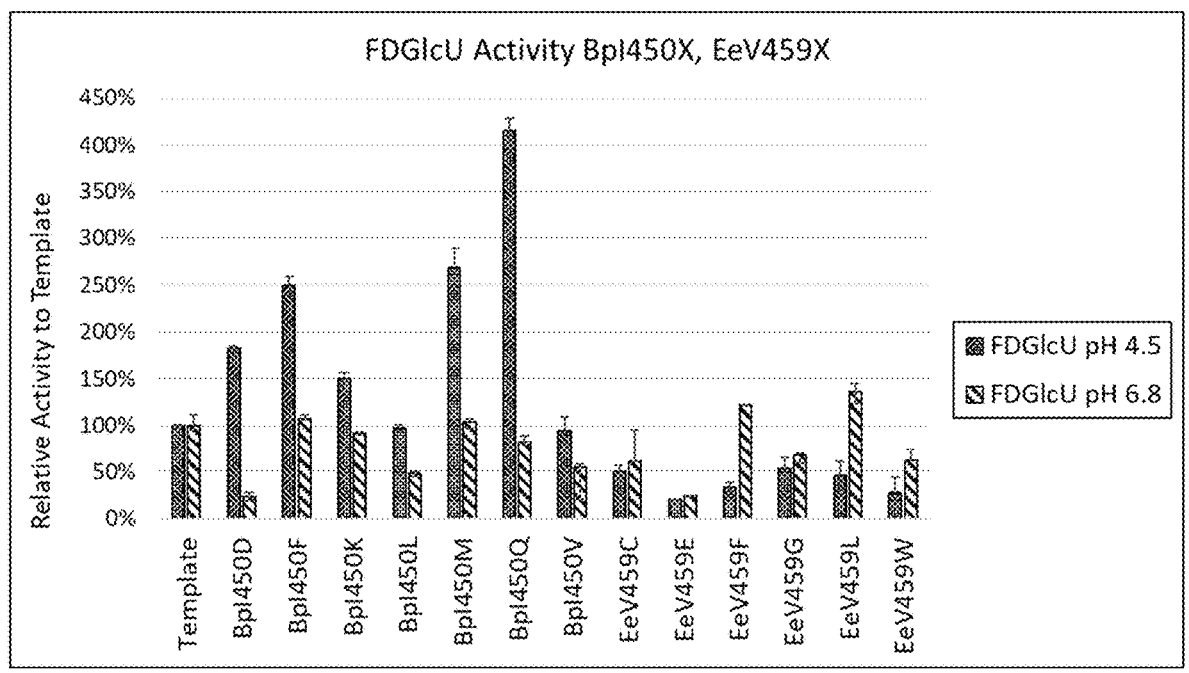
FIG. 19 is a bar graph showing the enzymatic activity of the BpI450X and EeV459X variant enzymes on the FDGlcU substrate.
Figure 20:
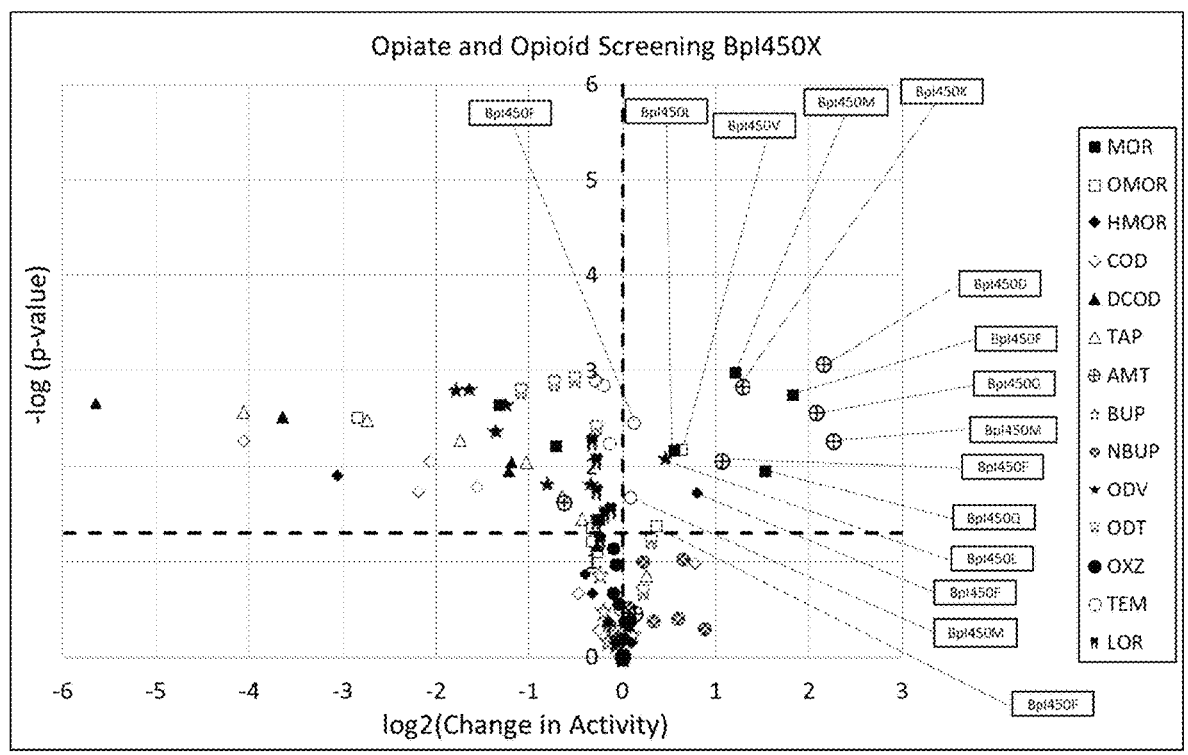
FIG. 20 is a graph showing the significant enzymatic activity of the BpI450X variant enzymes on a panel of opiate and opioid substrates.
Figure 21:
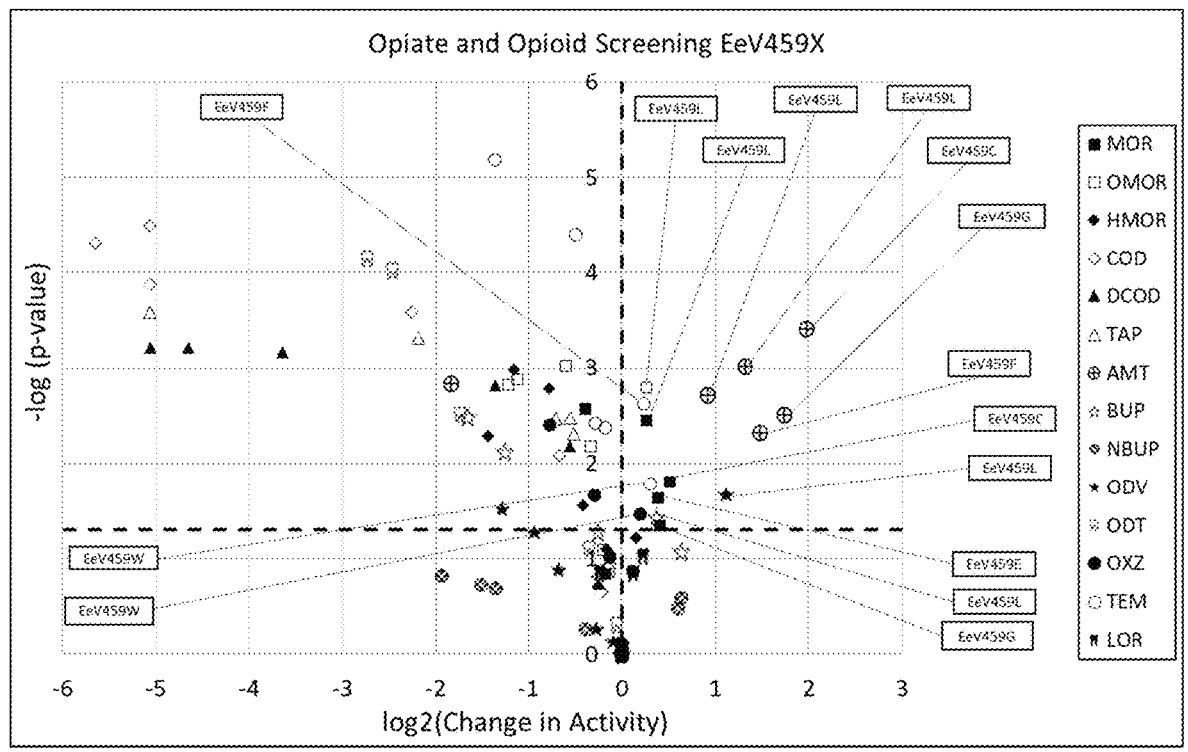
FIG. 21 is a graph showing the significant enzymatic activity of the EeV459X variant enzymes on a panel of opiate and opioid substrates.

In this example, the first amino acid residue within Variant Site 2 shown in FIG. 1 was mutated and the enzymatic activity of the variants tested on a panel of substrates. This residue corresponds to positions BpI450, EeV459, and Rxn3Y447. Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 18 for BpI450 and EeV459, and FIGS. 35 and 36 for Rxn3Y447. The results for the FDGlcU substrate, as compared to template, are shown in FIG. 19 for BpI450 and EeV459. The results for the BpI450 variants on a panel of opiates and opioids are shown in FIG. 20. The results for the EeV459 variants on a panel of opiates and opioids are shown in FIG. 21. The results for the Rxn3Y447 variants on a panel of opiates and opioids are shown in FIG. 37. In FIGS. 20, 21 and 37, variants indicated in the upper right quadrant of the graph exhibited increased activity as compared to template.

In summary, the results from FIGS. 18-20 demonstrate that the following BpGUS single point variants exhibited enhanced enzymatic activity against at least one, and often multiple, substrates as compared to the template from which the variant was derived: BpI450F, BpI450K, BpI450L, BpI450M, BpI450Q, BpI450D and BPI450V, the amino acid sequences of which are shown in SEQ ID NOs: 64-70, respectively.

In summary, the results from FIGS. 18, 19 and 21 demonstrate that the following EeGUS single point variants exhibited enhanced enzymatic activity against at least one, and often multiple, substrates as compared to the template from which the variant was derived: EeV459F, EeV459L, EeV459W, EeV459C, EeV459G and EeV459E, the amino acid sequences of which are shown in SEQ ID NOs: 71-76, respectively.

Figure 35:
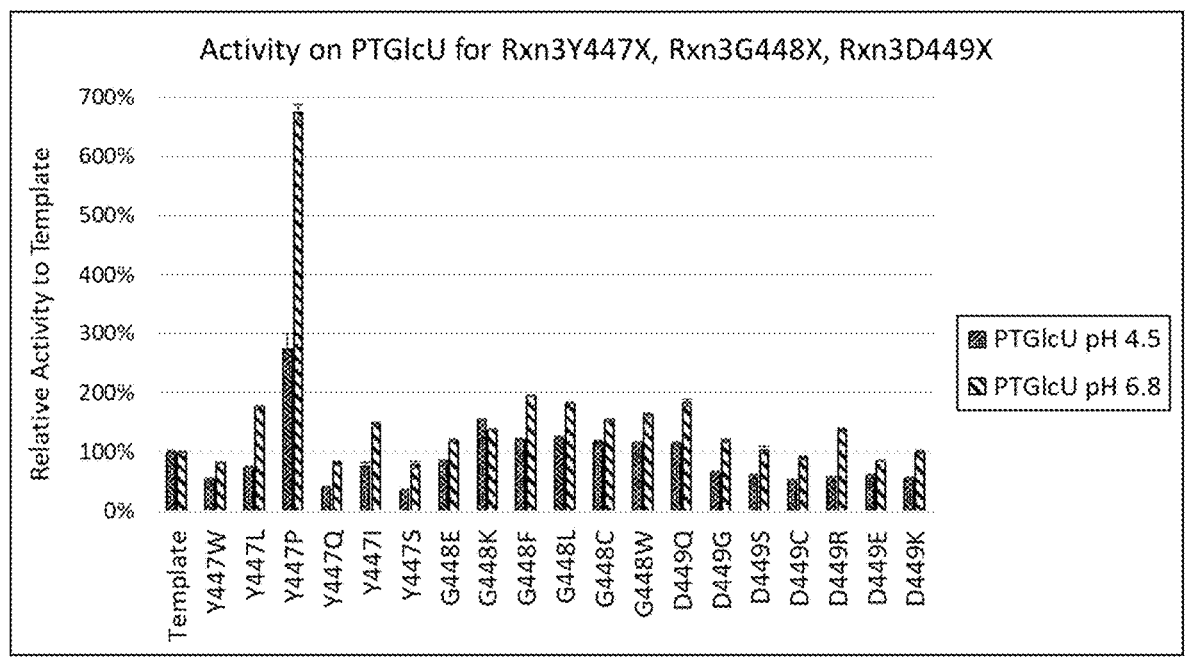
FIG. 35 is a bar graph showing the enzymatic activity of Rxn3Y447X. Rxn3G448X and Rxn3D449X variant enzymes on the PTGlcU substrate.
Figure 36:
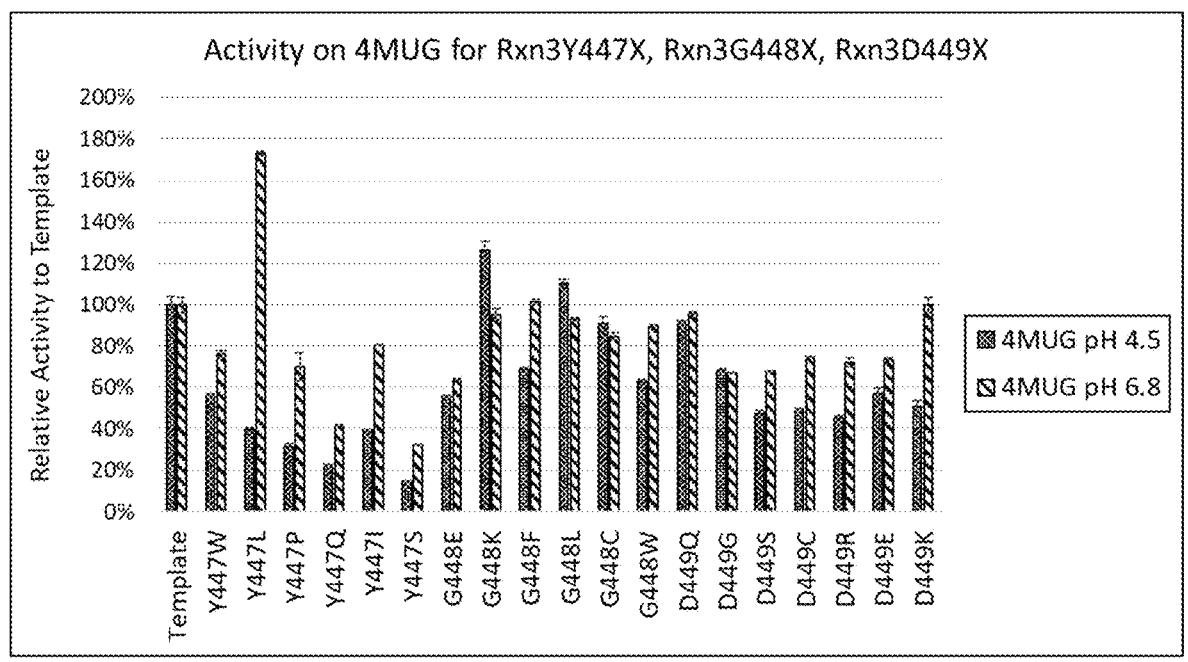
FIG. 36 is a bar graph showing the enzymatic activity of Rxn3Y447X. Rxn3G448X and Rxn3D449X variant enzymes on the 4MUG substrate.
Figure 37:
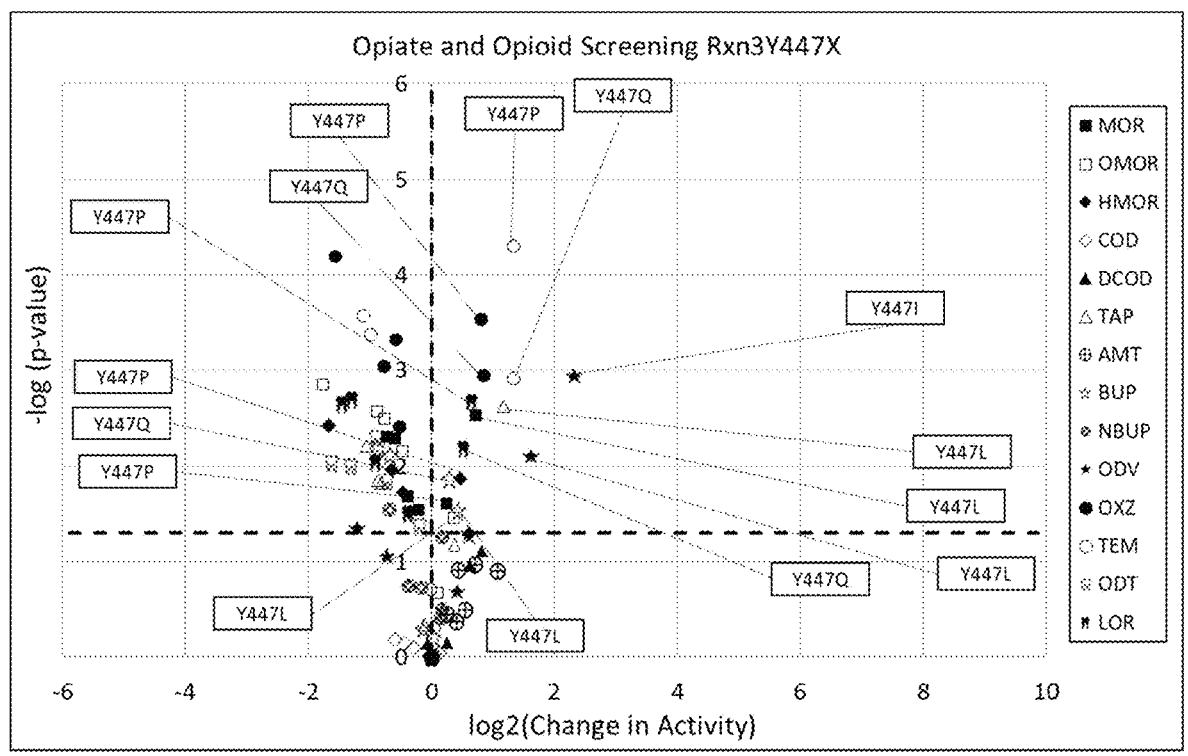
FIG. 37 is a graph showing the enzymatic activity of the Rxn3Y447X variant enzymes on a panel of opiate and opioid substrates.

In summary, the results from FIGS. 35, 36 and 37 demonstrate that the following Rxn3 single point variants exhibited enhanced enzymatic activity against at least one, and often multiple, substrates as compared to the template from which the variant was derived: Rxn3Y447L, Rxn3Y447P, Rxn3Y447I and Rxn3Y447Q, the amino acid sequences of which are shown in SEQ ID NOs: 121-124, respectively.

Example 11: Point Mutation at Residue Position Corresponding to BpQ451

Figure 22:
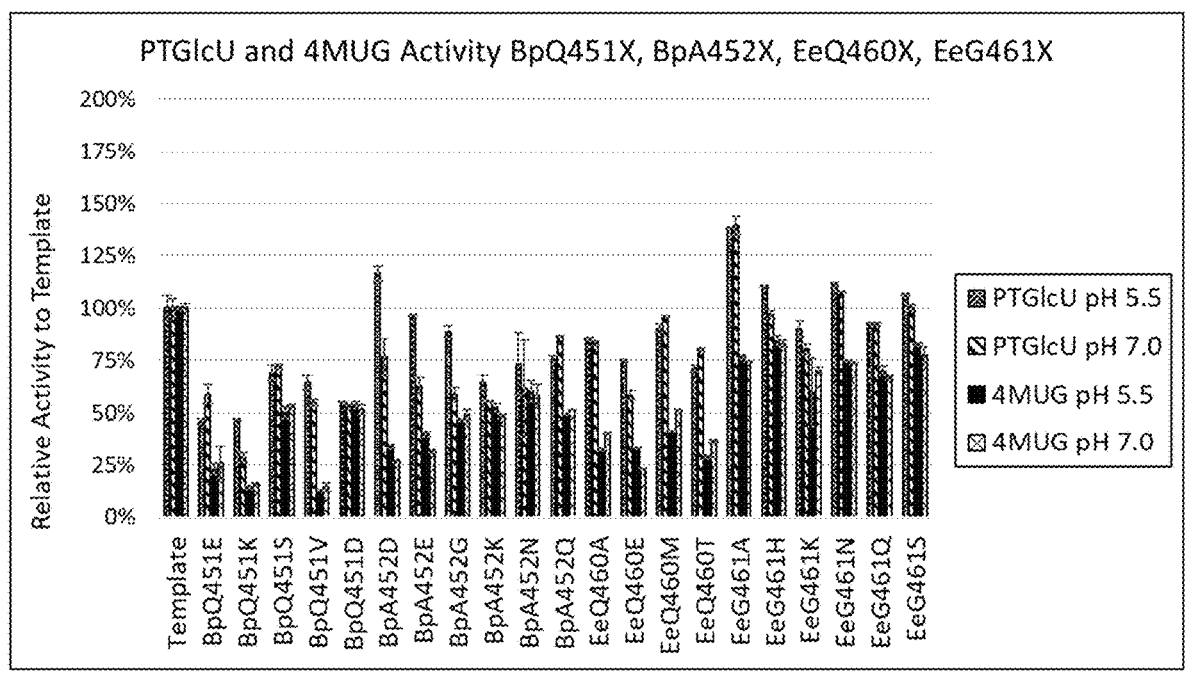
FIG. 22 is a bar graph showing the enzymatic activity of the BpQ451X, BpA452X. EeQ460X and EeG461X significant enzymes on the PTGlcU and 4MUG substrates.
Figure 23:
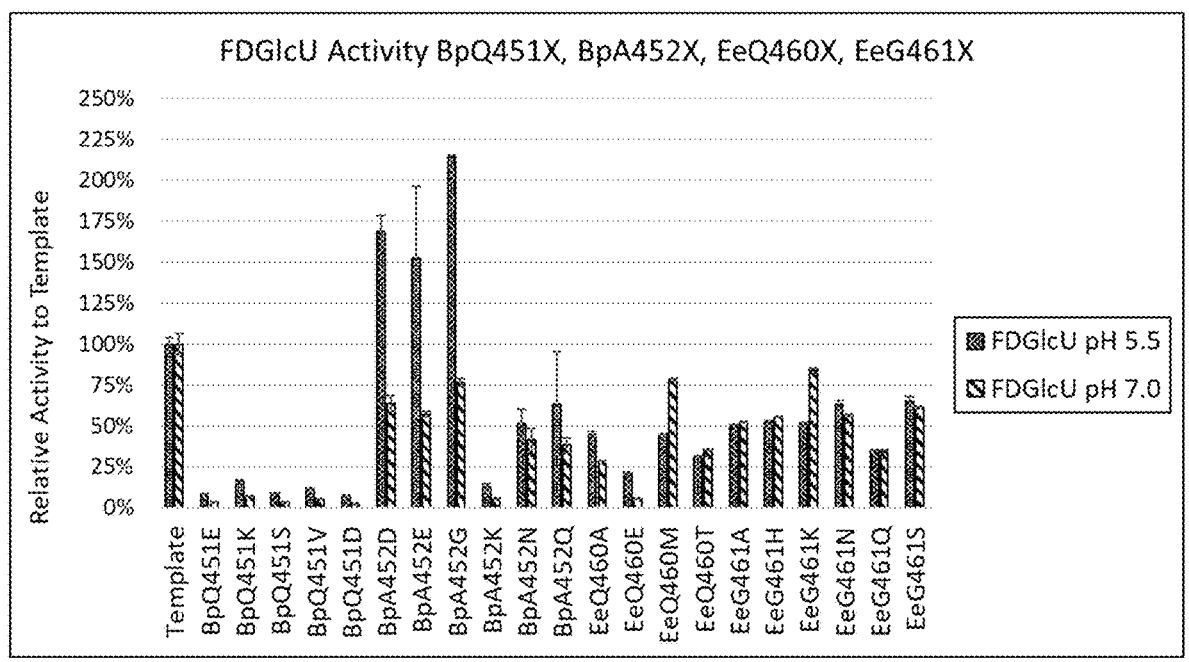
FIG. 23 is a bar graph showing the enzymatic activity of the BpQ451X. BpA452X, EeQ460X and EeG461X variant enzymes on the FDGlcU substrate.
Figure 24:
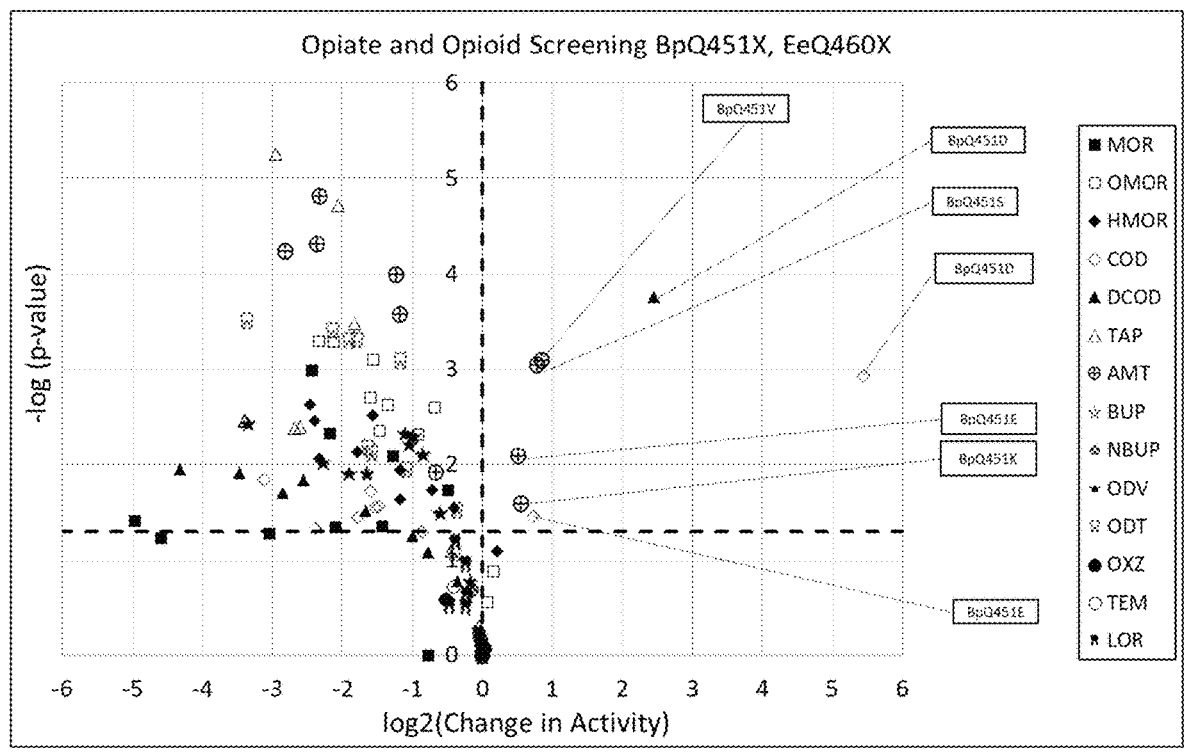
FIG. 24 is a graph showing the significant enzymatic activity of the BpQ451X and EeQ460X variant enzymes on a panel of opiate and opioid substrates.
Figure 38:
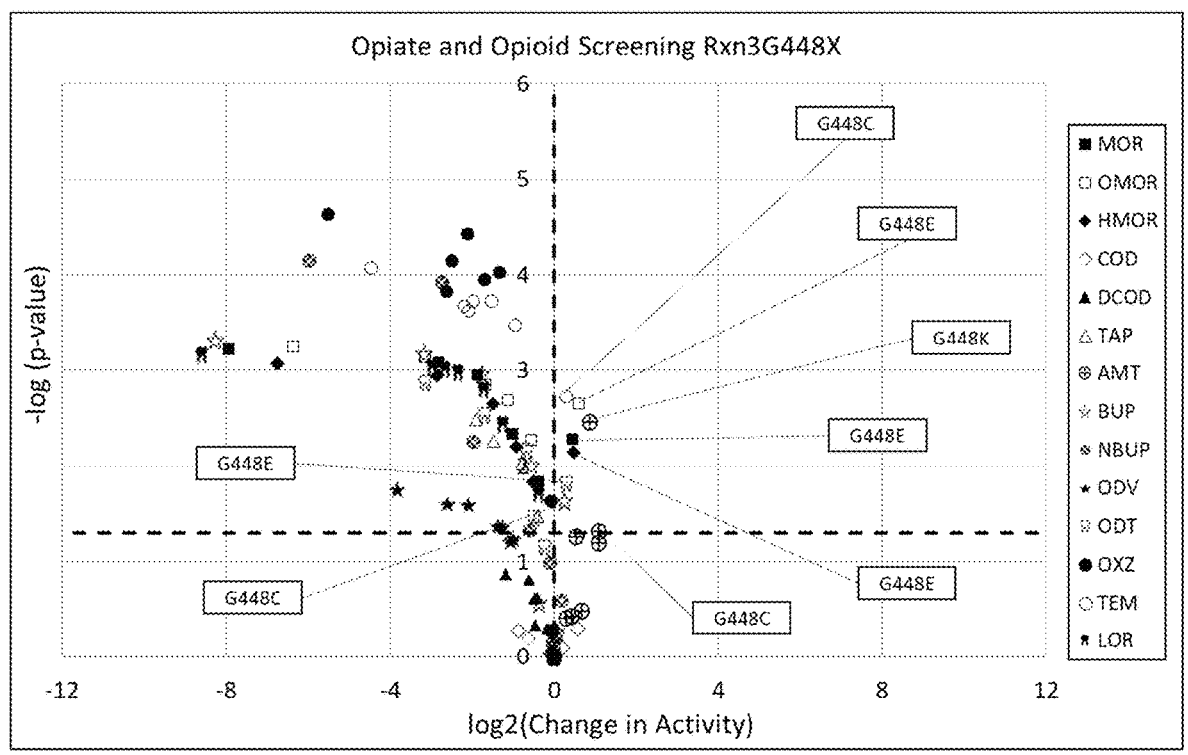
FIG. 38 is a graph showing the enzymatic activity of the Rxn3G448X variant enzymes on a panel of opiate and opioid substrates.

In this example, the second amino acid residue within Variant Site 2 shown in FIG. 1 was mutated and the enzymatic activity of the variants tested on a panel of substrates. This residue corresponds to positions BpQ451, EeQ460 and Rxn3G448. Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 22 for BpQ451 and EeQ460, and FIGS. 35 and 36 for Rxn3G448. The results for the FDGlcU substrate, as compared to template, are shown in FIG. 23 for BpQ451 and EeQ460. The results for BpQ451 and EeQ460 variants on a panel of opiates and opioids are shown in FIG. 24. The results for the Rxn3G448 variants on a panel of opiates and opioids are shown in FIG. 38. In FIGS. 24 and 38, variants indicated in the upper right quadrant of the graph exhibited increased activity as compared to template.

In summary, the results from FIGS. 22-24 demonstrate that the following BpGUS single point variants exhibited enhanced enzymatic activity against at least one, and often multiple, substrates as compared to the template from which the variant was derived: BpQ451D, BpQ451E, BpQ451G, BpQ451S, BpQ451V and BpQ451K, the amino acid sequences of which are shown in SEQ ID NOs: 77-82, respectively. Moreover, the data shown in FIG. 24 demonstrates that the BpQ451D showed exceptionally high enzymatic activity against the codeine-6-β-D-glucuronide (COD) substrate as compared to the parental BpGUS enzyme.

In summary, the results from FIGS. 35, 36 and 38 demonstrate that the following Rxn3 single point variants exhibited enhanced enzymatic activity against at least one, and often multiple, substrates as compared to the template from which the variant was derived: Rxn3G448E, Rxn3G448K, Rxn3G448F, Rxn3G448L, Rxn3G448C and Rxn3G448W, the amino acid sequences of which are shown in SEQ ID NOs: 125-130, respectively.

Example 12: Point Mutation at Residue Position Corresponding to BpA452

Figure 25:
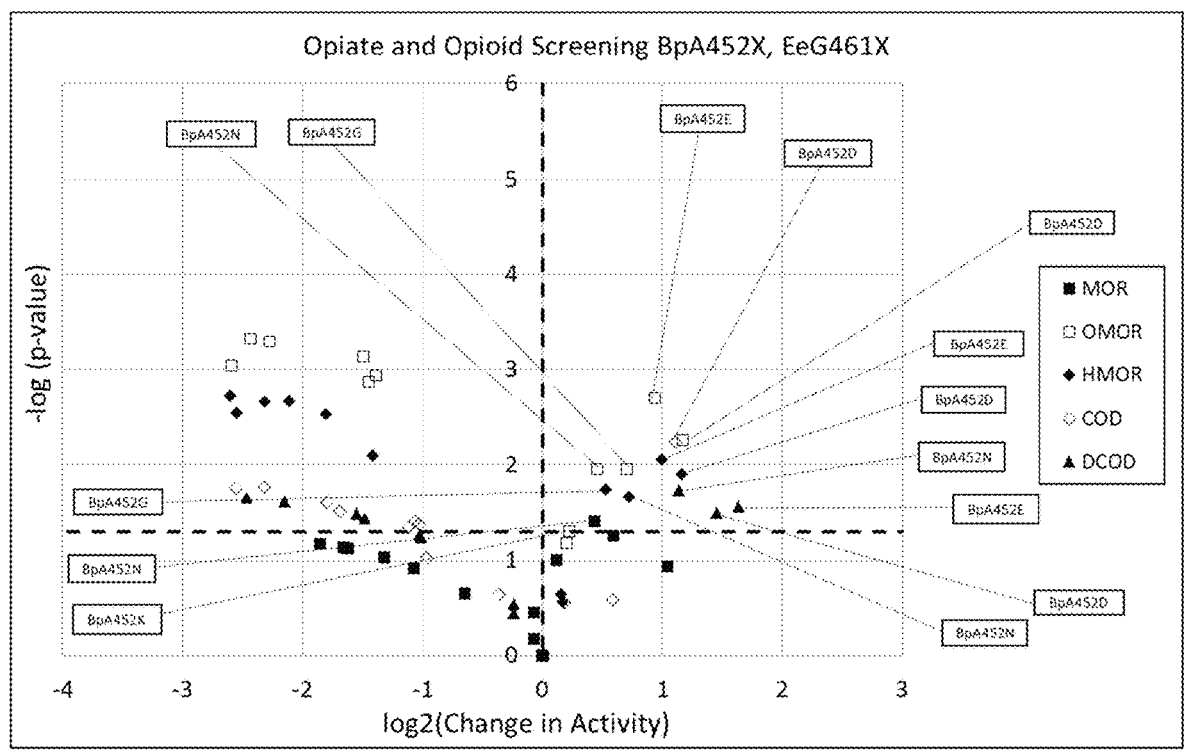
FIG. 25 is a graph showing the significant enzymatic activity of the BpA452X and EeG461X variant enzymes on a panel of opiate and opioid substrates.
Figure 26:
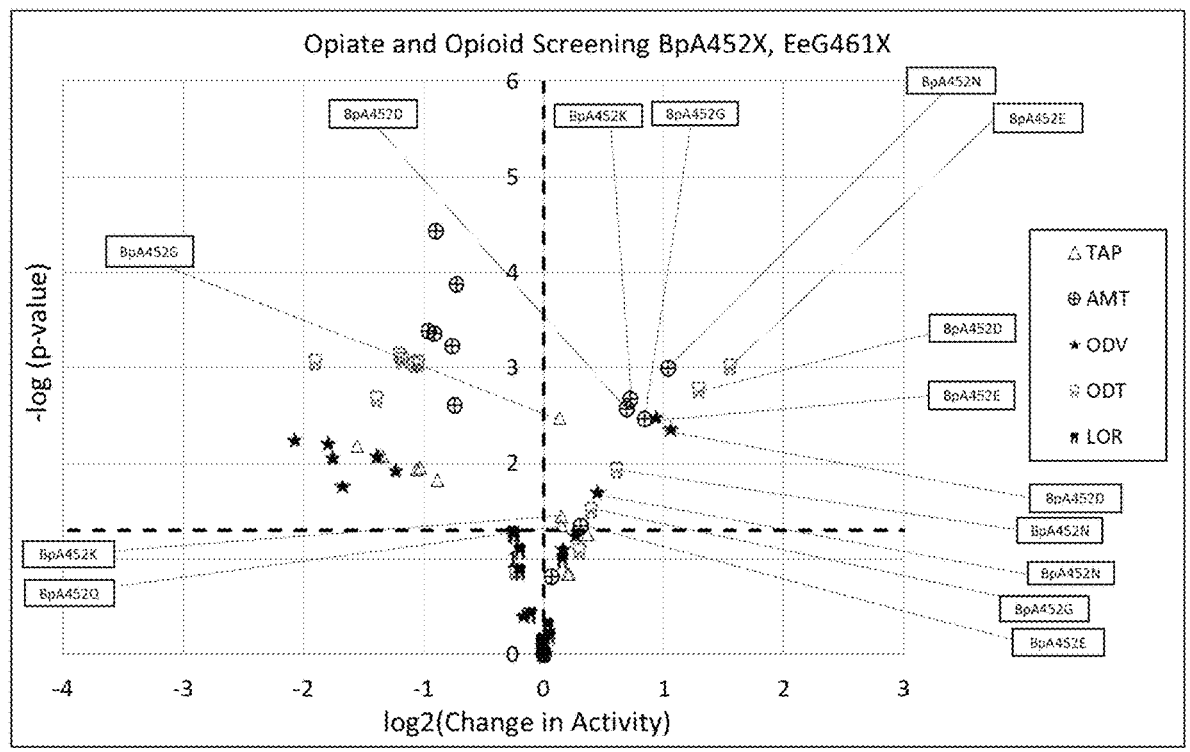
FIG. 26 is a bar graph showing the enzymatic activity of the BpA452X and EeG461X variant enzymes on a panel of opiate and opioid substrates.
Figure 39:
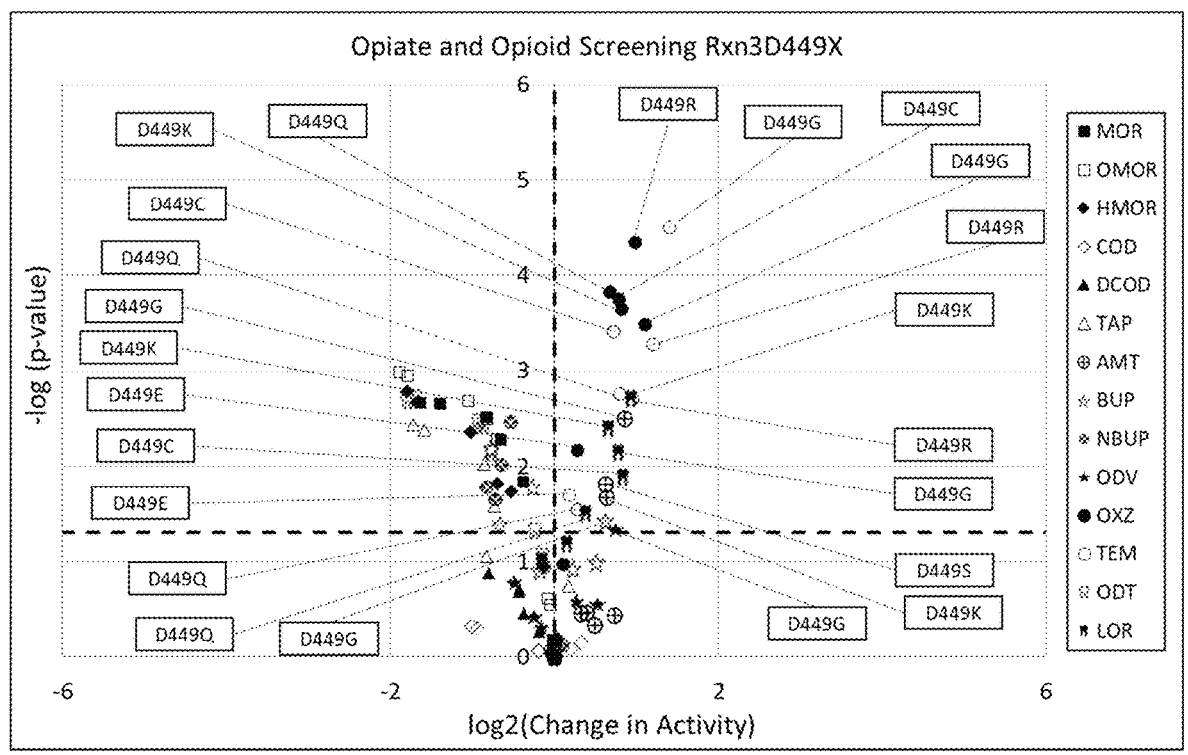
FIG. 39 is a graph showing the enzymatic activity of the Rxn3D449X variant enzymes on a panel of opiate and opioid substrates.

In this example, the third amino acid residue within Variant Site 2 shown in FIG. 1 was mutated and the enzymatic activity of the variants tested on a panel of substrates. This residue corresponds to positions BpA452, EeG461 and Rxn3D449. Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 22 for BpA452 and EeG461, and FIGS. 35 and 36 for Rxn3D449. The results for the FDGlcU substrate, as compared to template, are shown in FIG. 23 for BpA452 and EeG461. The results for these variants on two different panels of opiates and opioids are shown in FIGS. 25 and 26 for BpA452 and EeG461. The results for the Rxn3D449 variants on a panel of opiates and opioids are shown in FIG. 39. In FIGS. 25, 26 and 39, variants indicated in the upper right quadrant of the graph exhibited increased activity as compared to template.

In summary, the results from FIGS. 22, 23, 25 and 26 demonstrate that the following BpGUS single point variants exhibited enhanced enzymatic activity against at least one, and often multiple, substrates as compared to the template from which the variant was derived: BpA452D, BpA452K, BpA452N, BpA452G, BpA452E and BPA452Q, the amino acid sequences of which are shown in SEQ ID NOs: 83-88, respectively.

In summary, the results from FIGS. 22, 23, 25 and 26 demonstrate that the following EeGUS single point variants exhibited enhanced enzymatic activity against at least one, and often multiple, substrates as compared to the template from which the variant was derived: EeG461A, EeG461H, EeG461N and EeG461S, the amino acid sequences of which are shown in SEQ ID NOs: 89-92, respectively.

In summary, the results from FIGS. 35, 36 and 39 demonstrate that the following Rxn3 single point variants exhibited enhanced enzymatic activity against at least one, and often multiple, substrates as compared to the template from which the variant was derived: Rxn3D449Q, Rxn3D449G, Rxn3D449R, Rxn3D449K, Rxn3D449S, Rxn3D449C, and Rxn3D449E, the amino acid sequences of which are shown in SEQ ID NOs: 131-137, respectively.

Example 13: Point Mutation at Residue Position Corresponding to BpG563

Figure 27:
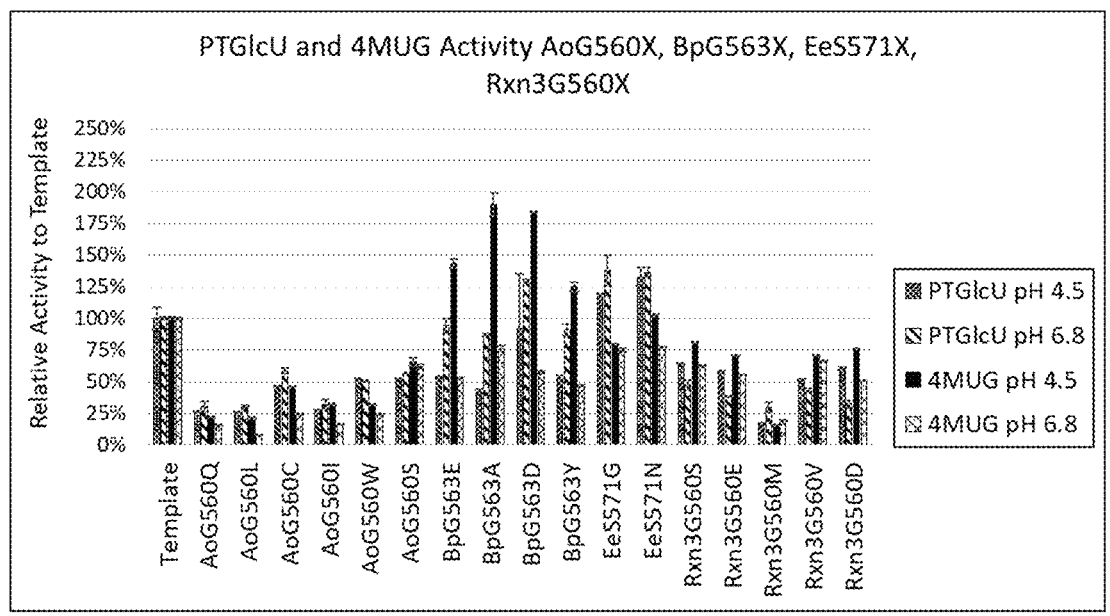
FIG. 27 is a bar graph showing the enzymatic activity of the AoG560X, BpG563X, EeS571X and Rxn3G560X variant enzymes on the PTGlcU and 4MUG substrates.
Figure 28:
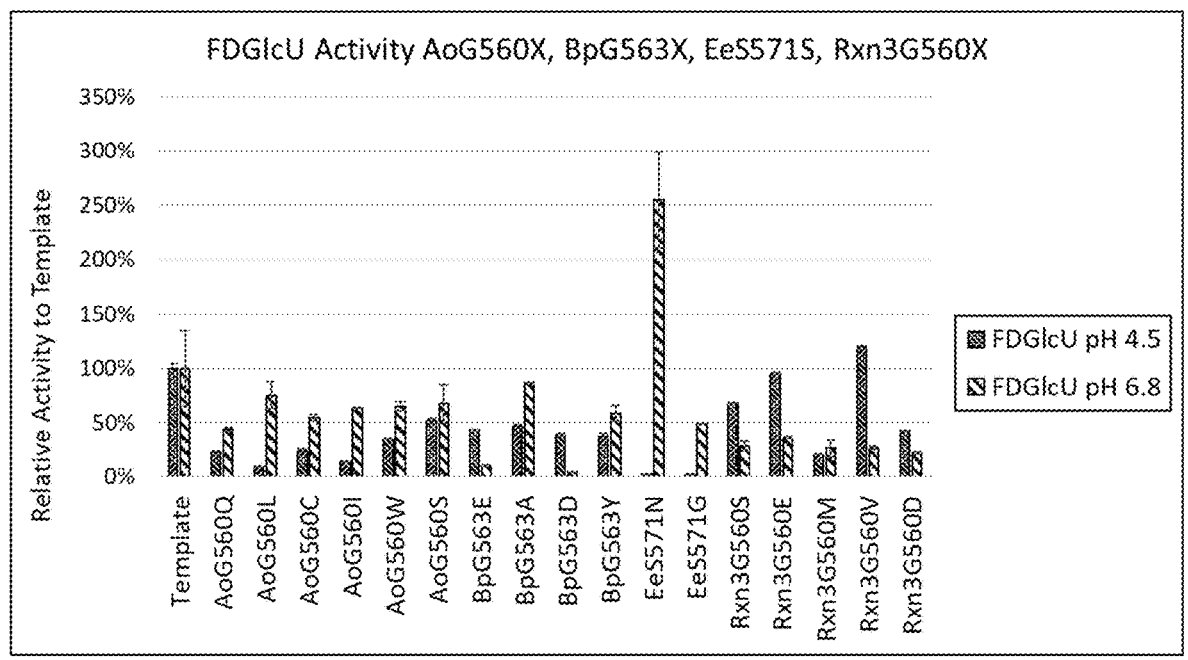
FIG. 28 is a bar graph showing the enzymatic activity of the AoG560X, BpG563X, EeS571X and Rxn3G560X variant enzymes on the FDGlcU substrate.
Figure 29:
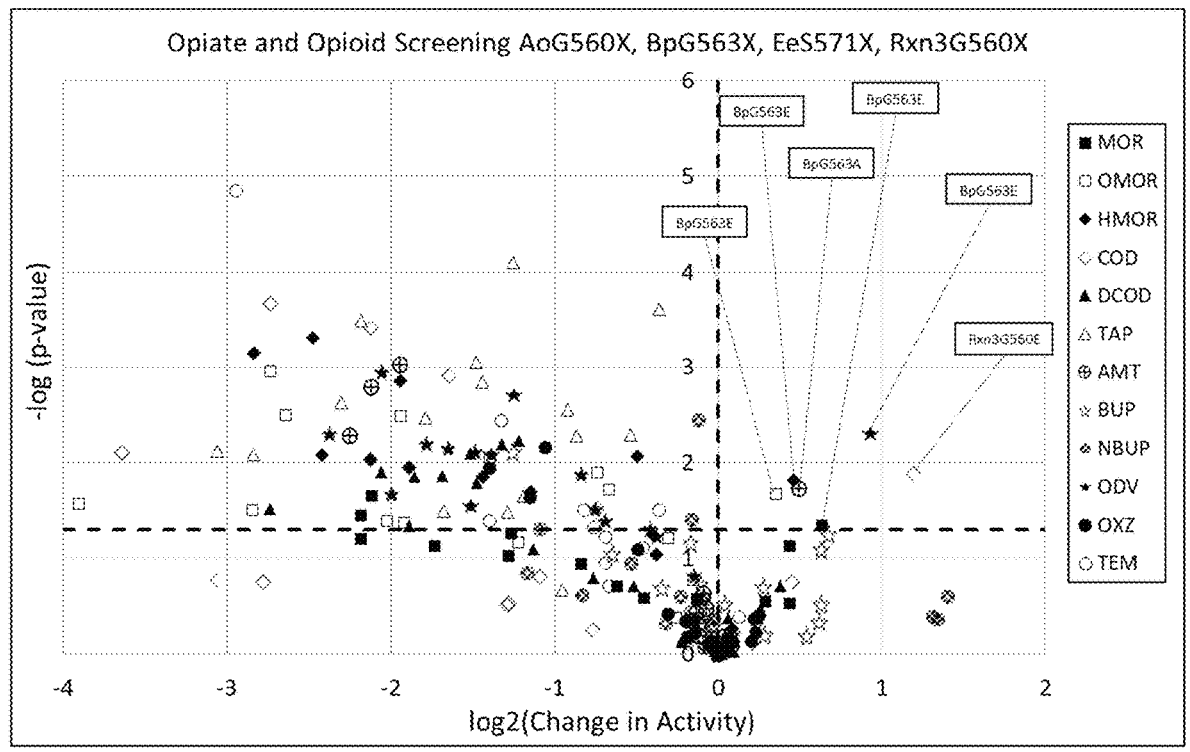
FIG. 29 is a graph showing the significant enzymatic activity of the AoG560X, BpG563X, EeS571X and Rxn3G560X variant enzymes on a panel of opiate and opioid substrates.

In this example, the amino acid residue at Variant Site 3 shown in FIG. 1 was mutated and the enzymatic activity of the variants tested on a panel of substrates. This residue corresponds to positions BpG563, EeS571, AoG560 and Rxn3G560. Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 27. The results for the FDGlcU substrate, as compared to template, are shown in FIG. 28. The results for these variants on a panel of opiates and opioids are shown in FIG. 29. In FIG. 29, variants indicated in the upper right quadrant of the graph exhibited increased activity as compared to template.

In summary, the results from FIGS. 27-29 demonstrate that the following BpGUS single point variants exhibited enhanced enzymatic activity against at least one, and often multiple, substrates as compared to the template from which the variant was derived: BpG563E, BpG563A, BpG563D and BpG563Y, the amino acid sequences of which are shown in SEQ ID NOs: 93-96, respectively.

In summary, the results from FIGS. 27-29 demonstrate that the following EeGUS single point variants exhibited enhanced enzymatic activity against at least one, and often multiple, substrates as compared to the template from which the variant was derived: EeS571G and EeS571N, the amino acid sequences of which are shown in SEQ ID NOs: 97 and 98, respectively.

In summary, the results from FIGS. 27-29 demonstrate that the following Rxn3 single point variants exhibited enhanced enzymatic activity against at least one, and often multiple, substrates as compared to the template from which the variant was derived: Rxn3G560V and Rxn3G560E, the amino acid sequences of which are shown in SEQ ID NOs: 99 and 100, respectively.

Example 14: Double Point Variants

Figure 30:
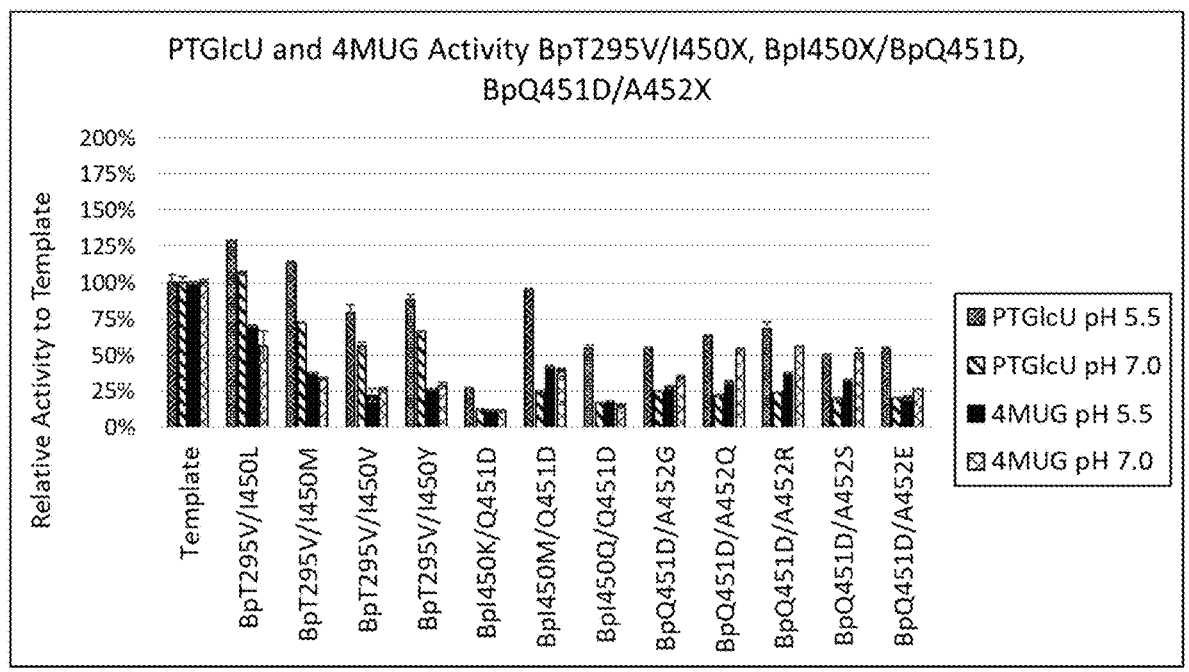
FIG. 30 is a bar graph showing the enzymatic activity of the BpT295V/I450X, BpI450X/Q451D and BpQ451D/A452X variant enzymes on the PTGlcU and 4MUG substrates.
Figure 31:
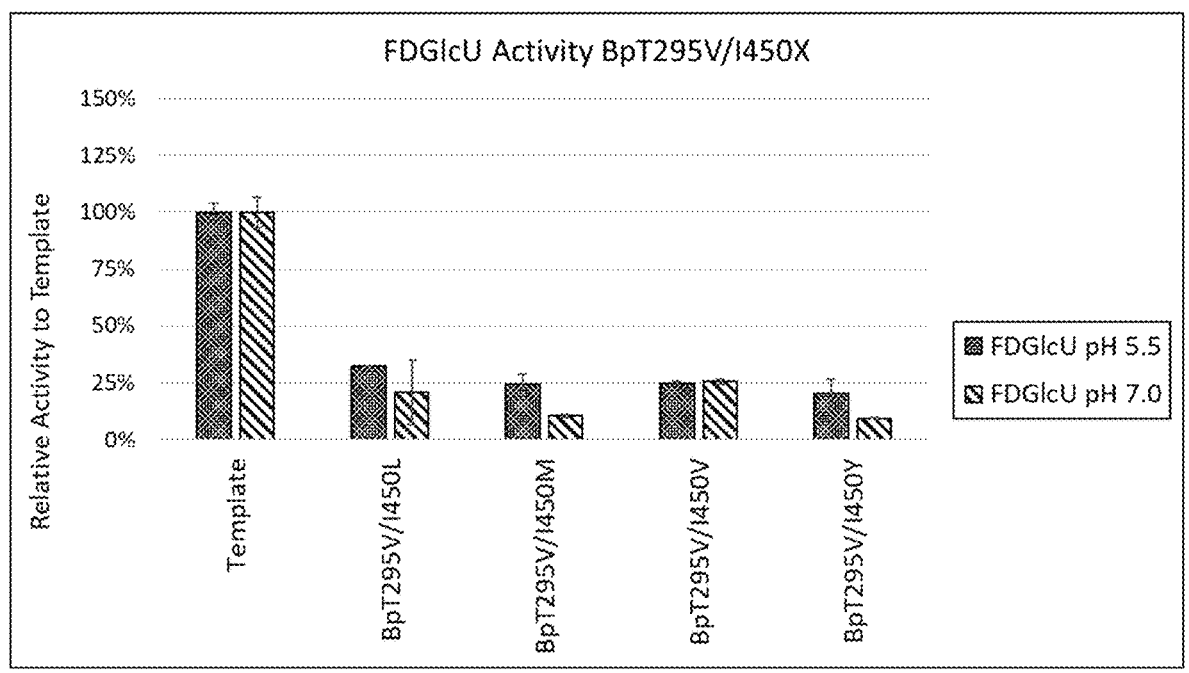
FIG. 31 is a bar graph showing the enzymatic activity of the BpT295V/I450X, BpI450X/Q451D and BpQ451D/A452X variant enzymes on the FDGlcU substrate.
Figure 32:
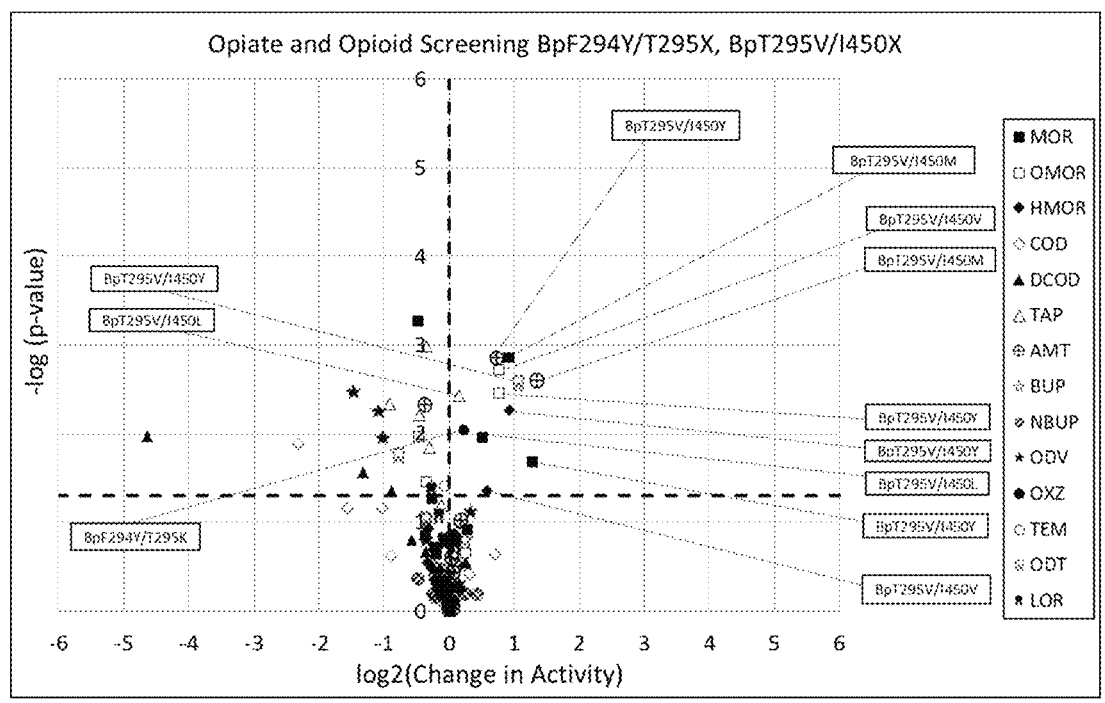
FIG. 32 is a graph showing the significant enzymatic activity of the BpF294Y/T295X and BpT295V/I450X variant enzymes on a panel of opiate and opioid substrates.
Figure 33:
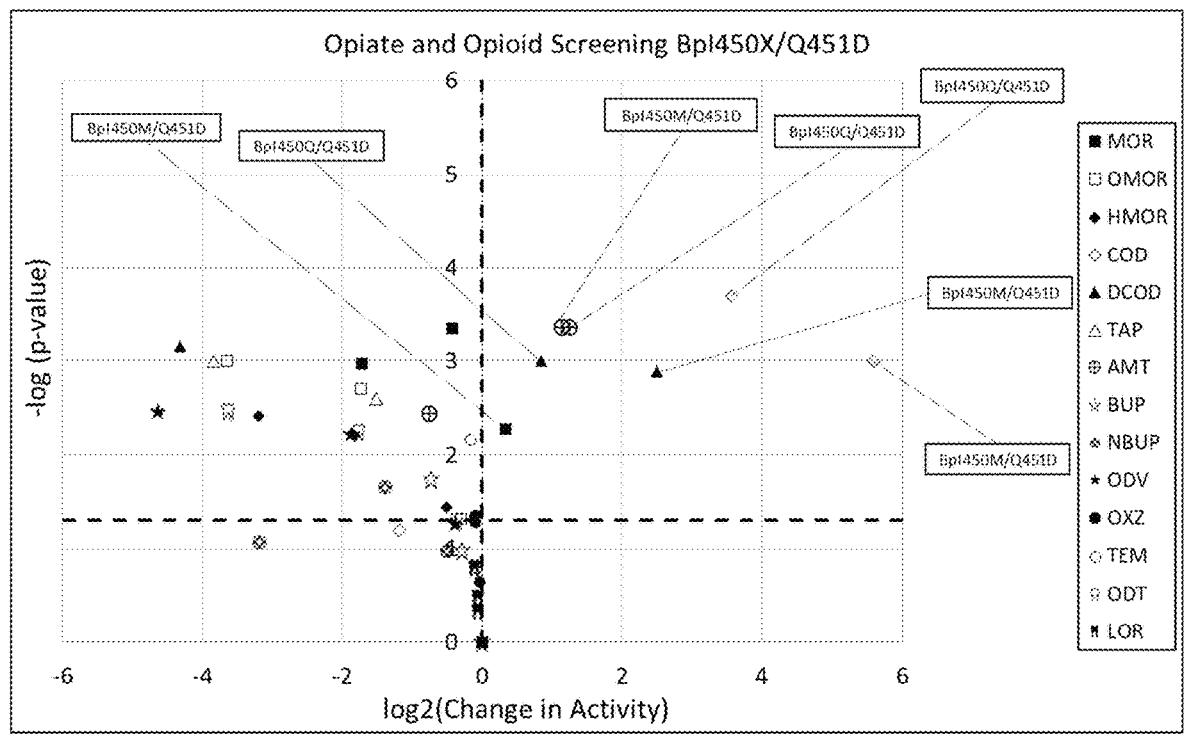
FIG. 33 is a graph showing the significant enzymatic activity of the BpI450X/Q451D variant enzymes on a panel of opiate and opioid substrates.
Figure 34:
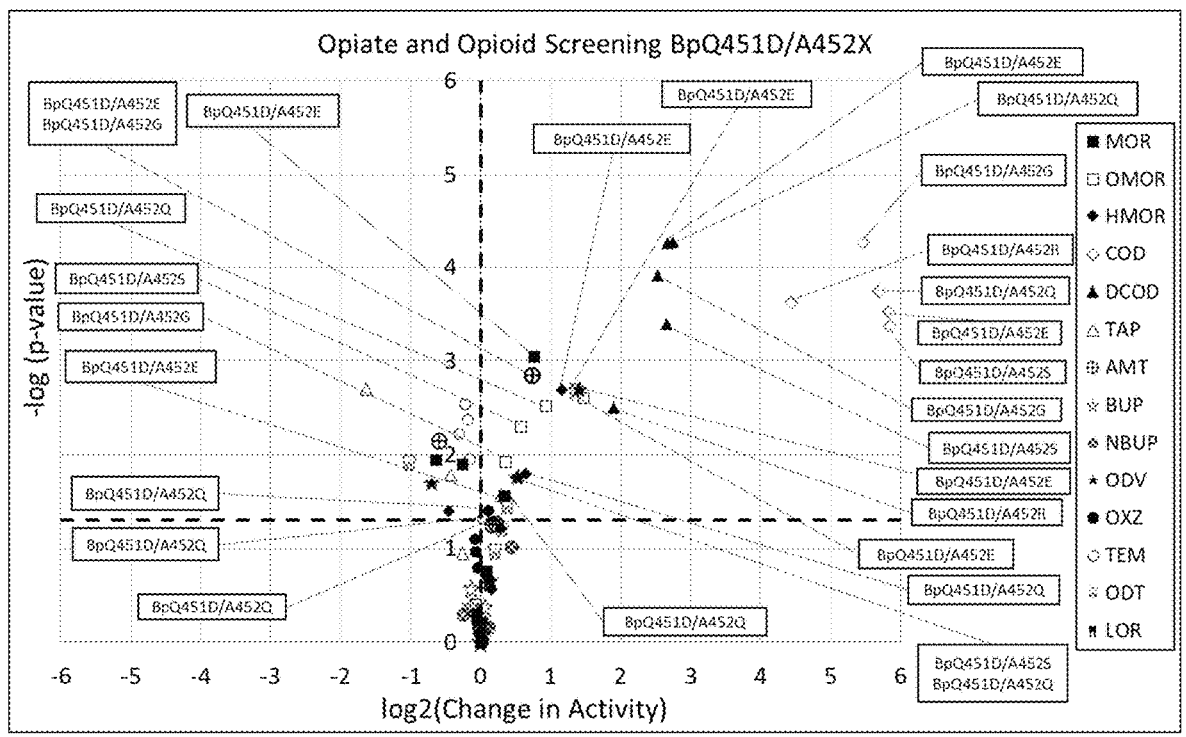
FIG. 34 is a graph showing the significant enzymatic activity of the BpQ451D/A452X variant enzymes on a panel of opiate and opioid substrates.

In this example, two point mutations were made at various combinations of amino acid residue with Variant Sites 1 and 2 shown in FIG. 1 and the enzymatic activity of the double point variants tested on a panel of substrates. These pairs of residues for the double variants tested correspond to positions BpF294/T295 (residues 1 and 2 of Variant Site 1), BpT295/I450 (residue 2 of Variant Site 1 and residue 1 of Variant Site 2), BpI450/Q451 (residues 1 and 2 of Variant Site 2) and BpQ451/A452 (residues 2 and 3 of Variant Site 2). Site-directed mutagenesis was performed as described in Example 7. The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIGS. 15 and 30. The results for the FDGlcU substrate, as compared to template, are shown in FIGS. 16 and 31. The results for the BpF294/T295 and BpT295/I450 variants on a panel of opiates and opioids are shown in FIG. 32. The results for the BpI450/Q451 variants on a panel of opiates and opioids are shown in FIG. 33. The results for the BpQ451/A452 variants on a panel of opiates and opioids are shown in FIG. 34. In FIGS. 32-34, variants indicated in the upper right quadrant of the graph exhibited increased activity as compared to template.

In summary, the results from FIGS. 15, 16 and 32 demonstrate that the following BpGUS F294/T295 double point variants exhibited enhanced enzymatic activity against at least one, and often multiple, substrates as compared to the template from which the variant was derived: BpF294Y/T295C, BpF294Y/T295I, BpF294Y/T295V, BpF294Y/T295F, BpF294Y/T295M, BpF294Y/T295K, the amino acid sequences of which are shown in SEQ ID NOs: 101-106.

In summary, the results from FIGS. 30-32 demonstrate that the following BpGUS T295/I450 double point variants exhibited enhanced enzymatic activity against at least one, and often multiple, substrates as compared to the template from which the variant was derived: BpT295V/I450L, BpT295V/I450M, BpT295V/I450Y and BpT295V/I450V, the amino acid sequences of which are shown in SEQ ID NOs: 107-110, respectively.

In summary, the results from FIGS. 30 and 33 demonstrate that the following BpGUS I450/Q451 double point variants exhibited enhanced enzymatic activity against at least one, and often multiple, substrates as compared to the template from which the variant was derived: BpI450M/Q451D and BpI450Q/Q451D, the amino acid sequences of which are shown in SEQ ID NOs: 111 and 112, respectively.

In summary, the results from FIGS. 30 and 34 demonstrate that the following BpGUS Q451/A452 double point variants exhibited enhanced enzymatic activity against at least one, and often multiple, substrates as compared to the template from which the variant was derived: BpQ451D/A452E, BpQ451D/A452G, BpQ451D/A452Q, BpQ451D/A452S and BpQ451D/A452R, the amino acid sequences of which are shown in SEQ ID NOs: 113-117, respectively. Moreover, the data shown in FIG. 34 demonstrates that the BpQ451D/A452E, BpQ451D/A452G, BpQ451D/A452Q, BpQ451D/A452S and BpQ451D/A452R variants showed exceptionally high enzymatic activity against the codeine-6-β-D-glucuronide (COD) substrate as compared to the parental BpGUS enzyme.

Example 15: EeGUS Cysteine Variants

In this example, cysteine substitutions were made at various amino acid positions within the EeGUS enzyme. Positions substituted with cysteine included Q8, L53, S73, K326, P489, H526, Q570 and K588, as either single or double mutations. Site-directed mutagenesis was performed as described in Example 7.

Figure 40:
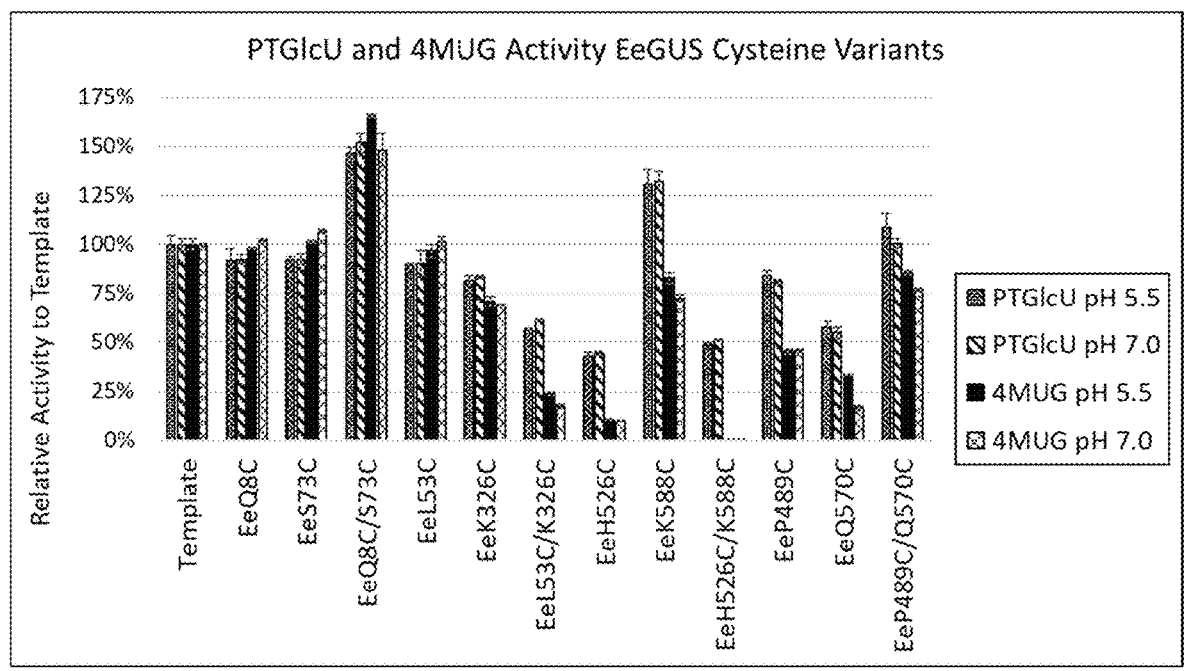
FIG. 40 is a bar graph showing the enzymatic activity of the indicated EeGUS cysteine variant enzymes on the PTGlcU and 4MUG substrates.

The enzymatic activity of the variants was compared to the parental enzyme (i.e., unmutated enzyme, also referred to herein as the template), often under two different pH conditions. The results using these variants, as compared to template, using the PTGlcU and 4MUG substrates are shown in FIG. 40. Furthermore, FIG. 41 displays the opiate and opioid activity of EeQ8C/S73C compared to template. EeQ8C/S73C had significant increases in activity on several different substrates where * indicates a p-value less than 0.05.

Figure 42:
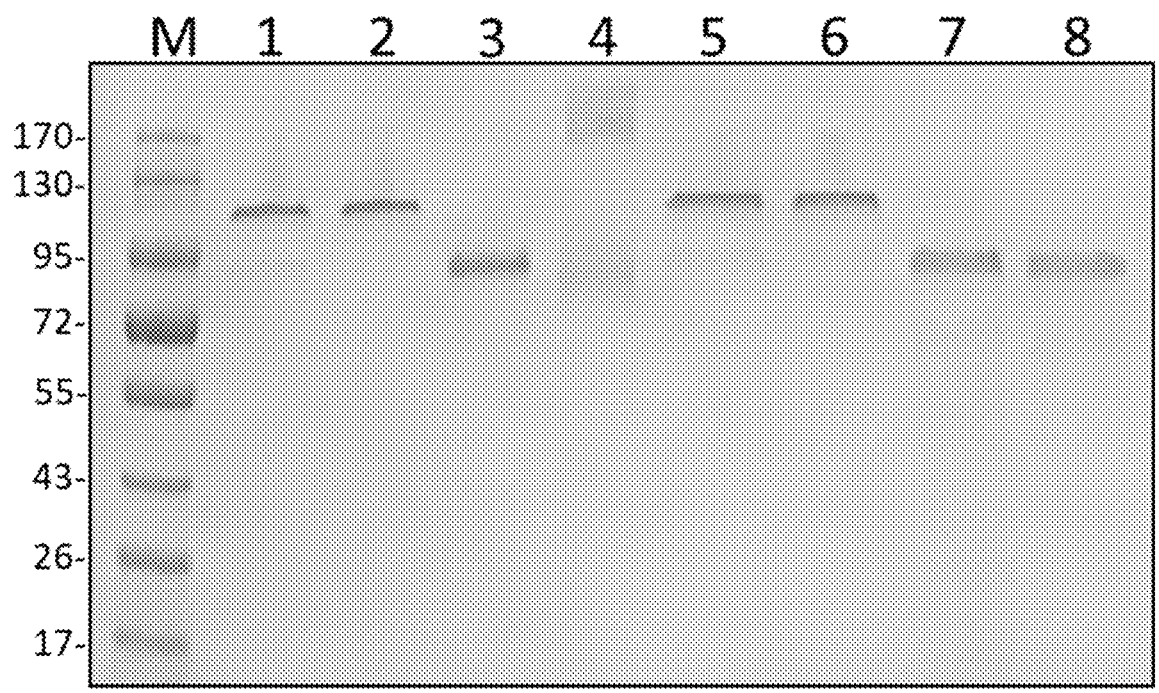
FIG. 42 is a photograph of a 10% SDS-PAGE of EeGUS and the EeQ8C/S73C variant enzyme showing the stability of BGUS enzymes in the presence of non-reducing conditions, reducing conditions, heat or combinations of each.

To examine the stability of the EeQ8C/S73C variants as compared to the parental EeGUS enzyme (template), the enzymes were subjected to various conditions that could affect enzyme stability. FIG. 42 shows the results of a 10% SDS-PAGE showing the stability of EeQ8C/S73C over template. The molecular weight marker lane is labeled with an "M". Lanes 1 and 2 were subjected to non-reducing conditions where lane 1 is template and lane 2 is EeQ8C/S73C. Lanes 3 and 4 were subjected to non-reducing conditions and heated at 100° C. for 10 minutes where lane 3 is template and lane 4 is EeQ8C/S73C. Lanes 5 and 6 were subjected to reducing conditions with 50 mM reducing agent Tris(2-carboxyethyl)phosphine (TCEP) where lane 5 was template and lane 6 was EeQ8C/S73C. Lanes 7 and 8 were subjected to reducing conditions with 50 mM reducing agent TCEP and heated at 100° C. for 10 minutes where lane 7 was template and lane 8 was EeQ8C/S73C. Each lane contained about 0.7 μg of protein.

Figure 41:
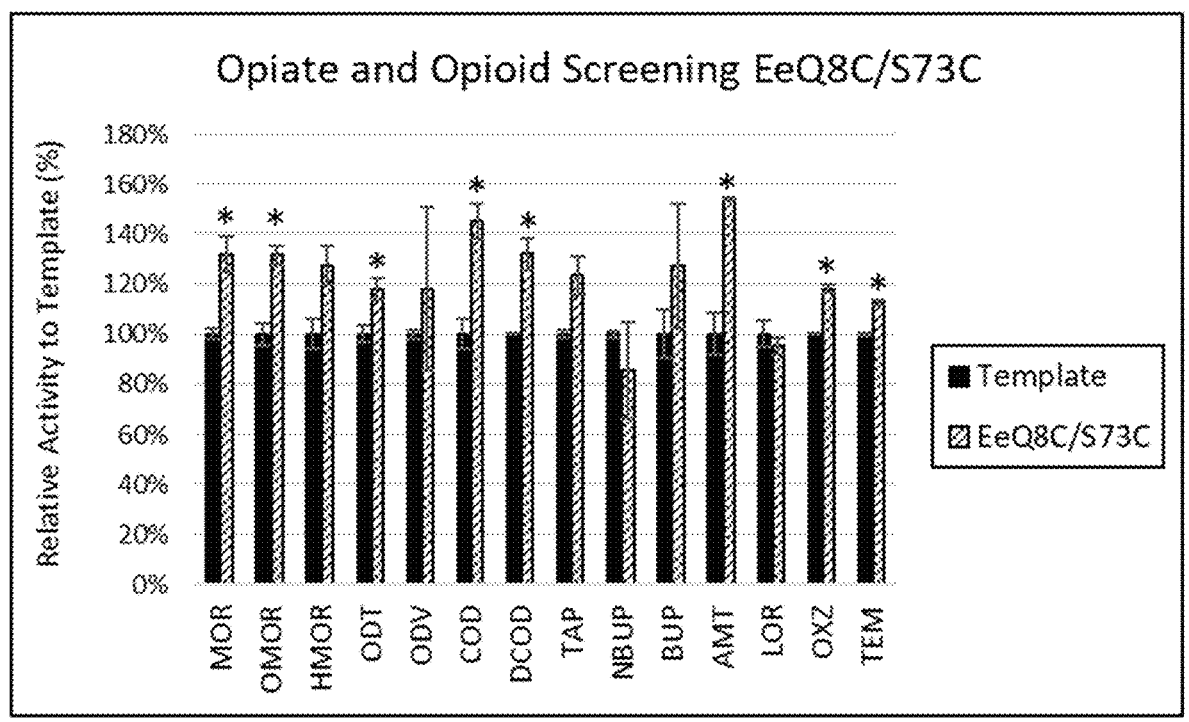
FIG. 41 is a bar graph showing the enzymatic activity of the variant EeQ8C/S73C on a panel of opiate and opioid substrates.

In summary, the results from FIGS. 40, 41 and 42 demonstrate that the following EeGUS cysteine variants exhibited enhanced stability and/or enhanced enzymatic activity against at least one, and often multiple, substrates as compared to the template from which the variant was derived: EeQ8C/S73C, EeK588C and EeP489C/Q570C, the amino acid sequences of which are shown in SEQ ID NOs: 118-120.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
|---|---|
| 1 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDTNIRGKGHDDAYMVHDFQLLHWMGANSFRTSHYPYAEEVMEYAD<br>RQGIVVIDETPAVGLAFSSGAGAQTSNPPATFSPDRINNKTREAHAQASRELIHRDKNH<br>PSVVMWSIANEPASNEDGAREYFAPLPKLARQLDPTRPVTFANVGLATYKADRIADL<br>FDVLCLNRYFGWYTQTAELDEAEAALEEELRGWTEKYDKPIVMTEYGADTVAGLHS<br>VMVTPWSEEFQVEMLDMYHRVFDRFEAMAGEQVWNFADFQTAVGVSRVDGNKKG<br>VFTRDRKPKAAAHLLRKRWTNLHNGTAEGSKTFQ<br>(AoGUS G600S: Aspergillus oryzae BGUS) |
| 2 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKWTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGKHEDSAVRGKGYDPAYMVHDFQLMDWMGANSFRTSHYPYAEEVMEF<br>ADRHGIVVIDETPAVGLAFSIGSGVSSEDSPQTFTPEGINNNTREAHKQAIRELIARDK<br>NHASVVMWSIANEPASQEVGAREYFAPLVDLAHELDPSRPVCFANYGDATYEVDRIS<br>DMFDVLCLNRYFGWYSQTGEVEEAEAALEKELLGWEGKYGKPIVITEYGADTMAGLH<br>SVLALPWSEEFQVQLLDMYHRVFDRIDSVVGEHVWNFADFQTAVGIIRVDGNKKGVF<br>TRERKPKAAAHTLKTRWSGMLGSDH<br>(AtGUS: Aspergillus terreus BGUS) |
| 3 | MKKLLAAAMLFMLNSWSCFSADTPRAEYPRPQFEREQWVNLNGTWTFDFDFGKSG<br>KDRRLQSAEKFDKNITVPFCPESKLSGVGYTDFIEQMWYQRNITIPSDWNGKKIFLNF<br>GAVDYCAEIYVDGKFVQRHFGGSSSFAVDLTRYVTPGKTHNLVVFVQDDLRSGLQTGG<br>KQCGNYYSGGCSYTRTTGIWQTVWMEAVSADGLKSVFVRPDIDQKQLVIEPEFYNES |

SUMMARY OF SEQUENCE LISTING

| SEQ ID NO: | DESCRIPTION |
|---|---|
| | ANTLEITLKDRNKTVAKKSVNCANSSVVVLPVKNMKLWSPEDPFLYDLVYQVKDAK GNVLDEVKSYAGMRKVHTANGRFYLNNQPYFQRLVLDQGFYPEGIWTAPSDEDLKN DIVLGKEAGFNGARLHQKVFEERYYYWADKLGYITWGESASWMLDVNKELAARNFL GEWSEVVVRDRNHPSLVTWTPFNETWGGGPDAYIRLVRDVYNITKAIDPTRPVNDA SGDNHVITDIWSVHNYEQDRAKLTEQLKMEEGKEPYRNARDKDFLAVYEGQPYMVD EFGGIPWMAEKDRKNSWGYGGMPENAEAFYKRLEGQIDAFIDSPHVTGFCYTQLTDV EQEKNGIYYYDRTPKLDMKRIKAIFEKIK (BfGUS: *Bacteroides fragilis* BGUS) |
| 4 | MKTLLKNSLTFLLMLMPVLAFAQQAPQIMNVSARQTTSLDGQWKTIVDPFENGYYD YRLKPYDGGYAQDKTYSDKTKLQEYDFETDKLLFVPGDWNTQRPQLYYYEGTVWYR KHFEYSLQPGKRLFLNFGAVNYEAIVWLNGKRLGRHIGGFTPFNFEITNLLKEGTNSL VVKVDNKRLPEAVPTVNADWWNFGGITRPVTLIEMPATYIRDYYVQLAKDDKNMIE GWVQLEGSDKEQKITLDIPELKVKKEVTTDANGYASFLIKSKPILWTPENPKLYAVNL ASETDKVSDEIGFRTIRTEGIKILLNDKEIFCRGISIHEETPYYSGRAYSKDHAHTLLSW AKELGCNFVRLAHYPHNEEMVREAERMGFLVWSEIPVYWTIHWENKDTYQNAEQQ LCDMIARDKNRCNIIIWSIANETPHSETRLTFLSNLANKARSLDSVRLIGAAMEKEEVQ PGVLTVNDPLGELLDIISFNEYVGWYDGDSEKCDRVNWTFDTQKPVFSSELGGGALYG RHGSPKERFTEEYQEDLYIRHVNMLKRIPGLAGTTPWILKDFRSPRRHVPEIQDDFNR KGLVSDKGQKKAFFVLQKWYKELTEAYK (BuGUS: *Bacteroides uniformis* BGUS) |
| 5 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFTGFGKHEDSEIAGRGYNPPVIKRDFELIKWVGANSFRTSHYPYSEEIMQAADRE GIVIIDEVAAVGMFDVGSVLNPSASKTDYFSLDEVHSKTKEVHKKAVEELIKRDKNHP SVVMWSLFNEPDTSKDEAVPYFEDIFNFAKSQDKQNLPKTFAAIQASSPGKCKCMHL CDVITLNRYYGWYFLGGYEIDMSEEKFREEMNLYSNMNKPVMFTEYGADTYAGVHK LPSVMWSEEYQCEYYEMNFKVFDSYDFIVGEQLWNFADFQTTEGIFRVDGNKKGIFT RNRQPKAVAHLIRSRWNKLPLDYKSKK (BpGUS: *Brachyspira pilosicoli* BGUS) |
| 6 | MVNSMLYPRESRTRRWDISGMWEFKIDSNNEGRKNGYANGLKDTTFIPVPSSFNDL FTDKNIREHAGDIWYETSFYLPLEWKDKNVNIRFGCATHEAAVYINGKEVCTHVGGF MPFNAPVNEAGIFGEKNKLVVVVNNELSNTTLPCGHTETKPSGKKYIKPSFDFFNYAG LNRPVKITVTNKEYIYDIDILSDINGSDGIVNYEVHTTGENKVFVKIYDEEGKEAASAEG KNGKIVIKNAKLWNPKAAYLYKFEACIKNGEELIDEYYLDFGIRTIKVEGTKFLINGKP FYFTGFGKHEDSETAGRGYNPPVIKRDFELIKWIGANSFRTSHYPYSEEIMQAADREGI VIIDEIAAVGMFDVGSVLNPGASKADYFSLEEVHTKTKEIHKKAVEELITRDKNHPSVV MWSLFNEPDTSKDEALPYFEDIFNFAKSIDKQNLPKTFAAIQASAPGKCKCMHLCDVI TLNRYYGWYFLGGYEIDMSEEKFREEMNLYKDMNKPVMFTEYGADTYAGVHKLPSV MWSEEYQCEYYEMNFKVFDSYDFIIGEQLWNFADFQTTEGIFRVDGNKKGIFTRTRQ PKAVAHYIRSRWTKLPLDYKK (BmGUS: *Brachyspira murdochii* BGUS) |
| 7 | MLYPHTESRQLIDLSGIWKFKLNEGNGLTEELSKAPLEDTIEMAVPSSYNDLVESQEV RDHVGWVWYERNFTIPKTLLNERIVLRFGSATHEAKVYLNGELLVEHKGGFTPFEAE INDLLVSGDNRLTVAVNNIIDETTLPVGLVKEVEVDGKKVIKNSVNPDFFNYAGIHRPV KIYTTPKSYIEDITIVTDFKENNGYVNYEVQAVGKCNIKVTIIDEENNIVAEGEGKEGKL TINNVHLWEPMNAYLYKLKVELLDDEEIIDTYFEEFGVRTVEVKDGKFLINNKPFYFK GFGKHEDSYVNGRGINEAINIKDFNLMKWIGANSFRTSHYPYSEEIMRLADREGIVVID ETPAVGLHLNFMATGFGGDAPKRDTWKEIGTKEAHERILRELVSRDKNHPCVVMWS VANEPDSDSEGAKEYFEPLIKLTKELDPQKRPVTVVTYLMSTPDRCKVGDIVDVLCLN RYYGWYVAGGDLEEAKRMLEDELKGWEERCPKTPIMFTEYGADTVAGLHDTVPVM FTEEYQVEYYKANHEVMDKCKNFVGEQVWNFADFATSQGIIRVQGNKKGIFTRERKP KMIAHSLRERWTNIPEFGYKK (CpGUS: *Clostridium perfringens* BGUS) |
| 8 | MLRPVETPTREIKKLDGLWAFSLDRENCGIDQRWWESALQESRAIAVPGSFNDQFAD ADIRNYAGNVWYQREVFIPKGWAGQRIVLRFDAVTHYGKVWVNNQEVMEHQGGYT PFEADVTPYVIAGKSVRITVCVNNELNWQTIPPGMVITDENGKKKQSYFHDFFNYAGI HRSVMLYTTPNTWVDDITVVTHVAQDCNHASVDWQVVANGDVSVELRDADQQVVA TGQGTSGTLQVVNPHLWQPGEGYLYELCVTAKSQTECDIYPLRVGIRSVAVKGEQFLI NHKPFYFTGFGRHEDADLRGKGFDNVLMVHDHALMDWIGANSYRTSHYPYAEEML DWADEHGIVVIDETAAVGFNLSLGIGFEAGNKPKELYSEEAVNGETQQAHLQAIKELI ARDKNHPSVVMWSIANEPDTRPQGAREYFAPLAEATRKLDPTRPITCVNVMFCDAH TDTISDLFDVLCLNRYYGWYVQSGDLETAEKVLEKELLAWQEKLHQPIIITEYGVDTL AGLHSMYTDMWSEEYQCAWLDMYHRVFDRVSAVVGEQVWNFADFATSQGILRVGG NKKGIFTRDRKPKSAAFLLQKRWTGMNFGEKPQQGGKQ (EcGUS: *Escherichia coli* BGUS) |

SUMMARY OF SEQUENCE LISTING

| SEQ ID NO: | DESCRIPTION |
|---|---|

9  MLRPVETPTREIKKLDGLWAFSLDRENCGIDQRWWESALQESRAIAVPGSFNDQFAD
   ADIRNYAGNVWYQREVFIPKGWAGQRIVLRFDAVTHYGKVWVNNQEVMEHQGGYT
   PFEADVTPYVIAGKSVRITVCVNNELNWQTIPPGMVITDENGKKKQSYFHDFFNYAGI
   HRSVMLYTTPNTWVDDITVVTHVAQDCNHASVDWQVVANGDVSVELRDADQQVVA
   TGQGTSGTLQVVNPHLWQPGEGYLYELCVTAKSQTECDIYPLRVGIRSVAVKGEQFLI
   NHKPFYFTGFGRHEDADLRGKGFDNVLMVHDHALMDWIGANSYRTSHYPYAEEML
   DWADEHGIVVIDETAAVGFNLSLGIGFEAGNKPKELYSEEAVNGETQQAHLQAIKELI
   ARDKNHPSVVMWSIANEPDTRPQGAREYFAPLAEATRKLDPTRPITCVNVMFCDAH
   TDTISDLFDVLCLNRYYGWYVQSGDLETAEKVLEKELLAWQEKLHQPIIITEYGVDTL
   AGLHSMYTDMWSEEYQCAWLDMYHRVFDRVSAVVGEQVWNFADFATSQSILRVGG
   NKKGIFTRDRKPKSAAFLLQKRWTGMNFGEKPQQGSKQGLCGR
   (EcE1F: IMCSzyme ® variant *Escherichia coli* K12 BGUS)

10 MLYPVLTQSRLLSDLSGVWDFKLDNGKGFEEKWYEKPLKDADTMPVPASYNDLKEG
   TDFRDHYGWVFYQRNISVPEYVKSQRIVLRCAAVTHYAMIYLNGKLICEHKGGFLPFE
   VELNDDLQDGDNLLTIAVNNVIDYTTLPVGGKANMMSGMMGGMGAGASDKPQNNP
   NFDFFNYCGITRPVKIYTTPETYINDITVTADIDFTKEEPSAVLNYNVEIKGKDYNNITC
   KVELFDEEGTKLSETEGSEGTFEISNVRLWQPLNAYLYKIKVTAGQDVYTLPYGVRSV
   RVDGTKFLINEKPFYFKGYGKHEDTFPNGRGINLPMNTKDISIMKWQHANSFRTSHY
   PYSEEMMRLCDEEGIVVIDETTAVGVNLQFGGGANFGGERIGTFDKEHGVQTQEHHK
   DVIRDLISRDKNHACVVMWSIANEPDSAAEGAYDYFKPLYDLARELDPQKRPCTLVSV
   QGTTADTDCSSQLSDVICLNRYYGWYFGGPDLEVSEIGLRKELSDWGKLGKPVMFTE
   YGADTVSGLHDTTSVMYTEEYQVEYYEMNNKVFDEFDFVVGEQAWNFADFATSQSL
   LRVQGNKKGLFTRDRKPKMVAHYFRNRWSTIPEFGYKTK
   (EeGUS: *Eubacterium eligens* BGUS)

11 MARGSAVAWAALGPLLWGCALGLQGGMLYPQESPSRECKELDGLWSFRADFSDNRR
   RGFEEQWYRRPLWESGPTVDMPVPSSFNDISQDWRLRHFVGWVWYEREVILPERW
   TQDLRTRVVLRIGSAHSYAIVWVNGVDTLEHEGGYLPFEADISNLVQVGPLPSRLRITI
   AINNTLTPTTLPPGTIQYLTDTSKYPKGYFVQNTYFDFFNYAGLQRSVLLYTTPTTYID
   DITVTTSVEQDSGLVNYQISVKGSNLFKLEVRLLLDAENKVVANGTGTQGQLKVPGVSL
   WWPYLMHERPAYLYSLEVQLTAQTSLGPVSDFYTLPVGIRTVAVTKSQFLINGKPFYF
   HGVNKHEDADIRGKGFDWPLLVKDFNLLRWLGANAFRTSHYPYAEEVMQMCDRYG
   IVVIDECPGVGLALPQFFNNVSLHHHMQVMEEVVRRDKNHPAVVMWSVANEPASHL
   ESAGYYLKMVIAHTKSLDPSRPVTFVSNSNYAADKGAPYVDVICLNSYYSWYHDYGHL
   ELIQLQLATQFENWYKKYQKPIIQSEYGAETIAGFHQDPPLMFTEEYQKSLLEQYHLG
   LDQKRRKYVVGELIWNFADFMTEQSPTRVLGNKKGIFTRQRQPKSAAFLLRERYWKI
   ANETRYPHSVAKSQCLENSLFT
   (HsGUS: *Homo sapiens* BGUS)

12 MLYPMETASRVVLDLSGVWRFMIDKEQIPVDVTRPLPATLSMAVPASFNDQTASKEI
   REHVGYVWYERCFELPQLLRQERLVLRFGSATHEAWVYLNGHLITHHKGGFTPFEVE
   INDDLVTGENRLTVKLSNMLDYTTLPVGHYKETQNETGQRVRQLDENFDFFNYAGL
   QRPVKIYSTPHSYIRDITLTPKVNLTNHSAVVNGEIETVGDVEQVVVTILDEDNQVVGT
   TSGKTLAIELNSVHLWQPGKAYLYRAKVELYQAGQVIDTYIETFGIRQIAVKAGKFLIN
   GQPFYFKGFGKHEDAYIHGRGLSEPQNVLDLSLMKQMGANSFRTSHYPYSEEMMRLC
   DREGIVVIDEVPAVGLMLSFTFDVSALEKDDFEDDTWEKLRTAEAHRQAITEMIDRD
   KNHASVVMWSISNEAANFSKGAYEYFKPLFDLARKLDPQQRPCTYTSIMMTTLKTDR
   CLALADVIALNRYYGWYMGNGDLKAAETATREELLAYQAKFPDKPIMYTEYGADTIA
   GLHSNYDEPFSEEFQEDYYRMCSRVFDEVTNFVGEQLWNFADFQTKFGIQRVQGNKK
   GIFTRAREPKMVVRYLTQRWRNIPDFNYKK
   (LbLR2D: *Lactobacillus brevis* BGUS)

13 MSLKWSACWVALGQLLCSCALALKGGMLFPKESPSRELKALDGLWHFRADLSNNRL
   QGFEQQWYRQPLRESGPVLDMPVPSSFNDITQEAALRDFIGWVWYEREAILPRRWT
   QDTDMRVVLRINSAHYYAVVWVNGIHVVEHEGGHLPFEADISKLVQSGPLTTCRITIA
   INNTLTPHTLPPGTIVYKTDTSMYPKGYFVQDTSFDFFNYAGLHRSVVLYTTPTTYID
   DITVITNVEQDIGLVTYWISVQGSEHFQLEVQLLDEGGKVVAHGTGNQGQLQVPSANL
   WWPYLMHEHPAYMYSLEVKVTTTESVTDYYTLPIGIRTVAVTKSKFLINGKPFYFQG
   VNKHEDSDIRGKGFDWPLLVKDFNLLRWLGANSFRTSHYPYSEEVLQLCDRYGIVVID
   ECPGVGIVLPQSFGNESLRHHLEVMEELVRRDKNHPAVVMWSVANEPSSALKPAAYY
   FKTLITHTKALDLTRPVTFVSNAKYDADLGAPYVDVICVNSYFSWYHDYGHLEVIQPQ
   LNSQFENWYKTHQKPIIQSEYGADAIPGIHEDPPRMFSEEYQKAVLENYHSVLDQKRK
   EYVVGELIWNFADFMTNQSPLRVIGNKKGIFTRQRQPKTSAFILRERYWRIANETGGH
   GSGPRTQCFGSRPFTF
   (*Mus musculus* BGUS)

14 MKRISIAFLSLFLCVASVWSMPRPEYPRPQFERAGWVNLNGEWTCSFDFGGSGMERE
   FYKSKGFDKKITVPFCPESKLSGIGYTDFINHFWYQRPITIPQEWNGKNILLNFGAVYY
   KSEVYIDGVLASRHFGGTSSFAVDITSLVKPGQTHSLVVYVESDVRGAKQAAGKQNLQ
   YASYGCNYTRTTGIWQTVWMEAVHPEGLQSIQLLTDIDQQQLVVRPRFYKEAGGKLQ
   VTLKDNGKVVASRTVSASSLSSVVLPVKKMKTWSPESPFLYDLEYKVLDKNGNIIDEV

SUMMARY OF SEQUENCE LISTING

| SEQ ID NO: | DESCRIPTION |
|---|---|
| | NGYAGMRKVHIEGNKIYLNNKPYYQRLVLDQGFYPDGIWTAPSDEALKRDIELSMEA<br>GFNGARLHQKVFEERFYYWADKMGYLTWGEASSWGMDCNDTETARNFITEWSEIV<br>QRDRNHPSLLIWTPTNEEFWPDRVQYPRLMHDLYNLTKMIDPTRPFHGASGGTHIA<br>TDIWTVHNYEQDPAKLKEKLYNGGKLMEAPKWEIHLMPMNIGYNGLKYTDQYAFPE<br>YKKDMPYLVDEFGGIKWNPSQQMESAQNTSWGYGEPPRSLEEFYARLEGQVDAVLS<br>LSNDIWGYCYTQLTDVEQEQNGIYYYDRTPKFDMKRIHAIFSKTPESK<br>(PmGUS: *Parabacteroides* sp. *merdae* BGUS) |
| 15 | MLYPINTETRGVFDLNGVWNFKLDYGKGLEEKWYESKLTDTISMAVPSSYNDIGVTK<br>EIRNHIGYVWYEREFTVPAYLKDQRIVLRFGSATHKAIVYVNGELVVEHKGGFLPFEA<br>EINNSLRDGMNRVTVAVDNILDDSTLPVGLYSERHEEGLGKVIRNKPNFDFFNYAGLH<br>RPVKIYTTPFTYVEDISVVTDFNGPTGTVTYTVDFQGKAETVKVSVVDEEGKVVASTE<br>GLSGNVEIPNVILWEPLNTYLYQIKVELVNDGLTIDVYEEPFGVRTVEVNDGKFLINNK<br>PFYFKGFGKHEDTPINGRGFNEASNVMDFNILKWIGANSFRTAHYPYSEELMRLADR<br>EGLVVIDETPAVGVHLNFMATTGLGEGSERVSTWEKIRTFEHHQDVLRELVSRDKNH<br>PSVVMWSIANEAATEEEGAYEYFKPLVELTKELDPQKRPVTIVLFVMATPETDKVAE<br>LIDVIALNRYNGWYFDGGDLEAAKVHLRQEFHAWNKRCPGKPIMITEYGADTVAGFH<br>DIDPVMFTEEYQVEYYQANHVVFDEFENFVGEQAWNFADFATSQGVMRVQGNKKG<br>VFTRDRKPKLAAHVFRERWTNIPDFGYKN<br>(StpGUS: *Staphylococcus* sp. RLH1 BGUS) |
| 16 | MLYPLLTKTRNTYDLGGIWNFKLGEHNPNELLPSDEVMVIPTSFNDLMVSKEKRDYI<br>GDFWYEKVIEVPKVSEGEEMVLRFGSVTHQAKIYVDGILVGEHKGGFTPFEVLVPECK<br>YNNEKIKVSICANNVLDYTTLPVGNYSEIIQEDGSIKKKVRENFDFFNYAGVHRPLKLM<br>IRPKNHISDITITSRLSDDLQSADLHFLVETNQKVDEVRISVFDEDNKLVGETKDSRLF<br>LSDVHLWEVLNAYLYTARVEIFVDNQLQDVYEENFGLREIEVTNGQPFLLNRKPIYFKG<br>FGKHEDTFINGRGLNEAANLMDLNLLKDIGANSFRTSHYPYSEEMMRLADRMGVLVI<br>DEVPAVGLFQNFNASLDLSPKDNGTWSLMQTKAAHEQAIQELVKRDKNHPSVVMW<br>VVANEPASHEAGAHDYFEPLVKLYKDLDPQKRPVTLVNILMATPDRDQVMDLVDVV<br>CLNRYYGWYVDHGDLTNAEVGLRKELLEWQDKFPDKPIIITEYGADTLPGLHSTWNI<br>PYTEEFQCDFYEMSHRVFDGIPNLVGEQVWNFADFETNLMILRVQGNHKGLFSRNR<br>QPKQVVKEFKKRWMTIPHYHNKKNSVK<br>(SaGUS: *Streptococcus agalactiae* BGUS) |
| 17 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKWTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGKHEDTNIRGKGHDDAYMVHDFQLLHWMGANSFRTSHYPYAEEVMEY<br>ADRQGIVVIDETPAVGLAFSIGAGAQTSNPPATFSPDRINNKTREAHAQAIRELIHRDK<br>NHPSVVMWSIANEPASNEDGAREYFAPLPKLARQLDPTRPVTFANVGLATYKADRIA<br>DLFDVLCLNRYFGWYTQTAELDEAEAALEEELRGWTEKYDKPIVMTEYGADTVAGL<br>HSVMVTPWSEEFQVEMLDMYHRVFDRFEAMAGEQVWNFADFQTAVGVSRVDGNK<br>KGVFTRDRKPKAAAHLLRKRWTNLHNGTAEGSKTFQ<br>(Rxn1 chimera) |
| 18 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGRHEDADLRGKGFDNVLMVHDHALMDWIGANSYRTSHYPYAEEMLDW<br>ADEHGIVVIDETAAVGFNLSLGIGFEAGNKPKELYSEEAVNGETQQAHLQAIKELIARD<br>KNHPSVVMWSIANEPDTRPQGAREYFAPLAEATRKLDPTRPITCVNVMFCDAHTDTI<br>SDLFDVLCLNRYYGWYVQSGDLETAEKVLEKELLAWQEKLHQPIIITEYGVDTLAGLH<br>SMYTDMWSEEYQCAWLDMYHRVFDRVSAVVGEQVWNFADFATSQSILRVGGNKKG<br>IFTRDRKPKSAAFLLQKRWTGMNFGEKPQQGSKTFQ<br>(Rxn2 chimera) |
| 19 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGDATYEVDRISDM<br>FDVLCLNRYFGWYSQTGEVEEAEAALEKELLGWEGKYKGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3 chimera) |

SUMMARY OF SEQUENCE LISTING

| SEQ ID NO: | DESCRIPTION |
|---|---|
| 20 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKWTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGRHEDADLRGKGFDNVLMVHDHALMDWIGANSYRTSHYPYAEEMLDW<br>ADEHGIVVIDETAAVGFNLSLGIGFEAGNKPKELYSEEAVNGETQQAHLQAIKELIARD<br>KNHPSVVMWSIANEPDTRPQGAREYFAPLAEATRKLDPTRPITCVNVMFCDAHTDTI<br>SDLFDVLCLNRYYGWYVQSGDLETAEKVLEKELLAWQEKLHQPIIITEYGVDTLAGLH<br>SMYTDMWSEEYQCAWLDMYHRVFDRVSAVVGEQVWNFADFATSQSILRVGGNKKG<br>IFTRDRKPKSAAFLLQKRWTGMNFGEKPQQGSDH<br>(Rxn4 chimera) |
| 21 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGRHEDADLRGKGFDNVLMVHDHALMDWIGANSYRTSHYPYAEEMLDW<br>ADEHGIVVIDETAAVGFNLSLGIGFEAGNKPKELYSEEAVNGETQQAHLQAIKELIARD<br>KNHPSVVMWSIANEPDTRPQGAREYFAPLAEATRKLDPTRPITCVNVMFCDAHTDTI<br>SDLFDVLCLNRYYGWYVQSGDLETAEKVLEKELLAWQEKLHQPIIITEYGVDTLAGLH<br>SMYTDMWSEEYQCAWLDMYHRVFDRVSAVVGEQVWNFADFATSQSILRVGGNKKG<br>IFTRDRKPKSAAFLLQKRWTGMNFGEKPQQGSKQGLCGR<br>(Rxn5 chimera) |
| 22 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGRHEDADLRGKGFDNVLMVHDHALMDWIGANSYRTSHYPYAEEMLDW<br>ADEHGIVVIDETAAVGFNLSLGIGFEAGNKPKELYSEEAVNGETQQAHLQAIKELIARD<br>KNHPSVVMWSIANEPDTRPQGAREYFAPLAEATRKLDPTRPITCVNVMFCDAHTDTI<br>SDLFDVLCLNRYYGWYVQSGDLETAEKVLEKELLAWQEKLHQPIIITEYGVDTLAGLH<br>SMYTDMWSEEYQCAWLDMYHRVFDRVSAVVGEQVWNFADFATSQSILRVGGNKKG<br>IFTRDRKPKSAAFLLQKRWTGMNFGEKPQQGSKQGLCGR<br>(Rxn8 chimera) |
| 23 | MLRPVETPTREIKKLDGLWAFSLDRENCGIDQRWWESALQESRAIAVPGSFNDQFAD<br>ADIRNYAGNVWYQREVFIPKGWAGQRIVLRFDAVTHYGKVWVNNQEVMEHQGGYT<br>PFEADVTPYVIAGKSVRITVCVNNELNWQTIPPGMVITDENGKKKQSYFHDFFNYAGI<br>HRSVMLYTTPNTWVDDITVVTHVAQDCNHASVDWQVVANGDVSVELRDADQQVVA<br>TGQGTSGTLQVVNPHLWQPGEGYLYELCVTAKSQTECDIYPLRVGIRSVAVKGEQFLI<br>NHKPFYFTGFGKHEDTNIRGKGHDDAYMVHDFQLLHWMGANSFRTSHYPYAEEVM<br>EYADRQGIVVIDETPAVGLAFSIGAGAQTSNPPATFSPDRINNKTREAHAQAIRELIHR<br>DKNHPSVVMWSIANEPASNEDGAREYFAPLPKLARQLDPTRPVTFANVGLATYKAD<br>RIADLFDVLCLNRYFGWYTQTAELDEAEAALEEELRGWTEKYDKPIVMTEYGADTVA<br>GLHSVMVTPWSEEFQVEMLDMYHRVFDRFEAMAGEQVWNFADFQTAVGVSRVDG<br>NKKGVFTRDRKPKAAAHLLRKRWTNLHNGTAEGSKQGLCGR<br>(Rxn9 chimera) |
| 24 | MLRPVETPTREIKKLDGLWAFSLDRENCGIDQRWWESALQESRAIAVPGSFNDQFAD<br>ADIRNYAGNWYQREVFIPKGWAGQRIVLRFDAVTHYGKVWVNNQEVMEHQGGYT<br>PFEADVTPYVIAGKSVRITVCVNNELNWQTIPPGMVITDENGKKKQSYFHDFFNYAGI<br>HRSVMLYTTPNTWVDDITVVTHVAQDCNHASVDWQVVANGDVSVELRDADQQVVA<br>TGQGTSGTLQWNPHLWQPGEGYLYELCVTAKSQTECDIYPLRVGIRSVAVKGEQFLI<br>NHKPFYFTGFGKHEDSAVRGKGYDPAYMVHDFQLMDWMGANSFRTSHYPYAEEVM<br>EFADRHGIVVIDETPAVGLAFSIGSGVSSEDSPQTFTPEGINNNTREAHKQAIRELIARD<br>KNHASVVMWSIANEPASQEVGAREYFAPLVDLAHELDPSRPVCFANYGDATYEVDRI<br>SDMFDVLCLNRYFGWYSQTGEVEEAEAALEKELLGWEGKYGKPIVITEYGADTMAGL<br>HSVLALPWSEEFQVQLLDMYHRVFDRIDSVVGEHVWNFADFQTAVGIIRVDGNKKGV<br>FTRERKPKAAAHTLKTRWSGMLGSKQGLCGR<br>(Rxn10 chimera) |
| 25 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGKHEDSAVRGKGYDPAYMVHDFQLMDWMGANSFRTSHYPYAEEVMEF<br>ADRHGIVVIDETPAVGLAFSIGSGVSSEDSPQTFTPEGINNNTREAHKQAIRELIARDK<br>NHASVVMWSIANEPASNEDGAREYFAPLPKLARQLDPTRPVTFANVGLATYKADRIA |

| SUMMARY OF SEQUENCE LISTING |
|---|

| SEQ ID NO: | DESCRIPTION |
|---|---|
| | DLFDVLCLNRYFGWYTQTAELDEAEAALEEELRGWTEKYDKPIVMTEYGADTVAGL<br>HSVMVTPWSEEFQVEMLDMYHRVFDRFEAMAGEQVWNFADFQTAVGVSRVDGNK<br>KGVFTRDRKPKAAAHLLKRWTNLHNGTAEGSKTFQ<br>(Save1 chimera) |
| 26 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDTNIRGKGHDDAYMVHDFQLLHWMGANSFRTSHYPYAEEVMEYAD<br>RQGIVVIDETPAVGLAFSIGAGAQTSNPPATFSPDRINNKTREAHAQAIRELIHRDKNH<br>PSVVMWSIANEPASQEVGAREYFAPLVDLAHELDPSRPVCFANYGDATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Save3 chimera) |
| 27 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGRHEDADLRGKGFDNVLMVHDHALMDWIGANSYRTSHYPYAEEMLDW<br>ADEHGIVVIDETPAVGLAFSIGSGVSSEDSPQTFTPEGINNNTREAHKQAIRELIARDK<br>NHASVVMWSIANEPDTRPQGAREYFAPLAEATRKLDPTRPITCVNVMFCDAHTDTIS<br>DLFDVLCLNRYYGWYVQSGDLETAEKVLEKELLAWQEKLHQPIIITEYGVDTLAGLHS<br>MYTDMWSEEYQCAWLDMYHRVFDRVSAVVGEQVWNFADFATSQSILRVGGNKKGI<br>FTRDRKPKSAAFLLQKRWTGMNFGEKPQQGSDH<br>(Save4 chimera) |
| 28 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGRHEDADLRGKGFDNVLMVHDHALMDWIGANSYRTSHYPYAEEMLDW<br>ADEHGIVVIDETPAVGLAFSIGAGAQTSNPPATFSPDRINNKTREAHAQAIRELIHRDK<br>NHPSVVMWSIANEPDTRPQGAREYFAPLAEATRKLDPTRPITCVNVMFCDAHTDTIS<br>DLFDVLCLNRYYGWYVQSGDLETAEKVLEKELLAWQEKLHQPIIITEYGVDTLAGLHS<br>MYTDMWSEEYQCAWLDMYHRVFDRVSAVVGEQVWNFADFATSQSILRVGGNKKGI<br>FTRDRKPKSAAFLLQKRWTGMNFGEKPQQGSKQGLCGR<br>(Save5 chimera) |
| 29 | MLRPVETPTREIKKLDGLWAFSLDRENCGIDQRWWESALQESRAIAVPGSFNDQFAD<br>ADIRNYAGNVWYQREVFIPKGWAGQRIVLRFDAVTHYGKVWVNNQEVMEHQGGYT<br>PFEADVTPYVIAGKSVRITCVNNELNWQTIPPGMVITDENGKKKQSYFHDFFNYAGI<br>HRSVMLYTTPNTWVDDITVVTHVAQDCNHASVDWQVVANGDVSVELRDADQQVVA<br>TGQGTSGTLQVVNPHLWQPGEGYLYELCVTAKSQTECDIYPLRVGIRSVAVKGEQFLI<br>NHKPFYFTGFGRHEDADLRGKGFDNVLMVHDHALMDWIGANSYRTSHYPYAEEML<br>DWADEHGIVVIDETAAVGFNLSLGIGFEAGNKPKELYSEEAVNGETQQAHLQAIKELI<br>ARDKNHPSVVMWSIANEPASNEDGAREYFAPLPKLARQLDPTRPVTFANVGLATYK<br>ADRIADLFDVLCLNRYGWYTQTAELDEAEAALEEELRGWTEKYDKPIVMTEYGADT<br>VAGLHSVMVTPWSEEFQVEMLDMYHRVFDRFEAMAGEQVWNFADFQTAVGVSRV<br>DGNKKGVFTRDRKPKAAAHLLKRWTNLHNGTAEGSKQGLCGR<br>(Save9 chimera) |
| 30 | MLRPVETPTREIKKLDGLWAFSLDRENCGIDQRWWESALQESRAIAVPGSFNDQFAD<br>ADIRNYAGNVWYQREVFIPKGWAGQRIVLRFDAVTHYGKVWVNNQEVMEHQGGYT<br>PFEADVTPYVIAGKSVRITCVNNELNWQTIPPGMVITDENGKKKQSYFHDFFNYAGI<br>HRSVMLYTTPNTWVDDITVVTHVAQDCNHASVDWQVVANGDVSVELRDADQQVVA<br>TGQGTSGTLQVVNPHLWQPGEGYLYELCVTAKSQTECDIYPLRVGIRSVAVKGEQFLI<br>NHKPFYFTGFGKHEDSAVRGKGYDPAYMVHDFQLMDWMGANSFRTSHYPYAEEVM<br>EFADRHGIVVIDETAAVGFNLSLGIGFEAGNKPKELYSEEAVNGETQQAHLQAIKELIA<br>RDKNHPSVVMWSIANEPASQEVGAREYFAPLVDLAHELDPSRPVCFANYGDATYEVD<br>RISDMFDVLCLNRYFGWYSQTGEVEEAEAALEKELLGWEGKYGKPIVITEYGADTMA<br>GLHSVLALPWSEEFQVQLLDMYHRVFDRIDSVVGEHVWNFADFQTAVGIIRVDGNKK<br>GVFTRERKPKAAAHTLKTRWSGMLGSKQGLCGR<br>(Save10 chimera) |
| 31 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR |

SUMMARY OF SEQUENCE LISTING

| SEQ ID NO: | DESCRIPTION |
|---|---|
| | SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDTNIRGKGHDDAYMVHDFQLLHWMGANSFRTSHYPYAEEVMEYAD<br>RQGIVVIDETPAVGLAFSIGSGVSSEDSPQTFTPEGINNNTREAHKQAIRELIARDKNH<br>ASVVMWSIANEPASNEDGAREYFAPLPKLARQLDPTRPVTFANVGLATYKADRIADL<br>FDVLCLNRYFGWYTQTAELDEAEAALEEELRGWTEKYDKPIVMTEYGADTVAGLHS<br>VMVTPWSEEFQVEMLDMYHRVFDRFEAMAGEQVWNFADFQTAVGVSRVDGNKKG<br>VFTRDRKPKAAAHLLRKRWTNLHNGTAEGSKTFQ<br>(L1 chimera) |
| 32 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGRHEDADLRGKGFDNVLMVHDHALMDWIGANSYRTSHYPYAEEMLDWAD<br>EHGIVVIDETAAVGFNLSLGIGFEAGNKPKELYSEEAVNGETQQAHLQAIKELIARDKN<br>HPSVVMWSIANEPASNEDGAREYFAPLPKLARQLDPTRPVTFANVGLATYKADRIAD<br>LFDVLCLNRYFGWYTQTAELDEAEAALEEELRGWTEKYDKPIVMTEYGADTVAGLH<br>SVMVTPWSEEFQVEMLDMYHRVFDRFEAMAGEQVWNFADFQTAVGVSRVDGNKK<br>GVFTRDRKPKAAAHLLRKRWTNLHNGTAEGSKTFQ<br>(L2 chimera) |
| 33 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYLYQFRASIVGLNDSVVDTYCVETGVRTVKVSGNRFLIND<br>KPFYFTGFGKHEDTNIRGKGHDDAYMVHDFQLLHWMGANSFRTSHYPYAEEVMEY<br>ADRQGIVVIDETPAVGLAFSIGAGAQTSNPPATFSPDRINNKTREAHAQAIRELIHRDK<br>NHPSVVMWSIANEPASQEVGAREYFAPLVDLAHELDPSRPVCFANYGDATYEVDRIS<br>DMFDVLCLNRYFGWYSQTGEVEEAEAALEKELLGWEGKYGKPIVITEYGADTMAGLH<br>SVLALPWSEEFQVQLLDMYHRVFDRIDSVVGEHVWNFADFQTAVGIIRVDGNKKGVF<br>TRERKPKAAAHTLKTRWSGMLGSDH<br>(L3 chimera) |
| 34 | MLKPRQTPFRDLISLDGLWKFALDSGDNATAAPWTGPLTTDLECPVPASYNDIFVDR<br>QIRDHVGWVYYQREAIVPRAWSQQQYLVRVDAATHQGRIYINDNLVAEHRGGYTPFE<br>ADITGLVSAGDSFRLTIAVNNELTHETIPPGRIEVEEYTGKRVQVYQHDFFNYAGLARS<br>VWLYSVPQQHIQDIKVVTHVKGSAGLINYLVTVSNSTTGRVKIDVIDKDGTTVAEASG<br>ARGSVTIDSVKLWQPGEAYIYQFRASIVGLNDSWDTYCVETGVRTVKVSGNRFLIND<br>KPFYFTGFGKHEDSAVRGKGYDPAYMVHDFQLMDWMGANSFRTSHYPYAEEVMEF<br>ADRHGIVVIDETAAVGFNLSLGIGFEAGNKPKELYSEEAVNGETQQAHLQAIKELIARD<br>KNHPSVVMWSIANEPASQEVGAREYFAPLVDLAHELDPSRPVCFANYGDATYEVDRI<br>SDMFDVLCLNRYFGWYSQTGEVEEAEAALEKELLGWEGKYGKPIVITEYGADTMAGL<br>HSVLALPWSEEFQVQLLDMYHRVFDRIDSVVGEHVWNFADFQTAVGIIRVDGNKKGV<br>FTRERKPKAAAHTLKTRWSGMLGSDH<br>(L4 chimera) |
| 35 | MLRPVETPTREIKKLDGLWAFSLDRENCGIDQRWWESALQESRAIAVPGSFNDQFAD<br>ADIRNYAGNVWYQREVFIPKGWAGQRIVLRFDAVTHYGKVWVNNQEVMEHQGGYT<br>PFEADVTPYVIAGKSVRITCVNNELNWQTIPPGMVITDENGKKKQSYFHDFFNYAGI<br>HRSVMLYTTPNTWVDDITVVTHVAQDCNHASVDWQVVANGDVSVELRDADQQVVA<br>TGQGTSGTLQVVNPHLWQPGEGYLYELCVTAKSQTECDIYPLRVGIRSVAVKGEQFLI<br>NHKPFYFTGFGKHEDTNIRGKGHDDAYMVHDFQLLHWMGANSFRTSHYPYAEEVM<br>EYADRQGIVVIDETPAVGLAFSIGAGAQTSNPPATFSPDRINNKTREAHAQAIRELIHR<br>DKNHPSVVMWSIANEPDTRPQGAREYFAPLAEATRKLDPTRPITCVNVMFCDAHTD<br>TISDLFDVLCLNRYYGWYVQSGDLETAEKVLEKELLAWQEKLHQPIIITEYGVDTLAG<br>LHSMYTDMWSEEYQCAWLDMYHRVFDRVSAVVGEQVWNFADFATSQSILRVGGNK<br>KGIFTRDRKPKSAAFLLQKRWTGMNFGEKPQQGSKQGLCGR<br>(L5 chimera) |
| 36 | MLRPVETPTREIKKLDGLWAFSLDRENCGIDQRWWESALQESRAIAVPGSFNDQFAD<br>ADIRNYAGNVWYQREVFIPKGWAGQRIVLRFDAVTHYGKVWVNNQEVMEHQGGYT<br>PFEADVTPYVIAGKSVRIWCVNNELNWQTIPPGMVITDENGKKKQSYFHDFFNYAGI<br>HRSVMLYTTPNTWVDDITVVTHVAQDCNHASVDWQVVANGDVSVELRDADQQVVA<br>TGQGTSGTLQVVNPHLWQPGEGYLYELCVTAKSQTECDIYPLRVGIRSVAVKGEQFLI<br>NHKPFYFTGFGRHEDADLRGKGFDNVLMVHDHALMDWIGANSYRTSHYPYAEEML<br>DWADEHGIVVIDETPAVGLAFSIGSGVSSEDSPQTFTPEGINNNTREAHKQAIRELIAR<br>DKNHASVVMWSIANEPDTRPQGAREYFAPLAEATRKLDPTRPITCVNVMFCDAHTD<br>TISDLFDVLCLNRYYGWYVQSGDLETAEKVLEKELLAWQEKLHQPIIITEYGVDTLAG |

SUMMARY OF SEQUENCE LISTING

| SEQ ID NO: | DESCRIPTION |
|---|---|
| | LHSMYTDMWSEEYQCAWLDMYHRVFDRVSAVVGEQVWNFADFATSQSILRVGGNK KGIFTRDRKPKSAAFLLQKRWTGMNFGEKPQQGSKQGLCGR (L6 chimera) |
| 37 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGGKANMMSGMMGGMGAGASDK PQNNPNFDFFNYAGLNRPVKITVTNKEYIHDIDILSDVNGSDGIVNYEVHTTGENKVYI KINDEEGKEVASCEGKSGKIVIKDAKLWNPKAAYLYKFIACIKNGDELIDEYYLDFGIR TVKVEGTKFLINGKPFYFTGFGKHEDSEIAGRGYNPPVIKRDFELIKWVGANSFRTSHY PYSEEIMQAADREGIVIIDEVAAVGMFDVGSVLNPSASKTDYFSLDEVHSKTKEVHKK AVEELIKRDKNHPSVVMWSLFNEPDTSKDEAVPYFEDIFNFAKSQDKQNLPKTFAAI QASSPGKCKCMHLCDVITLNRYYGWYFLGGYEIDMSEEKFREEMNLYSNMNKPVMF TEYGADTYAGVHKLPSVMWSEEYQCEYYEMNFKVFDSYDFIVGEQLWNFADFQTTE GIFRVDGNKKGIFTRNRQPKAVAHLIRSRWNKLPLDYKSKK (BpChimera1 chimera) |
| 38 | MVNSMLYPRESRTRRVVDISGMWEFKSDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFTGFGKHEDSEIAGRGYNPPVIKRDFELIKWVGANSFRTSHYPYSEEIMQAADRE GIVIIDEVAAVGMFDQGGGANFGGERIGTFDKEHGSKTKEVHKKAVEELIKRDKNHP SVVMWSLFNEPDTSKDEAVPYFEDIFNFAKSQDKQNLPKTFAAIQASSPGKCKCMHL CDVITLNRYYGWYFLGGYEIDMSEEKFREEMNLYSNMNKPVMFTEYGADTYAGVHK LPSVMWSEEYQCEYYEMNFKVFDSYDFIVGEQLWNFADFQTTEGIFRVDGNKKGIFT RNRQPKAVAHLIRSRWNKLPLDYKSKK (BpChimera2 chimera) |
| 39 | MVNSMLYPRESRTRRVVDISGMWEFKSDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGGKANMMSGMMGGMGAGASDK PQNNPNFDFFNYAGLNRPVKITVTNKEYIHDIDILSDVNGSDGIVNYEVHTTGENKVYI KINDEEGKEVASCEGKSGKIVIKDAKLWNPKAAYLYKFIACIKNGDELIDEYYLDFGIR TVKVEGTKFLINGKPFYFTGFGKHEDSEIAGRGYNPPVIKRDFELIKWVGANSFRTSHY PYSEEIMQAADREGIVIIDEVAAVGMFDQGGGANFGGERIGTFDKEHGSKTKEVHKK AVEELIKRDKNHPSVVMWSLFNEPDTSKDEAVPYFEDIFNFAKSQDKQNLPKTFAAI QASSPGKCKCMHLCDVITLNRYYGWYFLGGYEIDMSEEKFREEMNLYSNMNKPVMF TEYGADTYAGVHKLPSVMWSEEYQCEYYEMNFKVFDSYDFIVGEQLWNFADFQTTE GIFRVDGNKKGIFTRNRQPKAVAHLIRSRWNKLPLDYKSKK (BpChimera3 chimera) |
| 40 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFTGFGKHEDSEIAGRGYNPPVIKRDFELIKWVGANSFRTSHYPYSEEIMQAADRE GIVIIDEVAAVGMFDVGGGGANFGGERDYFSLDEVHSKTKEVHKKAVEELIKRDKNHP SVVMWSLFNEPDTSKDEAVPYFEDIFNFAKSQDKQNLPKTFAAIQASSPGKCKCMHL CDVITLNRYYGWYFLGGYEIDMSEEKFREEMNLYSNMNKPVMFTEYGADTYAGVHK LPSVMWSEEYQCEYYEMNFKVFDSYDFIVGEQLWNFADFQTTEGIFRVDGNKKGIFT RNRQPKAVAHLIRSRWNKLPLDYKSKK (BpChimera4 chimera) |
| 41 | MVNSMLYPRESRTRRVVDISGMWEFKSDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGGKANMMSGMMGGMGAGASDK PQNNPNFDFFNYAGLNRPVKITVTNKEYIHDIDILSDVNGSDGIVNYEVHTTGENKVYI KINDEEGKEVASCEGKSGKIVIKDAKLWNPKAAYLYKFIACIKNGDELIDEYYLDFGIR TVKVEGTKFLINGKPFYFTGFGKHEDSEIAGRGYNPPVIKRDFELIKWVGANSFRTSHY PYSEEIMQAADREGIVIIDEVAAVGMFDVGGGGANFGGERDYFSLDEVHSKTKEVHKK AVEELIKRDKNHPSVVMWSLFNEPDTSKDEAVPYFEDIFNFAKSQDKQNLPKTFAAI QASSPGKCKCMHLCDVITLNRYYGWYFLGGYEIDMSEEKFREEMNLYSNMNKPVMF TEYGADTYAGVHKLPSVMWSEEYQCEYYEMNFKVFDSYDFIVGEQLWNFADFQTTE GIFRVDGNKKGIFTRNRQPKAVAHLIRSRWNKLPLDYKSKK (BpChimera5 chimera) |
| 42 | MLYPVLTQSRLLSDLSGVWDFKLDNGKGFEEKWYEKPLKDADTMPVPASYNDLKEG TDFRDHYGWVFYQRNISVPEYVKSQRIVLRCAAVTHYAMIYLNGKLICEHKGGFLPFE VELNDDLQDGDNLLTIAVNNVIDYTTLPVGCGHTETKPSGKKYIKPSFDFFNYCGITRP VKIYTTPETYINDITVTADIDFTKEEPSAVLNYNVEIKGKDYNNITCKVELFDEEGTKLS |

SUMMARY OF SEQUENCE LISTING

| SEQ ID NO: | DESCRIPTION |
|---|---|
| | ETEGSEGTFEISNVRLWQPLNAYLYKIKVTAGQDVYTLPYGVRSVRVDGTKFLINEKP<br>FYFKGYGKHEDTFPNGRGINLPMNTKDISIMKWQHANSFRTSHYPYSEEMMRLCDE<br>EGIVVIDETTAVGVNLQFGGGANFGGERIGTFDKEHGVQTQEHHKDVIRDLISRDKNH<br>ACVVMWSIANEPDSAAEGAYDYFKPLYDLARELDPQKRPCTLVSVQGTTADTDCSSQ<br>LSDVICLNRYYGWYFGGPDLEVSEIGLRKELSDWGKLGKPVMFTEYGADTVSGLHDT<br>TSVMYTEEYQVEYYEMNNKVFDEFDFVVGEQAWNFADFATSQSLLRVQGNKKGLFT<br>RDRKPKMVAHYFRNRWSTIPEFGYKTK<br>(EeChimera1 chimera) |
| 43 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLVGSVLNPSASKTDYFSLDEVHVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeChimera2 chimera) |
| 44 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGCGHTETKPSGKKYIKPSFDFFNYCGITRP<br>VKIYTTPETYINDITVTADIDFTKEEPSAVLNYNVEIKGKDYNNITCKVELFDEEGTKLS<br>ETEGSEGTFEISNVRLWQPLNAYLYKIKVTAGQDVYTLPYGVRSVRVDGTKFLINEKP<br>FYFKGYGKHEDTFPNGRGINLPMNTKDISIMKWQHANSFRTSHYPYSEEMMRLCDE<br>EGIVVIDETTAVGVNLVGSVLNPSASKTDYFSLDEVHVQTQEHHKDVIRDLISRDKNH<br>ACVVMWSIANEPDSAAEGAYDYFKPLYDLARELDPQKRPCTLVSVQGTTADTDCSSQ<br>LSDVICLNRYYGWYFGGPDLEVSEIGLRKELSDWGKLGKPVMFTEYGADTVSGLHDT<br>TSVMYTEEYQVEYYEMNNKVFDEFDFVVGEQAWNFADFATSQSLLRVQGNKKGLFT<br>RDRKPKMVAHYFRNRWSTIPEFGYKTK<br>(EeChimera3 chimera) |
| 45 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFSVLNPSASKTIGTFDKEHGVQTQEHHKD<br>VIRDLISRDKNHACVVMWSIANEPDSAAEGAYDYFKPLYDLARELDPQKRPCTLVSVQ<br>GTTADTDCSSQLSDVICLNRYYGWYFGGPDLEVSEIGLRKELSDWGKLGKPVMFTEYG<br>ADTVSGLHDTTSVMYTEEYQVEYYEMNNKVFDEFDFVVGEQAWNFADFATSQSLLR<br>VQGNKKGLFTRDRKPKMVAHYFRNRWSTIPEFGYKTK<br>(EeChimera4 chimera) |
| 46 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGCGHTETKPSGKKYIKPSFDFFNYCGITRP<br>VKIYTTPETYINDITVTADIDFTKEEPSAVLNYNVEIKGKDYNNITCKVELFDEEGTKLS<br>ETEGSEGTFEISNVRLWQPLNAYLYKIKVTAGQDVYTLPYGVRSVRVDGTKFLINEKP<br>FYFKGYGKHEDTFPNGRGINLPMNTKDISIMKWQHANSFRTSHYPYSEEMMRLCDE<br>EGIVVIDETTAVGVNLQFSVLNPSASKTIGTFDKEHGVQTQEHHKDVIRDLISRDKNH<br>ACVVMWSIANEPDSAAEGAYDYFKPLYDLARELDPQKRPCTLVSVQGTTADTDCSSQ<br>LSDVICLNRYYGWYFGGPDLEVSEIGLRKELSDWGKLGKPVMFTEYGADTVSGLHDT<br>TSVMYTEEYQVEYYEMNNKVFDEFDFVVGEQAWNFADFATSQSLLRVQGNKKGLFT<br>RDRKPKMVAHYFRNRWSTIPEFGYKTK<br>(EeChimera5 chimera) |
| 47 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYATGPFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294A) |

SUMMARY OF SEQUENCE LISTING

| SEQ ID NO: | DESCRIPTION |
|---|---|
| 48 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYITGFGKHEDSEIAGRGYNPPVIKRDFELIKWVGANSFRTSHYPYSEEIMQAADREG<br>IVIIDEVAAVGMFDVGSVLNPSASKTDYFSLDEVHSKTKEVHKKAVEELIKRDKNHPS<br>VVMWSLFNEPDTSKDEAVPYFEDIFNFAKSQDKQNLPKTFAAIQASSPGKCKCMHLC<br>DVITLNRYYGWYFLGGYEIDMSEEKFREEMNLYSNMNKPVMFTEYGADTYAGVHKL<br>PSVMWSEEYQCEYYEMNFKVFDSYDFIVGEQLWNFADFQTTEGIFRVDGNKKGIFTR<br>NRQPKAVAHLIRSRWNKLPLDYKSKK<br>(BpF294I) |
| 49 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYVTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294V) |
| 50 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294Y) |
| 51 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYLTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294L) |
| 52 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYWTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294W) |
| 53 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYWKGYGKHEDTFPNGRGINLPMNTKDISIMKWQHANSFRTSH<br>YPYSEEMMRLCDEEGIVVIDETTAVGVNLQFGGGANFGGERIGTFDKEHGVQTQEHH |

SUMMARY OF SEQUENCE LISTING

| SEQ ID NO: | DESCRIPTION |
|---|---|
| | KDVIRDLISRDKNHACWMWSIANEPDSAAEGAYDYFKPLYDLARELDPQKRPCTLV SVQGTTADTDCSSQLSDVICLNRYYGWYFGGPDLEVSEIGLRKELSDWGKLGKPVMFT EYGADTVSGLHDTTSVMYTEEYQVEYYEMNNKVFDEFDFVVGEQAWNFADFATSQS LLRVQGNKKGLFTRDRKPKMVAHYFRNRWSTIPEFGYKTK (EeF303W) |
| 54 | MLYPVLTQSRLLSDLSGVWDFKLDNGKGFEEKWYEKPLKDADTMPVPASYNDLKEG TDFRDHYGWVFYQRNISVPEYVKSQRIVLRCAAVTHYAMIYLNGKLICEHKGGFLPFE VELNDDLQDGDNLLTIAVNNVIDYTTLPVGGKANMMSGMMGGMGAGASDKPQNNP NFDFFNYCGITRPVKIYTTPETYINDITVTADIDFTKEEPSAVLNYNVEIKGKDYNNITC KVELFDEEGTKLSETEGSEGTFEISNVRLWQPLNAYLYKIKVTAGQDVYTLPYGVRSV RVDGTKFLINEKPFYSKGYGKHEDTFPNGRGINLPMNTKDISIMKWQHANSFRTSHY PYSEEMMRLCDEEGIVVIDETTAVGVNLQFGGGANFGGERIGTFDKEHGVQTQEHHK DVIRDLISRDKNHACVVMWSIANEPDSAAEGAYDYFKPLYDLARELDPQKRPCTLVSV QGTTADTDCSSQLSDVICLNRYYGWYFGGPDLEVSEIGLRKELSDWGKLGKPVMFTE YGADTVSGLHDTTSVMYTEEYQVEYYEMNNKVFDEFDFVVGEQAWNFADFATSQSL LRVQGNKKGLFTRDRKPKMVAHYFRNRWSTIPEFGYKTK (EeF303S) |
| 55 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFAGFGKHEDSEIAGRGYNPPVIKRDFELIKWVGANSFRTSHYPYSEEIMQAADRE GIVIIDEVAAVGMFDVGSVLNPSASKTDYFSLDEVHSKTKEVHKKAVEEELIKRDKNHP SVVMWSLFNEPDTSKDEAVPYFEDIFNFAKSQDKQNLPKTFAAIQASSPGKCKCMHL CDVITLNRYYGWYFLGGYEIDMSEEKFREEMNLYSNMNKPVMFTEYGADTYAGVHK LPSVMWSEEYQCEYYEMNFKVFDSYDFIVGEQLWNFADFQTTEGIFRVDGNKKGIFT RNRQPKAVAHLIRSRWNKLPLDYKSKK (BpT295A) |
| 56 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFCGFGKHEDSEIAGRGYNPPVIKRDFELIKWVGANSFRTSHYPYSEEIMQAADRE GIVIIDEVAAVGMFDVGSVLNPSASKTDYFSLDEVHSKTKEVHKKAVEEELIKRDKNHP SVVMWSLFNEPDTSKDEAVPYFEDIFNFAKSQDKQNLPKTFAAIQASSPGKCKCMHL CDVITLNRYYGWYFLGGYEIDMSEEKFREEMNLYSNMNKPVMFTEYGADTYAGVHK LPSVMWSEEYQCEYYEMNFKVFDSYDFIVGEQLWNFADFQTTEGIFRVDGNKKGIFT RNRQPKAVAHLIRSRWNKLPLDYKSKK (BpT295C) |
| 57 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFFGFGKHEDSEIAGRGYNPPVIKRDFELIKWVGANSFRTSHYPYSEEIMQAADRE GIVIIDEVAAVGMFDVGSVLNPSASKTDYFSLDEVHSKTKEVHKKAVEEELIKRDKNHP SVVMWSLFNEPDTSKDEAVPYFEDIFNFAKSQDKQNLPKTFAAIQASSPGKCKCMHL CDVITLNRYYGWYFLGGYEIDMSEEKFREEMNLYSNMNKPVMFTEYGADTYAGVHK LPSVMWSEEYQCEYYEMNFKVFDSYDFIVGEQLWNFADFQTTEGIFRVDGNKKGIFT RNRQPKAVAHLIRSRWNKLPLDYKSKK (BpT295F) |
| 58 | MVNSMLYPRESRTRRVVDISGMWEFKIDINNEGRNSGYANGLKDTTFIPVPSSFNDLF TDKNIREHAGDVWYETSFYLPLEWKDKDVNVRFGCATHEATVYINGKEVCTHVGGF MPFNAPVNEAGIFGEKNKLVVVVNNELSNTTIPCGHTETKPSGKKYIKPSFDFFNYAG LNRPVKITVTNKEYIHDIDILSDVNGSDGIVNYEVHTTGENKVYIKINDEEGKEVASCE GKSGKIVIKDAKLWNPKAAYLYKFIACIKNGDELIDEYYLDFGIRTVKVEGTKFLINGK PFYFIGFGKHEDSEIAGRGYNPPVIKRDFELIKWVGANSFRTSHYPYSEEIMQAADREG IVIIDEVAAVGMFDVGSVLNPSASKTDYFSLDEVHSKTKEVHKKAVEEELIKRDKNHPS VVMWSLFNEPDTSKDEAVPYFEDIFNFAKSQDKQNLPKTFAAIQASSPGKCKCMHLC DVITLNRYYGWYFLGGYEIDMSEEKFREEMNLYSNMNKPVMFTEYGADTYAGVHKL PSVMWSEEYQCEYYEMNFKVFDSYDFIVGEQLWNFADFQTTEGIFRVDGNKKGIFTR NRQPKAVAHLIRSRWNKLPLDYKSKK (BpT295I) |

SUMMARY OF SEQUENCE LISTING

| SEQ ID NO: | DESCRIPTION |
|---|---|
| 59 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFKGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpT295K) |
| 60 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFSGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpT295S) |
| 61 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFVGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpT295V) |
| 62 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFAGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeK304A) |
| 63 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFVGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeK304V) |
| 64 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAFQASSPGKCKCMHL |

SUMMARY OF SEQUENCE LISTING

| SEQ ID NO: | DESCRIPTION |
|---|---|
| | CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(Bp1450F) |
| 65 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAKQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(Bp1450K) |
| 66 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAALQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(Bp1450L) |
| 67 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAMQASSPGKCKCMH<br>LCDVITLNRYYGWYFLGGYEIDMSEEKFREEMNLYSNMNKPVMFTEYGADTYAGVH<br>KLPSVMWSEEYQCEYYEMNFKVFDSYDFIVGEQLWNFADFQTTEGIFRVDGNKKGIF<br>TRNRQPKAVAHLIRSRWNKLPLDYKSKK<br>(Bp1450M) |
| 68 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAQQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(Bp1450Q) |
| 69 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAADQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(Bp1450D) |
| 70 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGSFGEKNKLVVVVNNELSNTTIPCGHTETKPSGKKYIKPSFDFFNYAG |

SUMMARY OF SEQUENCE LISTING

| SEQ ID NO: | DESCRIPTION |
|---|---|
| | LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAVQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpI450V) |
| 71 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSF<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeV459F) |
| 72 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFQNEKPFYFKGYGKHEDTFPNGRGSNLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSL<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeV459L) |
| 73 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVS<br>WQGTTADTDCSSQLSDVICLNRYYGWYFGGPDLEVSEIGLRKELSDWGKLGKPVMFT<br>EYGADTVSGLHDTTSVMYTEEYQVEYYEMNNKVFDEFDFVVGEQAWNFADFATSQS<br>LLRVQGNKKGLFTRDRKPKMVAHYFRNRWSTIPEFGYKTK<br>(EeV459W) |
| 74 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSC<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeV459C) |
| 75 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVS<br>GQGTTADTDCSSQLSDVICLNRYYGWYFGGPDLEVSEIGLRKELSDWGKLGKPVMFT |

-continued

SUMMARY OF SEQUENCE LISTING

| SEQ ID NO: | DESCRIPTION |
|---|---|
| | EYGADTVSGLHDTTSVMYTEEYQVEYYEMNNKVFDEFDFVVGEQAWNFADFATSQS<br>LLRVQGNKKGLFTRDRKPKMVAHYFRNRWSTIPEFGYKTK<br>(EeV459G) |
| 76 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSE<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeV459E) |
| 77 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIDASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451D) |
| 78 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIEASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451E) |
| 79 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIGASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451G) |
| 80 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAISASSPGKCKCMHLC<br>DVITLNRYYGWYFLGGYEIDMSEEKFREEMNLYSNMNKPVMFTEYGADTYAGVHKL<br>PSVMWSEEYQCEYYEMNFKVFDSYDFIVGEQLWNFADFQTTEGIFRVDGNKKGIFTR<br>NRQPKAVAHLIRSRWNKLPLDYKSKK<br>(BpQ451S) |
| 81 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE |

| SUMMARY OF SEQUENCE LISTING | |
|---|---|
| SEQ ID NO: | DESCRIPTION |
| | GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIVASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451V) |
| 82 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLWWNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIKASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451K) |
| 83 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQDSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpA452D) |
| 84 | MVNSMLYPRESRTRRVVDISGMWEFKSDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQKSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpA452K) |
| 85 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQNSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpA452N) |
| 86 | MVNSMLYPRESRTRRVVDISGMWEFKSDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQGSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpA452G) |

| SUMMARY OF SEQUENCE LISTING |
|---|

SEQ
ID
NO: DESCRIPTION

87 MVNSMLYPRESRTRRWDISGMWEFKIDINNEGRNSGYANGLKDTTFIPVPSSFNDLF
TDKNIREHAGDVWYETSFYLPLEWKDKDVNVRFGCATHEATVYINGKEVCTHVGGF
MPFNAPVNEAGIFGEKNKLVVVVNNELSNTTIPCGHTETKPSGKKYIKPSFDFFNYAG
LNRPVKITVTNKEYIHDIDILSDVNGSDGIVNYEVHTTGENKVYIKINDEEGKEVASCE
GKSGKIVIKDAKLWNPKAAYLYKFIACIKNGDELIDEYYLDFGIRTVKVEGTKFLINGK
PFYFTGFGKHEDSEIAGRGYNPPVIKRDFELIKWVGANSFRTSHYPYSEEIMQAADRE
GIVIIDEVAAVGMFDVGSVLNPSASKTDYFSLDEVHSKTKEVHKKAVEELIKRDKNHP
SVVMWSLFNEPDTSKDEAVPYFEDIFNFAKSQDKQNLPKTFAAIQESSPGKCKCMHL
CDVITLNRYYGWYFLGGYEIDMSEEKFREEMNLYSNMNKPVMFTEYGADTYAGVHK
LPSVMWSEEYQCEYYEMNFKVFDSYDFIVGEQLWNFADFQTTEGIFRVDGNKKGIFT
RNRQPKAVAHLIRSRWNKLPLDYKSKK
(BpA452E)

88 MVNSMLYPRESRTRRVVDISGMWEFKIDINNEGRNSGYANGLKDTTFIPVPSSFNDLF
TDKNIREHAGDVWYETSFYLPLEWKDKDVNVRFGCATHEATVYINGKEVCTHVGGF
MPFNAPVNEAGIFGEKNKLWWNNELSNTTIPCGHTETKPSGKKYIKPSFDFFNYAG
LNRPVKITVTNKEYIHDIDILSDVNGSDGIVNYEVHTTGENKVYIKINDEEGKEVASCE
GKSGKIVIKDAKLWNPKAAYLYKFIACIKNGDELIDEYYLDFGIRTVKVEGTKFLINGK
PFYFTGFGKHEDSEIAGRGYNPPVIKRDFELIKWVGANSFRTSHYPYSEEIMQAADRE
GIVIIDEVAAVGMFDVGSVLNPSASKTDYFSLDEVHSKTKEVHKKAVEELIKRDKNHP
SVVMWSLFNEPDTSKDEAVPYFEDIFNFAKSQDKQNLPKTFAAIQQSSPGKCKCMHL
CDVITLNRYYGWYFLGGYEIDMSEEKFREEMNLYSNMNKPVMFTEYGADTYAGVHK
LPSVMWSEEYQCEYYEMNFKVFDSYDFIVGEQLWNFADFQTTEGIFRVDGNKKGIFT
RNRQPKAVAHLIRSRWNKLPLDYKSKK
(BpA452Q)

89 MLYPVLTQSRLLSDLSGVWDFKLDNGKGFEEKWYEKPLKDADTMPVPASYNDLKEG
TDFRDHYGWVFYQRNISVPEYVKSQRIVLRCAAVTHYAMIYLNGKLICEHKGGFLPFE
VELNDDLQDGDNLLTIAVNNVIDYTTLPVGGKANMMSGMMGGMGAGASDKPQNNP
NFDFFNYCGITRPVKIYTTPETYINDITVTADIDFTKEEPSAVLNYNVEIKGKDYNNITC
KVELFDEEGTKLSETEGSEGTFEISNVRLWQPLNAYLYKIKVTAGQDVYTLPYGVRSV
RVDGTKFLINEKPFYFKGYGKHEDTFPNGRGINLPMNTKDISIMKWQHANSFRTSHY
PYSEEMMRLCDEEGIVVIDETTAVGVNLQFGGGANFGGERIGTFDKEHGVQTQEHHK
DVIRDLISRDKNHACVVMWSIANEPDSAAEGAYDYFKPLYDLARELDPQKRPCTLVSV
QATTADTDCSSQLSDVICLNRYYGWYFGGPDLEVSEIGLRKELSDWGKLGKPVMFTE
YGADTVSGLHDTTSVMYTEEYQVEYYEMNNKVFDEFDFVVGEQAWNFADFATSQSL
LRVQGNKKGLFTRDRKPKMVAHYFRNRWSTIPEFGYKTK
(EeG461A)

90 MLYPVLTQSRLLSDLSGVWDFKLDNGKGFEEKWYEKPLKDADTMPVPASYNDLKEG
TDFRDHYGWVFYQRNISVPEYVKSQRIVLRCAAVTHYAMIYLNGKLICEHKGGFLPFE
VELNDDLQDGDNLLTIAVNNVIDYTTLPVGGKANMMSGMMGGMGAGASDKPQNNP
NFDFFNYCGITRPVKIYTTPETYINDITVTADIDFTKEEPSAVLNYNVEIKGKDYNNITC
KVELFDEEGTKLSETEGSEGTFEISNVRLWQPLNAYLYKIKVTAGQDVYTLPYGVRSV
RVDGTKFLINEKPFYFKGYGKHEDTFPNGRGINLPMNTKDISIMKWQHANSFRTSHY
PYSEEMMRLCDEEGIVVIDETTAVGVNLQFGGGANFGGERIGTFDKEHGVQTQEHHK
DVIRDLISRDKNHACVVMWSIANEPDSAAEGAYDYFKPLYDLARELDPQKRPCTLVSV
QHTTADTDCSSQLSDVICLNRYYGWYFGGPDLEVSEIGLRKELSDWGKLGKPVMFTE
YGADTVSGLHDTTSVMYTEEYQVEYYEMNNKVFDEFDFVVGEQAWNFADFATSQSL
LRVQGNKKGLFTRDRKPKMVAHYFRNRWSTIPEFGYKTK
(EeG461H)

91 MLYPVLTQSRLLSDLSGVWDFKLDNGKGFEEKWYEKPLKDADTMPVPASYNDLKEG
TDFRDHYGWVFYQRNISVPEYVKSQRIVLRCAAVTHYAMIYLNGKLICEHKGGFLPFE
VELNDDLQDGDNLLTIAVNNVIDYTTLPVGGKANMMSGMMGGMGAGASDKPQNNP
NFDFFNYCGITRPVKIYTTPETYINDITVTADIDFTKEEPSAVLNYNVEIKGKDYNNITC
KVELFDEEGTKLSETEGSEGTFEISNVRLWQPLNAYLYKIKVTAGQDVYTLPYGVRSV
RVDGTKFLINEKPFYFKGYGKHEDTFPNGRGSNLPMNTKDISIMKWQHANSFRTSHY
PYSEEMMRLCDEEGIVVIDETTAVGVNLQFGGGANFGGERIGTFDKEHGVQTQEHHK
DVIRDLISRDKNHACVVMWSIANEPDSAAEGAYDYFKPLYDLARELDPQKRPCTLVSV
QNTTADTDCSSQLSDVICLNRYYGWYFGGPDLEVSEIGLRKELSDWGKLGKPVMFTE
YGADTVSGLHDTTSVMYTEEYQVEYYEMNNKVFDEFDFVVGEQAWNFADFATSQSL
LRVQGNKKGLFTRDRKPKMVAHYFRNRWSTIPEFGYKTK
(EeG461N)

92 MLYPVLTQSRLLSDLSGVWDFKLDNGKGFEEKWYEKPLKDADTMPVPASYNDLKEG
TDFRDHYGWVFYQRNISVPEYVKSQRIVLRCAAVTHYAMIYLNGKLICEHKGGFLPFE
VELNDDLQDGDNLLTIAVNNVIDYTTLPVGGKANMMSGMMGGMGAGASDKPQNNP
NFDFFNYCGITRPVKIYTTPETYINDITVTADIDFTKEEPSAVLNYNVEIKGKDYNNITC
KVELFDEEGTKLSETEGSEGTFEISNVRLWQPLNAYLYKIKVTAGQDVYTLPYGVRSV
RVDGTKFLINEKPFYFKGYGKHEDTFPNGRGINLPMNTKDISSMKWQHANSFRTSHY
PYSEEMMRLCDEEGIVVIDETTAVGVNLQFGGGANFGGERIGTFDKEHGVQTQEHHK

SUMMARY OF SEQUENCE LISTING

| SEQ ID NO: | DESCRIPTION |
|---|---|
| | DVIRDLISRDKNHACVVMWSIANEPDSAAEGAYDYFKPLYDLARELDPQKRPCTLVSV<br>QSTTADTDCSSQLSDVICLNRYYGWFGGPDLEVSEIGLRKELSDWGKLGKPVMFTEY<br>GADTVSGLHDTTSVMYTEEYQVEYYEMNNKVFDEFDFVVGEQAWNFADFATSQSLL<br>RVQGNKKGLFTRDRKPKMVAHYFRNRWSTIPEFGYKTK<br>(EeG461S) |
| 93 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGSFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEEIFRVDGNKKGIFT<br>RNRQPKAVAHLIRSRWNKLPLDYKSKK<br>(BpG563E) |
| 94 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEAIFRVDGNKKGIFT<br>RNRQPKAVAHLIRSRWNKLPLDYKSKK<br>(BpG563A) |
| 95 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEDIFRVDGNKKGIFT<br>RNRQPKAVAHLIRSRWNKLPLDYKSKK<br>(BpG563D) |
| 96 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEYIFRVDGNKKGIFT<br>RNRQPKAVAHLIRSRWNKLPLDYKSKK<br>(BpG563Y) |
| 97 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QSTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQGL<br>LRVQGNKKGLFTRDRKPKMVAHYFRNRWSTIPEFGYKTK<br>(EeS571G) |

SUMMARY OF SEQUENCE LISTING

| SEQ ID NO: | DESCRIPTION |
|---|---|
| 98 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQNL<br>LRVQGNKKGLFTRDRKPKMVAHYFRNRWSTIPEFGYKTK<br>(EeS571N) |
| 99 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGDATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVVIIRVDGNKKGVFTR<br>ERKPKAAAHTLKTRWSGMLGSDH<br>(Rxn3G560V) |
| 100 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGDATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVEIIRVDGNKKGVFTR<br>ERKPKAAAHTLKTRWSGMLGSDH<br>(Rxn3G560E) |
| 101 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYCGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294Y/T295C) |
| 102 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYIGFGKHEDSEIAGRGYNPPVIKRDFELIKWVGANSFRTSHYPYSEEIMQAADREG<br>IVIIDEVAAVGMFDVGSVLNPSASKTDYFSLDEVHSKTKEVHKKAVEELIKRDKNHPS<br>VVMWSLFNEPDTSKDEAVPYFEDIFNFAKSQDKQNLPKTFAAIQASSPGKCKCMHLC<br>DVITLNRYYGWYFLGGYEIDMSEEKFREEMNLYSNMNKPVMFTEYGADTYAGVHKL<br>PSVMWSEEYQCEYYEMNFKVFDSYDFIVGEQLWNFADFQTTEGIFRVDGNKKGIFTR<br>NRQPKAVAHLIRSRWNKLPLDYKSKK<br>(BpF294Y/T295I) |
| 103 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYVGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL |

SUMMARY OF SEQUENCE LISTING

| SEQ ID NO: | DESCRIPTION |
|---|---|
| | CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294Y/T295V) |
| 104 | MVNSMLYPRESRTRRVVDISGMWEFKSDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYFGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294Y/T295F) |
| 105 | MVNSMLYPRESRTRRVVDISGMWEFKSDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYMGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294Y/T295M) |
| 106 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYYKGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpF294Y/T295K) |
| 107 | MVNSMLYPRESRTRRVVDISGMWEFKSDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFVGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAALQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpT295V/I450L) |
| 108 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFVGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAMQASSPGKCKCMH<br>LCDVITLNRYYGWYFLGGYEIDMSEEKFREEMNLYSNMNKPVMFTEYGADTYAGVH<br>KLPSVMWSEEYQCEYYEMNFKVFDSYDFIVGEQLWNFADFQTTEGIFRVDGNKKGIF<br>TRNRQPKAVAHLIRSRWNKLPLDYKSKK<br>(BpT295V/I450M) |
| 109 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG |

| SUMMARY OF SEQUENCE LISTING |
|---|

| SEQ ID NO: | DESCRIPTION |
|---|---|
| | LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFVGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAYQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpT295V/I450Y) |
| 110 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFVGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAVQASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpT295V/I450V) |
| 111 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAMDASSPGKCKCMH<br>LCDVITLNRYYGWYFLGGYEIDMSEEKFREEMNLYSNMNKPVMFTEYGADTYAGVH<br>KLPSVMWSEEYQCEYYEMNFKVFDSYDFIVGEQLWNFADFQTTEGIFRVDGNKKGIF<br>TRNRQPKAVAHLIRSRWNKLPLDYKSKK<br>(BpI450M/Q451D) |
| 112 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAQDASSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpI450Q/Q451D) |
| 113 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIDESSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451D/A452E) |
| 114 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGSFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIDGSSPGKCKCMHL |

SUMMARY OF SEQUENCE LISTING

| SEQ ID NO: | DESCRIPTION |
|---|---|
| | CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451D/A452G) |
| 115 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGSFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIDQSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451D/A452Q) |
| 116 | MVNSMLYPRESRTRRVVDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIDSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451D/A452S) |
| 117 | MVNSMLYPRESRTRRWDISGMWEFKIDINNEGRNSGYANGLKDTTFIPVPSSFNDLF<br>TDKNIREHAGDVWYETSFYLPLEWKDKDVNVRFGCATHEATVYINGKEVCTHVGGF<br>MPFNAPVNEAGIFGEKNKLVVVVNNELSNTTIPCGHTETKPSGKKYIKPSFDFFNYAG<br>LNRPVKITVTNKEYIHDIDILSDVNGSDGIVNYEVHTTGENKVYIKINDEEGKEVASCE<br>GKSGKIVIKDAKLWNPKAAYLYKFIACIKNGDELIDEYYLDFGIRTVKVEGTKFLINGK<br>PFYFTGFGKHEDSEIAGRGYNPPVIKRDFELIKWVGANSFRTSHYPYSEEIMQAADRE<br>GIVIIDEVAAVGMFDVGSVLNPSASKTDYFSLDEVHSKTKEVHKKAVEELIKRDKNHP<br>SVVMWSLFNEPDTSKDEAVPYFEDIFNFAKSQDKQNLPKTFAAIDRSSPGKCKCMHL<br>CDVITLNRYYGWYFLGGYEIDMSEEKFREEMNLYSNMNKPVMFTEYGADTYAGVHK<br>LPSVMWSEEYQCEYYEMNFKVFDSYDFIVGEQLWNFADFQTTEGIFRVDGNKKGIFT<br>RNRQPKAVAHLIRSRWNKLPLDYKSKK<br>(BpQ451D/A452R) |
| 118 | MLYPVLTCSRLLSDLSGVWDFKLDNGKGFEEKWYEKPLKDADTMPVPASYNDLKEG<br>TDFRDHYGWVFYQRNICVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRKPKMVAHYFRNRWSTIPEFGYKTK<br>(EeQ8C/S73C) |
| 119 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP<br>NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGPDLEVSEIGLRKELSDWGKLGKPVMFTE<br>YGADTVSGLHDTTSVMYTEEYQVEYYEMNNKVFDEFDFVVGEQAWNFADFATSQSL<br>LRVQGNKKGLFTRDRCPKMVAHYFRNRWSTIPEFGYKTK<br>(EeK588C) |
| 120 | MLYPVLTQSRLLSDLSGVWDFKLDNGKGFEEKWYEKPLKDADTMPVPASYNDLKEG<br>TDFRDHYGWVFYQRNISVPEYVKSQRIVLRCAAVTHYAMIYLNGKLICEHKGGFLPFE<br>VELNDDLQDGDNLLTIAVNNVIDYTTLPVGGKANMMSGMMGGMGAGASDKPQNNP |

| SUMMARY OF SEQUENCE LISTING |
|---|

| SEQ ID NO: | DESCRIPTION |
|---|---|
| | NFDFFNYCGITRPVKIYTTPETYINDITVTADIDFTKEEPSAVLNYNVEIKGKDYNNITC<br>KVELFDEEGTKLSETEGSEGTFEISNVRLWQPLNAYLYKIKVTAGQDVYTLPYGVRSV<br>RVDGTKFLINEKPFYFKGYGKHEDTFPNGRGINLPMNTKDISIMKWQHANSFRTSHY<br>PYSEEMMRLCDEEGIVVIDETTAVGVNLQFGGGANFGGERIGTFDKEHGVQTQEHHK<br>DVIRDLISRDKNHACVVMWSIANEPDSAAEGAYDYFKPLYDLARELDPQKRPCTLVSV<br>QGTTADTDCSSQLSDVICLNRYYGWYFGGCDLEVSEIGLRKELSDWGKLGKPVMFTE<br>YGADTVSGLHDTTSVMYTEEYQVEYYEMNNKVFDEFDFVVGEQAWNFADFATSCSL<br>LRVQGNKKGLFTRDRKPKMVAHYFRNRWSTIPEFGYKTK<br>(EeP489C/Q570C) |
| 121 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANLGDATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3Y447L) |
| 122 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANPGDATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3Y447P) |
| 123 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNWASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANIGDATYEVDRISDMF<br>DVLCLNRYFGWYSQTGEVEEAEAALEKELLGWEGKYGKPIVITEYGADTMAGLHSVL<br>ALPWSEEFQVQLLDMYHRVFDRIDSVVGEHVWNFADFQTAVGIIRVDGNKKGVFTR<br>ERKPKAAAHTLKTRWSGMLGSDH<br>(Rxn3Y447I) |
| 124 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANQGDATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3Y447Q) |
| 125 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIWIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYEDATYEVDRISDM |

SUMMARY OF SEQUENCE LISTING

SEQ ID NO: DESCRIPTION

FDVLCLNRYFGWYSQTGEVEEAEAALEKELLGWEGKYGKPIVITEYGADTMAGLHSV
LALPWSEEFQVQLLDMYHRVFDRIDSWGEHVWNFADFQTAVGHRVDGNKKGVFTR
ERKPKAAAHTLKTRWSGMLGSDH
(Rxn3G448E)

126 MLKPQQTTTRDLISLDGLWKFALASDDNNTQPWTSQLKTSLECPVPASYNDIFADSK
IHDHVGWVYYQRDVIVPKGWSEERYLVRCEAATHHGRIYVNGNLVADHVGGYTPFE
ADITDLVAAGEQFRLTIAVDNELTYQTIPPGKVEILEATGKKVQTYQHDFYNYAGLAR
SVWLYSVPQQHIQDITVRTDVQGTTGLIDYNVVASTTQGTIQVAVIDEDGTTVATSSGS
NGTIHIPSVHLWQPGAAYLYQLHASIIDSSKKTIDTYKLATGIRTVKVQGTQFLINDKP
FYFTGFGKHEDSAVRGKGYDPAYMVHDFQLMDWMGANSFRTSHYPYAEEVMEFAD
RHGIVVIDETPAVGLAFSIGSGVSSEDSPQTFTPEGINNNTREAHKQAIRELIARDKNH
ASVVMWSIANEPASQEVGAREYFAPLVDLAHELDPSRPVCFANYKDATYEVDRISDM
FDVLCLNRYFGWYSQTGEVEEAEAALEKELLGWEGKYGKPIVITEYGADTMAGLHSV
LALPWSEEFQVQLLDMYHRVFDRIDSVVGEHVWNFADFQTAVGIIRVDGNKKGVFTR
ERKPKAAAHTLKTRWSGMLGSDH
(Rxn3G448K)

127 MLKPQQTTTRDLISLDGLWKFALASDDNNTQPWTSQLKTSLECPVPASYNDIFADSK
IHDHVGWVYYQRDVIVPKGWSEERYLVRCEAATHHGRIYVNGNLVADHVGGYTPFE
ADITDLVAAGEQFRLTIAVDNELTYQTIPPGKVEILEATGKKVQTYQHDFYNYAGLAR
SVWLYSVPQQHIQDITVRTDVQGTTGLIDYNVVASTTQGTIQVAVIDEDGTTVATSSGS
NGTIHIPSVHLWQPGAAYLYQLHASIIDSSKKTIDTYKLATGIRTVKVQGTQFLINDKP
FYFTGFGKHEDSAVRGKGYDPAYMVHDFQLMDWMGANSFRTSHYPYAEEVMEFAD
RHGIWIDETPAVGLAFSIGSGVSSEDSPQTFTPEGINNNTREAHKQAIRELIARDKNH
ASVVMWSIANEPASQEVGAREYFAPLVDLAHELDPSRPVCFANYFDATYEVDRISDM
FDVLCLNRYFGWYSQTGEVEEAEAALEKELLGWEGKYGKPIVITEYGADTMAGLHSV
LALPWSEEFQVQLLDMYHRVFDRIDSVVGEHVWNFADFQTAVGIIRVDGNKKGVFTR
ERKPKAAAHTLKTRWSGMLGSDH
(Rxn3G448F)

128 MLKPQQTTTRDLISLDGLWKFALASDDNNTQPWTSQLKTSLECPVPASYNDIFADSK
IHDHVGWVYYQRDVIVPKGWSEERYLVRCEAATHHGRIYVNGNLVADHVGGYTPFE
ADITDLVAAGEQFRLTIAVDNELTYQTIPPGKVEILEATGKKVQTYQHDFYNYAGLAR
SVWLYSVPQQHIQDITVRTDVQGTTGLIDYNVVASTTQGTIQVAVIDEDGTTVATSSGS
NGTIHIPSVHLWQPGAAYLYQLHASIIDSSKKTIDTYKLATGIRTVKVQGTQFLINDKP
FYFTGFGKHEDSAVRGKGYDPAYMVHDFQLMDWMGANSFRTSHYPYAEEVMEFAD
RHGIVVIDETPAVGLAFSIGSGVSSEDSPQTFTPEGINNNTREAHKQAIRELIARDKNH
ASVVMWSIANEPASQEVGAREYFAPLVDLAHELDPSRPVCFANYLDATYEVDRISDM
FDVLCLNRYFGWYSQTGEVEEAEAALEKELLGWEGKYGKPIVITEYGADTMAGLHSV
LALPWSEEFQVQLLDMYHRVFDRIDSVVGEHVWNFADFQTAVGIIRVDGNKKGVFTR
ERKPKAAAHTLKTRWSGMLGSDH
(Rxn3G448L)

129 MLKPQQTTTRDLISLDGLWKFALASDDNNTQPWTSQLKTSLECPVPASYNDIFADSK
IHDHVGWVYYQRDVIVPKGWSEERYLVRCEAATHHGRIYVNGNLVADHVGGYTPFE
ADITDLVAAGEQFRLTIAVDNELTYQTIPPGKVEILEATGKKVQTYQHDFYNYAGLAR
SVWLYSVPQQHIQDITVRTDVQGTTGLIDYNVVASTTQGTIQVAVIDEDGTTVATSSGS
NGTIHIPSVHLWQPGAAYLYQLHASIIDSSKKTIDTYKLATGIRTVKVQGTQFLINDKP
FYFTGFGKHEDSAVRGKGYDPAYMVHDFQLMDWMGANSFRTSHYPYAEEVMEFAD
RHGIVVIDETPAVGLAFSIGSGVSSEDSPQTFTPEGINNNTREAHKQAIRELIARDKNH
ASVVMWSIANEPASQEVGAREYFAPLVDLAHELDPSRPVCFANYCDATYEVDRISDM
FDVLCLNRYFGWYSQTGEVEEAEAALEKELLGWEGKYGKPIVITEYGADTMAGLHSV
LALPWSEEFQVQLLDMYHRVFDRIDSVVGEHVWNFADFQTAVGIIRVDGNKKGVFTR
ERKPKAAAHTLKTRWSGMLGSDH
(Rxn3G448C)

130 MLKPQQTTTRDLISLDGLWKFALASDDNNTQPWTSQLKTSLECPVPASYNDIFADSK
IHDHVGWVYYQRDVIVPKGWSEERYLVRCEAATHHGRIYVNGNLVADHVGGYTPFE
ADITDLVAAGEQFRLT1AVDNELTYQTIPPGKVEILEATGKKVQTYQHDFYNYAGLAR
SVWLYSVPQQHIQDITVRTDVQGTTGLIDYNVVASTTQGTIQVAVIDEDGTTVATSSGS
NGTIHIPSVHLWQPGAAYLYQLHASIIDSSKKTIDTYKLATGIRTVKVQGTQFLINDKP
FYFTGFGKHEDSAVRGKGYDPAYMVHDFQLMDWMGANSFRTSHYPYAEEVMEFAD
RHGIVVIDETPAVGLAFSIGSGVSSEDSPQTFTPEGINNNTREAHKQAIRELIARDKNH
ASVVMWSIANEPASQEVGAREYFAPLVDLAHELDPSRPVCFANYWDATYEVDRISD
MFDVLCLNRYFGWYSQTGEVEEAEAALEKELLGWEGKYGKPIVITEYGADTMAGLHS
VLALPWSEEFQVQLLDMYHRVFDRIDSVVGEHVWNFADFQTAVGIIRVDGNKKGVFT
RERKPKAAAHTLKTRWSGMLGSDH
(Rxn3G448W)

131 MLKPQQTTTRDLISLDGLWKFALASDDNNTQPWTSQLKTSLECPVPASYNDIFADSK
IHDHVGWVYYQRDVIVPKGWSEERYLVRCEAATHHGRIYVNGNLVADHVGGYTPFE
ADITDLVAAGEQFRLTIAVDNELTYQTIPPGKVEILEATGKKVQTYQHDFYNYAGLAR

SUMMARY OF SEQUENCE LISTING

| SEQ ID NO: | DESCRIPTION |
|---|---|
| | SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGQATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449Q) |
| 132 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGGATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449G) |
| 133 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGRATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449R) |
| 134 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASHDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGKATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449K) |
| 135 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGSATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449S) |
| 136 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNWASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGCATYEVDRISDM |

SUMMARY OF SEQUENCE LISTING

| SEQ ID NO: | DESCRIPTION |
|---|---|
| | FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449C) |
| 137 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQTYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASHDSSKKTIDTYKLATGIRTVKVQGTQFLINDKP<br>FYFTGFGKHEDSAVRGKGYDPAYMVHDFQLMDWMGANSFRTSHYPYAEEVMEFAD<br>RHGIVVIDETPAVGLAFSIGSGVSSEDSPQTFTPEGINNNTREAHKQAIRELIARDKNH<br>ASVVMWSIANEPASQEVGAREYFAPLVDLAHELDPSRPVCFANYGEATYEVDRISDM<br>FDVLCLNRYFGWYSQTGEVEEAEAALEKELLGWEGKYGKPIVITEYGADTMAGLHSV<br>LALPWSEEFQVQLLDMYHRVFDRIDSVVGEHVWNFADFQTAVGIIRVDGNKKGVFTR<br>ERKPKAAAHTLKTRWSGMLGSDH<br>(Rxn3D449E) |
| 138 | MLKPQQTTTRDLISLDGLWKFALASDDNNTQPWTSQLKTSLECPVPASYNDIFADSK<br>IHDHVGWVYYQRDVIVPKGWSEERYLVRCEAATHHGRIYVNGNLVADHVGGYTPFE<br>ADITDLVAAGEQFRLTIAVDNELTYQTIPPGKVEILEATGKKVQIYQHDFYNYAGLAR<br>SVWLYSVPQQHIQDITVRTDVQGTTGLIDYNVVASTTQGTIQVAVIDEDGTTVATSSGS<br>NGTIHIPSVHLWQPGAAYLYQLHASIIDSSKKTIDTYKLATGIRTVKVQGTQFLINDKP<br>FYFTGFGKHEDTNIRGKGHDDAYMVHDFQLLHWMGANSFRTSHYPYAEEVMEYAD<br>RQGIVVIDETPAVGLAFSIGAGAQTSNPPATFSPDRINNKTREAHAQAIRELIHRDKNH<br>PSVVMWSIANEPASNEDGAREYFAPLPKLARQLDPTRPVTFANVGLATYKADRIADL<br>FDVLCLNRYFGWYTQTAELDEAEAALEEELRGWTEKYDKPIVMTEYGADTVAGLHS<br>VMVTPWSEEFQVEMLDMYHRVFDRFEAMAGEQVWNFADFQTAVGVSRVDGNKKG<br>VFTRDRKPKAAAHLLRKRWTNLHNGTAEGGKTFQ<br>(AoGUS: *Aspergillus oryzae* BGUS) |

SEQUENCE LISTING

```
Sequence total quantity: 139
SEQ ID NO: 1            moltype = AA  length = 604
FEATURE                 Location/Qualifiers
source                  1..604
                        mol_type = protein
                        organism = Aspergillus oryzae
SEQUENCE: 1
MLKPQQTTTR DLISLDGLWK FALASDDNNT QPWTSQLKTS LECPVPASYN DIFADSKIHD   60
HVGWVYYQRD VIVPKGWSEE RYLVRCEAAT HHGRIYVNGN LVADHVGGYT PFEADITDLV  120
AAGEQFRLTI AVDNELTYQT IPPGKVEILE ATGKKVQTYQ HDFYNYAGLA RSVWLYSVPQ  180
QHIQDITVRT DVQGTTGLID YNVVASTTQG TIQVAVIDED GTTVATSSGS NGTIHIPSVH  240
LWQPGAAYLY QLHASIIDSS KKTIDTYKLA TGIRTVKVQG TQFLINDKPF YFTGFGKHED  300
TNIRGKGHDD AYMVHDFQLL HWMGANSFRT SHYPYAEEVM EYADRQGIVV IDETPAVGLA  360
FSIGAGAQTS NPPATFSPDR INNKTREAHA QAIRELIHRD KNHPSVVMWS IANEPASNED  420
GAREYFAPLP KLARQLDPTR PVTFANVGLA TYKADRIADL FDVLCLNRYF GWYTQTAELD  480
EAEAALEEEL RGWTEKYDKP IVMTEYGADT VAGLHSVMVT PWSEEFQVEM LDMYHRVFDR  540
FEAMAGEQVW NFADFQTAVG VSRVDGNKKG VFTRDRKPKA AAHLLRKRWT NLHNGTAEGS  600
KTFQ                                                               604

SEQ ID NO: 2            moltype = AA  length = 599
FEATURE                 Location/Qualifiers
source                  1..599
                        mol_type = protein
                        organism = Aspergillus terreus
SEQUENCE: 2
MLKPRQTPFR DLISLDGLWK FALDSGDNAT AAPWTGPLTT DLECPVPASY NDIFVDRQIR   60
DHVGWVYYQR EAIVPRAWSQ QQYLVRVDAA THQGRIYIND NLVAEHRGGY TPFEADITGL  120
VSAGDSFRLT IAVNNELTHE TIPPGRIEVE EYTGKRVQVY QHDFFNYAGL ARSVWLYSVP  180
QQHIQDIKVV THVKGSAGLI NYLVTVSNST TGRVKIDVID KDGTTVAEAS GARGSVTIDS  240
VKLWQPGEAY LYQFRASIVG LNDSVVDTYC VETGVRTVKV SGNRFLINDK PFYFTGFGKH  300
EDSAVRGKGY DPAYMVHDFQ LMDWMGANSF RTSHYPYAEE VMEFADRHGI VVIDETPAVG  360
LAFSIGSGVS SEDSPQTFTP EGINNNTREA HKQAIRELIA RDKNHASVVM WSIANEPASQ  420
EVGAREYFAP LVDLAHELDP SRPVCFANYG DATYEVDRIS DMFDVLCLNR YFGWYSQTGE  480
VEEAEAALEK ELLGWEGKYG KPIVITEYGA DTMAGLHSVL ALPWSEEFQV QLLDMYHRVF  540
DRIDSVVGEH VWNFADFQTA VGIIRVDGNK KGVFTRERKP KAAAHTLKTR WSGMLGSDH   599
```

```
SEQ ID NO: 3              moltype = AA  length = 594
FEATURE                   Location/Qualifiers
source                    1..594
                          mol_type = protein
                          organism = Bacteroides fragilis
SEQUENCE: 3
MKKLLAAAML FMLNSWSCFS ADTPRAEYPR PQFEREQWVN LNGTWTFDFD FGKSGKDRRL   60
QSAEKFDKNI TVPFCPESKL SGVGYTDFIE QMWYQRNITI PSDWNGKKIF LNFGAVDYCA  120
EIYVDGKFVQ RHFGGSSSFA VDLTRYVTPG KTHNLVVFVQ DDLRSGLQTG GKQCGNYYSG  180
GCSYTRTTGI WQTVWMEAVS ADGLKSVFVR PDIDQKQLVI EPEFYNESAN TLEITLKDRN  240
KTVAKKSVNC ANSSVVVLPV KNMKLWSPED PFLYDLVYQV KDAKGNVLDE VKSYAGMRKV  300
HTANGRFYLN NQPYFQRLVL DQGFYPEGIW TAPSDEDLKN DIVLGKEAGF NGARLHQKVF  360
EERYYYWADK LGYITWGESA SWMLDVNKEL AARNFLGEWS EVVVRDRNHP SLVTWTPFNE  420
TWGGGPDAYI RLVRDVYNIT KAIDPTRPVN DASGDNHVIT DIWSVHNYEQ DRAKLTEQLK  480
MEEGKEPYRN ARDKDFLAVY EGQPYMVDEF GGIPWMAEKD RKNSWGYGGM PENAEAFYKR  540
LEGQIDAFID SPHVTGFCYT QLTDVEQEKN GIYYYDRTPK LDMKRIKAIF EKIK        594

SEQ ID NO: 4              moltype = AA  length = 603
FEATURE                   Location/Qualifiers
source                    1..603
                          mol_type = protein
                          organism = Bacteroides uniformis
SEQUENCE: 4
MKTLLKNSLT FLLMLMPVLA FAQQAPQIMN VSARQTTSLD GQWKTIVDPF ENGYYDYRLK   60
PYDGGYAQDK TYSDKTKLQE YDFETDKLLF VPGDWNTQRP QLYYYEGTVW YRKHFEYSLQ  120
PGKRLFLNFG AVNYEAIVWL NGKRLGRHIG GFTPFNFEIT NLLKEGTNSL VVKVDNKRLP  180
EAVPTVNADW WNFGGITRPV TLIEMPATYI RDYYVQLAKD DKNMIEGWVQ LEGSDKEQKI  240
TLDIPELKVK KEVTTDANGY ASFLIKSKPI LWTPENPKLY AVNLASETDK VSDEIGFRTI  300
RTEGIKILLN DKEIFCRGIS IHEETPYYSG RAYSKDHAHT LLSWAKELGC NFVRLAHYPH  360
NEEMVREAER MGFLVWSEIP VYWTIHWENK DTYQNAEQQL CDMIARDKNR CNIIIWSIAN  420
ETPHSETRLT FLSNLANKAR SLDSVRLIGA AMEKEEVQPG VLTVNDPLGE LLDIISFNEY  480
VGWYDGDSEK CDRVNWTFDT QKPVFISELG GGALYGRHGS PKERFTEEYQ EDLYIRHVNM  540
LKRIPGLAGT TPWILKDFRS PRRHVPEIQD DFNRKGLVSD KGQKKAFFV LQKWYKELTE  600
AYK                                                                603

SEQ ID NO: 5              moltype = AA  length = 603
FEATURE                   Location/Qualifiers
source                    1..603
                          mol_type = protein
                          organism = Brachyspira pilosicoli
SEQUENCE: 5
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 6              moltype = AA  length = 601
FEATURE                   Location/Qualifiers
source                    1..601
                          mol_type = protein
                          organism = Brachyspira murdochii
SEQUENCE: 6
MVNSMLYPRE SRTRRVVDIS GMWEFKIDSN NEGRKNGYAN GLKDTTFIPV PSSFNDLFTD   60
KNIREHAGDI WYETSFYLPL EWKDKNVNIR FGCATHEAAV YINGKEVCTH VGGFMPFNAP  120
VNEAGIFGEK NKLVVVVNNE LSNTTLPCGH TETKPSGKKY IKPSFDFFNY AGLNRPVKIT  180
VTNKEYIYDI DILSDINGSD GIVNYEVHTT GENKVFVKIY DEEGKEAASA EGKNGKIVIK  240
NAKLWNPKAA YLYKFEACIK NGEELIDEYY LDFGIRTIKV EGTKFLINGK PFYFTGFGKH  300
EDSETAGRGY NPPVIKRDFE LIKWIGANSF RTSHYPYSEE IMQAADREGI VIIDEIAAVG  360
MFDVGSVLNP GASKADYFSL EEVHTKTKEI HKKAVEELIT RDKNHPSVVM WSLFNEPDTS  420
KDEALPYFED IFNFAKSIDK QNLPKTFAAI QASPGKCKC MHLCDVITLN RYYGWYFLGG   480
YEIDMSEEKF REEMNLYKDM NKPVMFTEYG ADTYAGVHKL PSVMWSEEYQ CEYYEMNFKV  540
FDSYDFIIGE QLWNFADFQT TEGIFRVDGN KKGIFTRTRQ PKAVAHYIRS RWTKLPLDYK  600
K                                                                  601

SEQ ID NO: 7              moltype = AA  length = 599
FEATURE                   Location/Qualifiers
source                    1..599
                          mol_type = protein
                          organism = Clostridium perfringens
SEQUENCE: 7
MLYPIITESR QLIDLSGIWK FKLNEGNGLT EELSKAPLED TIEMAVPSSY NDLVESQEVR   60
DHVGWVWYER NFTIPKTLLN ERIVLRFGSA THEAKVYLNG ELLVEHKGGF TPFEAEINDL  120
```

```
LVSGDNRLTV AVNNIIDETT LPVGLVKEVE VDGKKVIKNS VNFDFFNYAG IHRPVKIYTT    180
PKSYIEDITI VTDFKENNGY VNYEQVAVGK CNIKVTIIDE ENNIVAEGEG KEGKLTINNV    240
HLWEPMNAYL YKLKVELLDD EEIIDTYFEE FGVRTVEVKD GKFLINNKPF YFKGFGKHED    300
SYVNGRGINE AINIKDFNLM KWIGANSFRT SHYPYSEEIM RLADREGIVV IDETPAVGLH    360
LNFMATGFGG DAPKRDTWKE IGTKEAHERI LRELVSRDKN HPCVVMWSVA NEPDSDSEGA    420
KEYFEPLIKL TKELDPQKRP VTVVTYLMST PDRCKVGDIV DVLCLNRYYG WYVAGGDLEE    480
AKRMLEDELK GWEERCPKTP IMFTEYGADT VAGLHDTVPV MFTEEYQVEY YKANHEVMDK    540
CKNFVGEQVW NFADFATSQG IIRVQGNKKG IFTRERKPKM IAHSLRERWT NIPEFGYKK     599

SEQ ID NO: 8              moltype = AA   length = 603
FEATURE                   Location/Qualifiers
source                    1..603
                          mol_type = protein
                          organism = Escherichia coli
SEQUENCE: 8
MLRPVETPTR EIKKLDGLWA FSLDRENCGI DQRWWESALQ ESRAIAVPGS FNDQFADADI    60
RNYAGNVWYQ REVFIPKGWA GQRIVLRFDA VTHYGKVWVN NQEVMEHQGG YTPFEADVTP    120
YVIAGKSVRI TVCVNNELNW QTIPPGMVIT DENGKKKQSY FHDFFNYAGI HRSVMLYTTP    180
NTWVDDITVV THVAQDCNHA SVDWQVVANG DVSVELRDAD QQVVATGQGT SGTLQVVNPH    240
LWQPGEGYLY ELCVTAKSQT ECDIYPLRVG IRSVAVKGEQ FLINHKPFYF TGFGRHEDAD    300
LRGKGFDNVL MVHDHALMDW IGANSYRTSH YPYAEEMLDW ADEHGIVVID ETAAVGFNLS    360
LGIGFEAGNK PKELYSEEAV NGETQQAHLQ AIKELIARDK NHPSVVMWSI ANEPDTRPQG    420
AREYFAPLAE ATRKLDPTRP ITCVNVMFCD AHTDTISDLF DVLCLNRYYG WYVQSGDLET    480
AEKVLEKELL AWQEKLHQPI IITEYGVDTL AGLHSMYTDM WSEEYQCAWL DMYHRVFDRV    540
SAVVGEQVWN FADFATSQGI LRVGGNKKGI FTRDRKPKSA AFLLQKRWTG MNFGEKPQQG    600
GKQ                                                                 603

SEQ ID NO: 9              moltype = AA   length = 608
FEATURE                   Location/Qualifiers
source                    1..608
                          mol_type = protein
                          organism = synthetic construct
                          note = Description of Artificial Sequence: Synthetic
                          polypeptide
SEQUENCE: 9
MLRPVETPTR EIKKLDGLWA FSLDRENCGI DQRWWESALQ ESRAIAVPGS FNDQFADADI    60
RNYAGNVWYQ REVFIPKGWA GQRIVLRFDA VTHYGKVWVN NQEVMEHQGG YTPFEADVTP    120
YVIAGKSVRI TVCVNNELNW QTIPPGMVIT DENGKKKQSY FHDFFNYAGI HRSVMLYTTP    180
NTWVDDITVV THVAQDCNHA SVDWQVVANG DVSVELRDAD QQVVATGQGT SGTLQVVNPH    240
LWQPGEGYLY ELCVTAKSQT ECDIYPLRVG IRSVAVKGEQ FLINHKPFYF TGFGRHEDAD    300
LRGKGFDNVL MVHDHALMDW IGANSYRTSH YPYAEEMLDW ADEHGIVVID ETAAVGFNLS    360
LGIGFEAGNK PKELYSEEAV NGETQQAHLQ AIKELIARDK NHPSVVMWSI ANEPDTRPQG    420
AREYFAPLAE ATRKLDPTRP ITCVNVMFCD AHTDTISDLF DVLCLNRYYG WYVQSGDLET    480
AEKVLEKELL AWQEKLHQPI IITEYGVDTL AGLHSMYTDM WSEEYQCAWL DMYHRVFDRV    540
SAVVGEQVWN FADFATSQSI LRVGGNKKGI FTRDRKPKSA AFLLQKRWTG MNFGEKPQQG    600
SKQGLCGR                                                            608

SEQ ID NO: 10             moltype = AA   length = 611
FEATURE                   Location/Qualifiers
source                    1..611
                          mol_type = protein
                          organism = Eubacterium eligens
SEQUENCE: 10
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLPE KLICEHKGGF LPFEVELNDD    120
LQDGDNLLTI AVNNVIDYTT LPVGGKANMM SGMMGGMGAG ASDKPQNNPN FDFFNYCGIT    180
RPVKIYTTPE TYINDITVTA DIDFTKEEPS AVLNYNVEIK GKDYNNITCK VELFDEEGTK    240
LSETEGSEGT FEISNVRLWQ PLNAYLYKIK VTAGQDVYTL PYGVRSVRVD GTKFLINEKP    300
FYFKGYGKHE DTFPNGRGIN LPMNTKDISI MKWQHANSFR TSHYPYSEEM MRLCDEEGIV    360
VIDETTAVGV NLQFGGGANF GGERIGTFDK EHGVQTQEHH KDVIRDLISR DKNHACVVMW    420
SIANEPDSAA EGAYDYFKPL YDLARELDPQ KRPCTLVSVQ GTTADTDCSS QLSDVICLNR    480
YYGWYFGGPD LEVSEIGLRK ELSDWGKLGK PVMFTEYGAD TVSGLHDTTS VMYTEEYQVE    540
YYEMNNKVFD EFDFVVGEQA WNFADFATSQ SLLRVQGNKK GLFTRDRKPK MVAHYFRNRW    600
STIPEFGYKT K                                                        611

SEQ ID NO: 11             moltype = AA   length = 651
FEATURE                   Location/Qualifiers
source                    1..651
                          mol_type = protein
                          organism = Homo sapiens
SEQUENCE: 11
MARGSAVAWA ALGPLLWGCA LGLQGGMLYP QESPSRECKE LDGLWSFRAD FSDNRRRGFE    60
EQWYRRPLWE SGPTVDMPVP SSFNDISQDW RLRHFVGWVW YEREVILPER WTQDLRTRVV    120
LRIGSAHSYA IVWVNGVDTL EHEGGYLPFE ADISNLVQVG PLPSRLRITI AINNTLTPTT    180
LPPGTIQYLT DTSKYPKGYF VQNTYFDFFN YAGLQRSVLL YTTPTTYIDD ITVTTSVEQD    240
SGLVNYQISV KGSNLFKLEV RLLDAENKVV ANGTGTQGQL KVPGVSLWWP YLMHERPAYL    300
YSLEVQLTAQ TSLGPVSDFY TLPVGIRTVA VTKSQFLING KPFYFHGVNK HEDADIRGKG    360
FDWPLLVKDF NLLRWLGANA FRTSHYPYAE EVMQMCDRYG IVVIDECPGV GLALPQFFNN    420
VSLHHHMQVM EEVVRRDKNH PAVVMWSVAN EPASHLESAG YYLKMVIAHT KSLDPSRPVT    480
```

```
FVSNSNYAAD KGAPYVDVIC LNSYYSWYHD YGHLELIQLQ LATQFENWYK KYQKPIIQSE   540
YGAETIAGFH QDPPLMFTEE YQKSLLEQYH LGLDQKRRKY VVGELIWNFA DFMTEQSPTR   600
VLGNKKGIFT RQRQPKSAAF LLRERYWKIA NETRYPHSVA KSQCLENSLF T            651

SEQ ID NO: 12             moltype = AA   length = 603
FEATURE                   Location/Qualifiers
source                    1..603
                          mol_type = protein
                          organism = Lactobacillus brevis
SEQUENCE: 12
MLYPMETASR VVLDLSGVWR FMIDKEQIPV DVTRPLPATL SMAVPASFND QTASKEIREH   60
VGYVWYERCF ELPQLLRQER LVLRFGSATH EAWVYLNGHL ITHHKGGFTP FEVEINDDLV   120
TGENRLTVKL SNMLDYTTLP VGHYKETQNE TGQRVRQLDE NFDFFNYAGL QRPVKIYSTP   180
HSYIRDITLT PKVNLTNHSA VVNGEIETVG DVEQVVVTIL DEDNQVVGTT SGKTLAIELN   240
SVHLWQPGKA YLYRAKVELY QAGQVIDTYI ETFGIRQIAV KAGKFLINGQ PFYFKGFGKH   300
EDAYIHRGRL SEPQNVLDLS LMKQMGANSF RTSHYPYSEE MMRLCDREGI VVIDEVPAVG   360
LMLSFTFDVS ALEKDDFEDD TWEKLRTAEA HRQAITEMID RDKNHASVVM WSISNEAANF   420
SKGAYEYFKP LFDLARKLDP QQRPCTYTSI MMTTLKTDRC LALADVIALN RYYGWYMGNG   480
DLKAAETATR EELLAYQAKF PDKPIMYTEY GADTIAGLHS NYDEPFSEEF QEDYYRMCSR   540
VFDEVTNFVG EQLWNFADFQ TKFGIQRVQG NKKGIFTRAR EPKMVVRYLT QRWRNIPDFN   600
YKK                                                                 603

SEQ ID NO: 13             moltype = AA   length = 648
FEATURE                   Location/Qualifiers
source                    1..648
                          mol_type = protein
                          organism = Mus musculus
SEQUENCE: 13
MSLKWSACWV ALGQLLCSCA LALKGGMLFP KESPSRELKA LDGLWHFRAD LSNNRLQGFE   60
QQWYRQPLRE SGPVLDMPVP SSFNDITQEA ALRDFIGWVW YEREAILPRR WTQDTDMRVV   120
LRINSAHYYA VVWVNGIHVV EHEGGHLPFE ADISKLVQSG PLTTCRITIA INNTLTPHTL   180
PPGTIVYKTD TSMYPKGYFV QDTSFDFFNY AGLHRSVVLY TTPTTYIDDI TVITNVEQDI   240
GLVTYWISVQ GSEHFQLEVQ LLDEGGKVVA HGTGNQGQLQ VPSANLWWPY LMHEHPAYMY   300
SLEVKVTTTE SVTDYYTLPI GIRTVAVTKS KFLINGKPFY FQGVNKHEDS DIRGKGFDWP   360
LLVKDFNLLR WLGANSFRTS HYPYSEEVLQ LCDRYGIVVI DECPGVGIVL PQSFGNESLR   420
HHLEVMEELV RRDKNHPAVV MWSVANEPSS ALKPAAYYFK TLITHTKALD LTRPVTFVSN   480
AKYDADLGAP YVDVICVNSY FSWYHDYGHL EVIQPQLNSQ FENWYKTHQK PIIQSEYGAD   540
AIPGIHEDPP RMFSEEYQKA VLENYHSVLD QKRKEYVVGE LIWNFADFMT NQSPLRVIGN   600
KKGIFTRQRQ PKTSAFILRE RYWRIANETG GHGSGPRTQC FGSRPFTF                648

SEQ ID NO: 14             moltype = AA   length = 617
FEATURE                   Location/Qualifiers
source                    1..617
                          mol_type = protein
                          organism = Parabacteroides sp.
SEQUENCE: 14
MKRISIAFLS LFLCVASVWS MPRPEYPRPQ FERAGWVNLN GEWTCSFDFG GSGMEREFYK   60
SKGFDKKITV PFCPESKLSG IGYTDFINHF WYQRPITIPQ EWNGKNILLN FGAVYYKSEV   120
YIDGVLASRH FGGTSSFAVD ITSLVKPGQT HSLVVYVESD VRGAKQAAGK QNLQYASYGC   180
NYTRTTGIWQ TVWMEAVHPE GLQSIQLLTD IDQQQLVVRP RFYKEAGGKL QVTLKDNGKV   240
VASRTVSASS LSSVVLPVKK MKTWSPESPF LYDLEYKVLD KNGNIIDEVN GYAGMRKVHI   300
EGNKIYLNNK PYYQRLVLDQ GFYPDGIWTA PSDEALKRDI ELSMEAGFNG ARLHQKVFEE   360
RFYYWADKMG YLTWGEASSW GMDCNDTETA RNFITEWSEI VQRDRNHPSL LIWTPTNEEF   420
WPDRVQYPRL MHDLYNLTKM IDPTRPFHGA SGGTHIATDI WTVHNYEQDP AKLKEKLYNG   480
GKLMEAPKWE IHLMPMNIGY NGLKYTDQYA FPEYKKDMPY LVDEFGGIKW NPSQQMESAQ   540
NTSWGYGEPP RSLEEFYARL EGQVDAVLSL SNDIWGYCYT QLTDVEQEQN GIYYYDRTPK   600
FDMKRIHAIF SKTPESK                                                  617

SEQ ID NO: 15             moltype = AA   length = 602
FEATURE                   Location/Qualifiers
source                    1..602
                          mol_type = protein
                          organism = Staphylococcus sp.
SEQUENCE: 15
MLYPINTETR GVFDLNGVWN FKLDYGKGLE EKWYESKLTD TISMAVPSSY NDIGVTKEIR   60
NHIGYVWYER EFTVPAYLKD QRIVLRFGSA THKAIVYVNG ELVVEHKGGF LPFEAEINNS   120
LRDGMNRVTV AVDNILDDST LPVGLYSERH EEGLGKVIRN KPNFDFFNYA GLHRPVKIYT   180
TPFTYVEDIS VVTDFNGPTG TVTYTVDFQG KAETVKVSVV DEEGKVVAST EGLSGNVEIP   240
NVILWEPLNT YLYQIKVELV NDGLTIDVYE EPFGVRTVEV NDGKFLINNK PFYFKGFGKH   300
EDTPINGRGF NEASNVMDFN ILKWIGANSF RTAHYPYSEE LMRLADREGL VVIDETPAVG   360
VHLNFMATTG LGEGSERVST WEKIRTFEHH QDVLRELVSR DKNHPSVVMW SIANEAATEE   420
EGAYEYFKPL VELTKELDPQ KRPVTIVLFV MATPETDKVA ELIDVIALNR YNGWYFDGGD   480
LEAAKVHLRQ EFHAWNKRCP GKPIMITEYG ADTVAGFHDI DPVMFTEEYQ VEYYQANHVV   540
FDEFENFVGE QAWNFADFAT SQGVMRVQGN KKGVFTRDRK PKLAAHVFRE RWTNIPDFGY   600
KN                                                                  602

SEQ ID NO: 16             moltype = AA   length = 599
FEATURE                   Location/Qualifiers
source                    1..599
```

```
                            mol_type = protein
                            organism = Streptococcus agalactiae
SEQUENCE: 16
MLYPLLTKTR NTYDLGGIWN FKLGEHNPNE LLPSDEVMVI PTSFNDLMVS KEKRDYIGDF    60
WYEKVIEVPK VSEGEEMVLR FGSVTHQAKI YVDGILVGEH KGGFTPFEVL VPECKYNNEK   120
IKVSICANNV LDYTTLPVGN YSEIIQEDGS IKKKVRENFD FFNYAGVHRP LKLMIRPKNH   180
ISDITITSRL SDDLQSADLH FLVETNQKVD EVRISVFDED NKLVGETKDS RLFLSDVHLW   240
EVLNAYLYTA RVEIFVDNQL QDVYEENFGL REIEVTNGQF LLNRKPIYFK GFGKHEDTFI   300
NGRGLNEAAN LMDLNLLKDI GANSFRTSHY PYSEEMMRLA DRMGVLVIDE VPAVGLFQNF   360
NASLDLSPKD NGTWSLMQTK AAHEQAIQEL VKRDKNHPSV VMWVVANEPA SHEAGAHDYF   420
EPLVKLYKDL DPQKRPVTLV NILMATPDRD QVMDLVDVVC LNRYYGWYVD HGDLTNAEVG   480
LRKELLEWQD KFPDKPIIIT EYGADTLPGL HSTWNIPYTE EFQCDFYEMS HRVFDGIPNL   540
VGEQVWNFAD FETNLMILRV QGNHKGLFSR NRQPKQVVKE FKKRWMTIPH YHNKKNSVK    599

SEQ ID NO: 17               moltype = AA   length = 606
FEATURE                     Location/Qualifiers
source                      1..606
                            mol_type = protein
                            organism = synthetic construct
                            note = Description of Artificial Sequence: Synthetic
                             polypeptide
SEQUENCE: 17
MLKPRQTPFR DLISLDGLWK FALDSGDNAT AAPWTGPLTT DLECPVPASY NDIFVDRQIR    60
DHVGWVYYQR EAIVPRAWSQ QQYLVRVDAA THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGKH   300
EDTNIRGKGH DDAYMVHDFQ LLHWMGANSF RTSHYPYAEE VMEYADRQGI VVIDETPAVG   360
LAFSIGAGAQ TSNPPATFSP DRINNKTREA HAQAIRELIH RDKNHPSVVM WSIANEPASN   420
EDGAREYFAP LPKLARQLDP TRPVTFANVG LATYKADRIA DLFDVLCLNR YFGWYTQTAE   480
LDEAEAALEE ELRGWTEKYD KPIVMTEYGA DTVAGLHSVM VTPWSEEFQV EMLDMYHRVF   540
DRFEAMAGEQ VWNFADFQTA VGVSRVDGNK KGVFTRDRKP KAAAHLLRKR WTNLHNGTAE   600
GSKTFQ                                                              606

SEQ ID NO: 18               moltype = AA   length = 609
FEATURE                     Location/Qualifiers
source                      1..609
                            mol_type = protein
                            organism = synthetic construct
                            note = Description of Artificial Sequence: Synthetic
                             polypeptide
SEQUENCE: 18
MLKPRQTPFR DLISLDGLWK FALDSGDNAT AAPWTGPLTT DLECPVPASY NDIFVDRQIR    60
DHVGWVYYQR EAIVPRAWSQ QQYLVRVDAA THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGRH   300
EDADLRGKGF DNVLMVHDHA LMDWIGANSY RTSHYPYAEE MLDWADEHGI VVIDETAAVG   360
FNLSLGIGFE AGNKPKELYS EEAVNGETQQ AHLQAIKELI ARDKNHPSVV MWSIANEPDT   420
RPQGAREYFA PLAEATRKLD PTRPITCVNV MFCDAHTDTI SDLFDVLCLN RYYGWYVQSG   480
DLETAEKVLE KELLAWQEKL HQPIIITEYG VDTLAGLHSM YTDMWSEEYQ CAWLDMYHRV   540
FDRVSAVVGE QVWNFADFAT SQSILRVGGN KKGIFTRDRK PKSAAFLLQK RWTGMNFGEK   600
PQQGSKTFQ                                                           609

SEQ ID NO: 19               moltype = AA   length = 597
FEATURE                     Location/Qualifiers
source                      1..597
                            mol_type = protein
                            organism = synthetic construct
                            note = Description of Artificial Sequence: Synthetic
                             polypeptide
SEQUENCE: 19
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVN EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANYGDA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH      597

SEQ ID NO: 20               moltype = AA   length = 607
FEATURE                     Location/Qualifiers
source                      1..607
                            mol_type = protein
                            organism = synthetic construct
                            note = Description of Artificial Sequence: Synthetic
```

```
                        polypeptide
SEQUENCE: 20
MLKPRQTPFR DLISLDGLWK FALDSGDNAT AAPWTGPLTT DLECPVPASY NDIFVDRQIR    60
DHVGWVYYQR EAIVPRAWSQ QQYLRVDAA  THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGRH   300
EDADLRGKGF DNVLMVHDHA LMDWIGANSY RTSHYPYAEE MLDWADEHGI VVIDETAAVG   360
FNLSLGIGFE AGNKPKELYS EEAVNGETQQ AHLQAIKELI ARDKNHPSVV MWSIANEPDT   420
RPQGAREYFA PLAEATRKLD PTRPITCVNV MFCDAHTDTI SDLFDVLCLN RYYGWYVQSG   480
DLETAEKVLE KELLAWQEKL HQPIIITEYG VDTLAGLHSM YTDMWSEEYQ CAWLDMYHRV   540
FDRVSAVVGE QVWNFADFAT SQSILRVGGN KKGIFTRDRK PKSAAFLLQK RWTGMNFGEK   600
PQQGSDH                                                            607

SEQ ID NO: 21             moltype = AA  length = 612
FEATURE                   Location/Qualifiers
source                    1..612
                          mol_type = protein
                          organism = synthetic construct
                          note = Description of Artificial Sequence: Synthetic
                          polypeptide
SEQUENCE: 21
MLKPRQTPFR DLISLDGLWK FALDSGDNAT AAPWTGPLTT DLECPVPASY NDIFVDRQIR    60
DHVGWVYYQR EAIVPRAWSQ QQYLRVDAA  THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGRH   300
EDADLRGKGF DNVLMVHDHA LMDWIGANSY RTSHYPYAEE MLDWADEHGI VVIDETAAVG   360
FNLSLGIGFE AGNKPKELYS EEAVNGETQQ AHLQAIKELI ARDKNHPSVV MWSIANEPDT   420
RPQGAREYFA PLAEATRKLD PTRPITCVNV MFCDAHTDTI SDLFDVLCLN RYYGWYVQSG   480
DLETAEKVLE KELLAWQEKL HQPIIITEYG VDTLAGLHSM YTDMWSEEYQ CAWLDMYHRV   540
FDRVSAVVGE QVWNFADFAT SQSILRVGGN KKGIFTRDRK PKSAAFLLQK RWTGMNFGEK   600
PQQGSKQGLC GR                                                      612

SEQ ID NO: 22             moltype = AA  length = 612
FEATURE                   Location/Qualifiers
source                    1..612
                          mol_type = protein
                          organism = synthetic construct
                          note = Description of Artificial Sequence: Synthetic
                          polypeptide
SEQUENCE: 22
MLKPRQTPFR DLISLDGLWK FALDSGDNAT AAPWTGPLTT DLECPVPASY NDIFVDRQIR    60
DHVGWVYYQR EAIVPRAWSQ QQYLRVDAA  THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGRH   300
EDADLRGKGF DNVLMVHDHA LMDWIGANSY RTSHYPYAEE MLDWADEHGI VVIDETAAVG   360
FNLSLGIGFE AGNKPKELYS EEAVNGETQQ AHLQAIKELI ARDKNHPSVV MWSIANEPDT   420
RPQGAREYFA PLAEATRKLD PTRPITCVNV MFCDAHTDTI SDLFDVLCLN RYYGWYVQSG   480
DLETAEKVLE KELLAWQEKL HQPIIITEYG VDTLAGLHSM YTDMWSEEYQ CAWLDMYHRV   540
FDRVSAVVGE QVWNFADFAT SQSILRVGGN KKGIFTRDRK PKSAAFLLQK RWTGMNFGEK   600
PQQGSKQGLC GR                                                      612

SEQ ID NO: 23             moltype = AA  length = 605
FEATURE                   Location/Qualifiers
source                    1..605
                          mol_type = protein
                          organism = synthetic construct
                          note = Description of Artificial Sequence: Synthetic
                          polypeptide
SEQUENCE: 23
MLRPVETPTR EIKKLDGLWA FSLDRENCGI DQRWWESALQ ESRAIAVPGS FNDQFADADI    60
RNYAGNVWYQ REVFIPKGWA GQRIVLRFDA VTHYGKVWVN NQEVMEHQGG YTPFEADVTP   120
YVIAGKSVRI TVCVNNELNW QTIPPGMVIT DENGKKKQSY FHDFFNYAGI HRSVMLYTTP   180
NTWVDDITVV THVAQDCNHA SVDWQVVANG DVSVELRDAD QQVVATGQGT SGTLQVVNPH   240
LWQPGEGYLY ELCVTAKSQT ECDIYPLRVG IRSVAVKGEQ FLINHKPYF  TGFGKHEDTN   300
IRGKHDDAY  MVHDFQLLHW MGANSFRTSH YPYAEEVMEG ADRQGIVVID ETPAVGLAFS   360
IGAGAQTSNP PATFSPDRIN NKTREAHAQA IRELIHRDKN HPSVVMWSIA NEPASNEDGA   420
REYFAPLPKL ARQLDPTRPV TFANVGLATY KADRIADLFD VLCLNRYFGW YTQTAELDEA   480
EAALEEELRG WTEKYDKPIV MTEYGADTVA GLHSVMVTPW SEEFQVEMLD MYHRVFDRFE   540
AMAGEQVWNF ADFQTAVGVS RVDGNKKGVF TRDRKPKAAA HLLRKRWTNL HNGTAEGSKQ   600
GLCGR                                                              605

SEQ ID NO: 24             moltype = AA  length = 600
FEATURE                   Location/Qualifiers
source                    1..600
                          mol_type = protein
                          organism = synthetic construct
```

```
                        note = Description of Artificial Sequence: Synthetic
                        polypeptide
SEQUENCE: 24
MLRPVETPTR EIKKLDGLWA FSLDRENCGI DQRWWESALQ ESRAIAVPGS FNDQFADADI    60
RNYAGNVWYQ REVFIPKGWA GQRIVLRFDA VTHYGKVWVN NQEVMEHQGG YTPFEADVTP   120
YVIAGKSVRI TVCVNNELNW QTIPPGMVIT DENGKKKQSY FHDFFNYAGI HRSVMLYTTP   180
NTWVDDITVV THVAQDCNHA SVDWQVVANG DVSVELRDAD QQVVATGQGT SGTLQVVNPH   240
LWQPGEGYLY ELCVTAKSQT ECDIYPLRVG IRSVAVKGEQ FLINHKPFYF TGFGKHEDSA   300
VRGKGYDPAY MVHDFQLMDW MGANSFRTSH YPYAEEVMEF ADRHGIVVID ETPAVGLAFS   360
IGSGVSSEDS PQTFTPEGIN NNTREAHKQA IRELIARDKN HASVVMWSIA NEPASQEVGA   420
REYFAPLVDL AHELDPSRPV CFANYGDATY EVDRISDMFD VLCLNRYFGW YSQTGEVEEA   480
EAALEKELLG WEGKYGKPIV ITEYGADTMA GLHSVLALPW SEEFQVQLLD MYHRVFDRID   540
SVVGEHVWNF ADFQTAVGII RVDGNKKGVF TRERKPAAA HTLKTRWSGM LGSKQGLCGR    600

SEQ ID NO: 25           moltype = AA  length = 606
FEATURE                 Location/Qualifiers
source                  1..606
                        mol_type = protein
                        organism = synthetic construct
                        note = Description of Artificial Sequence: Synthetic
                        polypeptide
SEQUENCE: 25
MLKPRQTPFR DLISLDGLWK FALDSGDNAT AAPWTGPLTT DLECPVPASY NDIFVDRQIR    60
DHVGWVYYQR EAIVPRAWSQ QQYLVRVDAA THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGKH   300
EDSAVRGKGY DPAYMVHDFQ LMDWMGANSF RTSHYPYAEE VMEFADRHGI VVIDETPAVG   360
LAFSIGSGVS SEDSPQTFTP EGINNNTREA HKQAIRELIA RDKNHASVVM WSIANEPASN   420
EDGAREYFAP LPKLARQLDP TRPVTFANVG LATYKADRIA DLFDVLCLNR YFGWYTQTAE   480
LDEAEAALEE ELRGWTEKYD KPIVMTEYGA DTVAGLHSVM VTPWSEEFQV EMLDMYHRVF   540
DRFEAMAGEQ VWNFADFQTA VGVSRVDGNK KGVFTRDRKP KAAAHLLRKR WTNLHNGTAE   600
GSKTFQ                                                             606

SEQ ID NO: 26           moltype = AA  length = 597
FEATURE                 Location/Qualifiers
source                  1..597
                        mol_type = protein
                        organism = synthetic construct
                        note = Description of Artificial Sequence: Synthetic
                        polypeptide
SEQUENCE: 26
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
TNIRGKGHDD AYMVHDFQLL HWMGANSFRT SHYPYAEEVM EYADRQGIVV IDETPAVGLA   360
FSIGAGAQTS NPPATFSPDR INNKTREAHA QAIRELIHRD KNHPSVVMWS IANEPASQEV   420
GAREYFAPLV DLAHELDPSR PVCFANYGDA TYEVDRISDM FDVLCLNRYF GWYSQTGEVE   480
EAAALEKEL LGWEGKYGKP IVITEYGADT MAGLHSVLAL PWSEEFQQL LDMYHRVFDR    540
IDSVVGEHVW NFADFQTAVG IIRVDGNKKG VFTRERKPKA AAHTLKTRWS GMLGSDH     597

SEQ ID NO: 27           moltype = AA  length = 606
FEATURE                 Location/Qualifiers
source                  1..606
                        mol_type = protein
                        organism = synthetic construct
                        note = Description of Artificial Sequence: Synthetic
                        polypeptide
SEQUENCE: 27
MLKPRQTPFR DLISLDGLWK FALDSGDNAT AAPWTGPLTT DLECPVPASY NDIFVDRQIR    60
DHVGWVYYQR EAIVPRAWSQ QQYLVRVDAA THQGRIYIND NLVAEHRGGY TPFEADITGL   120
VSAGDSFRLT IAVNNELTHE TIPPGRIEVE EYTGKRVQVY QHDFFNYAGL ARSVWLYSVP   180
QQHIQDIKVV THVKGSAGLI NYLVTVSNST TGRVKIDVID KDGTTVAEAS GARGSVTIDS   240
VKLWQPGEAY LYQFRASIVG LNDSVVDTYC VETGVRTVKV SGNRFLINDK PFYFTGFGRH   300
EDADLRGKGF DNVLMVHDHA LMDWIGANSY RTSHYPYAEE MLDWADEHGI VVIDETPAVG   360
LAFSIGSGVS SEDSPQTFTP EGINNNTREA HKQAIRELIA RDKNHASVVM WSIANEPDTR   420
PQGAREYFAP LAEATRKLDP TRPITCVNVM FCDAHTDTIS DLFDVLCLNR YYGWYVQSGD   480
LETAEKVLEK ELLAWQEKLH QPIIITEYGV DTLAGLHSMY TDMWSEEYQC AWLDMYHRVF   540
DRVSAVVGEQ VWNFADFATS QSILRVGGNK KGIFTRDRKP KSAAFLLQKR WTGMNFGEKP   600
QQGSDH                                                             606

SEQ ID NO: 28           moltype = AA  length = 611
FEATURE                 Location/Qualifiers
source                  1..611
                        mol_type = protein
                        organism = synthetic construct
                        note = Description of Artificial Sequence: Synthetic
```

```
                               -continued polypeptide
SEQUENCE: 28
MLKPRQTPFR DLISLDGLWK FALDSGDNAT AAPWTGPLTT DLECPVPASY NDIFVDRQIR     60
DHVGWVYYQR EAIVPRAWSQ QQYLVRVDAA THQGRIYIND NLVAEHRGGY TPFEADITGL    120
VSAGDSFRLT IAVNNELTHE TIPPGRIEVE EYTGKRVQVY QHDFFNYAGL ARSVWLYSVP    180
QQHIQDIKVV THVKGSAGLI NYLVTVSNST TGRVKIDVID KDGTTVAEAS GARGSVTIDS    240
VKLWQPGEAY LYQFRASIVG LNDSVVDTYC VETGVRTVKV SGNRFLINDK PFYFTGFGRH    300
EDADLRGKGF DNVLMVHDHA LMDWIGANSY RTSHYPYAEE MLDWADEHGI VVIDETPAVG    360
LAFSIGAGAQ TSNPPATFSP DRINNKTREA HAQAIRELIH RDKNHPSVVM WSIANEPDTR    420
PQGAREYFAP LAEATRKLDP TRPITCVNVM FCDAHTDTIS DLFDVLCLNR YYGWYVQSGD    480
LETAEKVLEK ELLAWQEKLH QPIIITEYGV DTLAGLHSMY TDMWSEEYQC AWLDMYHRVF    540
DRVSAVVGEQ VWNFADFATS QSILRVGGNK KGIFTRDRKP KSAAFLLQKR WTGMNFGEKP    600
QQGSKQGLCG R                                                        611

SEQ ID NO: 29            moltype = AA  length = 606
FEATURE                  Location/Qualifiers
source                   1..606
                         mol_type = protein
                         organism = synthetic construct
                         note = Description of Artificial Sequence: Synthetic
                         polypeptide
SEQUENCE: 29
MLRPVETPTR EIKKLDGLWA FSLDRENCGI DQRWWESALQ ESRAIAVPGS FNDQFADADI     60
RNYAGNVWYQ REVFIPKGWA GQRIVLRFDA VTHYGKVWVN NQEVMEHQGG YTPFEADVTP    120
YVIAGKSVRI TVCVNNELNW QTIPPGMVIT DENGKKKQSY FHDFFNYAGI HRSVMLYTTP    180
NTWVDDITVV THVAQDCNHA SVDWQVVANG DVSVELRDAD QQVVATGQGT SGTLQVVNPH    240
LWQPGEGYLY ELCVTAKSQT ECDIYPLRVG IRSVAVKGEQ FLINHKPFYF TGFGRHEDAD    300
LRGKGFDNVL MVHDHALMDW IGANSYRTSH YPYAEEMLDW ADEHGIVVID ETAAVGFNLS    360
LGIGFEAGNK PKELYSEEAV NGETQQAHLQ AIKELIARDK NHPSVVMWSI ANEPASNEDG    420
AREYFAPLPK LARQLDPTRP VTFANVGLAT YKADRIADLF DVLCLNRYFG WYTQTAELDE    480
AEAALEEELR GWTEKYDKPI VMTEYGADTV AGLHSVMVTP WSEEFQVEML DMYHRVFDRF    540
EAMAGEQVWN FADFQTAVGV SRVDGNKKGV FTRDRKPKAA AHLLRKRWTN LHNGTAEGSK    600
QGLCGR                                                              606

SEQ ID NO: 30            moltype = AA  length = 601
FEATURE                  Location/Qualifiers
source                   1..601
                         mol_type = protein
                         organism = synthetic construct
                         note = Description of Artificial Sequence: Synthetic
                         polypeptide
SEQUENCE: 30
MLRPVETPTR EIKKLDGLWA FSLDRENCGI DQRWWESALQ ESRAIAVPGS FNDQFADADI     60
RNYAGNVWYQ REVFIPKGWA GQRIVLRFDA VTHYGKVWVN NQEVMEHQGG YTPFEADVTP    120
YVIAGKSVRI TVCVNNELNW QTIPPGMVIT DENGKKKQSY FHDFFNYAGI HRSVMLYTTP    180
NTWVDDITVV THVAQDCNHA SVDWQVVANG DVSVELRDAD QQVVATGQGT SGTLQVVNPH    240
LWQPGEGYLY ELCVTAKSQT ECDIYPLRVG IRSVAVKGEQ FLINHKPFYF TGFGKHEDSA    300
VRGKGYDPAY MVHDFQLMDW MGANSFRTSH YPYAEEVMEF ADRHGIVVID ETAAVGFNLS    360
LGIGFEAGNK PKELYSEEAV NGETQQAHLQ AIKELIARDK NHPSVVMWSI ANEPASQEVG    420
AREYFAPLVD LAHELDPSRP VCFANYGDAT YEVDRISDMF DVLCLNRYFG WYSQTGEVEE    480
AEAALEKELL GWEGKYGKPI VITEYGADTM AGLHSVLALP WSEEFQVQLL DMYHRVFDRI    540
DSVVGEHVWN FADFQTAVGI IRVDGNKKGV FTRERKPKAA AHTLKTRWSG MLGSKQGLCG    600
R                                                                   601

SEQ ID NO: 31            moltype = AA  length = 604
FEATURE                  Location/Qualifiers
source                   1..604
                         mol_type = protein
                         organism = synthetic construct
                         note = Description of Artificial Sequence: Synthetic
                         polypeptide
SEQUENCE: 31
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
TNIRGKGHDD AYMVHDFQLL HWMGANSFRT SHYPYAEEVM EYADRQGIVV IDETPAVGLA    360
FSIGSGVSSE DSPQTFTPEG INNNTREAHK QAIRELIARD KNHASVVMWS IANEPASNED    420
GAREYFAPLP KLARQLDPTR PVTFANVGLA TYKADRIADL FDVLCLNRYF GWYTQTAELD    480
EAEAALEEEL RGWTEKYDKP IVMTEYGADT VAGLHSVMVT PWSEEFQVEM LDMYHRVFDR    540
FEAMAGEQVW NFADFQTAVG VSRVDGNKKG VFTRDRKPKA AAHLLRKRWT NLHNGTAEGS    600
KTFQ                                                                604

SEQ ID NO: 32            moltype = AA  length = 605
FEATURE                  Location/Qualifiers
source                   1..605
                         mol_type = protein
                         organism = synthetic construct
```

```
                        note = Description of Artificial Sequence: Synthetic
                        polypeptide
SEQUENCE: 32
MLKPQQTTTR  DLISLDGLWK  FALASDDNNT  QPWTSQLKTS  LECPVPASYN  DIFADSKIHD   60
HVGWVYYQRD  VIVPKGWSEE  RYLVRCEAAT  HHGRIYVNGN  LVADHVGGYT  PPEADITDLV  120
AAGEQFRLTI  AVDNELTYQT  IPPGKVEILE  ATGKKVQTYQ  HDFYNYAGLA  RSVWLYSVPQ  180
QHIQDITVRT  DVQGTTGLID  YNVVASTTQG  TIQVAVIDED  GTTVATSSGS  NGTIHIPSVH  240
LWQPGAAYLY  QLHASIIDSS  KKTIDTYKLA  TGIRTVKVQG  TQFLINDKPF  YFTGFGRHED  300
ADLRGKGFDN  VLMVHDHALM  DWIGANSYRT  SHYPYAEEMRL DWADEHGIVV  IDETAAVGFN  360
LSLGIGFEAG  NKPKELYSEE  AVNGETQQAH  LQAIKELIAR  DKNHPSVVMW  SIANEPASNE  420
DGAREYFAPL  PKLARQLDPT  RPVTFANVGL  ATYKADRIAD  LFDVLCLNRY  FGWYTQTAEL  480
DEAEAALEEE  LRGWTEKYDK  PIVMTEYGAD  TVAGLHSVMV  TPWSEEFQVE  MLDMYHRVFD  540
RFEAMAGEQV  WNFADFQTAV  GVSRVDGNKK  GVFTRDRKPK  AAAHLLRKRW  TNLHNGTAEG  600
SKTFQ                                                                  605

SEQ ID NO: 33           moltype = AA   length = 599
FEATURE                 Location/Qualifiers
source                  1..599
                        mol_type = protein
                        organism = synthetic construct
                        note = Description of Artificial Sequence: Synthetic
                        polypeptide
SEQUENCE: 33
MLKPRQTPFR  DLISLDGLWK  FALDSGDNAT  AAPWTGPLTT  DLECPVPASY  NDIFVDRQIR   60
DHVGWVYYQR  EAIVPRAWSQ  QQYLVRVDAA  THQGRIYIND  NLVAEHRGGY  TPFEADITGL  120
VSAGDSFRLT  IAVNNELTHE  TIPPGRIEVE  EYTGKRVQVY  QHDFFNYAGL  ARSVWLYSVP  180
QQHIQDIKVV  THVKGSAGLI  NYLVTVSNST  TGRVKIDVID  KDGTTVAEAS  GARGSVTIDS  240
VKLWQPGEAY  LYQFRASIVG  LNDSVVDTYC  VETGVRTVKV  SGNRFLINDK  PFYFTGFGKH  300
EDTNIRGKGH  DDAYMVHDFQ  LLHWMGANSF  RTSHYPYAEE  VMEYADRQGI  VVIDETPAVG  360
LAFSIGAGAQ  TSNPPATFSP  DRINNKTREA  HAQAIRELIH  RDKNHPSVVM  WSIANEPASQ  420
EVGAREYFAP  LVDLAHELDP  SRPVCFANYG  DATYEVDRIS  DMFDVLCLNR  YFGWYSQTGE  480
VEEEAEAALEK ELLGWEGKYG  KPIVITEYGA  DTMAGLHSVL  ALPWSEEFQV  QLLDMYHRVF  540
DRIDSVVGEH  VWNFADFQTA  VGIIRVDGNK  KGVFTRERKP  KAAAHTLKTR  WSGMLGSDH   599

SEQ ID NO: 34           moltype = AA   length = 600
FEATURE                 Location/Qualifiers
source                  1..600
                        mol_type = protein
                        organism = synthetic construct
                        note = Description of Artificial Sequence: Synthetic
                        polypeptide
SEQUENCE: 34
MLKPRQTPFR  DLISLDGLWK  FALDSGDNAT  AAPWTGPLTT  DLECPVPASY  NDIFVDRQIR   60
DHVGWVYYQR  EAIVPRAWSQ  QQYLVRVDAA  THQGRIYIND  NLVAEHRGGY  TPFEADITGL  120
VSAGDSFRLT  IAVNNELTHE  TIPPGRIEVE  EYTGKRVQVY  QHDFFNYAGL  ARSVWLYSVP  180
QQHIQDIKVV  THVKGSAGLI  NYLVTVSNST  TGRVKIDVID  KDGTTVAEAS  GARGSVTIDS  240
VKLWQPGEAY  LYQFRASIVG  LNDSVVDTYC  VETGVRTVKV  SGNRFLINDK  PFYFTGFGKH  300
EDSAVRGKGY  DPAYMVHDFQ  LMDWMGANSF  RTSHYPYAEE  VMEFADRHGI  VVIDETAAVG  360
FNLSLGIGFE  AGNKPKELYS  EEAVNGETQQ  AHLQAIKELI  ARDKNHPSVV  MWSIANEPAS  420
QEVGAREYFA  PLVDLAHELD  PSRPVCFANY  GDATYEVDRI  SDMFDVLCLN  RYFGWYSQTG  480
EVEEEAEAALE KELLGWEGKY  GKPIVITEYG  ADTMAGLHSV  LALPWSEEFQ  VQLLDMYHRV  540
FDRIDSVVGE  HVWNFADFQT  AVGIIRVDGN  KKGVFTRERK  PKAAAHTLKT  RWSGMLGSDH  600

SEQ ID NO: 35           moltype = AA   length = 607
FEATURE                 Location/Qualifiers
source                  1..607
                        mol_type = protein
                        organism = synthetic construct
                        note = Description of Artificial Sequence: Synthetic
                        polypeptide
SEQUENCE: 35
MLRPVETPTR  EIKKLDGLWA  FSLDRENCGI  DQRWWESALQ  ESRAIAVPGS  FNDQFADADI   60
RNYAGNVWYQ  REVFIPKGWA  GQRIVLRFDA  VTHYGKVWVN  NQEVMEHQGG  TYPFEADVTG  120
YVIAGKSVRI  TVCVNNELNW  QTIPPGMVIT  DENGKKKQSY  FHDFFNYAGI  HRSVMLYTTP  180
NTWVDDITVV  THVAQDCNHA  SVDWQVVANG  DVSVELRDAD  QQVVATGQGT  SGTLQVVNPH  240
LWQPGEGYLY  ELCVTAKSQT  ECDIYPLRVG  IRSVAVKGEQ  FLINHKPYF   TGFGKHEDTN  300
IRGKGHDDAY  MVHDFQLLHW  MGANSFRTSH  YPYAEEVMEY  ADRQGIVVID  ETPAVGLAFS  360
IGAGAQTSNP  PATFSPDRIN  NKTREAHAQA  IRELIHRDKN  HPSVVMWSIA  NEPDTRPQGA  420
REYFAPLAEA  TRKLDPTRPI  TCVNVMFCDA  HTDTISDLFD  VLCLNRYYGW  YVQSGDLETA  480
EKVLEKELLA  WQEKLHQPII  ITEYGVDTLA  GLHSMYTDMW  SEEYQCAWLD  MYHRVFDRVS  540
AVVGEQVWNF  ADFATSQSIL  RVGGNKKGIF  TRDRKPKSAA  FLLQKRWTGM  NFGEKPQQGS  600
KQGLCGR                                                                607

SEQ ID NO: 36           moltype = AA   length = 607
FEATURE                 Location/Qualifiers
source                  1..607
                        mol_type = protein
                        organism = synthetic construct
                        note = Description of Artificial Sequence: Synthetic
```

```
                              polypeptide
SEQUENCE: 36
MLRPVETPTR EIKKLDGLWA FSLDRENCGI DQRWWESALQ ESRAIAVPGS FNDQFADADI   60
RNYAGNVWYQ REVFIPKGWA GQRIVLRFDA VTHYGKWVN NQEVMEHQGG YTPFEADVTP   120
YVIAGKSVRI TVCVNNELNW QTIPPGMVIT DENGKKKQSY PHDFFNYAGI HRSVMLYTTP  180
NTWVDDITVV THVAQDCNHA SVDWQVVANG DVSVELRDAD QQVVATGQGT SGTLQVVNPH  240
LWQPGEGYLY ELCVTAKSQT ECDIYPLRVG IRSVAVKGEQ FLINHKPFYF TGFGRHEDAD  300
LRGKGFDNVL MVHDHALMDW IGANSYRTSH YPYAEEMLDW ADEHGIVVID ETPAVGLAFS  360
IGSGVSSEDS PQTFTPEGIN NNTREAHKQA IRELIARDKN HASVVMWSIA NEPDTRPQGA  420
REYFAPLAEA TRKLDPTRPI TCVNVMFCDA HTDTISDLFD VLCLNRYYGW YVQSGDLETA  480
EKVLEKELLA WQEKLHQPII ITEYGVDTLA GLHSMYTDMW SEEYQCAWLD MYHRVFDRVS  540
AVVGEQVWNF ADFATSQSIL RVGGNKKGIF TRDRKPKSAA FLLQKRWTGM NFGEKPQQGS  600
KQGLCGR                                                           607

SEQ ID NO: 37           moltype = AA  length = 614
FEATURE                 Location/Qualifiers
source                  1..614
                        mol_type = protein
                        organism = synthetic construct
                        note = Description of Artificial Sequence: Synthetic
                              polypeptide
SEQUENCE: 37
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGG KANMMSGMMG GMGAGASDKP QNNPNFDFFN  180
YAGLNRPVKI TVTNKEYIHD IDILSDVNGS DGIVNYEVHT TGENKVYIKI NDEEGKEVAS  240
CEGKSGKIVI KDAKLWNPKA AYLYKFIACI KNGDELIDEY YLDFGIRTVK VEGTKFLING  300
KPFYFTGFGK HEDSEIAGRG YNPPVIKRDF ELIKWVGANS FRTSHYPYSE EIMQAADREG  360
IVIIDEVAAV GMFDVGSVLN PSASKTDYFS LDEVHSKTKE VHKKAVEELI KRDKNHPSVV  420
MWSLFNEPDT SKDEAVPYFE DIFNFAKSQD KQNLPKTFAA IQASSPGKCK CMHLCDVITL  480
NRYYGWYFLG GYEIDMSEEK FREEMNLYSN MNKPVMFTEY GADTYAGVHK LPSVMWSEEY  540
QCEYYEMNFK VFDSYDFIVG EQLWNFADFQ TTEGIFRVDG NKKGIFTRNR QPKAVAHLIR  600
SRWNKLPLDY KSKK                                                   614

SEQ ID NO: 38           moltype = AA  length = 603
FEATURE                 Location/Qualifiers
source                  1..603
                        mol_type = protein
                        organism = synthetic construct
                        note = Description of Artificial Sequence: Synthetic
                              polypeptide
SEQUENCE: 38
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDQFGGGAN FGGERIGTFD KEHGSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRP KAVAHLIRS RWNKLPLDYK  600
SKK                                                               603

SEQ ID NO: 39           moltype = AA  length = 614
FEATURE                 Location/Qualifiers
source                  1..614
                        mol_type = protein
                        organism = synthetic construct
                        note = Description of Artificial Sequence: Synthetic
                              polypeptide
SEQUENCE: 39
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGG KANMMSGMMG GMGAGASDKP QNNPNFDFFN  180
YAGLNRPVKI TVTNKEYIHD IDILSDVNGS DGIVNYEVHT TGENKVYIKI NDEEGKEVAS  240
CEGKSGKIVI KDAKLWNPKA AYLYKFIACI KNGDELIDEY YLDFGIRTVK VEGTKFLING  300
KPFYFTGFGK HEDSEIAGRG YNPPVIKRDF ELIKWVGANS FRTSHYPYSE EIMQAADREG  360
IVIIDEVAAV GMFDQFGGGA NFGGERIGTF DKEHGSKTKE VHKKAVEELI KRDKNHPSVV  420
MWSLFNEPDT SKDEAVPYFE DIFNFAKSQD KQNLPKTFAA IQASSPGKCK CMHLCDVITL  480
NRYYGWYFLG GYEIDMSEEK FREEMNLYSN MNKPVMFTEY GADTYAGVHK LPSVMWSEEY  540
QCEYYEMNFK VFDSYDFIVG EQLWNFADFQ TTEGIFRVDG NKKGIFTRNR QPKAVAHLIR  600
SRWNKLPLDY KSKK                                                   614

SEQ ID NO: 40           moltype = AA  length = 603
FEATURE                 Location/Qualifiers
source                  1..603
                        mol_type = protein
                        organism = synthetic construct
```

```
                          note = Description of Artificial Sequence: Synthetic
                          polypeptide
SEQUENCE: 40
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFTGFGKH   300
EDSEIAGRGY NPPVIKRDFE LIKWVGANSF RTSHYPYSEE IMQAADREGI VIIDEVAAVG   360
MFDVGGGGAN FGGERDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 41             moltype = AA  length = 614
FEATURE                   Location/Qualifiers
source                    1..614
                          mol_type = protein
                          organism = synthetic construct
                          note = Description of Artificial Sequence: Synthetic
                          polypeptide
SEQUENCE: 41
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGG KANMMSGMMG GMGAGASADKP QNNPNFDFFN   180
YAGLNRPVKI TVTNKEYIHD IDILSDVNGS DGIVNYEVHT TGENKVYIKI NDEEGKEVAS   240
CEGKSGKIVI KDAKLWNPKA AYLYKFIACI KNGDELIDEY YLDFGIRTVK VEGTKFLING   300
KPFYFTGFGK HEDSEIAGRG YNPPVIKRDF ELIKWVGANS FRTSHYPYSE EIMQAADREG   360
IVIIDEVAAV GMFDVGGGGA NFGGERDYFS LDEVHSKTKE VHKKAVEELI KRDKNHPSVV   420
MWSLFNEPDT SKDEAVPYFE DIFNFAKSQD KQNLPKTFAA IQASSPGKCK CMHLCDVITL   480
NRYYGWYFLG GYEIDMSEEK FREEMNLYSN MNKPVMFTEY GADTYAGVHK LPSVMWSEEY   540
QCEYYEMNFK VFDSYDFIVG EQLWNFADFQ TTEGIFRVDG NKKGIFTRNR QPKAVAHLIR   600
SRWNKLPLDY KSKK                                                    614

SEQ ID NO: 42             moltype = AA  length = 602
FEATURE                   Location/Qualifiers
source                    1..602
                          mol_type = protein
                          organism = synthetic construct
                          note = Description of Artificial Sequence: Synthetic
                          polypeptide
SEQUENCE: 42
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGCGHTET KPSGKKYIKP SFDFFNYCGI TRPVKIYTTP   180
ETYINDITVT ADIDFTKEEP SAVLNYNVEI KGKDYNNITC KVELFDEEGT KLSETEGSEG   240
TFEISNVRLW QPLNAYLYKI KVTAGQDVYT LPYGVRSVRV DGTKFLINEK PFYFKGYGKH   300
EDTFPNGRGI NLPMNTKDIS IMKWQHANSF RTSHYPYSEE MMRLCDEEGI VVIDETTAVG   360
VNLQFGGGAN FGGERIGTFD KEHGVQTQEH HKDVIRDLIS RDKNHACVVM WSIANEPDSA   420
AEGAYDYFKP LYDLARELDP QKRPCTLVSV QGTTADTDCS SQLSDVICLN RYYGWYFGGP   480
DLEVSEIGLR KELSDWGKLG KPVMFTEYGA DTVSGLHDTT SVMYTEEYQV EYYEMNNKVF   540
DEFDFVVGEQ AWNFADFATS QSLLRVQGNK KGLFTRDRKP KMVAHYFRNR WSTIPEFGYK   600
TK                                                                 602

SEQ ID NO: 43             moltype = AA  length = 611
FEATURE                   Location/Qualifiers
source                    1..611
                          mol_type = protein
                          organism = synthetic construct
                          note = Description of Artificial Sequence: Synthetic
                          polypeptide
SEQUENCE: 43
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLVGSVLNPS ASKTDYFSLD EVHVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                       611

SEQ ID NO: 44             moltype = AA  length = 602
FEATURE                   Location/Qualifiers
source                    1..602
                          mol_type = protein
```

```
                            organism = synthetic construct
                            note = Description of Artificial Sequence: Synthetic
                                polypeptide
SEQUENCE: 44
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGCGHTET KPSGKKYIKP SFDFFNYCGI TRPVKIYTTP   180
ETYINDITVT ADIDFTKEEP SAVLNYNVEI KGKDYNNITC KVELFDEEGT KLSETEGSEG   240
TFEISNVRLW QPLNAYLYKI KVTAGQDVYT LPYGVRSVRV DGTKFLINEK PFYFKGYGKH   300
EDTFPNGRGI NLPMNTKDIS IMKWQHANSF RTSHYPYSEE MMRLCDEEGI VVIDETTAVG   360
VNLVGSVLNP SASKTDYFSL DEVHVQTQEH HKDVIRDLIS RDKNHACVVM WSIANEPDSA   420
AEGAYDYFKP LYDLARELDP QKRPCTLVSV QGTTADTDCS SQLSDVICLN RYYGWYFGGP   480
DLEVSEIGLR KELSDWGKLG KPVMFTEYGA DTVSGLHDTT SVMYTEEYQV EYYEMNNKVF   540
DEFDFVVGEQ AWNFADFATS QSLLRVQGNK KGLFTRDRKP KMVAHYFRNR WSTIPEFGYK   600
TK                                                                 602

SEQ ID NO: 45           moltype = AA  length = 611
FEATURE                 Location/Qualifiers
source                  1..611
                        mol_type = protein
                        organism = synthetic construct
                        note = Description of Artificial Sequence: Synthetic
                            polypeptide
SEQUENCE: 45
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFSVLNPS ASKTIGTFDK EHGVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                       611

SEQ ID NO: 46           moltype = AA  length = 602
FEATURE                 Location/Qualifiers
source                  1..602
                        mol_type = protein
                        organism = synthetic construct
                        note = Description of Artificial Sequence: Synthetic
                            polypeptide
SEQUENCE: 46
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGCGHTET KPSGKKYIKP SFDFFNYCGI TRPVKIYTTP   180
ETYINDITVT ADIDFTKEEP SAVLNYNVEI KGKDYNNITC KVELFDEEGT KLSETEGSEG   240
TFEISNVRLW QPLNAYLYKI KVTAGQDVYT LPYGVRSVRV DGTKFLINEK PFYFKGYGKH   300
EDTFPNGRGI NLPMNTKDIS IMKWQHANSF RTSHYPYSEE MMRLCDEEGI VVIDETTAVG   360
VNLQFSVLNP SASKTIGTFD KEHGVQTQEH HKDVIRDLIS RDKNHACVVM WSIANEPDSA   420
AEGAYDYFKP LYDLARELDP QKRPCTLVSV QGTTADTDCS SQLSDVICLN RYYGWYFGGP   480
DLEVSEIGLR KELSDWGKLG KPVMFTEYGA DTVSGLHDTT SVMYTEEYQV EYYEMNNKVF   540
DEFDFVVGEQ AWNFADFATS QSLLRVQGNK KGLFTRDRKP KMVAHYFRNR WSTIPEFGYK   600
TK                                                                 602

SEQ ID NO: 47           moltype = AA  length = 603
FEATURE                 Location/Qualifiers
source                  1..603
                        mol_type = protein
                        organism = synthetic construct
                        note = Description of Artificial Sequence: Synthetic
                            polypeptide
SEQUENCE: 47
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYATGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 48           moltype = AA  length = 603
FEATURE                 Location/Qualifiers
source                  1..603
```

```
                    mol_type = protein
                    organism = synthetic construct
                    note = Description of Artificial Sequence: Synthetic
                    polypeptide
SEQUENCE: 48
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYITGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 49           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 49
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYVTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 50           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 50
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYYTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 51           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 51
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYLTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 52           moltype = AA  length = 603
FEATURE                 Location/Qualifiers
```

```
source                  1..603
                        mol_type = protein
                        organism = synthetic construct
                        note = Description of Artificial Sequence: Synthetic
                           polypeptide
SEQUENCE: 52
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYWTGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 53           moltype = AA  length = 611
FEATURE                 Location/Qualifiers
source                  1..611
                        mol_type = protein
                        organism = synthetic construct
                        note = Description of Artificial Sequence: Synthetic
                           polypeptide
SEQUENCE: 53
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYWKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                       611

SEQ ID NO: 54           moltype = AA  length = 611
FEATURE                 Location/Qualifiers
source                  1..611
                        mol_type = protein
                        organism = synthetic construct
                        note = Description of Artificial Sequence: Synthetic
                           polypeptide
SEQUENCE: 54
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYSKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                       611

SEQ ID NO: 55           moltype = AA  length = 603
FEATURE                 Location/Qualifiers
source                  1..603
                        mol_type = protein
                        organism = synthetic construct
                        note = Description of Artificial Sequence: Synthetic
                           polypeptide
SEQUENCE: 55
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFAGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 56           moltype = AA  length = 603
```

```
FEATURE            Location/Qualifiers
source             1..603
                   mol_type = protein
                   organism = synthetic construct
                   note = Description of Artificial Sequence: Synthetic
                   polypeptide
SEQUENCE: 56
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFCGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 57       moltype = AA  length = 603
FEATURE            Location/Qualifiers
source             1..603
                   mol_type = protein
                   organism = synthetic construct
                   note = Description of Artificial Sequence: Synthetic
                   polypeptide
SEQUENCE: 57
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFFGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 58       moltype = AA  length = 603
FEATURE            Location/Qualifiers
source             1..603
                   mol_type = protein
                   organism = synthetic construct
                   note = Description of Artificial Sequence: Synthetic
                   polypeptide
SEQUENCE: 58
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFIGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 59       moltype = AA  length = 603
FEATURE            Location/Qualifiers
source             1..603
                   mol_type = protein
                   organism = synthetic construct
                   note = Description of Artificial Sequence: Synthetic
                   polypeptide
SEQUENCE: 59
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFKGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603
```

```
SEQ ID NO: 60              moltype = AA   length = 603
FEATURE                    Location/Qualifiers
source                     1..603
                           mol_type = protein
                           organism = synthetic construct
                           note = Description of Artificial Sequence: Synthetic
                            polypeptide
SEQUENCE: 60
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFSGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                 603

SEQ ID NO: 61              moltype = AA   length = 603
FEATURE                    Location/Qualifiers
source                     1..603
                           mol_type = protein
                           organism = synthetic construct
                           note = Description of Artificial Sequence: Synthetic
                            polypeptide
SEQUENCE: 61
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFVGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                 603

SEQ ID NO: 62              moltype = AA   length = 611
FEATURE                    Location/Qualifiers
source                     1..611
                           mol_type = protein
                           organism = synthetic construct
                           note = Description of Artificial Sequence: Synthetic
                            polypeptide
SEQUENCE: 62
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFAGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTCSS QLSDVICLNR    480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611

SEQ ID NO: 63              moltype = AA   length = 611
FEATURE                    Location/Qualifiers
source                     1..611
                           mol_type = protein
                           organism = synthetic construct
                           note = Description of Artificial Sequence: Synthetic
                            polypeptide
SEQUENCE: 63
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFVGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTCSS QLSDVICLNR    480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611
```

```
SEQ ID NO: 64            moltype = AA   length = 603
FEATURE                  Location/Qualifiers
source                   1..603
                         mol_type = protein
                         organism = synthetic construct
                         note = Description of Artificial Sequence: Synthetic
                            polypeptide
SEQUENCE: 64
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAF QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 65            moltype = AA   length = 603
FEATURE                  Location/Qualifiers
source                   1..603
                         mol_type = protein
                         organism = synthetic construct
                         note = Description of Artificial Sequence: Synthetic
                            polypeptide
SEQUENCE: 65
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAK QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 66            moltype = AA   length = 603
FEATURE                  Location/Qualifiers
source                   1..603
                         mol_type = protein
                         organism = synthetic construct
                         note = Description of Artificial Sequence: Synthetic
                            polypeptide
SEQUENCE: 66
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAL QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                                603

SEQ ID NO: 67            moltype = AA   length = 603
FEATURE                  Location/Qualifiers
source                   1..603
                         mol_type = protein
                         organism = synthetic construct
                         note = Description of Artificial Sequence: Synthetic
                            polypeptide
SEQUENCE: 67
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAM QASSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
```

```
SKK                                                                         603

SEQ ID NO: 68           moltype = AA   length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 68
MVNSMLYPRE SRTRRVVDIS GMWEFKIDIN NEGRNSGYAN GLKDTTFIPV PSSFNDLFTD  60
KNIREHAGDV WYETSFYLPL EWKDKDVNVR FGCATHEATV YINGKEVCTH VGGFMPFNAP 120
VNEAGIFGEK NKLVVVVNNE LSNTTIPCGH TETKPSGKKY IKPSFDFFNY AGLNRPVKIT 180
VTNKEYIHDI DILSDVNGSD GIVNYEVHTT GENKVYIKIN DEEGKEVASC EGKSGKIVIK 240
DAKLWNPKAA YLYKFIACIK NGDELIDEYY LDFGIRTVKV EGTKFLINGK PFYFTGFGKH 300
EDSEIAGRGY NPPVIKRDFE LIKWVGANSF RTSHYPYSEE IMQAADREGI VIIDEVAAVG 360
MFDVGSVLNP SASKTDYFSL DEVHSKTKEV HKKAVEELIK RDKNHPSVVM WSLFNEPDTS 420
KDEAVPYFED IFNFAKSQDK QNLPKTFAAQ QASSPGKCKC MHLCDVITLN RYYGWYFLGG 480
YEIDMSEEKF REEMNLYSNM NKPVMFTEYG ADTYAGVHKL PSVMWSEEYQ CEYYEMNFKV 540
FDSYDFIVGE QLWNFADFQT TEGIFRVDGN KKGIFTRNRQ PKAVAHLIRS RWNKLPLDYK 600
SKK                                                                         603

SEQ ID NO: 69           moltype = AA   length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 69
MVNSMLYPRE SRTRRVVDIS GMWEFKIDIN NEGRNSGYAN GLKDTTFIPV PSSFNDLFTD  60
KNIREHAGDV WYETSFYLPL EWKDKDVNVR FGCATHEATV YINGKEVCTH VGGFMPFNAP 120
VNEAGIFGEK NKLVVVVNNE LSNTTIPCGH TETKPSGKKY IKPSFDFFNY AGLNRPVKIT 180
VTNKEYIHDI DILSDVNGSD GIVNYEVHTT GENKVYIKIN DEEGKEVASC EGKSGKIVIK 240
DAKLWNPKAA YLYKFIACIK NGDELIDEYY LDFGIRTVKV EGTKFLINGK PFYFTGFGKH 300
EDSEIAGRGY NPPVIKRDFE LIKWVGANSF RTSHYPYSEE IMQAADREGI VIIDEVAAVG 360
MFDVGSVLNP SASKTDYFSL DEVHSKTKEV HKKAVEELIK RDKNHPSVVM WSLFNEPDTS 420
KDEAVPYFED IFNFAKSQDK QNLPKTFAAD QASSPGKCKC MHLCDVITLN RYYGWYFLGG 480
YEIDMSEEKF REEMNLYSNM NKPVMFTEYG ADTYAGVHKL PSVMWSEEYQ CEYYEMNFKV 540
FDSYDFIVGE QLWNFADFQT TEGIFRVDGN KKGIFTRNRQ PKAVAHLIRS RWNKLPLDYK 600
SKK                                                                         603

SEQ ID NO: 70           moltype = AA   length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 70
MVNSMLYPRE SRTRRVVDIS GMWEFKIDIN NEGRNSGYAN GLKDTTFIPV PSSFNDLFTD  60
KNIREHAGDV WYETSFYLPL EWKDKDVNVR FGCATHEATV YINGKEVCTH VGGFMPFNAP 120
VNEAGIFGEK NKLVVVVNNE LSNTTIPCGH TETKPSGKKY IKPSFDFFNY AGLNRPVKIT 180
VTNKEYIHDI DILSDVNGSD GIVNYEVHTT GENKVYIKIN DEEGKEVASC EGKSGKIVIK 240
DAKLWNPKAA YLYKFIACIK NGDELIDEYY LDFGIRTVKV EGTKFLINGK PFYFTGFGKH 300
EDSEIAGRGY NPPVIKRDFE LIKWVGANSF RTSHYPYSEE IMQAADREGI VIIDEVAAVG 360
MFDVGSVLNP SASKTDYFSL DEVHSKTKEV HKKAVEELIK RDKNHPSVVM WSLFNEPDTS 420
KDEAVPYFED IFNFAKSQDK QNLPKTFAAV QASSPGKCKC MHLCDVITLN RYYGWYFLGG 480
YEIDMSEEKF REEMNLYSNM NKPVMFTEYG ADTYAGVHKL PSVMWSEEYQ CEYYEMNFKV 540
FDSYDFIVGE QLWNFADFQT TEGIFRVDGN KKGIFTRNRQ PKAVAHLIRS RWNKLPLDYK 600
SKK                                                                         603

SEQ ID NO: 71           moltype = AA   length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 71
MLYPVLTQSR LLSDLSGVWD FKLDNGKGFE EKWYEKPLKD ADTMPVPASY NDLKEGTDFR  60
DHYGWVFYQR NISVPEYVKS QRIVLRCAAV THYAMIYLNG KLICEHKGGF LPFEVELNDD 120
LQDGDNLLTI AVNNVIDYTT LPVGGKANMM SGMMGGMGAG ASDKPQNNPN FDFFNYCGIT 180
RPVKIYTTPE TYINDITVTA DIDFTKEEPS AVLNYNVEIK GKDYNNITCK VELFDEEGTK 240
LSETEGSEGT FEISNVRLWQ PLNAYLYKIK VTAGQDVYTL PYGVRSVRVD GTKFLINEKP 300
FYFKGYGKHE DTFPNGRGIN LPMNTKDISI MKWQHANSFR TSHYPYSEEM MRLCDEEGIV 360
VIDETTAVGV NLQFGGGANF GGERIGTFDK EHGVQTQEHH KDVIRDLISR DKNHACVVMW 420
SIANEPDSAA EGAYDYFKPL YDLARELDPQ KRPCTLVSFQ GTTADTDCSS QLSDVICLNR 480
YYGWYFGGPD LEVSEIGLRK ELSDWGKLGK PVMFTEYGAD TVSGLHDTTS VMYTEEYQVE 540
```

```
YYEMNNKVFD EFDFVVGEQA WNFADFATSQ SLLRVQGNKK GLFTRDRKPK MVAHYFRNRW   600
STIPEFGYKT K                                                        611

SEQ ID NO: 72           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 72
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSLQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611

SEQ ID NO: 73           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 73
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSWQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611

SEQ ID NO: 74           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 74
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSCQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611

SEQ ID NO: 75           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 75
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSGQ GTTADTDCSS QLSDVICLNR   480
```

```
YYGWYFGGPD LEVSEIGLRK ELSDWGKLGK PVMFTEYGAD TVSGLHDTTS VMYTEEYQVE    540
YYEMNNKVFD EFDFVVGEQA WNFADFATSQ SLLRVQGNKK GLFTRDRKPK MVAHYFRNRW    600
STIPEFGYKT K                                                        611

SEQ ID NO: 76           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 76
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD    120
LQDGDNLLTI AVNNVIDYTT LPVGGKANMM SGMMGGMGAG ASDKPQNNPN FDFFNYCGIT    180
RPVKIYTTPE TYINDITVTA DIDFTKEEPS AVLNYNVEIK GKDYNNITCK VELFDEEGTK    240
LSETEGSEGT FEISNVRLWQ PLNAYLYKIK VTAGQDVYTL PYGVRSVRVD GTKFLINEKP    300
FYFKGYGKHE DTFPNGRGIN LPMNTKDISI MKWQHANSFR TSHYPYSEEM MRLCDEEGIV    360
VIDETTAVGV NLQFGGGANF GGERIGTFDK EHGVQTQEHH KDVIRDLISR DKNHACVVMW    420
SIANEPDSAA EGAYDYFKPL YDLARELDPQ KRPCTLVSEQ GTTADTDCSS QLSDVICLNR    480
YYGWYFGGPD LEVSEIGLRK ELSDWGKLGK PVMFTEYGAD TVSGLHDTTS VMYTEEYQVE    540
YYEMNNKVFD EFDFVVGEQA WNFADFATSQ SLLRVQGNKK GLFTRDRKPK MVAHYFRNRW    600
STIPEFGYKT K                                                        611

SEQ ID NO: 77           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 77
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI DASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 78           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 78
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI EASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 79           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 79
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
```

```
KDEAVPYFED IFNFAKSQDK QNLPKTFAAI GASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 80           moltype = AA  length = 603
FEATURE                 Location/Qualifiers
source                  1..603
                        mol_type = protein
                        organism = synthetic construct
                        note = Description of Artificial Sequence: Synthetic
                         polypeptide
SEQUENCE: 80
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI SASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 81           moltype = AA  length = 603
FEATURE                 Location/Qualifiers
source                  1..603
                        mol_type = protein
                        organism = synthetic construct
                        note = Description of Artificial Sequence: Synthetic
                         polypeptide
SEQUENCE: 81
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI VASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 82           moltype = AA  length = 603
FEATURE                 Location/Qualifiers
source                  1..603
                        mol_type = protein
                        organism = synthetic construct
                        note = Description of Artificial Sequence: Synthetic
                         polypeptide
SEQUENCE: 82
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI KASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 83           moltype = AA  length = 603
FEATURE                 Location/Qualifiers
source                  1..603
                        mol_type = protein
                        organism = synthetic construct
                        note = Description of Artificial Sequence: Synthetic
                         polypeptide
SEQUENCE: 83
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
```

```
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QDSSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 84           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 84
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QKSSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 85           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 85
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QNSSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 86           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 86
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QGSSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 87           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 87
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
```

```
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QESSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                               603

SEQ ID NO: 88           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 88
MVNSMLYPRE SRTRRVVDIS GMWEFKIDIN NEGRNSGYAN GLKDTTFIPV PSSFNDLFTD   60
KNIREHAGDV WYETSFYLPL EWKDKDVNVR FGCATHEATV YINGKEVCTH VGGFMPFNAP  120
VNEAGIFGEK NKLVVVVNNE LSNTTIPCGH TETKPSGKKY IKPSFDFFNY AGLNRPVKIT  180
VTNKEYIHDI DILSDVNGSD GIVNYEVHTT GENKVYIKIN DEEGKEVASC EGKSGKIVIK  240
DAKLWNPKAA YLYKFIACIK NGDELIDEYY LDFGIRTVKV EGTKFLINGK PFYFTGFGKH  300
EDSEIAGRGY NPPVIKRDFE LIKWVGANSF RTSHYPYSEE IMQAADREGI VIIDEVAAVG  360
MFDVGSVLNP SASKTDYFSL DEVHSKTKEV HKKAVEELIK RDKNHPSVVM WSLFNEPDTS  420
KDEAVPYFED IFNFAKSQDK QNLPKTFAAI QQSSPGKCKC MHLCDVITLN RYYGWYFLGG  480
YEIDMSEEKF REEMNLYSNM NKPVMFTEYG ADTYAGVHKL PSVMWSEEYQ CEYYEMNFKV  540
FDSYDFIVGE QLWNFADFQT TEGIFRVDGN KKGIFTRNRQ PKAVAHLIRS RWNKLPLDYK  600
SKK                                                               603

SEQ ID NO: 89           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 89
MLYPVLTQSR LLSDLSGVWD FKLDNGKGFE EKWYEKPLKD ADTMPVPASY NDLKEGTDFR   60
DHYGWVFYQR NISVPEYVKS QRIVLRCAAV THYAMIYLNG KLICEHKGGF LPFEVELNDD  120
LQDGDNLLTI AVNNVIDYTT LPVGGKANMM SGMMGGMGAG ASDKPQNNPN FDFFNYCGIT  180
RPVKIYTTPE TYINDITVTA DIDFTKEEPS AVLNYNVEIK GKDYNNITCK VELFDEEGTK  240
LSETEGSEGT FEISNVRLWQ PLNAYLYKIK VTAGQDVYTL PYGVRSVRVD GTKFLINEKP  300
FYFKGYGKHE DTFPNGRGIN LPMNTKDISI MKWQHANSFR TSHYPYSEEM MRLCDEEGIV  360
VIDETTAVGV NLQFGGGANF GGERIGTFDK EHGVQTQEHH KDVIRDLISR DKNHACVVMW  420
SIANEPDSAA EGAYDYFKPL YDLARELDPQ KRPCTLVSVQ ATTADTDCSS QLSDVICLNR  480
YYGWYFGGPD LEVSEIGLRK ELSDWGKLGK PVMFTEYGAD TVSGLHDTTS VMYTEEYQVE  540
YYEMNNKVFD EFDFVVGEQA WNFADFATSQ SLLRVQGNKK GLFTRDRKPK MVAHYFRNRW  600
STIPEFGYKT K                                                      611

SEQ ID NO: 90           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 90
MLYPVLTQSR LLSDLSGVWD FKLDNGKGFE EKWYEKPLKD ADTMPVPASY NDLKEGTDFR   60
DHYGWVFYQR NISVPEYVKS QRIVLRCAAV THYAMIYLNG KLICEHKGGF LPFEVELNDD  120
LQDGDNLLTI AVNNVIDYTT LPVGGKANMM SGMMGGMGAG ASDKPQNNPN FDFFNYCGIT  180
RPVKIYTTPE TYINDITVTA DIDFTKEEPS AVLNYNVEIK GKDYNNITCK VELFDEEGTK  240
LSETEGSEGT FEISNVRLWQ PLNAYLYKIK VTAGQDVYTL PYGVRSVRVD GTKFLINEKP  300
FYFKGYGKHE DTFPNGRGIN LPMNTKDISI MKWQHANSFR TSHYPYSEEM MRLCDEEGIV  360
VIDETTAVGV NLQFGGGANF GGERIGTFDK EHGVQTQEHH KDVIRDLISR DKNHACVVMW  420
SIANEPDSAA EGAYDYFKPL YDLARELDPQ KRPCTLVSVQ HTTADTDCSS QLSDVICLNR  480
YYGWYFGGPD LEVSEIGLRK ELSDWGKLGK PVMFTEYGAD TVSGLHDTTS VMYTEEYQVE  540
YYEMNNKVFD EFDFVVGEQA WNFADFATSQ SLLRVQGNKK GLFTRDRKPK MVAHYFRNRW  600
STIPEFGYKT K                                                      611

SEQ ID NO: 91           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 91
MLYPVLTQSR LLSDLSGVWD FKLDNGKGFE EKWYEKPLKD ADTMPVPASY NDLKEGTDFR   60
DHYGWVFYQR NISVPEYVKS QRIVLRCAAV THYAMIYLNG KLICEHKGGF LPFEVELNDD  120
LQDGDNLLTI AVNNVIDYTT LPVGGKANMM SGMMGGMGAG ASDKPQNNPN FDFFNYCGIT  180
RPVKIYTTPE TYINDITVTA DIDFTKEEPS AVLNYNVEIK GKDYNNITCK VELFDEEGTK  240
```

```
LSETEGSEGT FEISNVRLWQ PLNAYLYKIK VTAGQDVYTL PYGVRSRVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ NTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611

SEQ ID NO: 92           moltype = AA  length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 92
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSRVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ STTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                        611

SEQ ID NO: 93           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 93
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFTGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEEIFRVDGN KKGIFTRNRQ PKAVAHLIRS RWNKLPLDYK   600
SKK                                                                 603

SEQ ID NO: 94           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 94
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFTGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI QASSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEAIFRVDGN KKGIFTRNRQ PKAVAHLIRS RWNKLPLDYK   600
SKK                                                                 603

SEQ ID NO: 95           moltype = AA  length = 603
FEATURE                 Location/Qualifiers
source                  1..603
                        mol_type = protein
                        organism = synthetic construct
                        note = Description of Artificial Sequence: Synthetic
                        polypeptide
SEQUENCE: 95
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
```

```
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEDIFRVDGN KKGIFTRNRQ PKAVAHLIRS RWNKLPLDYK    600
SKK                                                                 603

SEQ ID NO: 96             moltype = AA  length = 603
FEATURE                   Location/Qualifiers
source                    1..603
                          mol_type = protein
                          organism = synthetic construct
                          note = Description of Artificial Sequence: Synthetic
                          polypeptide
SEQUENCE: 96
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEYIFRVDGN KKGIFTRNRQ PKAVAHLIRS RWNKLPLDYK    600
SKK                                                                 603

SEQ ID NO: 97             moltype = AA  length = 611
FEATURE                   Location/Qualifiers
source                    1..611
                          mol_type = protein
                          organism = synthetic construct
                          note = Description of Artificial Sequence: Synthetic
                          polypeptide
SEQUENCE: 97
MLYPVLTQSR LLSDLSGVWD FKLDNGKGFE EKWYEKPLKD ADTMPVPASY NDLKEGTDFR     60
DHYGWVFYQR NISVPEYVKS QRIVLRCAAV THYAMIYLNG KLICEHKGGF LPFEVELNDD    120
LQDGDNLLTI AVNNVIDYTT LPVGGKANMM SGMMGGMGAG ASDKPQNNPN FDFFNYCGIT    180
RPVKIYTTPE TYINDITVTA DIDFTKEEPS AVLNYNVEIK GKDYNNITCK VELFDEEGTK    240
LSETEGSEGT FEISNVRLWQ PLNAYLYKIK VTAGQDVYTL PYGVRSVRVD GTKFLINEKP    300
FYFKGYGKHE DTFPNGRGIN LPMNTKDISI MKWQHANSFR TSHYPYSEEM MRLCDEEGIV    360
VIDETTAVGV NLQFGGGANF GGERIGTFDK EHGVQTQEHH KDVIRDLISR DKNHACVVMW    420
SIANEPDSAA EGAYDYFKPL YDLARELDPQ KRPCTLVSVQ GTTADTDCSS QLSDVICLNR    480
YYGWYFGGPD LEVSEIGLRK ELSDWGKLGK PVMFTEYGAD TVSGLHDTTS VMYTEEYQVE    540
YYEMNNKVFD EFDFVVGEQA WNFADFATSQ GLLRVQGNKK GLFTRDRKPK MVAHYFRNRW    600
STIPEFGYKT K                                                        611

SEQ ID NO: 98             moltype = AA  length = 611
FEATURE                   Location/Qualifiers
source                    1..611
                          mol_type = protein
                          organism = synthetic construct
                          note = Description of Artificial Sequence: Synthetic
                          polypeptide
SEQUENCE: 98
MLYPVLTQSR LLSDLSGVWD FKLDNGKGFE EKWYEKPLKD ADTMPVPASY NDLKEGTDFR     60
DHYGWVFYQR NISVPEYVKS QRIVLRCAAV THYAMIYLNG KLICEHKGGF LPFEVELNDD    120
LQDGDNLLTI AVNNVIDYTT LPVGGKANMM SGMMGGMGAG ASDKPQNNPN FDFFNYCGIT    180
RPVKIYTTPE TYINDITVTA DIDFTKEEPS AVLNYNVEIK GKDYNNITCK VELFDEEGTK    240
LSETEGSEGT FEISNVRLWQ PLNAYLYKIK VTAGQDVYTL PYGVRSVRVD GTKFLINEKP    300
FYFKGYGKHE DTFPNGRGIN LPMNTKDISI MKWQHANSFR TSHYPYSEEM MRLCDEEGIV    360
VIDETTAVGV NLQFGGGANF GGERIGTFDK EHGVQTQEHH KDVIRDLISR DKNHACVVMW    420
SIANEPDSAA EGAYDYFKPL YDLARELDPQ KRPCTLVSVQ GTTADTDCSS QLSDVICLNR    480
YYGWYFGGPD LEVSEIGLRK ELSDWGKLGK PVMFTEYGAD TVSGLHDTTS VMYTEEYQVE    540
YYEMNNKVFD EFDFVVGEQA WNFADFATSQ NLLRVQGNKK GLFTRDRKPK MVAHYFRNRW    600
STIPEFGYKT K                                                        611

SEQ ID NO: 99             moltype = AA  length = 597
FEATURE                   Location/Qualifiers
source                    1..597
                          mol_type = protein
                          organism = synthetic construct
                          note = Description of Artificial Sequence: Synthetic
                          polypeptide
SEQUENCE: 99
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
```

```
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYGDA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVV IIRVDGNKKG VFTRERKPKA AAHTLKTRWS GMLGSDH      597

SEQ ID NO: 100          moltype = AA  length = 597
FEATURE                 Location/Qualifiers
source                  1..597
                        mol_type = protein
                        organism = synthetic construct
                        note = Description of Artificial Sequence: Synthetic
                            polypeptide
SEQUENCE: 100
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYGDA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVE IIRVDGNKKG VFTRERKPKA AAHTLKTRWS GMLGSDH      597

SEQ ID NO: 101          moltype = AA  length = 603
FEATURE                 Location/Qualifiers
source                  1..603
                        mol_type = protein
                        organism = synthetic construct
                        note = Description of Artificial Sequence: Synthetic
                            polypeptide
SEQUENCE: 101
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYYCGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 102          moltype = AA  length = 603
FEATURE                 Location/Qualifiers
source                  1..603
                        mol_type = protein
                        organism = synthetic construct
                        note = Description of Artificial Sequence: Synthetic
                            polypeptide
SEQUENCE: 102
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYYIGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 103          moltype = AA  length = 603
FEATURE                 Location/Qualifiers
source                  1..603
                        mol_type = protein
                        organism = synthetic construct
                        note = Description of Artificial Sequence: Synthetic
                            polypeptide
SEQUENCE: 103
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
```

```
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYYVGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 104           moltype = AA   length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 104
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYYFGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 105           moltype = AA   length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 105
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYYMGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 106           moltype = AA   length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 106
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYYKGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 107           moltype = AA   length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 107
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
```

```
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFVGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAL QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 108           moltype = AA  length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 108
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFVGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAM QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 109           moltype = AA  length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 109
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFVGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAY QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 110           moltype = AA  length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 110
MVNSMLYPRE SRTRRVVDIS GMWEFKIDIN NEGRNSGYAN GLKDTTFIPV PSSFNDLFTD     60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFVGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAV QASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                 603

SEQ ID NO: 111           moltype = AA  length = 603
FEATURE                  Location/Qualifiers
source                   1..603
                         mol_type = protein
                         organism = synthetic construct
                         note = Description of Artificial Sequence: Synthetic
                         polypeptide
SEQUENCE: 111
MVNSMLYPRE SRTRRVVDIS GMWEFKIDIN NEGRNSGYAN GLKDTTFIPV PSSFNDLFTD     60
```

```
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAM DASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 112              moltype = AA  length = 603
FEATURE                     Location/Qualifiers
source                      1..603
                            mol_type = protein
                            organism = synthetic construct
                            note = Description of Artificial Sequence: Synthetic
                            polypeptide
SEQUENCE: 112
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAQ DASSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 113              moltype = AA  length = 603
FEATURE                     Location/Qualifiers
source                      1..603
                            mol_type = protein
                            organism = synthetic construct
                            note = Description of Artificial Sequence: Synthetic
                            polypeptide
SEQUENCE: 113
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI DESSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 114              moltype = AA  length = 603
FEATURE                     Location/Qualifiers
source                      1..603
                            mol_type = protein
                            organism = synthetic construct
                            note = Description of Artificial Sequence: Synthetic
                            polypeptide
SEQUENCE: 114
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP    120
VNEAGIFGEK NKLVVVVNNE LSNTTIPCGH TETKPSGKKY IKPSFDFFNY AGLNRPVKIT    180
VTNKEYIHDI DILSDVNGSD GIVNYEVHTT GENKVYIKIN DEEGKEVASC EGKSGKIVIK    240
DAKLWNPKAA YLYKFIACIK NGDELIDEYY LDFGIRTVKV EGTKFLINGK PFYFTGFGKH    300
EDSEIAGRGY NPPVIKRDFE LIKWVGANSF RTSHYPYSEE IMQAADREGI VIIDEVAAVG    360
MFDVGSVLNP SASKTDYFSL DEVHSKTKEV HKKAVEELIK RDKNHPSVVM WSLFNEPDTS    420
KDEAVPYFED IFNFAKSQDK QNLPKTFAAI DGSSPGKCKC MHLCDVITLN RYYGWYFLGG    480
YEIDMSEEKF REEMNLYSNM NKPVMFTEYG ADTYAGVHKL PSVMWSEEYQ CEYYEMNFKV    540
FDSYDFIVGE QLWNFADFQT TEGIFRVDGN KKGIFTRNRQ PKAVAHLIRS RWNKLPLDYK    600
SKK                                                                  603

SEQ ID NO: 115              moltype = AA  length = 603
FEATURE                     Location/Qualifiers
source                      1..603
                            mol_type = protein
                            organism = synthetic construct
                            note = Description of Artificial Sequence: Synthetic
                            polypeptide
SEQUENCE: 115
```

```
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFTGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI DQSSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 116         moltype = AA   length = 603
FEATURE                Location/Qualifiers
source                 1..603
                       mol_type = protein
                       organism = synthetic construct
                       note = Description of Artificial Sequence: Synthetic
                         polypeptide
SEQUENCE: 116
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFTGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI DSSSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 117         moltype = AA   length = 603
FEATURE                Location/Qualifiers
source                 1..603
                       mol_type = protein
                       organism = synthetic construct
                       note = Description of Artificial Sequence: Synthetic
                         polypeptide
SEQUENCE: 117
MVNSMLYPRE SRTRRVVDIS GMWEFKIDIN NEGRNSGYAN GLKDTTFIPV PSSFNDLFTD    60
KNIREHAGDV WYETSFYLPL EWKDKDVNVR FGCATHEATV YINGKEVCTH VGGFMPFNAP   120
VNEAGIFGEK NKLVVVVNNE LSNTTIPCGH TETKPSGKKY IKPSFDFFNY AGLNRPVKIT   180
VTNKEYIHDI DILSDVNGSD GIVNYEVHTT GENKVYIKIN DEEGKEVASC EGKSGKIVIK   240
DAKLWNPKAA YLYKFIACIK NGDELIDEYY LDFGIRTVKV EGTKFLINGK PFYFTGFGKH   300
EDSEIAGRGY NPPVIKRDFE LIKWVGANSF RTSHYPYSEE IMQAADREGI VIIDEVAAVG   360
MFDVGSVLNP SASKTDYFSL DEVHSKTKEV HKKAVEELIK RDKNHPSVVM WSLFNEPDTS   420
KDEAVPYFED IFNFAKSQDK QNLPKTFAAI DRSSPGKCKC MHLCDVITLN RYYGWYFLGG   480
YEIDMSEEKF REEMNLYSNM NKPVMFTEYG ADTYAGVHKL PSVMWSEEYQ CEYYEMNFKV   540
FDSYDFIVGE QLWNFADFQT TEGIFRVDGN KKGIFTRNRQ PKAVAHLIRS RWNKLPLDYK   600
SKK                                                                603

SEQ ID NO: 118         moltype = AA   length = 611
FEATURE                Location/Qualifiers
source                 1..611
                       mol_type = protein
                       organism = synthetic construct
                       note = Description of Artificial Sequence: Synthetic
                         polypeptide
SEQUENCE: 118
MLYPVLTCSR LLSDLSGVWD FKLDNGKGFE EKWYEKPLKD ADTMPVPASY NDLKEGTDFR    60
DHYGWVFYQR NICVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGDVYTL PYGVRSVRVD GTKFLINEKP    300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRKPK MVAHYFRNRW   600
STIPEFGYKT K                                                       611

SEQ ID NO: 119         moltype = AA   length = 611
FEATURE                Location/Qualifiers
source                 1..611
                       mol_type = protein
                       organism = synthetic construct
                       note = Description of Artificial Sequence: Synthetic
                         polypeptide
```

```
SEQUENCE: 119
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGPD LEVSEIGLRK ELSDWGKLGK PVMFTEYGAD TVSGLHDTTS VMYTEEYQVE   540
YYEMNNKVFD EFDFVVGEQA WNFADFATSQ SLLRVQGNKK GLFTRDRCPK MVAHYFRNRW   600
STIPEFGYKT K                                                       611

SEQ ID NO: 120          moltype = AA   length = 611
FEATURE                 Location/Qualifiers
source                  1..611
                        mol_type = protein
                        organism = synthetic construct
                        note = Description of Artificial Sequence: Synthetic
                        polypeptide
SEQUENCE: 120
MLYPVLTQSR LLSDLSGVWD FKLDNGKGFE EKWYEKPLKD ADTMPVPASY NDLKEGTDFR    60
DHYGWVFYQR NISVPEYVKS QRIVLRCAAV THYAMIYLNG KLICEHKGGF LPFEVELNDD   120
LQDGDNLLTI AVNNVIDYTT LPVGGKANMM SGMMGGMGAG ASDKPQNNPN FDFFNYCGIT   180
RPVKIYTTPE TYINDITVTA DIDFTKEEPS AVLNYNVEIK GKDYNNITCK VELFDEEGTK   240
LSETEGSEGT FEISNVRLWQ PLNAYLYKIK VTAGQDVYTL PYGVRSVRVD GTKFLINEKP   300
FYFKGYGKHE DTFPNGRGIN LPMNTKDISI MKWQHANSFR TSHYPYSEEM MRLCDEEGIV   360
VIDETTAVGV NLQFGGGANF GGERIGTFDK EHGVQTQEHH KDVIRDLISR DKNHACVVMW   420
SIANEPDSAA EGAYDYFKPL YDLARELDPQ KRPCTLVSVQ GTTADTDCSS QLSDVICLNR   480
YYGWYFGGCD LEVSEIGLRK ELSDWGKLGK PVMFTEYGAD TVSGLHDTTS VMYTEEYQVE   540
YYEMNNKVFD EFDFVVGEQA WNFADFATSC SLLRVQGNKK GLFTRDRKPK MVAHYFRNRW   600
STIPEFGYKT K                                                       611

SEQ ID NO: 121          moltype = AA   length = 597
FEATURE                 Location/Qualifiers
source                  1..597
                        mol_type = protein
                        organism = synthetic construct
                        note = Description of Artificial Sequence: Synthetic
                        polypeptide
SEQUENCE: 121
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANLGDA TYEVDRISDM FDVLCLNRYF GWYSQTGEVE   480
EAEAAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH      597

SEQ ID NO: 122          moltype = AA   length = 597
FEATURE                 Location/Qualifiers
source                  1..597
                        mol_type = protein
                        organism = synthetic construct
                        note = Description of Artificial Sequence: Synthetic
                        polypeptide
SEQUENCE: 122
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANPGDA TYEVDRISDM FDVLCLNRYF GWYSQTGEVE   480
EAEAAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH      597

SEQ ID NO: 123          moltype = AA   length = 597
FEATURE                 Location/Qualifiers
source                  1..597
                        mol_type = protein
                        organism = synthetic construct
                        note = Description of Artificial Sequence: Synthetic
                        polypeptide
SEQUENCE: 123
```

```
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANIGDA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH     597

SEQ ID NO: 124              moltype = AA  length = 597
FEATURE                     Location/Qualifiers
source                      1..597
                            mol_type = protein
                            organism = synthetic construct
                            note = Description of Artificial Sequence: Synthetic
                            polypeptide
SEQUENCE: 124
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANQGDA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH     597

SEQ ID NO: 125              moltype = AA  length = 597
FEATURE                     Location/Qualifiers
source                      1..597
                            mol_type = protein
                            organism = synthetic construct
                            note = Description of Artificial Sequence: Synthetic
                            polypeptide
SEQUENCE: 125
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANYEDA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH     597

SEQ ID NO: 126              moltype = AA  length = 597
FEATURE                     Location/Qualifiers
source                      1..597
                            mol_type = protein
                            organism = synthetic construct
                            note = Description of Artificial Sequence: Synthetic
                            polypeptide
SEQUENCE: 126
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANYKDA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH     597

SEQ ID NO: 127              moltype = AA  length = 597
FEATURE                     Location/Qualifiers
source                      1..597
                            mol_type = protein
                            organism = synthetic construct
                            note = Description of Artificial Sequence: Synthetic
                            polypeptide
SEQUENCE: 127
MLKPQQTTTR DLISLDGLWK FALASDDNNT QPWTSQLKTS LECPVPASYN DIFADSKIHD    60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
```

```
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYFDA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH      597

SEQ ID NO: 128           moltype = AA   length = 597
FEATURE                  Location/Qualifiers
source                   1..597
                         mol_type = protein
                         organism = synthetic construct
                         note = Description of Artificial Sequence: Synthetic
                         polypeptide
SEQUENCE: 128
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYLDA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH      597

SEQ ID NO: 129           moltype = AA   length = 597
FEATURE                  Location/Qualifiers
source                   1..597
                         mol_type = protein
                         organism = synthetic construct
                         note = Description of Artificial Sequence: Synthetic
                         polypeptide
SEQUENCE: 129
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYCDA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH      597

SEQ ID NO: 130           moltype = AA   length = 597
FEATURE                  Location/Qualifiers
source                   1..597
                         mol_type = protein
                         organism = synthetic construct
                         note = Description of Artificial Sequence: Synthetic
                         polypeptide
SEQUENCE: 130
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYWDA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH      597

SEQ ID NO: 131           moltype = AA   length = 597
FEATURE                  Location/Qualifiers
source                   1..597
                         mol_type = protein
                         organism = synthetic construct
                         note = Description of Artificial Sequence: Synthetic
                         polypeptide
SEQUENCE: 131
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
```

```
FSIGSGVSSE DSPQTFTPEG INNNTREAHK QAIRELIARD KNHASVVMWS IANEPASQEV    420
GAREYFAPLV DLAHELDPSR PVCFANYGQA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH       597

SEQ ID NO: 132          moltype = AA   length = 597
FEATURE                 Location/Qualifiers
source                  1..597
                        mol_type = protein
                        organism = synthetic construct
                        note = Description of Artificial Sequence: Synthetic
                          polypeptide
SEQUENCE: 132
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYGGA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH       597

SEQ ID NO: 133          moltype = AA   length = 597
FEATURE                 Location/Qualifiers
source                  1..597
                        mol_type = protein
                        organism = synthetic construct
                        note = Description of Artificial Sequence: Synthetic
                          polypeptide
SEQUENCE: 133
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYGRA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH       597

SEQ ID NO: 134          moltype = AA   length = 597
FEATURE                 Location/Qualifiers
source                  1..597
                        mol_type = protein
                        organism = synthetic construct
                        note = Description of Artificial Sequence: Synthetic
                          polypeptide
SEQUENCE: 134
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYGKA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
IDSVVGEHVW NFADFQTAVG IIRVDGNKKG VFTRERKPKA AAHTLKTRWS GMLGSDH       597

SEQ ID NO: 135          moltype = AA   length = 597
FEATURE                 Location/Qualifiers
source                  1..597
                        mol_type = protein
                        organism = synthetic construct
                        note = Description of Artificial Sequence: Synthetic
                          polypeptide
SEQUENCE: 135
MLKPQQTTTR DLISLDGLWK FALASDDNNT QPWTSQLKTS LECPVPASYN DIFADSKIHD     60
HVGWVYYQRD VIVPKGWSEE RYLVRCEAAT HHGRIYVNGN LVADHVGGYT PFEADITDLV    120
AAGEQFRLTI AVDNELTYQT IPPGKVEILE ATGKKVQTYQ HDFYNYAGLA RSVWLYSVPQ    180
QHIQDITVRT DVQGTTGLID YNVVASTTQG TIQVAVIDED GTTVATSSGS NGTIHIPSVH    240
LWQPGAAYLY QLHASIIDSS KKTIDTYKLA TGIRTVKVQG TQFLINDKPF YFTGFGKHED    300
SAVRGKGYDP AYMVHDFQLM DWMGANSFRT SHYPYAEEVM EFADRHGIVV IDETPAVGLA    360
FSIGSGVSSE DSPQTFTPEG INNNTREAHK QAIRELIARD KNHASVVMWS IANEPASQEV    420
GAREYFAPLV DLAHELDPSR PVCFANYGSA TYEVDRISDM FDVLCLNRYF GWYSQTGEVE    480
EAEAALEKEL LGWEGKYGKP IVITEYGADT MAGLHSVLAL PWSEEFQVQL LDMYHRVFDR    540
```

```
IDSVVGEHVW NFADFQTAVG IIRVDGNKKG VFTRERKPKA AAHTLKTRWS GMLGSDH      597

SEQ ID NO: 136          moltype = AA  length = 597
FEATURE                 Location/Qualifiers
source                  1..597
                        mol_type = protein
                        organism = synthetic construct
                        note = Description of Artificial Sequence: Synthetic
                           polypeptide
SEQUENCE: 136
MLKPQQTTTR DLISLDGLWK FALASDDNNT QPWTSQLKTS LECPVPASYN DIFADSKIHD   60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANYGCA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH      597

SEQ ID NO: 137          moltype = AA  length = 597
FEATURE                 Location/Qualifiers
source                  1..597
                        mol_type = protein
                        organism = synthetic construct
                        note = Description of Artificial Sequence: Synthetic
                           polypeptide
SEQUENCE: 137
MLKPQQTTTR DLISLDGLWK FALASDDNNT QPWTSQLKTS LECPVPASYN DIFADSKIHD   60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
SAVRGKGYDP AYMVHDFQLM DWMGANSFRT SHYPYAEEVM EFADRHGIVV IDETPAVGLA   360
FSIGSGVSSE DSPQTFTPEG INNNTREAHK QAIRELIARD KNHASVVMWS IANEPASQEV   420
GAREYFAPLV DLAHELDPSR PVCFANYGEA TYEVDRISDM FDVLCLNRYF GWYSQTGEVE   480
EAEAALEKEL LGWEGKYGKP IVITEYGADT MAGLHSVLAL PWSEEFQVQL LDMYHRVFDR   540
IDSVVGEHVW NFADFQTAVG IIRVDGNKKG VFTRERKPKA AAHTLKTRWS GMLGSDH      597

SEQ ID NO: 138          moltype = AA  length = 604
FEATURE                 Location/Qualifiers
source                  1..604
                        mol_type = protein
                        organism = Aspergillus oryzae
SEQUENCE: 138
MLKPQQTTTR DLISLDGLWK FALASDDNNT QPWTSQLKTS LECPVPASYN DIFADSKIHD   60
HVGWVYYQRD VIVPKGWSEE RYLVRCEAAT HHGRIYVNGN LVADHVGGYT PFEADITDLV   120
AAGEQFRLTI AVDNELTYQT IPPGKVEILE ATGKKVQTYQ HDFYNYAGLA RSVWLYSVPQ   180
QHIQDITVRT DVQGTTGLID YNVVASTTQG TIQVAVIDED GTTVATSSGS NGTIHIPSVH   240
LWQPGAAYLY QLHASIIDSS KKTIDTYKLA TGIRTVKVQG TQFLINDKPF YFTGFGKHED   300
TNIRGKGHDD AYMVHDFQLL HWMGANSFRT SHYPYAEEVM EYADRQGIVV IDETPAVGLA   360
FSIGAGAQTS NPPATFSPDR INNKTREAHA QAIRELIHRD KNHPSVVMWS IANEPASNED   420
GAREYFAPLP KLARQLDPTR PVTFANVGLA TYKADRIADL FDVLCLNRYF GWYTQTAELD   480
EAEAALEEEL RGWTEKYDKP IVMTEYGADT VAGLHSVMVT PWSEEFQVEM LDMYHRVFDR   540
FEAMAGEQVW NFADFQTAVG VSRVDGNKKG VFTRDRKPKA AAHLLRKRWT NLHNGTAEGG   600
KTFQ                                                               604

SEQ ID NO: 139          moltype = AA  length = 6
FEATURE                 Location/Qualifiers
source                  1..6
                        mol_type = protein
                        organism = synthetic construct
                        note = Description of Artificial Sequence: Synthetic 6xHis
                           tag
SEQUENCE: 139
HHHHHH                                                             6
```

What is claimed:

1. A variant *Brachyspira pilosicoli* beta-glucuronidase (BpBGUS) enzyme comprising an amino acid sequence at least 95% homologous to a parental BpBGUS amino acid sequence shown in SEQ ID NO: 5, wherein the variant comprises a substitution at amino acid position Q451, wherein the substitution is selected from the group consisting of aspartic acid (D), glutamic acid (E), serine(S), valine (V) and lysine (K), and wherein the variant exhibits an increased level of enzymatic activity for one or more substrates as compared to the parental BpBGUS enzyme, wherein the one or more substrates are selected from the group consisting of morphine-3-β-D-glucuronide (MOR), oxymorphone-3-β-D-glucuronide (OMOR), codeine-6-β-D-glucuronide (COD), dihydrocodeine-6-β-D-glucuronide (DCOD) and amitriptyline-N-β-D-glucuronide (AMT gluc).

2. The variant BpBGUS enzyme of claim 1, wherein the substitution is aspartic acid (D).

3. The variant BpBGUS enzyme of claim 2, which comprises the amino acid sequence shown in SEQ ID NO: 77.

4. The variant BpBGUS enzyme of claim 2, which further comprises a methionine (M) substitution at amino acid position 1450 of SEQ ID NO: 5.

5. The variant BpBGUS enzyme of claim 4, which comprises the amino acid sequence shown in SEQ ID NO: 111.

6. The variant BpBGUS enzyme of claim 2, which further comprises a glutamine (Q) substitution at amino acid position 1450 of SEQ ID NO: 5.

7. The variant BpBGUS enzyme of claim 6, which comprises the amino acid sequence shown in SEQ ID NO: 112.

8. The variant BpBGUS enzyme of claim 2, which further comprises a glutamic acid (E) substitution at amino acid position A452 of SEQ ID NO: 5.

9. The variant BpBGUS enzyme of claim 8, which comprises the amino acid sequence of SEQ ID NO: 113.

10. The variant BpBGUS enzyme of claim 2, which further comprises a glycine (G) substitution at amino acid position A452 of SEQ ID NO: 5.

11. The variant BpBGUS enzyme of claim 10, which comprises the amino acid sequence of SEQ ID NO: 114.

12. The variant BpBGUS enzyme of claim 2, which further comprises a glutamine (Q) substitution at amino acid position A452 of SEQ ID NO: 5.

13. The variant BpBGUS enzyme of claim 12, which comprises the amino acid sequence of SEQ ID NO: 115.

14. The variant BpBGUS enzyme of claim 2, which further comprises a serine(S) substitution at amino acid position A452 of SEQ ID NO: 5.

15. The variant BpBGUS enzyme of claim 14, which comprises the amino acid sequence of SEQ ID NO: 116.

16. The variant BpBGUS enzyme of claim 2, which further comprises an arginine (R) substitution at amino acid position A452 of SEQ ID NO: 5.

17. The variant BpBGUS enzyme of claim 16, which comprises the amino acid sequence of SEQ ID NO: 117.

18. The variant BpBGUS enzyme of claim 1, wherein the substitution is glutamic acid (E).

19. The variant BpBGUS enzyme of claim 18, which comprises the amino acid sequence shown in SEQ ID NO: 78.

20. The variant BpBGUS enzyme of claim 1, wherein the substitution is serine(S).

21. The variant BpBGUS enzyme of claim 20, which comprises the amino acid sequence shown in SEQ ID NO: 80.

22. The variant BpBGUS enzyme of claim 1, wherein the substitution is valine (V).

23. The variant BpBGUS enzyme of claim 22, which comprises the amino acid sequence shown in SEQ ID NO: 81.

24. The variant BpBGUS enzyme of claim 1, wherein the substitution is lysine (K).

25. The variant BpBGUS enzyme of claim 24, which comprises the amino acid sequence shown in SEQ ID NO: 82.

26. A formulation comprising the variant BpBGUS enzyme of claim 1 and at